(12) United States Patent
Arancio et al.

(10) Patent No.: US 9,783,525 B2
(45) Date of Patent: Oct. 10, 2017

(54) MAP KINASE MODULATORS AND USES THEREOF

(71) Applicants: THE TRUSTEES OF COLUMBIA UNIVERSITY IN THE CITY OF NEW YORK, New York, NY (US); Northwestern University, Evanston, IL (US)

(72) Inventors: Ottavio Arancio, New York, NY (US); Daniel Martin Watterson, Douglas, MI (US); Jeffrey Claude Pelletier, Lafayette Hill, PA (US); Saktimayee Mitra Roy, Evanston, IL (US)

(73) Assignees: THE TRUSTEES OF COLUMBIA UNIVERSITY IN THE CITY OF NEW YORK, New York, NY (US); NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/855,035

(22) Filed: Sep. 15, 2015

(65) Prior Publication Data
US 2016/0130253 A1    May 12, 2016

Related U.S. Application Data

(63) Continuation-in-part of application No. PCT/US2014/030260, filed on Mar. 17, 2014.

(60) Provisional application No. 61/790,207, filed on Mar. 15, 2013.

(51) Int. Cl.
*C07D 401/14* (2006.01)
*C07D 401/04* (2006.01)

(52) U.S. Cl.
CPC ......... *C07D 401/14* (2013.01); *C07D 401/04* (2013.01)

(58) Field of Classification Search
CPC .......................... C07D 401/14; C07D 401/04
See application file for complete search history.

(56) References Cited

U.S. PATENT DOCUMENTS

| | | |
|---|---|---|
| 7,919,485 B2 | 4/2011 | Watterson et al. |
| 8,063,047 B2 | 11/2011 | Watterson et al. |
| 8,158,627 B2 | 4/2012 | Watterson et al. |
| 8,188,096 B2 | 5/2012 | Watterson et al. |
| 8,367,672 B2 | 2/2013 | Watterson et al. |
| 2010/0016587 A1* | 1/2010 | Watterson ............. A61K 31/50 544/238 |
| 2010/0104536 A1 | 4/2010 | Modi et al. |
| 2012/0289511 A1 | 11/2012 | Alam |

FOREIGN PATENT DOCUMENTS

| | | |
|---|---|---|
| EP | 1196167 | 4/2002 |
| EP | 1606283 | 12/2005 |
| EP | 2426134 | 3/2012 |
| WO | WO-03/059891 | 7/2003 |
| WO | WO-2006/050389 | 5/2006 |
| WO | WO-2010/074783 | 7/2010 |
| WO | WO-2011/072243 A1 | 6/2011 |
| WO | WO-2012/088420 A1 | 6/2012 |
| WO | WO-2012/154814 A1 | 11/2012 |

OTHER PUBLICATIONS

Alamed et al., "Two-day radial-arm water maze learning and memory task; robust resolution of amyloid-related memory deficits in transgenic mice," Nat. Protoc. 1, pp. 1671-1679 (2006).
Yeung et al., "Interleukins in glioblastoma pathophysiology: implications for therapy," Br. J Pharmacol. 168, pp. 591-606 (2013).
Bachstetter and Van Eldik, "The p38 MAP kinase family as regulators of proinflammatory cytokine production in degenerative diseases of the CNS," Aging and Disease 1, pp. 199-211 (2010).
Bachstetter et al., "Microglial p38a MAPK is a key regulator of proinflammatory cytokine up-regulation induced by toll-like receptor (TLR) ligands or beta-amyloid (Aβ)," J. Neuroinflammation 8(79) 12 pages (2011).
Barone et al., "SB 239063, a Second-Generation p38 Mitogen-Activated Protein Kinase Inhibitor, Reduces Brain Injury and Neurological Deficits in Cerebral Focal Ischemia," Journal of Pharmacology and Experimental Therapeutics 296(2), pp. 312-321 (2001).
Berge, et al., "Pharmaceutical salts," J. Pharm. Sci. 66(1), pp. 1-19 (1977).
Chico et al., "Targeting protein kinases in central nervous system disorders," Nature Rev. Drug Discovery 8, pp. 892-909 (2009).
Corrêa and Eales, "The role of p38 MAPK and its substrates in neuronal plasticity and neurodegenerative disease," J. Signal Transduction, Epub, Article ID 649079, pp. 1-12 (2012).
Cullen et al., "Block of LTP in rat hippocampus in vivo by β-amyloid precursor protein fragments," NeuroReport. 8, pp. 3213-3217 (1997).
Dominguez et al., "p38 Map kinase inhibitors: many are made, but few are chosen," Curr. Opin. Drug Disc. Dev. 8, pp. 421-430 (2005).
Fabbro et al., "Targeting cancer with small-molecular-weight kinase inhibitors," Methods Mol. Biol. 795, pp. 1-34 (2012).
Fischer et al., "p38α mitogen-activated protein kinase inhibitors, a patent review (2005-2011)," Exp. Opin. Ther. Patents 21(12), pp. 1843-1866 (2011).
Giovannini et al., "β-Amyloid-Induced Inflammation and Cholinergic Hypofunction in the Rat Brain in Vivo: Involvement of the p38MAPK Pathway," Neurobiol. Dis. 11, 257-274 (2002).
Glover et al., "A step-up approach for cell therapy in stroke: translational hurdles of bone marrow-derived stem cells," Transl. Stroke Res. 3, pp. 90-98 (2012).
Gong et al., "Persistent improvement in synaptic and cognitive functions in an Alzheimer mouse model after rolipram treatment," J. Clin. Invest. 114(11), pp. 1624-1634 (2004).

(Continued)

*Primary Examiner* — Sahar Javanmard
(74) *Attorney, Agent, or Firm* — Wilmer Cutler Pickering Hale and Dorr LLP

(57) ABSTRACT

The invention provides for novel MAP kinase inhibitors and compositions comprising the same. In some embodiments, the MAP kinase inhibitors are p38α MAP kinase inhibitors. The invention further provides for methods for treatment of diseases comprising administration of MAP kinase inhibitors or compositions comprising MAP kinase inhibitors. In some embodiments, the disease is Alzheimer's Disease, ALS, Huntington's Disease or Parkinson's Disease.

17 Claims, 70 Drawing Sheets

(56) References Cited

OTHER PUBLICATIONS

Graziosi et al., "Mechanistic role of p38 MAPK in gastric cancer dissemination in a rodent model peritoneal metastasis," Eur. J Pharm. 674, pp. 143-152 (2012).
Hensley et al., "p38 kinase is activated in the Alzheimer's disease brain," J. Neurochem. 72, pp. 2053-2058 (1999).
Holcomb et al., "Accelerated Alzheimer-type phenotype in transgenic mice carrying both mutant *amyloid precursor protein and presenilin 1 transgenes*," Nat. Med. 4, pp. 97-100 (1998).
Hsiao et al., "Correlative memory deficits, Aβ elevation, and amyloid plaques in transgenic mice," Science 274, 99-102 (1996).
Hu et al., "Development of a novel therapeutic suppressor of brain proinflammatory cytokine up-regulation that attenuates synaptic dysfunction and behavioral deficits," Bioorg. Med. Chem. Lett. 17, pp. 414-418 (2007).
International Search Report and Written Opinion for International Patent Application No. PCT/US2014/030260 dated Oct. 3, 2014 (11 pages).
Itoh et al., "Impairments of long-term potentiation in hippocampal slices of β-amyloid-infused rats," Eur. J. Pharmacol. 382(3), pp. 167-175 (1999).
Klyubin et al., "Amyloid β protein immunotherapy neutralizes Aβ oligomers that disrupt synaptic plasticity in vivo," Nat. Med. 11, pp. 556-561 (2005).
Kumar et al., "p38 MAP kinases: key signalling molecules as therapeutic targets for inflammatory diseases," Nat. Rev. Drug Disc. 2, pp. 717-726 (2003).
La Merie Publishing, "Competitor Analysis—p38 Mitogen-Activated Protein Kinase (MAPK) Inhibitors," 25 Pages (Nov. 2010).
Lambert et al., "Diffusible, nonfibrillar ligands derived from $A\beta_{1-42}$ are potent central nervous system neurotoxins," Proc. Natl. Acad. Sci. U.S.A. 95, pp. 6448-6453 (1998).
Li et al., "Interleukin-1 mediates pathological effects of microglia on tau phosphorylation and on synaptophysin synthesis in cortical neurons through a p38-MAPK pathway," J. Neurosci. 23(5), pp. 1605-1611 (2003).
Yang et al., "Mitogen-activated protein kinases regulate vascular reactivity after hemorrhagic shock through myosin light chain phosphorylation pathway," J. Trauma Acute Care Surg. 74, pp. 1033-1043 (2013).
Kurt et al., "Neurodegenerative changes associated with β-amyloid deposition in the brains of mice carrying mutant amyloid precursor protein and mutant presenilin-1 transgenes," Exp. Neurol. 171(1), pp. 59-71 (2001).
Marshall-Batty and Nakai, "trans-Targeting of the Phage Mu Repressor Is Promoted by Conformational Changes That Expose Its ClpX Recognition Determinant," J. Biol. Chem. 278(3), pp. 1612-1617 (2003).
Masliah, "Mechanisms of synaptic dysfunction in Alzheimer's disease," Histol. Histopathol. 10, pp. 509-519 (1995).
McGowan et al., "Amyloid phenotype characterization of transgenic mice overexpressing both mutant amyloid precursor protein and mutant presenilin 1 transgenes," Neurobiol. Dis. 6, pp. 231-244 (1999).
Morfini et al., "Inhibition of Fast Axonal Transport by Pathogenic SOD1 Involves Activation of p38 MAP Kinase," PLoS ONE 2013, 8(6), e65235 (2013) (15 pages).
Munoz and Ammit, "Targeting p38 MAPK pathway for the treatment of Alzheimer's disease," Neuropharmacology 58, pp. 561-568 (2010).
Munoz et al., "A novel p38α MAPK inhibitor suppresses brain proinflammatory cytokine up-regulation and attenuates synaptic dysfunction and behavioral deficits in an Alzheimer's disease mouse model," J. Neuroinflammation 4:21 (2007) (14 pages).
O'Keefe et al., "Chemical genetics define the roles of p38α and p38β in acute and chronic inflammation," J. Biol. Chem. 282(48), pp. 34663-34671 (2007).
Oddo et al., "Triple-transgenic model of Alzheimer's disease with plaques and tangles: intracellular Aβ and synaptic dysfunction," Neuron 39, pp. 409-421 (2003).
Origlia et al., "Microglial Receptor for Advanced Glycation End Product-Dependent Signal Pathway Drives β-Amyloid-Induced Synaptic Depression and Long-Term Depression Impairment in Entorhinal Cortex," J. Neurosci. 30(34), pp. 11414-11425 (2010).
Origlia et al., "Receptor for advanced glycation end product-dependent activation of p38 mitogen-activated protein kinase contributes to amyloid-β-mediated cortical synaptic dysfunction," J. Neurosci. 28, pp. 3521-3530 (2008).
Partial Supplementary European Search Report issued by the European Patent Office for Application No. 14762602.2 dated Jul. 13, 2016 (6 pages).
Puzzo et al., "Amyloid-β peptide inhibits activation of the nitric oxide/cGMP/cAMP-responsive element-binding protein pathway during hippocampal synaptic plasticity," J. Neurosci. 25, pp. 6887-6897 (2005).
Puzzo et al., "Behavioral assays with mouse models of Alzheimer's disease: Practical considerations and guidelines," Biochem Pharmacol. 88, pp. 450-467 (2014).
Puzzo et al., "Picomolar amyloid-β positively modulates synaptic plasticity and memory in hippocampus," J. Neurosci. 28, pp. 14537-14545 (2008).
Ricci and Ruzziconi, "Regioselectively nucleus and/or side-chain fluorinated 2-(Phenanthryl)propionic acids by an effective combination of radical and organometallic chemistry," J. Org. Chem. 70, pp. 611-623 (2005).
Rogers et al., "Behavioral and functional analysis of mouse phenotype: SHIRPA, a proposed protocol for comprehensive phenotype assessment," Mammalian Genome 8, pp. 711-713 (1997).
Rowan et al., "Synaptic plasticity in animal models of early Alzheimer's disease," Philos. Trans. R. Soc. Lond. B. 358, pp. 821-828 (2003).
Sant'Angelo et al., "Usefulness of behavioral and electrophysiological studies in transgenic models of Alzheimer's disease," Neurochem. Res. 28, pp. 1009-1015 (2003).
Schmitt et al., "Use of 4-bromo pyridazine 3,6-dione for building 3-amino pyridazine libraries," Molecular Diversity 10, pp. 429-434, Epub (2006).
Selkoe, "Alzheimer's disease is a synaptic failure," Science 298, pp. 789-791 (2002).
Selkoe, "Soluble oligomers of the amyloid β-protein impair synaptic plasticity and behavior," Behav. Brain Res. 192, pp. 106-113 (2008).
Sheng et al., "Interleukin-1 promotion of MAPK-p38 overexpression in experimental animals and in Alzheimer's disease: potential significance for tau protein phosphorylation," Neurochem. Intl. 39, pp. 341-348 (2001).
Sipos et al., "β-amyloid pathology in the entorhinal cortex of rats induces memory deficits: implications for Alzheimer's disease," Neuroscience 147(1), pp. 28-36, Epub (2007).
Sun et al., "p38 MAP kinase is activated at early stages in Alzheimer's disease brain," Exp. Neurol. 183, pp. 394-405 (2003).
Tamayo et al., "Design and synthesis of potent pyridazine inhibitors of p38 MAP kinase," Bioorg. Med. Chem. Lett. 15, pp. 2409-2413 (2005).
Yamamoto et al., "Reversal of Neuropathology and Motor Dysfunction in a Conditional Model of Huntington's Disease," Cell 101(1), pp. 57-66 (2000).
Teich and Arancio "Is the Amyloid Hypothesis of Alzheimer's Disease Therapeutically Relevant?" Biochem. J. 446, pp. 165-177 (2012).
Tong et al., "Brain-derived neurotrophic factor-dependent synaptic plasticity is suppressed by interleukin-1β via p38 mitogen-activated protein kinase," J. Neurosci. 32(49), 17714-17724 (2012).
Trinchese et al., "Progressive age-related development of Alzheimer-like pathology in APP/PS1 mice," Ann. Neurol. 55(6), pp. 801-814 (2004).
Vitolo et al., "Amyloid β-peptide inhibition of the PKA/CREB pathway and long-term potentiation: Reversibility by drugs that enhance cAMP signaling," Proc. Natl. Acad. Sci. U.S.A. 99, pp. 13217-13221 (2002).

(56) References Cited

OTHER PUBLICATIONS

Vitolo et al., "Protection against β-amyloid induced abnormal synaptic function and cell death by Ginkgolide J," Neurobiol. Aging 30, pp. 257-265 (2009).
Voets et al., "Synthesis and evaluation of heteroaryl-substituted dihydronaphthalenes and indenes: potent and selective inhibitors of aldosterone synthase (CYP11B2) for the treatment of congestive heart failure and myocardial fibrosis," J. Med. Chem. 49(7), pp. 2222-2231 (2006).
Wagner and Nebreda "Signal integration by JNK and p38 MAPK pathways in cancer development," Nat. Rev. Cancer 9, pp. 537-549 (2009).
Walsh et al., "Naturally secreted oligomers of amyloid β protein potently inhibit hippocampal long-term potentiation in vivo," Nature 416, pp. 535-539 (2002).
Xing et al., "Microglial p38α MAPK is critical for LPS-induced neuron degeneration, through a mechanism involving TNFα," Molecular Neurodegeneration 6(84), pp. 1-12 (2011).
Watterson et al., "Development of Novel In Vivo Chemical Probes to Address CNS Protein Kinase Involvement in Synaptic Dysfunction," PLOS ONE 8, p. e66226 (2013) (16 pages).

\* cited by examiner

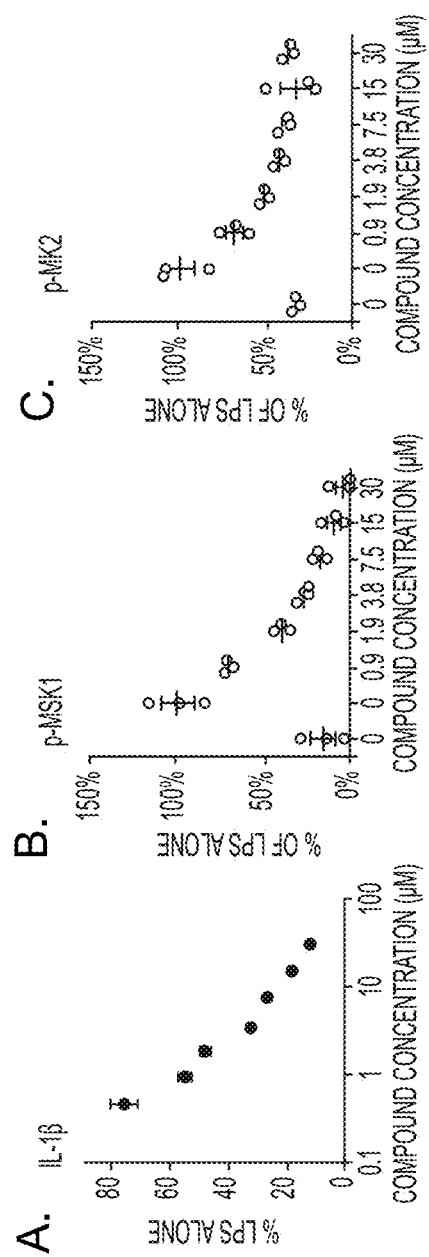
FIG. 1A-C

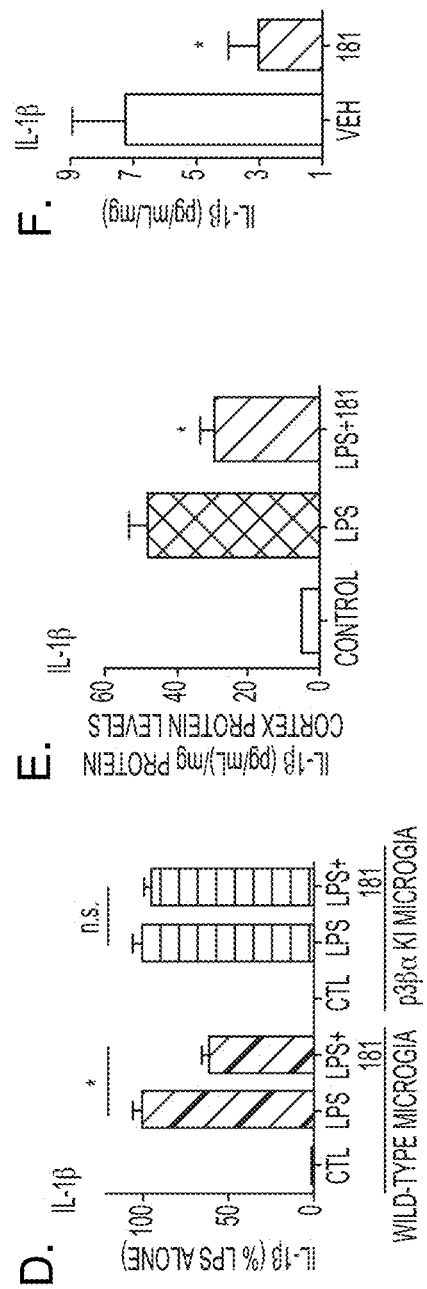
FIG. 1D-F

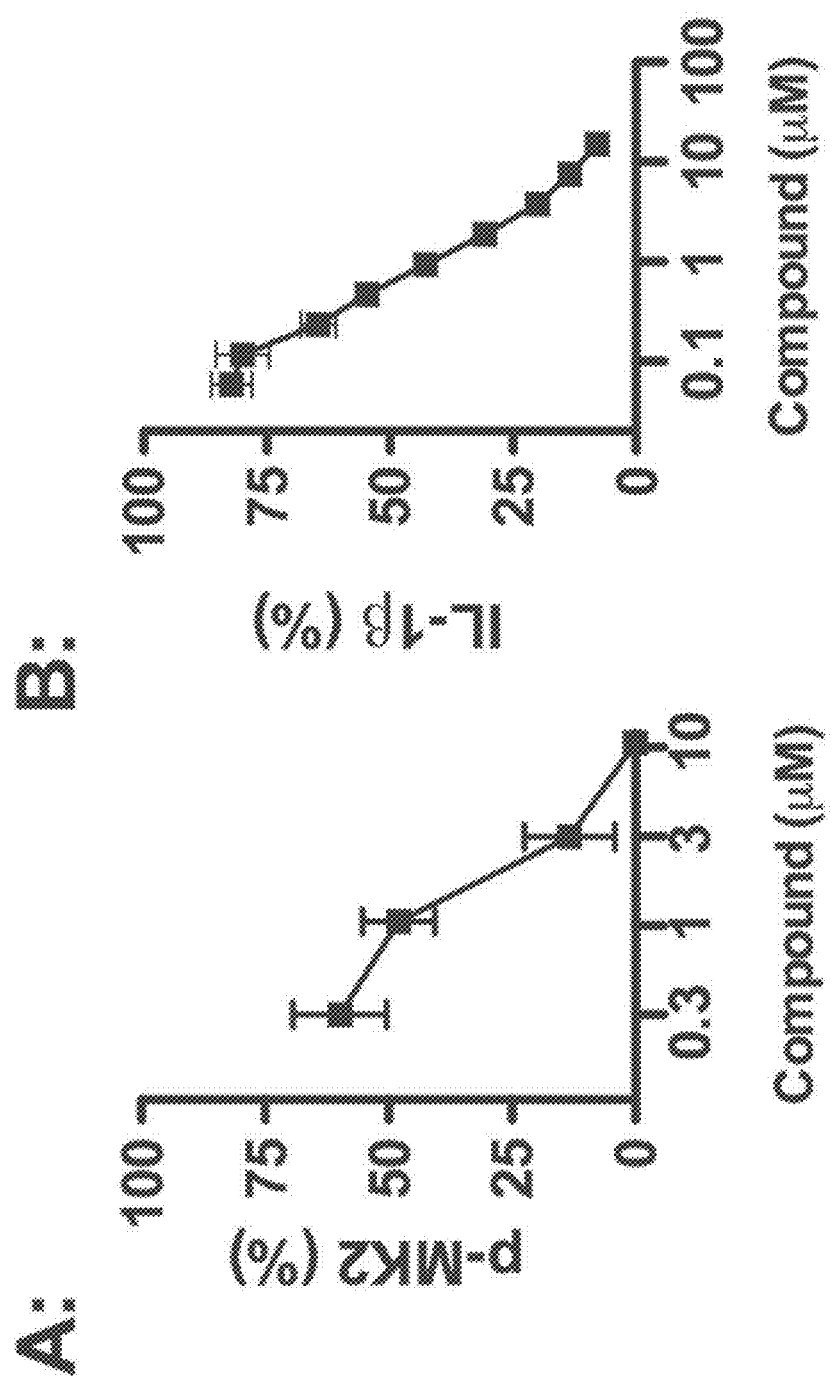
FIGS. 2A-B

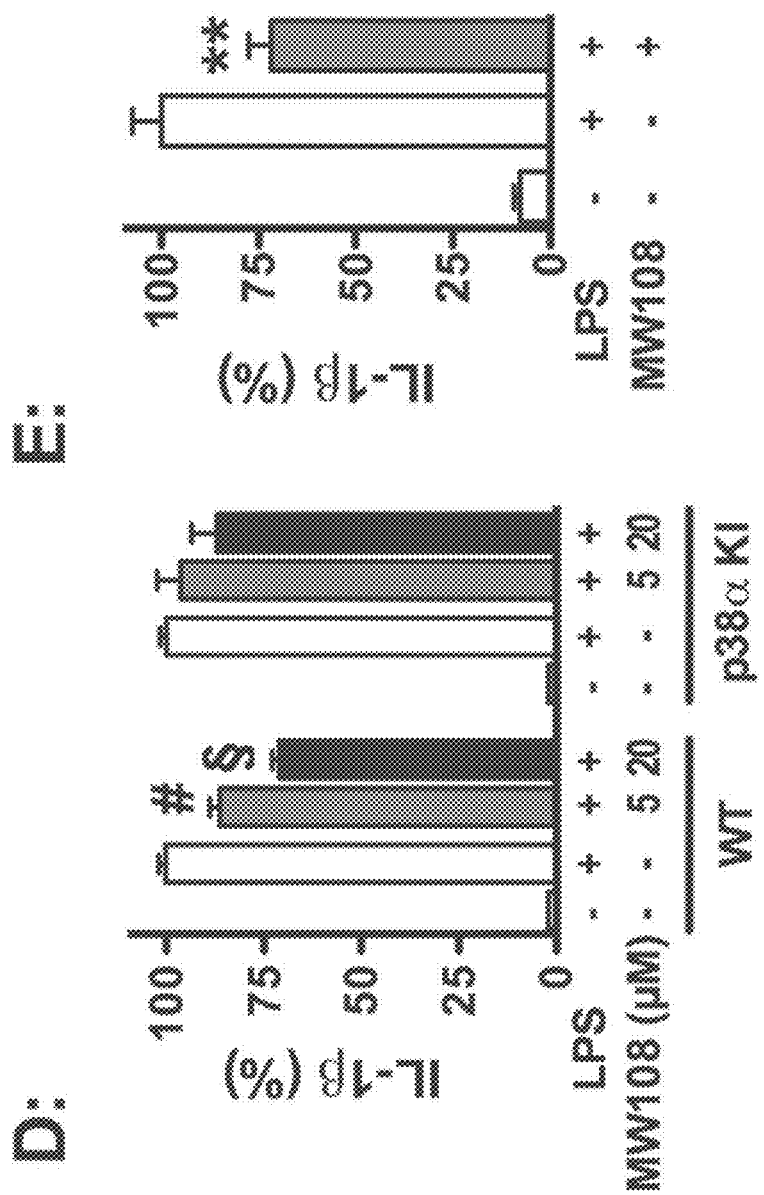
FIGS. 2D-E

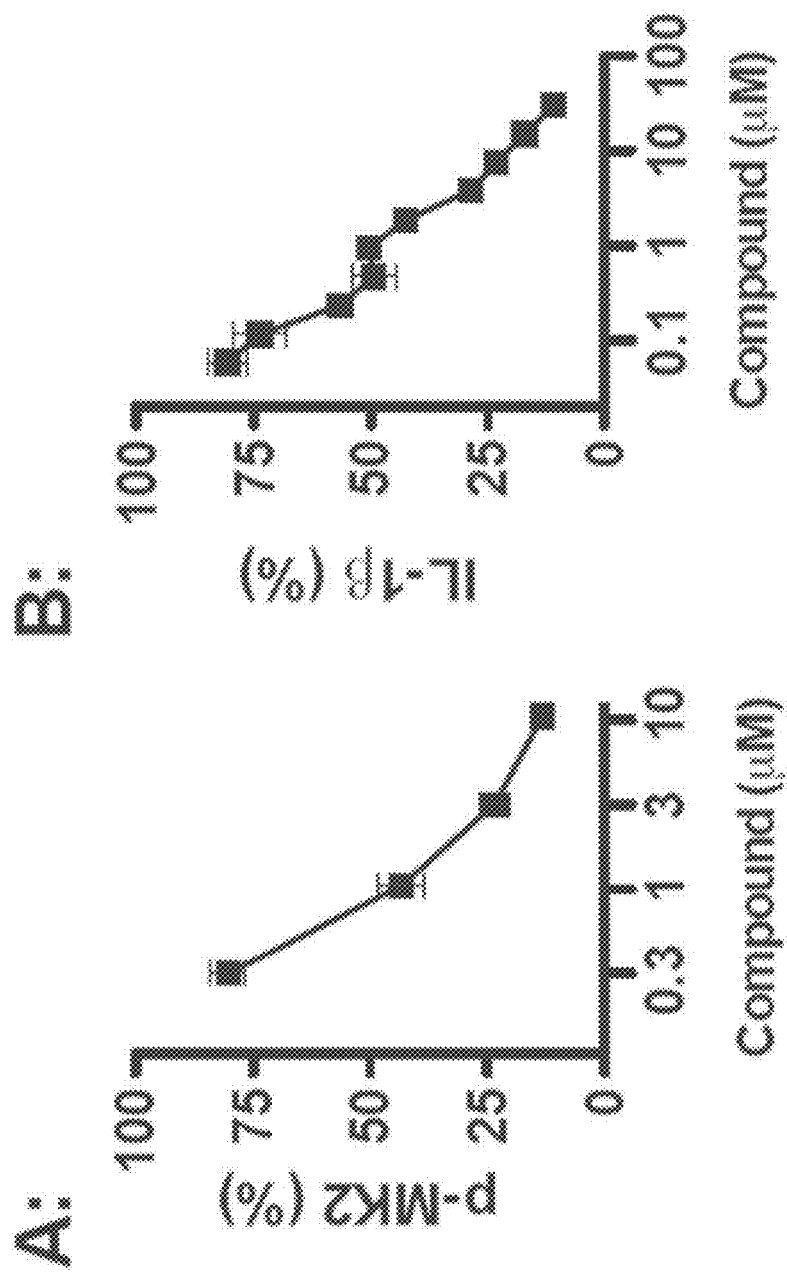
FIGS. 3A-B

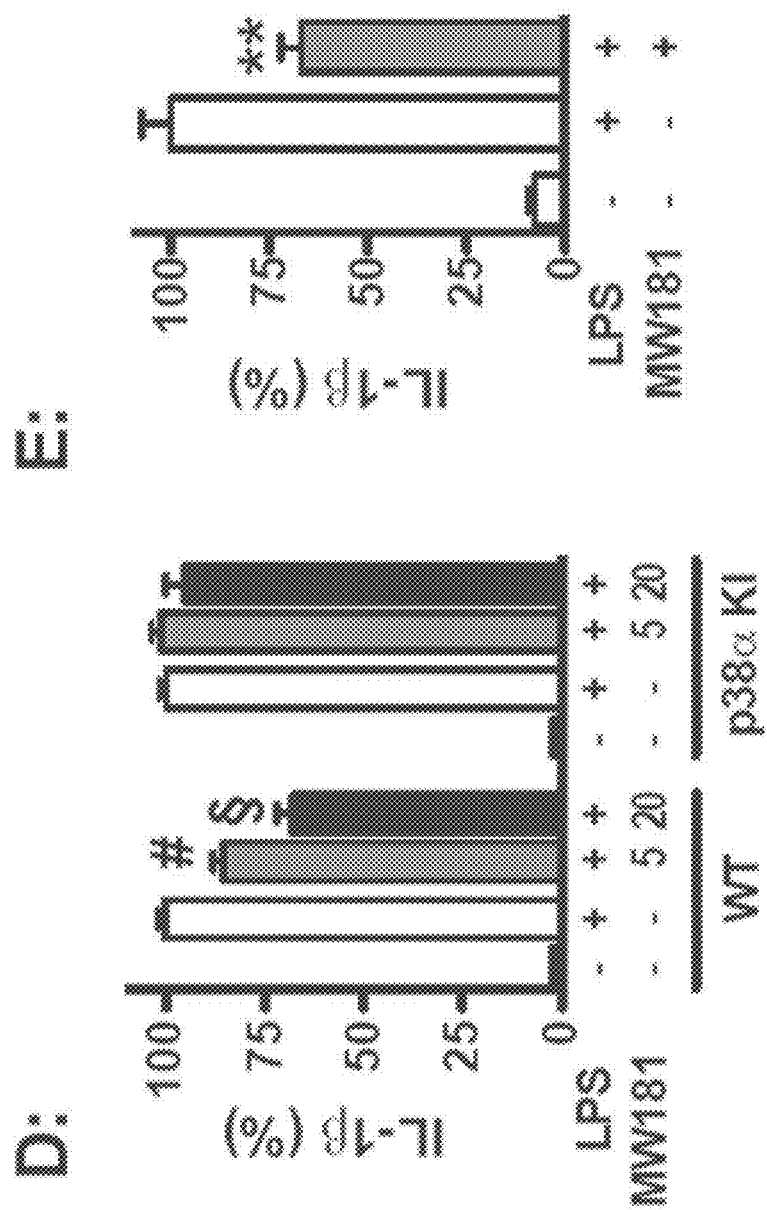
FIGS. 3D-E

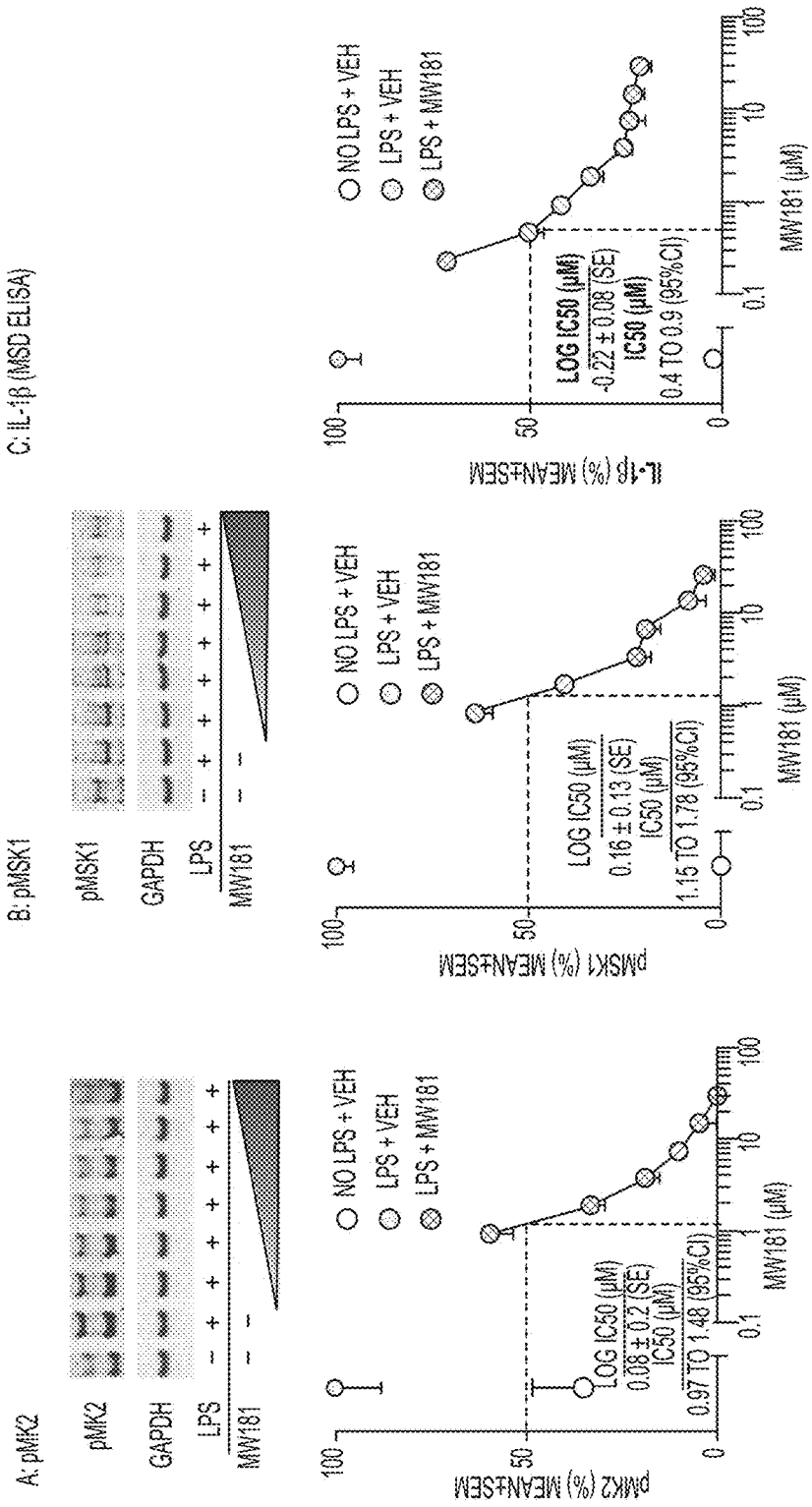
FIG. 4A-C

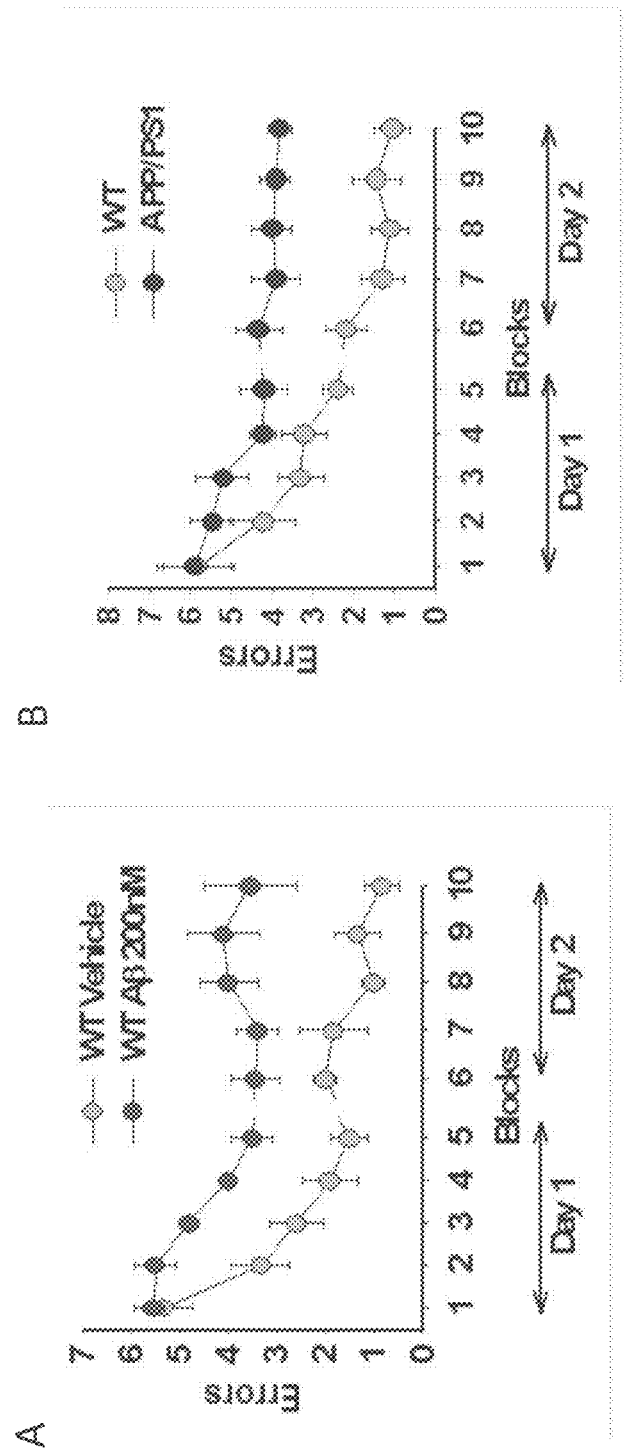
FIGS. 7A-B

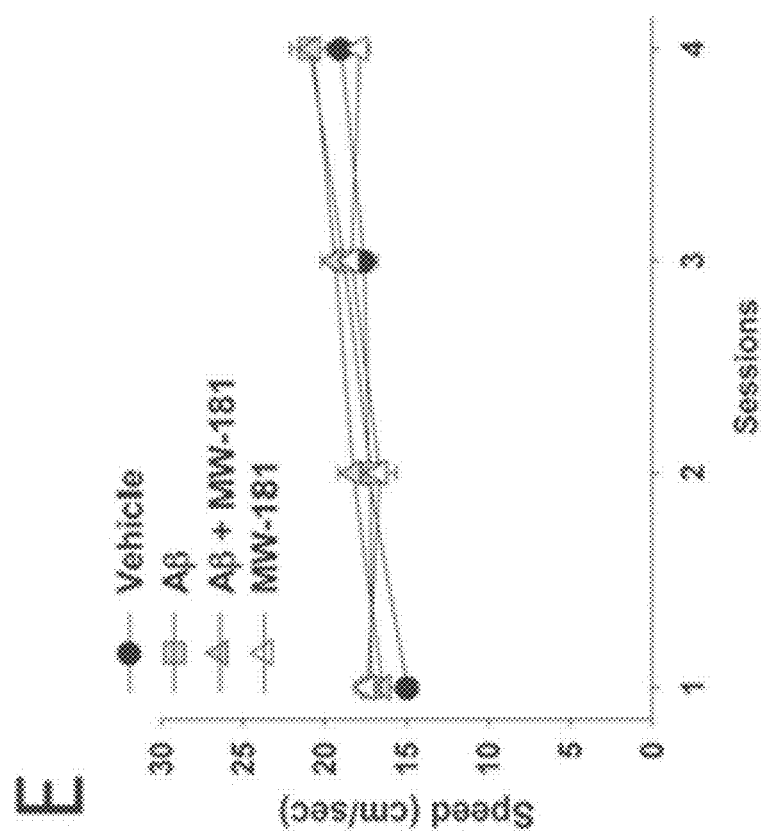

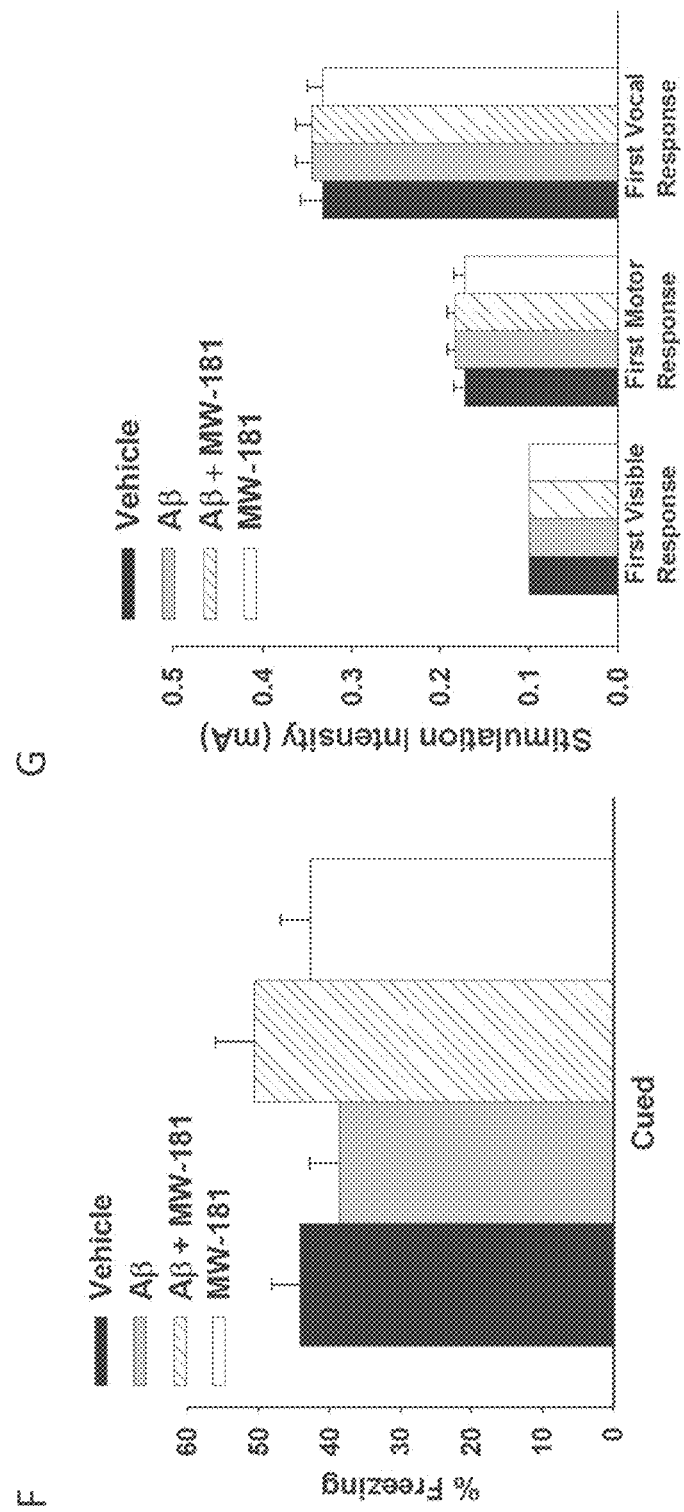
FIGS. 8F-G

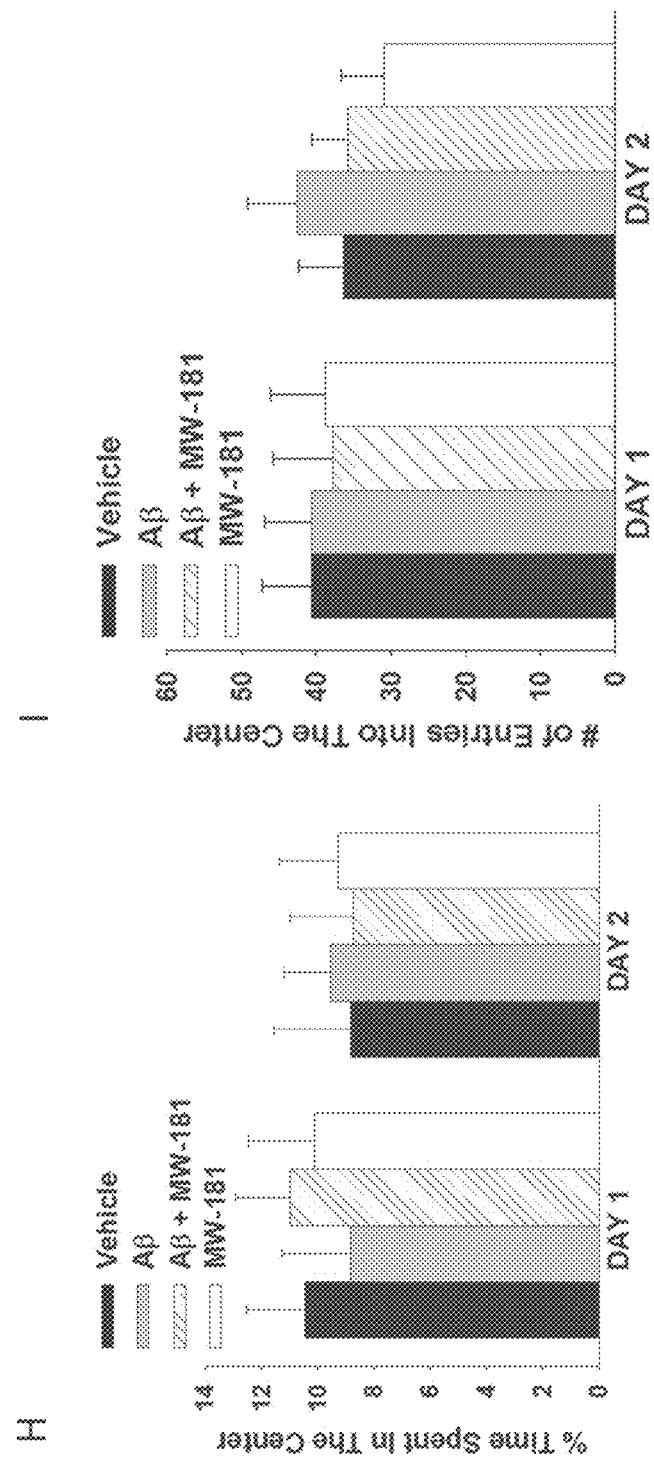
FIGS. 8H-I

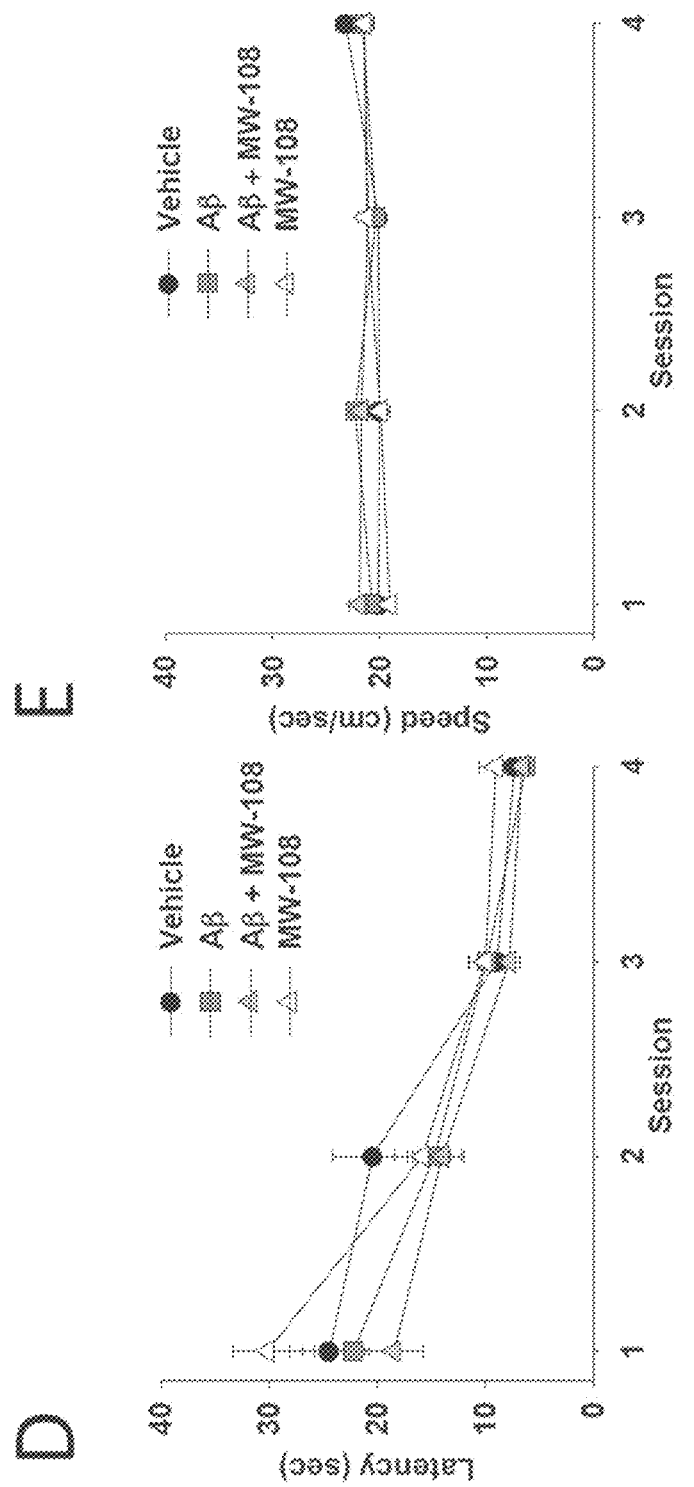
FIGS. 9D-E

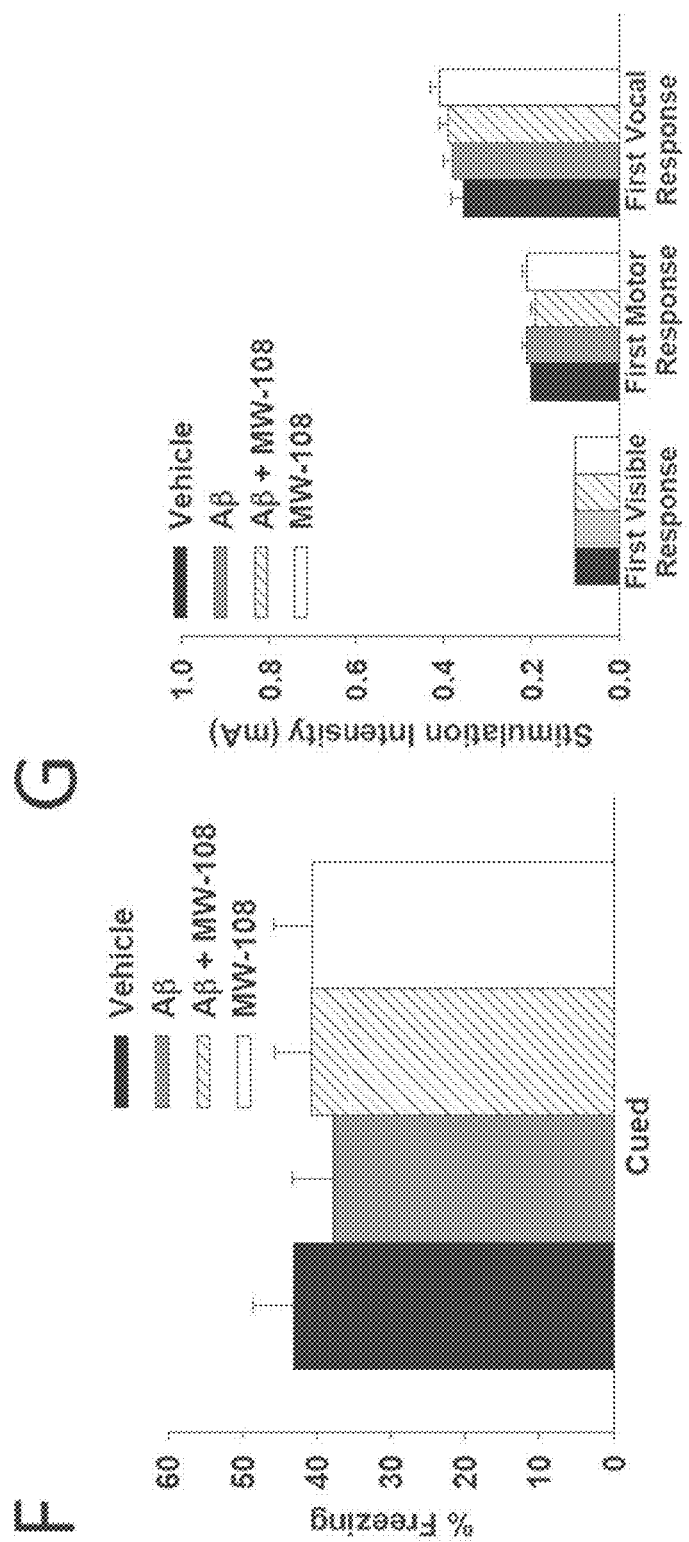
FIGS. 9F-G

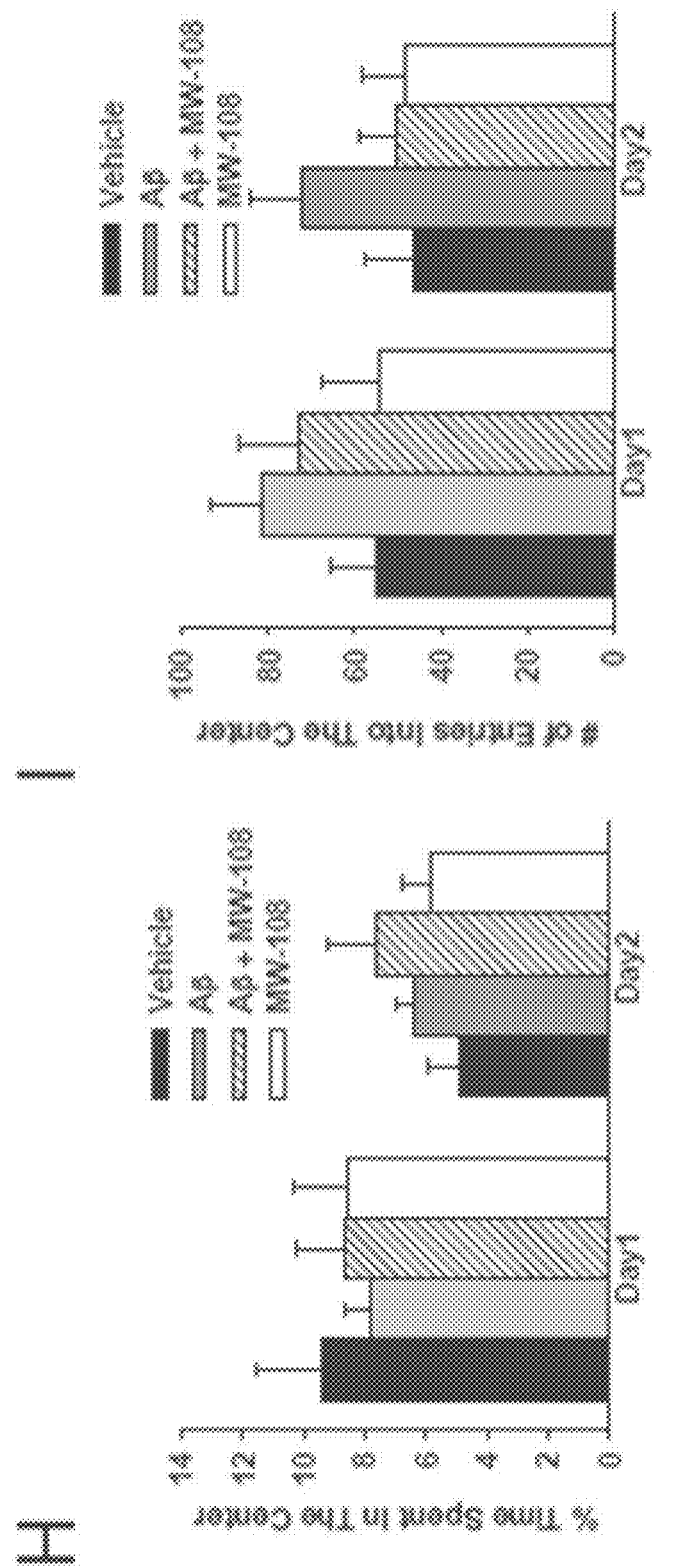
FIGS. 9H-I

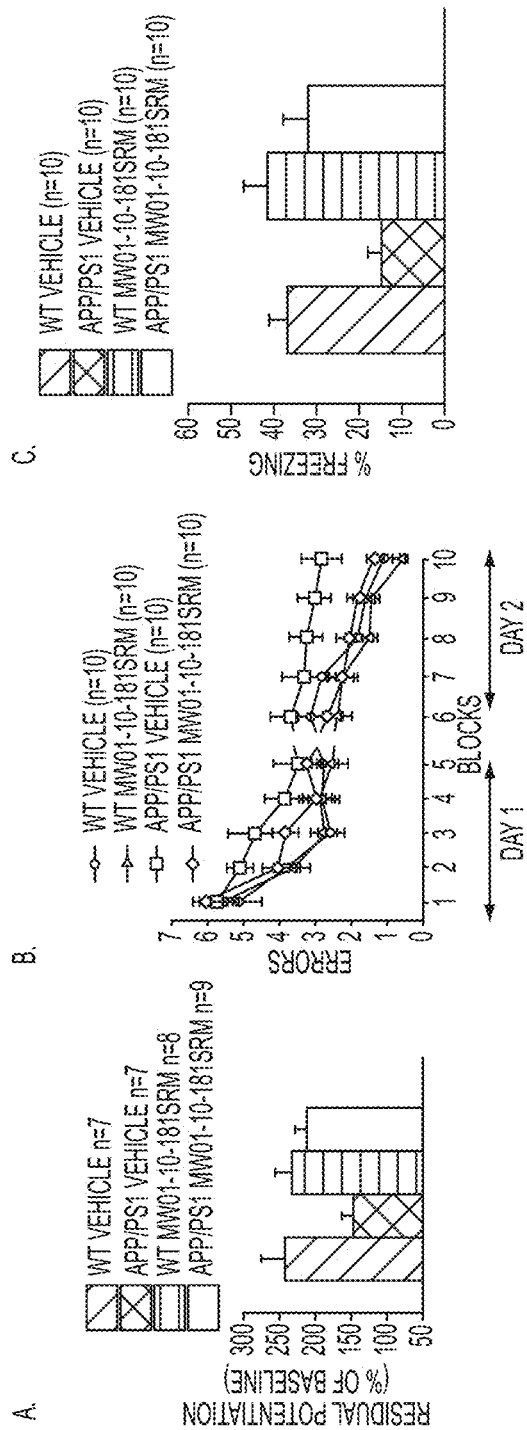
FIG. 10A-C

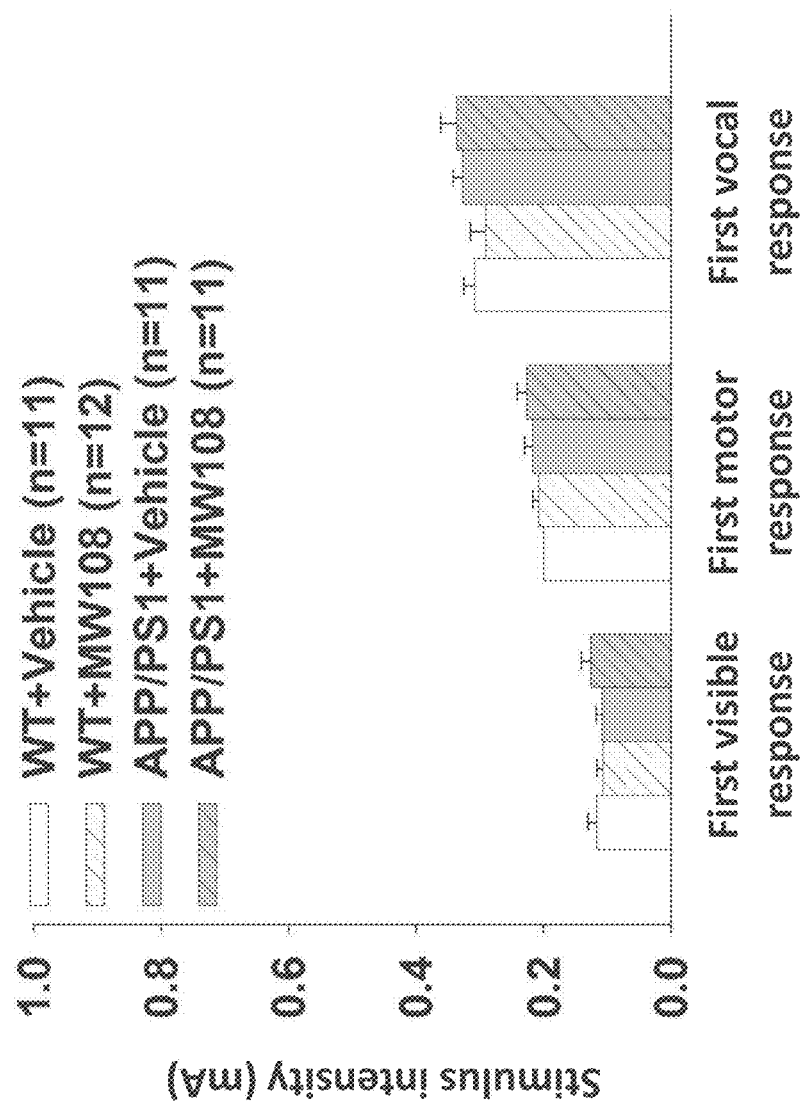

MAP KINASE MODULATORS AND USES THEREOF

This application is a continuation-in-part of International Patent Application No. PCT/US2014/030260, filed Mar. 17, 2014, which claims priority to U.S. Provisional Patent Application No. 61/790,207, filed Mar. 15, 2013, the entire contents of which are hereby incorporated by reference in their entirety.

GOVERNMENT SUPPORT

This invention was made with government support under grant AG043415 awarded by the National Institutes of Health. The Government has certain rights in this invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Protein kinases related to mitogen activated protein kinase (MAPK or MAP kinase) are part of stress-related signal transduction pathways. p38 MAPK is a serine/threonine kinase that has recently become a target for modulation of cytokine production as it is implicated in multiple signaling pathways activated during inflammation. Inhibitors of p38 MAPK are being studied for treatment of inflammatory diseases such as rheumatoid arthritis, psoriasis and pain.

Alzheimer's Disease (AD) is a progressive and terminal condition characterized by debilitating memory loss and extensive deterioration of cognitive and functional abilities. Currently available therapies for AD are palliative and neither cure nor arrest progression of the disease. Cholinesterase inhibitors such as Razadyne® (galantamine), Exelon® (rivastigmine), Aricept® (donepezil), and Cognex® (tacrine) have been prescribed for early stages of AD, and may temporarily delay or halt progression of symptoms. However, as AD progresses, the brain loses less acetylcholine, thereby rendering cholinesterase inhibitors ineffective. Namenda® (memantine), an N-methyl D-aspartate (NMDA) antagonist, is also prescribed to treat moderate to severe Alzheimer's disease; however only temporary benefits are realized.

There is a need for novel MAP kinase inhibitors. There is also a need for novel treatments for a variety of disease states for which MAP kinase is implicated. There is a further need for novel and effective treatments for neurodegenerative diseases and neurological disorders. In particular, there is a continuing need for treatments of dementia and memory loss associated with Alzheimer's Disease.

SUMMARY OF THE INVENTION

In one aspect, the invention is directed to a class of compounds of formula (I)

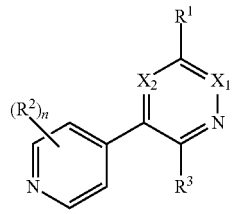

wherein
$X_1$ is N and $X_2$ is CH, or $X_1$ is CH and $X_2$ is N;
$R^1$ is —$N(R^4)_2$, cyclopropyl, or $R^5$-piperidin-4-yl;
$R^2$ is independently D or halogen;
$R^3$ is naphthyl, quinolinyl, isoquinolinyl, or indolyl, wherein said naphthyl, quinolinyl, isoquinolinyl or indolyl is optionally independently substituted with at least one D, halogen, $(C_1-C_3)$-alkoxy, or $(C_1-C_3)$-alkoxy substituted with at least one D;
$R^4$ is independently H, $(C_1-C_4)$-alkyl, $(C_1-C_4)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S, wherein the 3-7 membered heterocyclic ring is optionally substituted with a $(C_1-C_3)$-alkyl;
$R^5$ is H or $(C_1-C_3)$-alkyl, or $(C_1-C_3)$-alkyl substituted with at least one D;
$R^6$ is H, $(C_1-C_3)$-alkyl, $(C_1-C_3)$-alkyl substituted with at least one D, or pyrimidin-2-yl; and
n is an integer from 0-4; or a pharmaceutically acceptable salt thereof,
wherein when $R^3$ is indol-4-yl and n is 0, $R^1$ is not N-methyl-piperazinyl.

In another aspect, the invention is directed to compositions comprising a compound of formula (I) and a pharmaceutically acceptable carrier.

In another aspect, the invention is directed to a method of treating neurodegeneration in a subject comprising administration of a therapeutically effective amount of a compound of formula (I).

In another aspect, the invention is directed to a method of treating neurodegenerative disease in a subject comprising administration of a therapeutically effective amount of a compound of formula (I).

In another aspect, the invention is directed to a method of increasing long-term potentiation in a subject having a neurodegenerative disease comprising administration of a therapeutically effective amount of a compound of formula (I).

In another aspect, the invention is directed to a method of improving memory in a subject having a neurodegenerative disease comprising administration of a therapeutically effective amount of a compound of formula (I).

In another aspect, the invention is directed to a method of improving synaptic function in a subject having a neurodegenerative disease comprising administration of a therapeutically effective amount of a compound of formula (I).

In another aspect, the invention is directed to a method of restoring memory loss in a subject having a neurodegenerative disease comprising administration of a therapeutically effective amount of a compound of formula (I).

In some embodiments, the disease is ALS, Huntington's Disease, Parkinson's Disease or Alzheimer's Disease. In some embodiments, the disease is ALS, Parkinson's Disease or Alzheimer's Disease. In some embodiments, the disease is ALS. In some embodiments, the disease is Huntington's Disease. In some embodiments, the disease is Parkinson's Disease. In some embodiments, the disease is Alzheimer's Disease.

In another aspect, the invention is directed to a method of treating ischemia in a subject in need thereof comprising administration of a therapeutically effective amount of a compound of formula (I).

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

BRIEF DESCRIPTION OF THE FIGURES

FIGS. 1A-F show MW-181 (1) suppresses (A) IL-1β production, (B) phospho-MSK1, (C) phospho-MK2 in BV-2 microglia cell line, (D) IL-1β in primary microglia from WT mice but not from p38α (T106M) KI microglia, (E) LPS-induced IL-1β increase in mouse cortex of WT mice, (F) IL-1β levels in cortex of APP/PS1 mice back to control levels after single 2.5 mg/kg administration, 3×/week over 5 months.

FIGS. 2A-E show cellular target engagement and mechanism of action of MW-108 (2). (A). MW-108 inhibited phosphorylation of the p38α substrate MK2 in a concentration-dependent manner in LPS-stimulated BV-2 microglial cells. (B). MW-108 inhibited LPS-induced IL-1β production in a concentration-dependent manner in BV-2 cells. (C). MW-108 suppressed IL-1β production in BV-2 cells stimulated with diverse TLR ligands. BV-2 cells were treated with ligands for TLR2, TLR4, TLR7/8, and TLR9 in the absence (white bars) or presence (gray bars) of MW-108. ‡ p<0.0001 compared to TLR ligand in the absence of compound. (D). MW-108 inhibited LPS induced IL-1β production in primary microglia from wild-type (WT) mice, but not from drug resistant p38α MAPK knock-in (p38α KI) mice. # p <0.01, §p<0.001 compared to LPS alone. (E). MW-108 suppressed LPS-induced IL-1β levels in vivo. **p<0.01 compared to LPS alone (n=6 saline/vehicle; n=24 LPS/vehicle; n=15 LPS/MW-108). Data in all panels are expressed as a percent of the maximal levels, where levels in the presence of stressor alone were normalized to 100%.

FIGS. 3A-E show cellular target engagement and mechanism of action of MW-181 (1). (A). MW-181 inhibited phosphorylation of the p38α substrate MK2 in a concentration-dependent manner in LPS stimulated BV-2 microglial cells. (B). MW-181 inhibited LPS-induced IL-1β production in a concentration-dependent manner in BV-2 cells. (C). MW-181 suppressed IL-1β production in BV-2 cells stimulated with diverse TLR ligands. BV-2 cells were treated with ligands for TLR2, TLR4, TLR7/8, and TLR9 in the absence (white bars) or presence (gray bars) of MW-181. ‡ p<0.0001 compared to TLR ligand in the absence of compound. (D) MW-181 inhibited LPS-induced IL-1β production in primary microglia from wild-type (WT) mice, but not from drug-resistant p38α MAPK knock-in (p38α KI) mice. # p<0.01, §p<0.001 compared to LPS alone. (E) MW-181 suppressed LPS-induced IL-1β levels in vivo. **p<0.01 compared to LPS alone (n=6 saline/vehicle; n=24 LPS/vehicle; n=15 LPS/MW-181). Data in all panels are expressed as a percent of the maximal levels, where levels in the presence of stressor alone were normalized to 100%.

FIGS. 4A-C show (A) phosphorylation state of pMK2 is increased at 1 hr after LPS addition and the increase is attenuated in a dose dependent manner by MW-181 (1); (B) phosphorylation state of pMSK1 is increased at 1 hr after LPS addition and the increase is attenuated in a dose dependent manner by MW-181; and (C) IL-1β protein levels in cell lysates at 18 hrs after LPS addition in MSD ELISA measurements with vehicle, LPS+vehicle and LPS+MW-181.

FIGS. 7A-B show two-day RAWM performance is impaired following treatment with 200 nM Aβ and in APP/PS1 mice. (A). Mice that received bilateral injections of Aβ$_{42}$ [200 nM in a final volume of 1 µl over 1 min; twice on each testing day: 15 min prior to the 1st trial (for the 1st group of tests) and 15 min prior to the 7th trial (for the 2nd group of tests)]) into dorsal hippocampi, failed to reach the learning criterion (~1 error) by block 8 and 9 of day 2 compared to vehicle-infused mice (n=8 for both; P<0.001). (B). APP/PS1 mice failed to reach the criterion over 2 days of testing compared to WT littermate.

FIGS. 8A-I show beneficial effect of MW-181 (1) on Aβ$_{42}$-induced synaptic and cognitive dysfunction. (A) MW-181 (10 µM) ameliorated the LTP deficit in Aβ$_{42}$-treated slices (vehicle: n=7 slices; Aβ: n=8; Aβ+MW-181: n=7; MW-181: n=7; F(1,13)=6.651, p=0.0229, compared to slices treated only with Aβ$_{42}$). The horizontal bar represents the time of application of Aβ$_{42}$ and MW-181. Error bars indicate SEM in this and the remaining panels. (B) MW-181 (5 mg/kg, i.p., 30 min before the 1st and 2nd group of tests for the RAWM) ameliorated the reference memory deficit in Aβ$_{42}$-infused mice. Aβ$_{42}$ (200 nM, in a final volume of 1 µl over 1 min) was bilaterally infused 20 min prior to the 1st trial (for the 1st group of tests in a 2-day RAWM test assessing reference memory and 20 min prior to the 7th trial (for the 2nd group of tests of the RAWM), into dorsal hippocampus (vehicle: n=10 animals; Aβ: n=10; Aβ+MW-181: n=10; MW-181: n=10; F(1,18)=5.851, p=0.0264 comparing Aβ-infused mice vs. compound+Aβ infused animals). (C) MW-181 (5 mg/kg, i.p. 30 min before the electric shock) ameliorated the contextual fear memory deficit in Aβ$_{42}$-infused mice. Aβ$_{42}$ (200 nM, in a final volume of 1 µl over 1 min) was given 20 min prior to the foot shock (vehicle: n=15 animals; Aβ: n=15; Aβ+MW-181: n=16; MW-181: n=15; p=0.0005 comparing Aβ-infused mice vs. compound+Aβ infused animals). (D, E) No difference was detected between different groups of mice regardless of treatment with MW-181 (5 mg/kg, i.p., 30 min before testing) with and without Aβ$_{42}$ (200 nM, in a final volume of 1 µl over 1 min, 20 min before testing) when tested for visual-motor-motivational deficits with the visible platform test; speed and time to the platform are shown in D and E, respectively (vehicle: n=10; Aβ: n=10; Aβ+MW-181: n=10; MW-181: n=10; p>0.05 comparing Aβ-infused mice vs. compound+Aβ infused animals for both). (F) The same animals that underwent contextual fear conditioning testing were assessed for cued learning 24 hrs after the contextual learning. No difference was detected between different groups of mice regardless of treatment with MW-181 with and without $A\beta_{42}$ (vehicle: n=15 animals; Aβ: n=15; Aβ+MW-181: n=16; MW-181: n=15; p>0.05 comparing Aβ-infused mice vs. compound+Aβ infused animals). (G) Sensory threshold was not affected regardless of treatment with MW-108 with and without $A\beta_{42}$ (vehicle: n=9 animals; Aβ: n=9; Aβ+MW-108: n=9; MW-108: n=9; p>0.05 comparing Aβ-infused mice vs. compound+Aβ infused animals). (H, I) No difference in exploratory behavior as shown by a similar percentage of time spent in the center compartment (H) and the number of entries into the center compartment (I) were observed regardless of treatment with MW-181 with and without $A\beta_{42}$ (vehicle: n=9 animals; Aβ: n=9; Aβ+MW-181: n=9; MW-181: n=9; p>0.05 comparing Aβ-infused mice vs. compound+Aβ infused animals).

FIGS. 9A-I show beneficial effect of MW-108 (2) on $A\beta_{42}$-induced synaptic and cognitive dysfunction. (A) MW-108 (10 µM) ameliorated the LTP deficit in $A\beta_{42}$-treated slices (vehicle: n=7 slices; Aβ: n=7; Aβ+MW-108: n=8; MW-108: n=8; F(1,13)=17.25, p=0.0011, compared to slices treated only with $A\beta_{42}$). The horizontal bar represents the time of application of $A\beta_{42}$ and MW-108. Error bars indicate SEM in this and the remaining panels. (B) MW-108 (5 mg/kg, i.p., 30 min before the 1st and 2nd group of tests for the RAWM) ameliorated the reference memory deficit in $A\beta_{42}$-infused mice. $A\beta_{42}$ (200 nM, in a final volume of 1 µl over 1 min) was bilaterally infused 20 min prior to the 1st trial (for the 1st group of tests in a 2-day RAWM test assessing reference memory and 20 min prior to the 7th trial (for the 2nd group of tests of the RAWM), into dorsal hippocampus (vehicle: n=10 animals; Aβ: n=12; Aβ+MW-108: n=14; MW-108: n=13; F(1,24)=1.827, p=0.0001 comparing Aβ-infused mice vs. compound+Aβ infused animals). (C) MW-108 (5 mg/kg, i.p. 30 min before the electric shock) ameliorated the contextual fear memory deficit in $A\beta_{42}$-infused mice. $A\beta_{42}$ (200 nM, in a final volume of 1 µl over 1 min) was given 20 min prior to the foot shock (vehicle: n=16 animals; Aβ: n=17; Aβ+MW-108: n=17; MW-108: n=18; p=0.009 comparing Aβ-infused mice vs. compound+Aβ infused animals). (D-E) No difference was detected between different groups of mice regardless of treatment with MW-108 (5 mg/kg, i.p., 30 min before testing) with and without $A\beta_{42}$ (200 nM, in a final volume of 1 µl over 1 min, 20 min before testing) when tested for visual-motor-motivational deficits with the visible platform test; speed and time to the platform are shown in D and E, respectively (vehicle: n=10; Aβ: n=12; Aβ+MW-108: n=14; MW-108: n=13; p>0.05 comparing Aβ-infused mice vs. compound+Aβ infused animals for both). (F) The same animals that underwent contextual fear conditioning testing were assessed for cued learning 24 hrs after the contextual learning. No difference was detected between different groups of mice regardless of treatment with MW-108 with and without $A\beta_{42}$ (vehicle: n=16 animals; A13: n=17; A13+MW-108: n=17; MW-108: n=18; p>0.05 comparing Aβ-infused mice vs. compound+Aβ infused animals). (G) Sensory threshold was not affected regardless of treatment with MW-108 with and without $A\beta_{42}$ (vehicle: n=13 animals; AP: n=16; Aβ+MW-108: n=17; MW-108: n=15; p>0.05 comparing Aβ-infused mice vs. compound+Aβ infused animals). (H-I) No difference in exploratory behavior as shown by a similar percentage of time spent in the center compartment (H) and the number of entries into the center compartment (I) were observed regardless of treatment with MW-108 with and without Aβ42 (vehicle: n=13 animals; AP: n=16; Aβ+MW-108: n=17; MW-108: n=15; p>0.05 comparing Aβ-infused mice vs. compound+Aβ infused animals).

FIGS. 10A-C show (A) potentiation as a percent of baseline in WT, APP/PS1, WT+MW-181 (1), and APP/PS1+MW-181 treated mice; (B) RAWM results for WT, APP/PS1, WT+MW-181, and APP/PS1+MW-181 treated mice; and (C) FC results for WT, APP/PS1, WT+MW-181, and APP/PS1+MW-181 treated mice. MW-181 is beneficial against the defects in LPT (A), RAWM performance (B) and FC (C).

FIGS. 11A-J show (A) potentiation as a percent of baseline in WT, APP/PS1, WT+MW-108 (2), and APP/PS1+MW-108 treated mice; (B) RAWM results for WT, APP/PS1, WT+MW-108, and APP/PS1+MW-108 treated mice; and (C) FC results for WT, APP/PS1, WT+MW-108, and APP/PS1+MW-108 treated mice. The remaining panels show controls for input/output relationship (D), latency and speed to the visible platform (E, F), cued conditioning (G), sensory threshold assessment (H), number of entries into the center (I) and percent time spent in the center (J) during open field assessment.

(FIG. 26C) Quantification by a board-certified neuropathologist blinded to the treatment groups was done by analysis of a brain sagittal section from each mouse in which the total number of well formed β-amyloid plaques in the entire section were counted. Error bars show standard error of the mean (n=4 for each group). (FIG. 26D) In a separate experiment with APP/PS1 knock-in (KI) mice, Aβ plaques were quantified from KI mice treated with MW-150 or vehicle. In both AD mouse S15 models, there are no effects of MW-150 treatment on the amyloid plaque burden.

DETAILED DESCRIPTION OF THE INVENTION

Figure 2C:
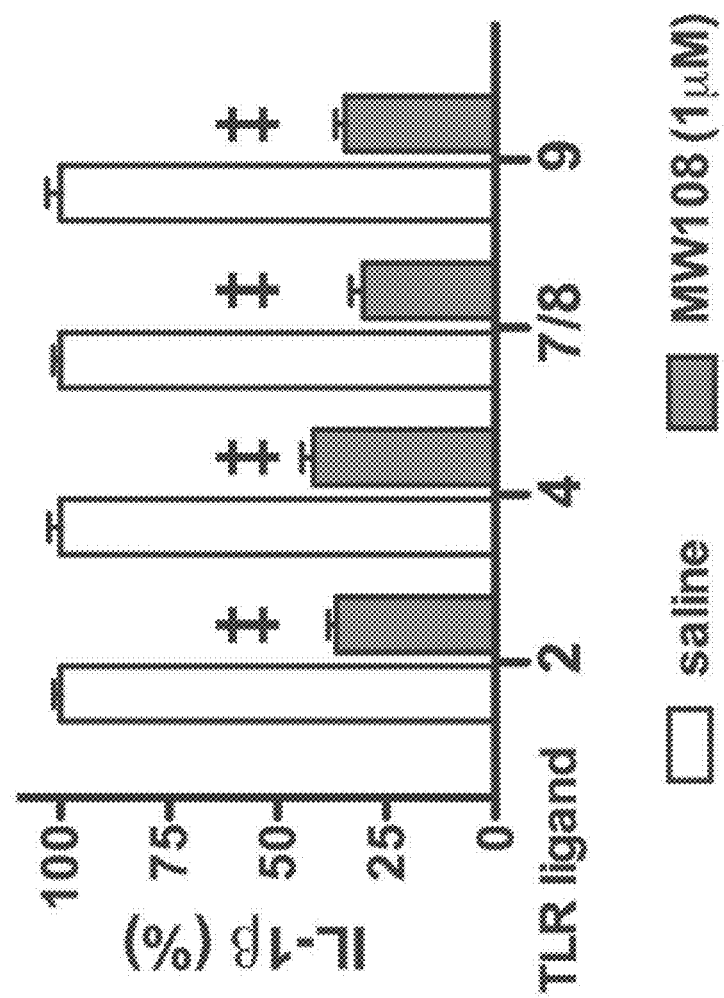

Glia are innate immunity cells of the central nervous system (CNS) that are key to homeostasis and health. However, they can be transformed into activated or effector type cells capable of releasing small proteins such as cytokines and other cytoactive factors that contribute to complex disease states. In some cases, transformed glia can become autonomous by creating a microenvironment, such as in glioma, where there is increased production of proinflammatory cytokines and dysfunction in signaling pathways. Upregulated cytokine production by other types of transformed glia can result in dysfunction in a critical physiological axis, such as the perturbation of glia-neuronal interactions. This can result in synaptic dysfunction, a common element of disease progression evident in diverse neurodegenerative diseases, post traumatic injury or complex syndromes evident in aged individuals. The term "synaptopathy" is often used to encompass a series of diseases that, despite manifesting with different symptoms, have much more in common that clinically evident. The need for neurons to maintain healthy and functional synapses is challenging as high polarization with axons, branched dentritic trees and numerous synaptic contacts is a key feature. A consequence of faltering synapses is onset of numerous neurodegenerative disorders, many with aging. Molecular mechanisms relevant to normal synaptic function are altered in the states, leading to synaptopathy, oftin in a cause/effect relationship that is connected with etiopathogenesis of the specific disease, or as a side consequence of the alteration of the mechanisms underlying synaptic transmission.

A variety of efforts are being expended to control the physiological effects of glia transformation as a sequealae of acute injury and as one component of progressive diseases such as neurodegeneration, dementia and glioma proliferation/metastasis. A prevailing theme is a focus on modulation of intracellular pathways in glia and their linkage to intercellular or organismal networks. The intracellular stress activated pathways controlled by enzymes called protein kinases are often targeted with small molecule drugs that inhibit multiple protein kinases in parallel or by targeting a single kinase with a causative linkage to disease or pathology progression. One of the single molecular target efforts are those focused on the stress activated kinase called p38 •MAPK, a regulator of cellular stress response and phenotypic switching.

Protein kinase inhibitors for CNS disorders are preferably CNS penetrant and avoid inhibition of other key signaling pathways that may contribute to adverse events. There is interest in novel small molecules for disease modification where glia functions are involved in the pathology progression.

p38 MAPK, a stress related protein kinase involved in eukaryotic signal transduction, has recently become the focus of drug discovery efforts targeted at neurodegeneration and central nervous system related diseases. p38 MAPK is a serine/threonine kinase, which exists as at least four isoforms or subtypes, namely $\alpha$, $\beta$ (and P2), $\delta$, and $\gamma$, each of which are encoded by separate genes and have varying sensitivity to inhibitors.

Intracellular protein kinases such as p38 MAPK, sometimes called stress kinases due to their activation with injury and disease, activate a cascade of downstream events in the cell that can result in pathology within a given tissue. When there is coincident activation of these pathways in integrated cellular networks, such as glia and neurons in the central nervous system, the impact of the system can be significant due to potential synergies among cells in the network. In the CNS, this can be manifest in cellular dysfunctions such as intracellular fast axonal transport or intercellular connections such as synapses. These effects are due to internal changes within neurons, with the biological effects potentially amplified through the activation of the p38 MAPK mediated pathways within glia, which can result in overproduction of proinflammatory cytokines that further stress or injure the neurons. Therefore, the CNS offers an interesting opportunity to target the same molecular target in the two distinct major cell types, glia and neurons, in order to modulate the system wide pathology via attenuation of intracellular cascades regulated by p38 MAPK. Synaptic dysfunction, in which activation of p38 MAPK has been established as a causative contributor, is considered a fundamental event in diverse diseases and injury sequelae, including, for example, Alzheimer's disease, ALS, dementias, cognitive impairment and morbidity from injury, and other neurological diseases. Therefore, the availability of highly selective, CNS penetrant, p38 MAPK inhibitor drugs would be a major contribution towards developing new therapeutic paradigms for disease alteration. Potential applications further include therapeutic intervention for CNS diseases and injuries, oncology where tumor immunology and microenvironment involves cytokine alterations that are regulated by p38 MAPK, and other applications related to p38 MAPK.

The alpha isoform, p38$\alpha$, has been the most thoroughly studied, and is a potential target for modulation of cytokine production as it is implicated in multiple signaling pathways activated during inflammation (Dominguez C. et al., *Curr. Opin. Drug Disc. Dev.* 2005, 8, 421-430; herein incorporated by reference in its entirety). Indeed, p38 MAPK inhibitors are in clinical trials to treat inflammatory diseases such as rheumatoid arthritis, psoriasis and pain ("Competitor Analysis-p38 MAPK inhibitors 2010" La Merie Publishing, p 21. 2010 (http://www.researchandmarkets.com/research/bee137/competitor_analysi); herein incorporated by reference in its entirety). There is also accumulating evidence that p38 MAPK plays a role in AD. AD is characterized by neuroinflammation due to glial cell activation and the production of inflammatory mediators (Munoz, L. and Ammit, A., *Neuropharmacology,* 2010, 58, 561-568; Munoz, L., et al., *J. Neuroinflammation,* 2007, 4, 21; each herein incorporated by reference in its entirety). This inflammation has a detrimental result on AD pathology. AD patients may benefit from treatment with p38 MAPK inhibitors (See, e.g., Watterson, D. M., et al., *PLoS One* (8)6: e66226 (2013); Munoz, L., et al., *J. Neuroinflammation,* 2007, 4, 21; each herein incorporated by reference in its entirety). Alzheimer's Disease (AD) is a leading cause of death in the United States, with only few treatment options for the afflicted patient. Current treatment options are merely palliative and do not cure or arrest progression of the disease.

AD is not the only disease in which p38•MAPK has been found to be altered. Animal model studies are consistent with the involvement of the p38$\alpha$ MAPK in AD related pathology progression and in other diseases characterized by glia transformation (e.g, ALS and glioma). p38 MAPK is at the crossroad of multiple signaling mechanisms including a) those activated by inflammatory cytokines binding to specific receptors at the cell surface, and promoting activation of interleukin-1 receptor associated kinase, TNF receptor-associated factor 2/6 leading to activation of MKKKs, and subsequently phosphorylation of MKK3 and MKK6, that, in turn, activate p38 MAPK; b) those activated by glutamate that, once released from the presynaptic terminal, binds to glutamate receptors (AMPA and NMDA, as well as metabotropic receptors) and either directly or indirectly (see metabotropic receptor that activates RAP1 which, in turn, phosphorylates MKK3/6) activate p38 MAPK (See, e.g., Correa et al, *J. Signal Transduction* 2012, Article ID 649079, doi:10.1155/2012/649079; herein incorporated by reference in its entirety). Thus, p38 MAPK is involved in a multitude of physiologic and pathologic chains of reactions that eventually lead to normal synaptic plasticity, the cellular bases of learning and memory, and neurodegenerative diseases characterized by cognitive disorders and inflammation. Inhibitors of p38 MAPK can be beneficial, for example, in several disorders and neurodegenerative diseases characterized by altered cellular function, synaptic dysfunction, fast axonal transport, and neuroinflammation. Alzheimer's disease, Parkinson's disease, Huntington disease, Down syndrome, head trauma, traumatic brain injury (TBI), brain injury due to cerebral focal ischemia, attention deficit disorder, neuronal degeneration with brain iron accumulation type I (Hallervorden-Spatz disease), Lytico-Bodig disease (Parkinson-dementia complex of Guam), pure autonomic failure, REM sleep behavior disorder, mild cognitive impairment (MCI), cerebral amyloid angiopathy (CAA), mild cognitive deficits, aging, vascular dementias mixed with Alzheimer's disease, any neurodegenerative disease characterized by abnormal amyloid deposition, or any combination thereof, Adrenoleukodystrophy (ALD), Alcoholism, Alexander's disease, Alper's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Rett's syndrome, Tau-positive FrontoTemporal dementia, Tau-negative FrontoTemporal dementia, Dementia pugilistica (chronic traumatic encephalopathy), Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy, Inclusion body myositis. Neuroinflammation has been also found to play a role in psychiatric illnesses. Indeed, a link between psychiatric symptoms and autoimmunity in autoimmune diseases, neuroimmunological abnormalities occur in classical psychiatric disorders (for example, major depressive, bipolar, schizophrenia, and obsessive compulsive disorders).

Proof of concept studies show that the p38 MAPK inhibitors rescue the Alzheimer's disease phenotype in animal models. These types of inhibitors can be used against brain injury and neuronal deficits in cerebral focal ischemia (Barone et al, *J. of Pharmacology and Experimental Therapeutics.* 296: 312, 2001; herein incorporated by reference in its entirety), as well as to counteract increase of cytokines. Additionally, increase in activation of p38 MAPK has been observed in specific pathologic conditions such as familial forms of ALS (Morfini et al, *Plos One* 8: e65235, 2013; herein incorporated by reference in its entirety), and therefore p38 MAPK inhibitors can be used in these diseases. Similar to soluble forms of beta amyloid that have been tested with p38 MAPK inhibitors in the context of Alzheimer's Disease, and soluble forms of tau have been associated with synaptic dysfunction and memory loss. Effect of the inhibitors onto tauopathies such as FrontoTemporal dementia, Niemann Pick disease, Progressive Supranuclear Palsy, TBI, Dementia pugilistica (chronic traumatic encephalopathy), Lytico-Bodig disease (Parkinsondementia complex of Guam), lead encephalopathy, tuberous sclerosis, Hallervorden-Spatz disease, and lipofuscinosis, corticobasal degeneration, Argyrophilic grain disease (AGD), and Frontotemporal lobar degeneration is also being studied. For example, a model of tauopathy has been developed in which tau oligomers are exogenously administered to the mouse brain, leading to impairment of synaptic plasticity and memory (Puzzo et al., Behavioral assays with mouse models of Alzheimer's disease: Practical considerations and guidelines. *Biochem Pharmacol.* 2014 Jan. 21. pii: S0006-2952 (14)00035-5. doi: 0.1016/j.bcp.2014.01.011. [Epub ahead of print] Review. PMID: 24462904; herein incorporated by reference in its entirety).

Thus, testing of compounds of the invention in AD models such as the APP/PS1 mouse (a transgenic mouse that produces high amounts of amyloid beta and deposits it in amyloid plaques in the brain) show rescue both synaptic plasticity defect and abnormal cognitive function. Consistent with broader indications for CNS diseases and injuries in which p38 MAPK activity is increased, compounds of the invention exhibit concentration dependent suppression of LPS induced proinflammatory cytokine by glia in a peripheral LPS stress test.

Other relevant applications related to MAPK and pharmacological studies are described, for example, in the following publications, each of which is incorporated herein by reference in its entirety:

Alam J J, Compositions and method for treating Alzheimer's Disease, WO 2012/154814;

Alamed J. et al., (2006) Two-day radial-arm water maze learning and memory task; robust resolution of amyloid-related memory deficits in transgenic mice. *Nat Protoc* 1: 1671-1679;

Bachstetter A D and Van Eldik, U (2010) The p38 MAP kinase family as regulators of proinflammatory cytokine production in degenerative diseases of the CNS. *Aging and Disease* 1: 199-211;

Barone F C et al., (2001) SB 239063, a second-generation p38 mitogen-activated protein kinase inhibitor, reduces brain injury and neurological deficits in cerebral focal ischemia, *J. Pharm. Exp. Ther.* 296:312-321;

Correa S A L, Eales K L (2012) The role of p38 MAPK and its substrates in neuronal plasticity and neurodegenerative disease, *J. Signal Transduction* Article ID 649079;

Chico L K et al., (2009) Targeting protein kinases in central nervous system disorders. *Nature Rev Drug Discovery* 8: 892-909;

Chico L K et al., (2009) Molecular properties and CYP2D6 substrates: central nervous system therapeutics case study and pattern analysis of a substrate database. *Drug Metab Disp* 37:2204-2211;

Giovannini, M G et al., (2002) Beta-amyloid-induced inflammation and cholinergic hypofunction in the rat brain in vivo: involvement of the p38MAPK pathway. *Neurobiol Dis* 11: 257-274;

Glover L E et al. A step-up approach for cell therapy in stroke: translational hurdles of bone marrow-derived stem cells. *Transl Stroke Res* 2012; 3:90-98. PMCID: PMC3284662;

Gong B et al., (2004) Persistent improvement in synaptic and cognitive functions in an Alzheimer mouse model after rolipram treatment. *J Clin Invest* 114: 1624-1634;

Graziosi L et al., (2012) Mechanistic role of p38 MAPK in gastric cancer dissemination in a rodent model peritoneal metastasis, *Eur. J. Pharm.* 674:143-152;

Hensley K et al. (1999) p38 kinase is activated in the Alzheimer's disease brain. *J Neurochem* 72: 2053-2058;

Li Y et al., (2003) Interleukin-1 mediates pathological effects of microglia on tau phosphorylation and on synaptophysin synthesis in cortical neurons through a p38-MAPK pathway. *J Neurosci* 23: 1605-1611;

Masliah E (1995) Mechanisms of synaptic dysfunction in Alzheimer's disease. *Histol Histopathol* 10: 509-519;

Morfini G A et al., Inhibition of Fast Axonal Transport by Pathogenic SOD1 Involves Activation of p38 MAP Kinase. *PLoS ONE* 2013, 8(6): e65235;

Munoz L et al., (2007) A novel p38 alpha MAPK inhibitor suppresses brain proinflammatory cytokine up-regulation and attenuates synaptic dysfunction and behavioral deficits in an Alzheimer's disease mouse model. *J Neuroinflammation* 4:21;

Oddo S et al., (2003) Triple-transgenic model of Alzheimer's disease with plaques and tangles: intracellular Abeta and synaptic dysfunction. *Neuron* 39: 409-421;

Rowan M J et al., (2003) Synaptic plasticity in animal models of early Alzheimer's disease. *Philos Trans R Soc Lond B Biol Sci* 358: 821-828;

Selkoe D J (2002) Alzheimer's disease is a synaptic failure. *Science* 298: 789-791;

Selkoe D J (2008) Soluble oligomers of the amyloid beta-protein impair synaptic plasticity and behavior. *Behav Brain Res* 192: 106-113;

Sheng J G et al., (2001) Interleukin-1 promotion of MAPK-p38 overexpression in experimental animals and in Alzheimer's disease: potential significance for tau protein phosphorylation. *Neurochem Intl* 39: 341-348;

Sun A et al., (2003) p38 MAP kinase is activated at early stages in Alzheimer's disease brain. *Exp Neurol* 183: 394-405;

Teich A F and Arancio O (2012) Is the Amyloid Hypothesis of Alzheimer's Disease Therapeutically Relevant? *Biochem J.* 446: 165-177;

Tong L et al., (2012) *J. Neurosci.* 32(49): 17714-17724;

Vitolo O V et al., Pathway and long-term potentiation: reversibility by drugs that enhance cAMP signaling. *Proc Natl Acad Sci USA* 99: 13217-13221;

Wagner E F and Nebreda A R (2009) Signal integration by JNK and p38 MAPK pathways in cancer development, *Nat. Rev. Cancer* 9:537-549;

Watterson D M et al., (2013) Development of novel in vivo chemical probes to address CNS protein kinase involvement in synaptic dysfunction. *PLOS One* 8: e66226;

Xing B et al., (2011) Microglia p38α MAPK is critical for LPS-induced neuron degeneration through a mechanism involving TNFα. *Molecular Neurodegeneration* 6: 84;

Walsh D M et al., (2002) Naturally secreted oligomers of amyloid beta protein potently inhibit hippocampal long-term potentiation in vivo. *Nature* 416: 535-539;

Yang G et al., (2013) Mitogen-activated protein kinases regulate vascular reactivity after hemorrhagic shock through myosin light chain phosphorylation pathway, *J. Trauma Acute Care Surg.* 74:1033-1043; and Yeung Y T et al., (2013) Interleukins in glioblastoma pathophysiology: implications for therapy, *Br. J. Pharmacol.* 168: 591-606.

MAPK inhibitors are described, for example, in U.S. Pat. Nos. 7,919,485; 8,188,096; U.S. Patent Publication Nos. 2010/0104536, 2012/0289511; European Patent No. EP1196167, EP2426134; EP1606283; Kumar, S., et al., *Nat. Rev. Drug Disc.* 2003, 2, 717; Munoz, L., et al., *J. Neuroinflammation* 2007, 4, 21; and Watterson, D. M., et al., *PLoS One* (8)6: e66226 (2013); and references therein; each herein incorporated by reference in its entirety. Most p38 MAPK inhibitors are multi-kinase inhibitors and exhibit relatively unselective inhibition of several kinases such as p38, JNK, ERK and upstream and downstream protein kinases. Pharmacological profiles of such compounds risk unexpected outcomes in terms of efficacy, toxicity and side effect profile. Target engagement studies were performed along with signal transduction in cell culture and in vivo pharmacology. In some embodiments, the compounds of the invention selectively inhibit p38α MAPK. In some embodiments, the compound of formula (I) is a pyridazine derivative. In some embodiments, the compound of formula (I) is a pyrazine derivative.

In some embodiments of formula (I), $X_1$ is N and $X_2$ is CH, or $X_1$ is CH and $X_2$ is N;

$R^1$ is $-N(R^4)_2$, cyclopropyl, or $R^5$-piperidin-4-yl;

$R^2$ is independently D or halogen;

$R^3$ is naphthyl, quinolinyl, isoquinolinyl, or indolyl, wherein said naphthyl, quinolinyl, isoquinolinyl or indolyl is optionally independently substituted with at least one D, halogen, $(C_1-C_3)$-alkoxy, or $(C_1-C_3)$-alkoxy substituted with at least one D;

$R^4$ is independently H, $(C_1-C_3)$-alkyl, $(C_1-C_3)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S;

$R^5$ is H or $(C_1-C_3)$-alkyl, or $(C_1-C_3)$-alkyl substituted with at least one D;

$R^6$ is H, $(C_1-C_3)$-alkyl, or $(C_1-C_3)$-alkyl substituted with at least one D; and n is an integer from 0-4; or a pharmaceutically acceptable salt thereof, wherein when $R^3$ is indol-4-yl and n is 0, $R^1$ is not N-methyl-piperazinyl.

In some embodiments of formula (I), $X_1$ is N and $X_2$ is CH;

$R^1$ is $-N(R^4)_2$, cyclopropyl, or $R^5$-piperidin-4-yl;

$R^2$ is independently D or halogen;

$R^3$ is naphthyl, quinolinyl, isoquinolinyl, or indolyl, wherein said naphthyl, quinolinyl, isoquinolinyl or indolyl is optionally independently substituted with at least one D, halogen, $(C_1-C_3)$-alkoxy, or $(C_1-C_3)$-alkoxy substituted with at least one D;

$R^4$ is independently H, $(C_1-C_3)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S;

$R^5$ is H or $(C_1-C_3)$-alkyl, or $(C_1-C_3)$-alkyl substituted with at least one D;

$R^6$ is H, $(C_1-C_3)$-alkyl, or $(C_1-C_3)$-alkyl substituted with at least one D; and n is an integer from 0-4; or a pharmaceutically acceptable salt thereof In some embodiments of formula (I), $X_1$ is CH and $X_2$ is N;

$R^1$ is $-N(R^4)_2$, cyclopropyl, or $R^5$-piperidin-4-yl;

$R^2$ is independently D or halogen;

$R^3$ is naphthyl, quinolinyl, isoquinolinyl, or indolyl, wherein said naphthyl, quinolinyl, isoquinolinyl or indolyl is optionally independently substituted with at least one D, halogen, $(C_1-C_3)$-alkoxy, or $(C_1-C_3)$-alkoxy substituted with at least one D;

$R^4$ is independently H, $(C_1-C_3)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S;

$R^5$ is H or $(C_1-C_3)$-alkyl, or $(C_1-C_3)$-alkyl substituted with at least one D;

$R^6$ is H, $(C_1-C_3)$-alkyl, or $(C_1-C_3)$-alkyl substituted with at least one D; and n is an integer from 0-4; or a pharmaceutically acceptable salt thereof In some embodiments of formula (I), $R^2$ is independently halogen;

$R^3$ is naphthalen-1-yl, naphthalen-2-yl, quinolin-8-yl, isoquinolin-5-yl, or indol-5-yl, wherein said naphthalen-1-yl, naphthalen-2-yl, quinolin-8-yl, isoquinolin-5-yl, or indol-5-yl is optionally independently substituted with at least one halogen or $(C_1-C_3)$-alkoxy;

$R^4$ is independently H, $(C_1-C_3)$-alkyl, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S;

$R^5$ is H or $(C_1-C_3)$-alkyl; and $R^6$ is H or $(C_1-C_3)$-alkyl.

In some embodiments of formula (I), $R^3$ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with at least one halogen or $(C_1-C_3)$-alkoxy;

$R^4$ is independently H, $(C_1-C_3)$-alkyl, $(C_3-C_5)$-cycloalkyl, or each $R^4$ together with the nitrogen to which they are attached form N-methyl piperazine, piperazine, piperidine, pyrrolidine, azetidine, or morpholine; and n is an integer from 0-2.

In some embodiments of formula (I), $R^1$ is $-N(R^4)_2$ or cyclopropyl;

$R^2$ is independently halogen;

$R^3$ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with at least one halogen or $(C_1-C_3)$-alkoxy;

$R^4$ is independently H, $(C_1-C_3)$-alkyl, $(C_3-C_5)$-cycloalkyl, or each $R^4$ together with the nitrogen to which they are attached form $NR^6$-piperazine, piperidine, pyrrolidine, azetidine, or morpholine;

$R^6$ is H, methyl or $CD_3$; and and n is an integer from 0-2.

In some embodiments of formula (I), $R^1$ is $-N(R^4)_2$ or cyclopropyl; $R^2$ is fluorine; $R^3$ is naphthalen-1-yl or naphthalen-2-yl; $R^4$ is independently H, $(C_1-C_3)$-alkyl, $(C_3-C_5)$-cycloalkyl, or each $R^4$ together with the nitrogen to which they are attached form

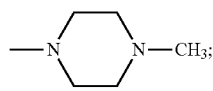

and n is 0 or 1.

In some embodiments of formula (I), $R^1$ is $-N(R^4)_2$ or cyclopropyl;

$R^2$ is independently halogen;

$R^3$ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with one or more fluorine atoms;

$R^4$ is independently H, $(C_1-C_3)$-alkyl, $(C_3-C_5)$-cycloalkyl, or each $R^4$ together with the nitrogen to which they are attached form $NR^6$-piperazine, piperidine, pyrrolidine, azetidine, or morpholine;

$R^6$ is H, methyl or $CD_3$; and and n is an integer from 0-2.

In some embodiments of formula (I), $R^1$ is $-N(CH_3)_2$, cyclopropyl, or

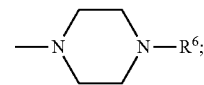

$R^3$ is naphthalen-1-yl or naphthalen-2-yl;

$R^6$ is H, methyl or $CD_3$; and n is 0.

In some embodiments of formula (I), $R^1$ is

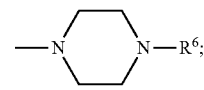

$R^3$ is naphthalen-1-yl or naphthalen-2-yl; $R^6$ is H, methyl or $CD_3$; and n is 0.

In some embodiments of formula (I), $R^1$ is

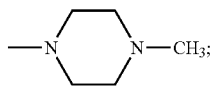

$R^3$ is naphthalen-1-yl or naphthalen-2-yl; and n is 0.

In some embodiments of formula (I), the compound is

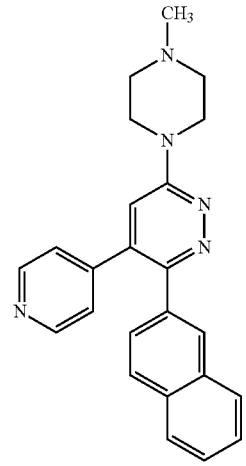

In some embodiments of formula (I), $R^1$ is $-N(CH_3)_2$ or cyclopropyl; $R^2$ is F; $R^3$ is naphthalen-1-yl or naphthalen-2-yl; and n is 0 or 1.

In some embodiments of formula (I), $R^1$ is $-N(CH_3)_2$, cyclopropyl or

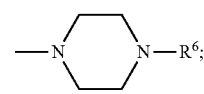

$R^2$ is halogen; $R^3$ is naphthalen-1-yl or naphthalen-2-yl; $R^6$ is H, methyl or $CD_3$; and n is 1.

In some embodiments of formula (I), $R^1$ is $-N(CH_3)_2$, cyclopropyl or

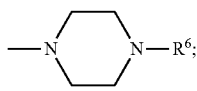

$R^3$ is naphthalen-1-yl or naphthalen-2-yl; $R^6$ is H, methyl or $CD_3$; and n is 0.

In some embodiments of formula (I), $R^1$ is —N(CH$_3$)$_2$; $R^3$ is naphthalen-1-yl or naphthalen-2-yl; and n is 0.

In some embodiments of formula (I), $R^1$ is —N(CH$_3$)$_2$, cyclopropyl or N-methyl-piperazinyl; $R^2$ is fluoro; $R^3$ is naphthalen-1-yl or naphthalen-2-yl; and n is 1; or a pharmaceutically acceptable salt thereof.

In some embodiments of formula (I), $R^1$ is —N(CH$_3$)$_2$, cyclopropyl or N-methyl-piperazinyl; $R^3$ is naphthalen-1-yl or naphthalen-2-yl; and n is 0; or a pharmaceutically acceptable salt thereof.

In some embodiments of formula (I), the compound is

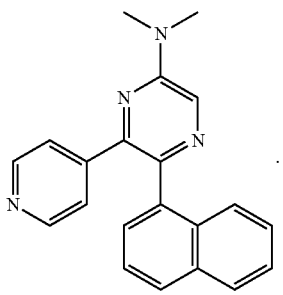 [SMILES: CN(C)c1cnc(-c2cccc3ccccc23)c(-c2ccncc2)n1]

In some embodiments of formula (I), $X_1$ is N and $X_2$ is CH, or $X_1$ is CH and $X_2$ is N. In some embodiments of formula (I), $X_1$ is N and $X_2$ is CH. In some embodiments of formula (I), $X_1$ is CH and $X_2$ is N.

In some embodiments of formula (I), $R^1$ is —N(CH$_3$)$_2$, —NH(CH$_3$), or cyclopropyl; $R^2$ is independently halogen; $R^3$ is naphthyl; and n is an integer from 0-4; or a pharmaceutically acceptable salt thereof.

In some embodiments of formula (I), $R^1$ is —N(R$^4$)$_2$, cyclopropyl, or R$^5$-piperidin-4-yl. In some embodiments of formula (I), $R^1$ is —N(CH$_3$)$_2$, cyclopropyl, or

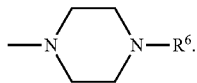

In some embodiments of formula (I), $R^1$ is

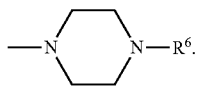

In some embodiments of formula (I), $R^1$ is

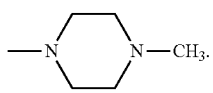

In some embodiments of formula (I), $R^1$ is —N(R$^4$)$_2$, cyclopropyl, or N-methyl piperazinyl. In some embodiments of formula (I), $R^1$ is —N(CH$_3$)$_2$, cyclopropyl, or N-methyl piperazinyl. In some embodiments of formula (I), $R^1$ is —N(R$^4$)$_2$ or cyclopropyl. In some embodiments of formula (I), $R^1$ is —N(CH$_3$)$_2$ or cyclopropyl. In some embodiments of formula (I), $R^1$ is —N(CH$_3$)$_2$ or —NH(CH$_3$). In some embodiments of formula (I), $R^1$ is cyclopropyl.

In some embodiments of formula (I), $R^2$ is independently D or halogen. In some embodiments of formula (I), $R^2$ is halogen. In some embodiments of formula (I), $R^2$ is D. In some embodiments of formula (I), $R^2$ is chlorine or fluorine. In some embodiments of formula (I), $R^2$ is chlorine. In some embodiments of formula (I), $R^2$ is fluorine.

In some embodiments of formula (I), $R^3$ is naphthyl, quinolinyl, isoquinolinyl, or indolyl, wherein said naphthyl, quinolinyl, isoquinolinyl or indolyl is optionally independently substituted with at least one D, halogen, (C$_1$-C$_3$)-alkoxy, or (C$_1$-C$_3$)-alkoxy substituted with at least one D. In some embodiments of formula (I), $R^3$ is naphthyl, quinolinyl, isoquinolinyl, or indolyl, wherein said naphthyl, quinolinyl, isoquinolinyl or indolyl is optionally independently substituted with at least one D, halogen, (C$_1$-C$_3$)-alkoxy, or (C$_1$-C$_3$)-alkoxy substituted with at least one D; and wherein said indolyl is not indol-4-yl. In some embodiments of formula (I), $R^3$ is naphthyl, quinolinyl, isoquinolinyl, or indol-5-yl, wherein said naphthyl, quinolinyl, isoquinolinyl or indol-5-yl is optionally independently substituted with at least one D, halogen, (C$_1$-C$_3$)-alkoxy, or (C$_1$-C$_3$)-alkoxy substituted with at least one D. In some embodiments of formula (I), $R^3$ is naphthyl, quinolinyl, isoquinolinyl, or indolyl, wherein said naphthyl, quinolinyl, isoquinolinyl or indolyl is optionally independently substituted with one or more halogen atoms or (C$_1$-C$_3$)-alkoxy. In some embodiments of formula (I), $R^3$ is naphthyl, quinolinyl, isoquinolinyl, or indolyl, wherein said naphthyl, quinolinyl, isoquinolinyl or indolyl is optionally independently substituted with one or more halogen atoms or (C$_1$-C$_3$)-alkoxy. In some embodiments of formula (I), $R^3$ is naphthyl, quinolinyl, isoquinolinyl, or indol-5-yl, wherein said naphthyl, quinolinyl, isoquinolinyl or indol-5-yl is optionally independently substituted with one or more halogen atoms or (C$_1$-C$_3$)-alkoxy. In some embodiments of formula (I), $R^3$ is naphthyl, quinolinyl, or isoquinolinyl, wherein said naphthyl, quinolinyl, or isoquinolinyl is optionally independently substituted with one or more halogen atoms or (C$_1$-C$_3$)-alkoxy. In some embodiments of formula (I), $R^3$ is naphthyl, quinolinyl, or isoquinolinyl, wherein said naphthyl, quinolinyl, or isoquinolinyl is optionally independently substituted with one or more halogen atoms. In some embodiments of formula (I), $R^3$ is naphthyl, quinolinyl, or isoquinolinyl. In some embodiments of formula (I), $R^3$ is naphthalen-1-yl, naphthalen-2-yl, quinolin-8-yl, isoquinolin-5-yl, or indol-5-yl, wherein said naphthalen-1-yl, naphthalen-2-yl, quinolin-8-yl, isoquinolin-5-yl, or indol-5-yl is optionally independently substituted with at least one D, halogen, (C$_1$-C$_3$)-alkoxy, or (C$_1$-C$_3$)-alkoxy substituted with at least one D. In some embodiments of formula (I), $R^3$ is naphthalen-1-yl, naphthalen-2-yl, quinolin-8-yl, isoquinolin-5-yl, or indol-5-yl, wherein naphthalen-1-yl, naphthalen-2-yl, quinolin-8-yl, isoquinolin-5-yl, or indol-5-yl is optionally independently substituted with one or more halogen atoms or (C$_1$-C$_3$)-alkoxy. In some embodiments of formula (I), $R^3$ is naphthalen-1-yl, naphthalen-2-yl, quinolin-8-yl, isoquinolin-5-yl, or indol-5-yl. In some embodiments of formula (I), $R^3$ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with at least one halogen or (C$_1$-C$_3$)-alkoxy. In some embodiments of formula (I), R³ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl, is optionally independently substituted with one or more halogen atoms. In some embodiments of formula (I), R³ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with one fluorine atom. In some embodiments of formula (I), R³ is naphthalen-1-yl or naphthalen-2-yl, optionally substituted with one or more halogen atoms. In some embodiments of formula (I), R³ is naphthalen-1-yl or naphthalen-2-yl.

In some embodiments of formula (I), R³ is

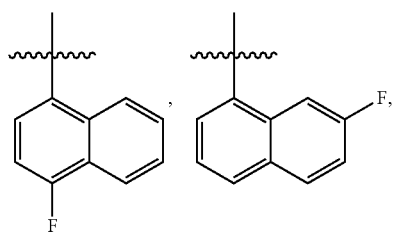

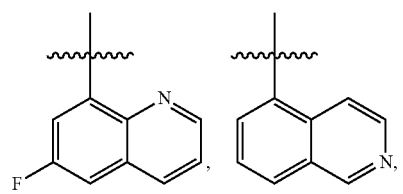

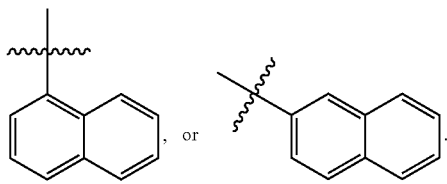

In some embodiments of formula (I), R³ is

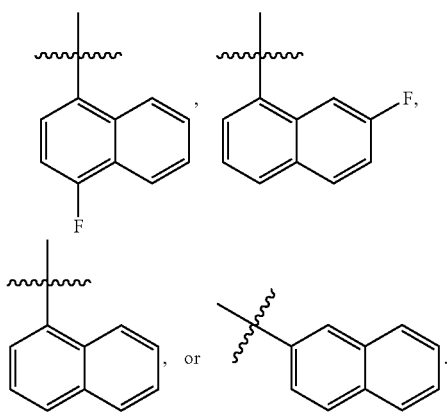

In some embodiments of formula (I), R³ is

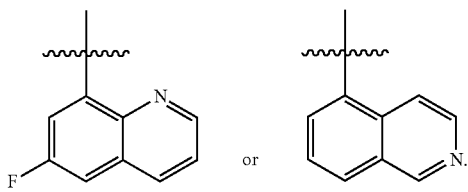 [SMILES: *c1cc(F)cc2cccnc12 ; *c1cccc2cnccc12]

or

In some embodiments of formula (I), R³ is

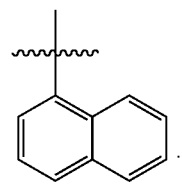 [SMILES: *c1cccc2ccccc12]

In some embodiments of formula (I), R³ is

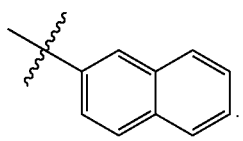 [SMILES: *c1ccc2ccccc2c1]

In some embodiments of formula (I), R³ is naphthyl, quinolinyl or isoquinolinyl.

In some embodiments of formula (I), R³ is naphthyl, independently substituted with one or more halogen atoms. In some embodiments of formula (I), R³ is naphthalen-1-yl or naphthalen-2-yl, independently substituted with one or more halogen atoms. In some embodiments of formula (I), R³ is quinolinyl, independently substituted with one or more halogen atoms. In some embodiments of formula (I), R³ is quinolinyl. In some embodiments of formula (I), R³ is quinolin-8-yl, independently substituted with one or more halogen atoms. In some embodiments of formula (I), R³ is quinolin-8-yl. In some embodiments of formula (I), R³ is isoquinolinyl, independently substituted with one or more halogen atoms. In some embodiments of formula (I), R³ is isoquinolinyl. In some embodiments of formula (I), R³ is isoquinolin-5-yl, independently substituted with one or more halogen atoms. In some embodiments of formula (I), R³ is isoquinolin-5-yl. In some embodiments of formula (I), R³ is indolyl. In some embodiments of formula (I), R³ is indolyl, independently substituted with one or more halogen atoms. In some embodiments of formula (I), R³ is indol-5-yl, independently substituted with one or more halogen atoms. In some embodiments of formula (I), R³ is indol-5-yl.

In some embodiments of formula (I), R³ is independently substituted with one or more halogen atoms. In some embodiments of formula (I), R³ is independently substituted with one or more D. In some embodiments of formula (I), R³ is independently substituted with one D.

In some embodiments of formula (I), the halogen atom is chlorine or fluorine. In some embodiments of formula (I), the halogen atom is chlorine. In some embodiments of formula (I), halogen atom is fluorine.

In some embodiments of formula (I), R⁴ is independently H, ($C_1$-$C_4$)-alkyl substituted with at least one D, ($C_3$-$C_5$)-cycloalkyl, or each R⁴ together with the nitrogen to which they are attached form a 3-7 membered heterocyclic ring, wherein one of the carbon atoms is optionally replaced with $NR^6$, O or S. In some embodiments of formula (I), $R^4$ is independently H, $(C_1-C_3)$-alkyl, $(C_1-C_3)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S. In some embodiments of formula (I), $R^4$ is independently H, $(C_1-C_3)$-alkyl, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S. In some embodiments of formula (I), $R^4$ is independently H, $(C_1-C_3)$-alkyl, $(C_3-C_5)$-cycloalkyl, or each $R^4$ together with the nitrogen to which they are attached form N-methyl piperazine, piperazine, piperidine, pyrrolidine, azetidine, or morpholine. In some embodiments of formula (I), $R^4$ is independently H, $(C_1-C_3)$-alkyl, or each $R^4$ together with the nitrogen to which they are attached form

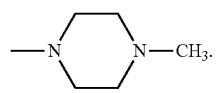

In some embodiments of formula (I), each $R^4$ together with the nitrogen to which they are attached form

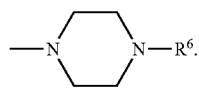

In some embodiments of formula (I), $R^4$ is independently H or methyl. In some embodiments of formula (I), $R^4$ is independently H, methyl or ethyl. In some embodiments of formula (I), $R^4$ is independently propyl or butyl. In some embodiments of formula (I), $R^4$ is independently methyl or ethyl. In some embodiments of formula (I), $R^4$ is independently methyl. In some embodiments of formula (I), $R^4$ is independently ethyl.

In some embodiments of formula (I), $R^4$ is independently H or $CD_3$. In some embodiments of formula (I), $R^4$ is independently H, $CD_3$ or $CH_2CD_3$. In some embodiments of formula (I), $R^4$ is independently $CD_3$ or $CH_2CD_3$. In some embodiments of formula (I), $R^4$ is independently $CD_3$. In some embodiments of formula (I), $R^4$ is independently $CH_2CD_3$.

In some embodiments of formula (I), $R^5$ is H or $(C_1-C_3)$-alkyl, or $(C_1-C_3)$-alkyl substituted with at least one D. In some embodiments of formula (I), $R^5$ is H or $(C_1-C_3)$-alkyl. In some embodiments of formula (I), $R^5$ is H or methyl. In some embodiments of formula (I), $R^5$ is H. In some embodiments of formula (I), $R^5$ is H, methyl or ethyl. In some embodiments of formula (I), $R^5$ is methyl or ethyl. In some embodiments of formula (I), $R^5$ is methyl. In some embodiments of formula (I), $R^5$ is ethyl.

In some embodiments of formula (I), $R^5$ is H or $CD_3$. In some embodiments of formula (I), $R^5$ is H, $CD_3$ or $CH_2CD_3$. In some embodiments of formula (I), $R^5$ is $CD_3$ or $CH_2CD_3$. In some embodiments of formula (I), $R^5$ is $CD_3$. In some embodiments of formula (I), $R^5$ is $CH_2CD_3$.

In some embodiments of formula (I), $R^6$ is H or $(C_1-C_3)$-alkyl, or $(C_1-C_3)$-alkyl substituted with at least one D. In some embodiments of formula (I), $R^6$ is H or $(C_1-C_3)$-alkyl. In some embodiments of formula (I), $R^6$ is H or methyl. In some embodiments of formula (I), $R^6$ is H. In some embodiments of formula (I), $R^6$ is H, methyl or ethyl. In some embodiments of formula (I), $R^6$ is methyl or ethyl. In some embodiments of formula (I), $R^6$ is methyl. In some embodiments of formula (I), $R^6$ is ethyl.

In some embodiments of formula (I), $R^6$ is H, methyl or $CD_3$. In some embodiments of formula (I), $R^6$ is H or $CD_3$. In some embodiments of formula (I), $R^6$ is H, $CD_3$ or $CH_2CD_3$. In some embodiments of formula (I), $R^6$ is $CD_3$ or $CH_2CD_3$. In some embodiments of formula (I), $R^6$ is $CD_3$. In some embodiments of formula (I), $R^6$ is $CH_2CD_3$.

In some embodiments of formula (I), n is an integer from 0-4. In some embodiments of formula (I), n is an integer from 0-3. In some embodiments of formula (I), n is an integer from 0-2. In some embodiments of formula (I), n is an integer from 0-1. In some embodiments of formula (I), n is an integer from 1-2. In some embodiments of formula (I), n is 0. In some embodiments of formula (I), n is 1. In some embodiments of formula (I), n is 2.

In some embodiments, $R^3$ is not indolyl. In some embodiments, $R^3$ is not indolyl when n is 0. In some embodiments, $R^3$ is not indol-4-yl. In some embodiments, $R^3$ is not indol-4-yl when n is 0. In some embodiments, $R^4$ is not H or $(C_1-C_3)$-alkyl when $R^3$ is indolyl and n is 0. In some embodiments, when $R^3$ is indol-4-yl and n is 0, $R^1$ is not N-methyl-piperazinyl.

Abbreviations and Definitions

The term "compound of the invention" as used herein means a compound of formula (I) or any subgenus or species thereof. The term is also intended to encompass salts, hydrates, and solvates thereof.

The term "composition(s) of the invention" as used herein means compositions comprising a compound of the invention. The compositions of the invention may further comprise other agents such as, for example, carriers, excipients, stabilants, lubricants, solvents, and the like.

The term "D" refers to a deuterium atom, and is known in the art to refer to a deuterium enriched species, that is, where D is present above its natural isotopic abundance.

A "pharmaceutical composition" refers to a mixture of one or more of the compounds of the invention with other chemical components, such as physiologically acceptable carriers and excipients. The purpose of a pharmaceutical composition is to facilitate administration of a compound to an organism or subject.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (*J. Pharm. Sci.* 1977, 66(1), 1; hereby incorporated by reference in its entirety).

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, 21$^{st}$ Ed. (Lippincot, Williams & Wilkins (2005); Modern Pharmaceutics, vol. 121 (Gilbert Banker and Christopher Rhodes, CRC Press (2002); each of which hereby incorporated by reference in its entirety).

In some embodiments of the compound of formula (I), $R^1$ is —N(CH$_3$)$_2$ or —NH(CH$_3$); $R^3$ is

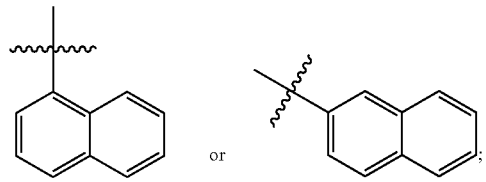 [SMILES: *c1cccc2ccccc12 ; *c1ccc2ccccc2c1]

or and n is 0.

In some embodiments of the compound of formula (I), $R^1$ is —N(CH$_3$)$_2$; $R^3$ is

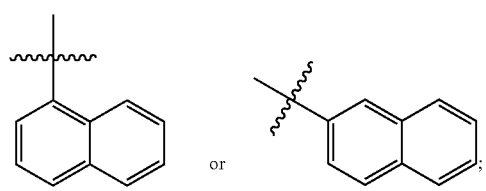 [SMILES: *c1cccc2ccccc12 ; *c1ccc2ccccc2c1]

or and n is 0.

In some embodiments of the compound of formula (I), $R^1$ is —N(CH$_3$)$_2$; $R^3$ is

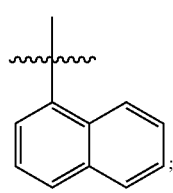 [SMILES: *c1cccc2ccccc12]

and n is 0.

In some embodiments of the compound of formula (I), $R^1$ is —N(CH$_3$)$_2$; $R^3$ is

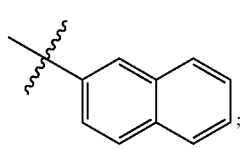 [SMILES: *c1ccc2ccccc2c1]

and n is 0.

In some embodiments of formula (I), $R^1$ is cyclopropyl; $R^2$ is halogen; and $R^3$ is

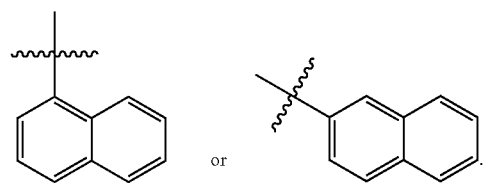 [SMILES: *c1cccc2ccccc12 ; *c1ccc2ccccc2c1]

or

In some embodiments of formula (I), $R^1$ is cyclopropyl; $R^2$ is halogen; and $R^3$ is

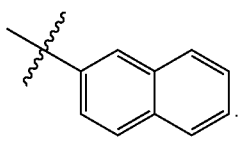 [SMILES: *c1ccc2ccccc2c1]

In some embodiments of formula (I), $R^1$ is cyclopropyl; $R^2$ is halogen; and $R^3$ is

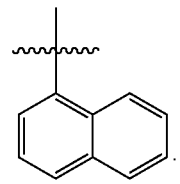 [SMILES: *c1cccc2ccccc12]

In some embodiments of formula (I), $R^1$ is cyclopropyl; $R^2$ is fluorine; $R^3$ is

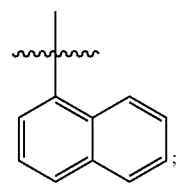 [SMILES: *c1cccc2ccccc12]

and n is 1.

In some embodiments of formula (I), $R^1$ is cyclopropyl; $R^2$ is fluorine; $R^3$ is

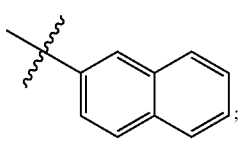 [SMILES: *c1ccc2ccccc2c1]

and n is 1.

In some embodiments of formula (I), the compound is selected from

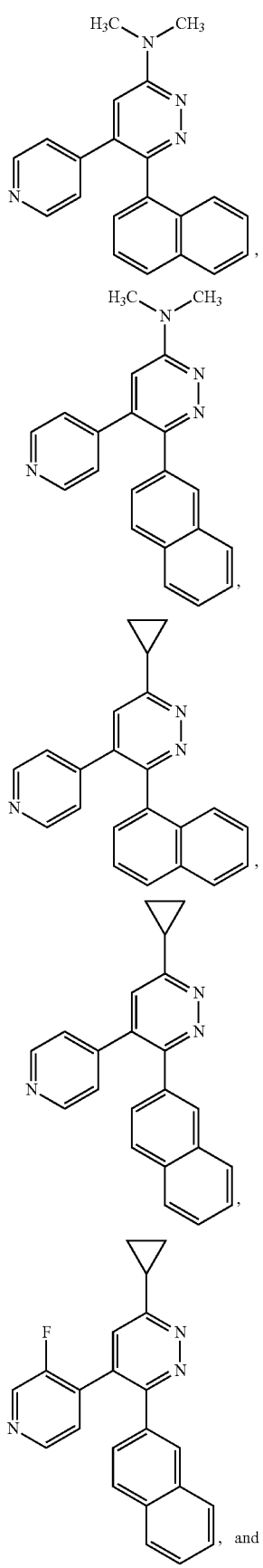
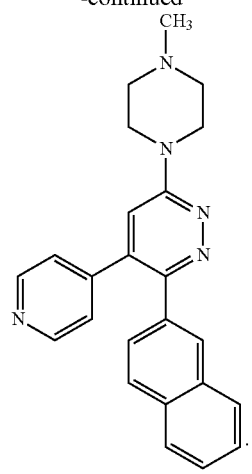
In some embodiments of formula (I), the compound is selected from
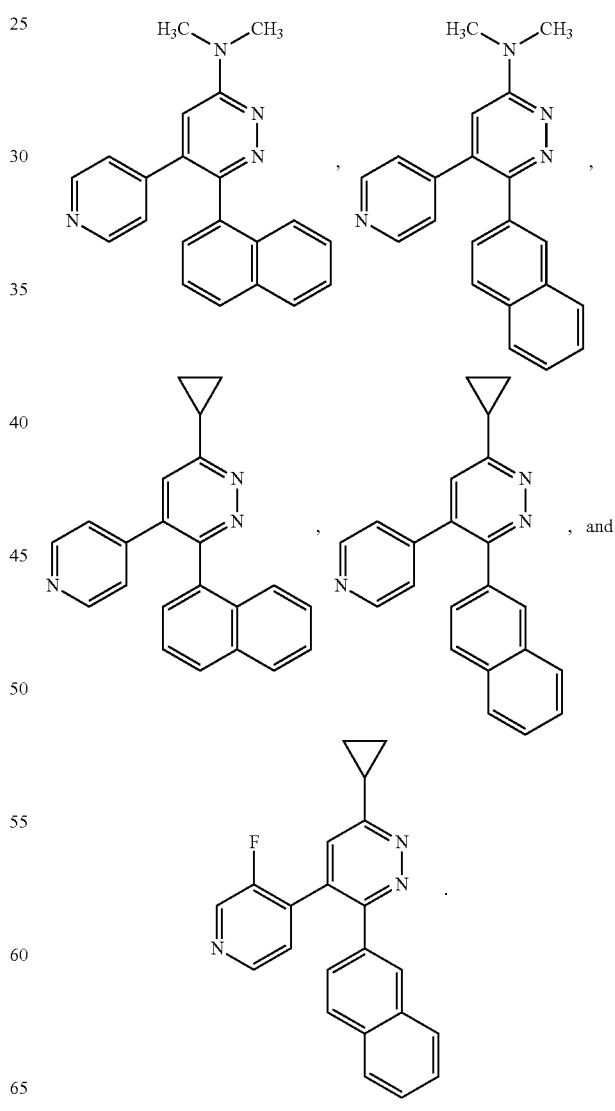

In some embodiments of formula (I), the compound is

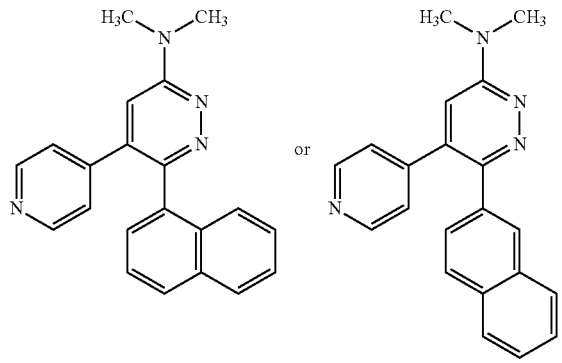

or

In some embodiments of formula (I), the compound is selected from

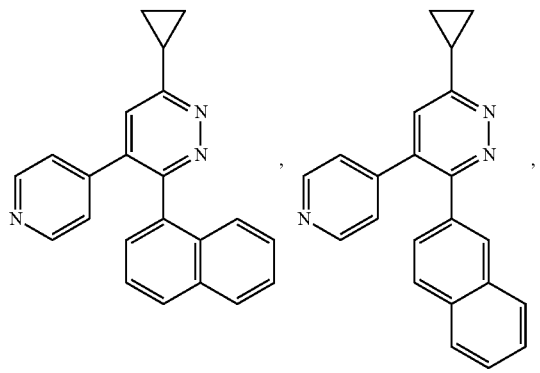

In some embodiments of formula (I), the compound is selected from

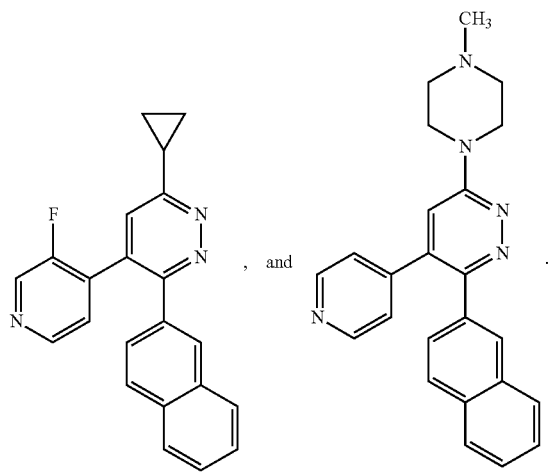

, and

In some embodiments of formula (I), the compound is

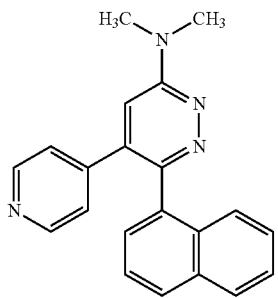 [SMILES: CN(C)c1cc(-c2ccncc2)c(-c2cccc3ccccc23)nn1]

In some embodiments of formula (I), the compound is (also referred to herein is (1) or MW-181).

In some embodiments of formula (I), the compound is

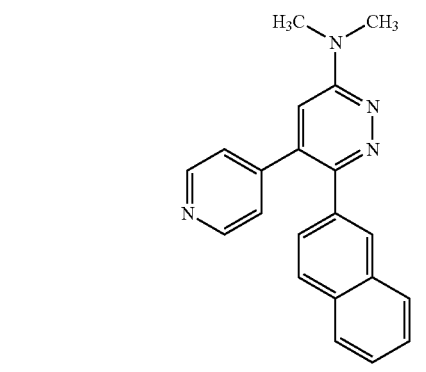 [SMILES: CN(C)c1cc(-c2ccncc2)c(-c2ccc3ccccc3c2)nn1]

(also referred to herein is (2) or MW-108).

In some embodiments of formula (I), the compound is

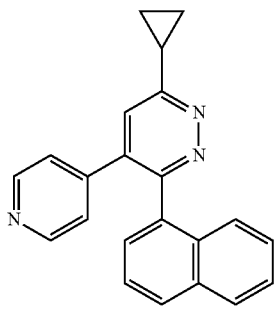 [SMILES: c1ccc2c(-c3nnc(C4CC4)cc3-c3ccncc3)cccc2c1]

(also referred to herein is (7) or MW-077).

In some embodiments of formula (I), the compound is

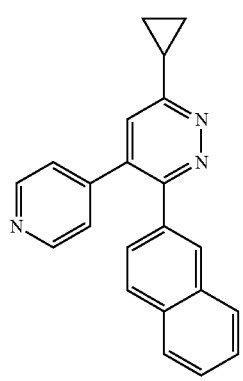 [SMILES: c1ccc2cc(-c3nnc(C4CC4)cc3-c3ccncc3)ccc2c1]

(also referred to herein is (9) or MW-125).

In some embodiments of formula (I), the compound is

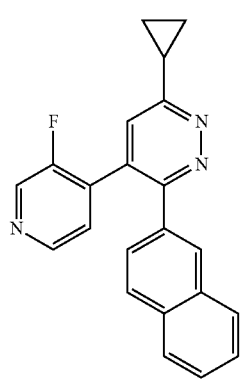 [SMILES: Fc1cnccc1-c1cc(C2CC2)nnc1-c1ccc2ccccc2c1]

(also referred to herein is (10) or MW-167).

In some embodiments of formula (I), the compound is

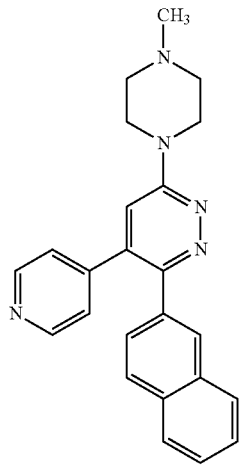

(also referred to herein is (27) or MW-150).

In some embodiments of formula (I), the compound is

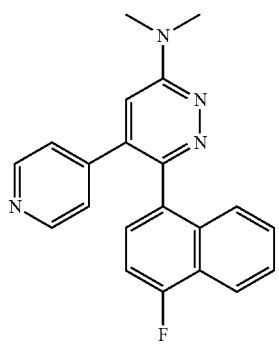 [SMILES: CN(C)c1cc(-c2ccncc2)c(-c2ccc(F)c3ccccc23)nn1]

(also referred to herein is (17) or MW-078).

In some embodiments of formula (I), the compound is

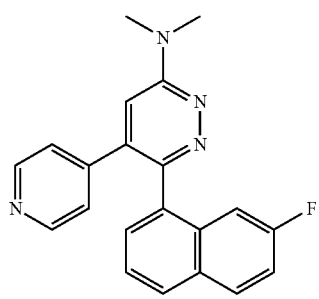 [SMILES: CN(C)c1cc(-c2ccncc2)c(-c2cccc3ccc(F)cc23)nn1]

(also referred to herein is (18) or MW-085).

In some embodiments of formula (I), the compound is

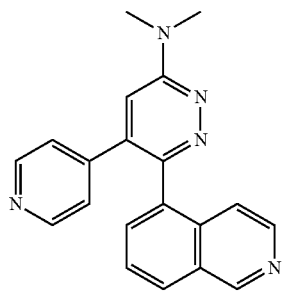 [SMILES: CN(C)c1cc(-c2ccncc2)c(-c2cccc3cnccc23)nn1]

(also referred to herein is (20) or MW-082).

In some embodiments of formula (I), the compound is

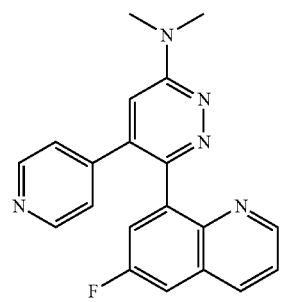 [SMILES: CN(C)c1cc(-c2ccncc2)c(-c2cc(F)cc3cccnc23)nn1]

(also referred to herein is (21) or MW-165).

In some embodiments of formula (I), the compound is

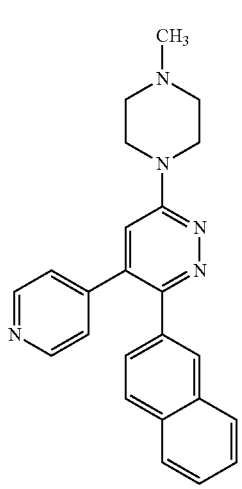 [SMILES: CN1CCN(c2cc(-c3ccncc3)c(-c3ccc4ccccc4c3)nn2)CC1]

(also referred to herein is (27) or MW-150).

In some embodiments, the compound is selected from the compounds listed in Table 1. In some embodiments, the compound is a compound of Table 1.

TABLE 1

Representative MAPK Modulators.

| Compound | | $R^3$ | $R^1$ |
|---|---|---|---|
| 1 (MW-181) | | | —N(CH$_3$)$_2$ |
| 2 (MW-108) | | | —N(CH$_3$)$_2$ |
| 7 (MW-077) | | | |

TABLE 1-continued
| # | | | |
|---|---|---|---|
| 9 (MW-125) | 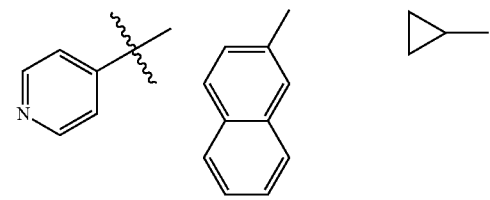 |  | 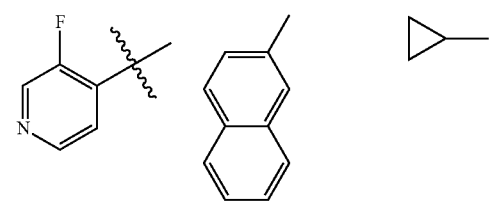 |
| 10 (MW-167) |  | 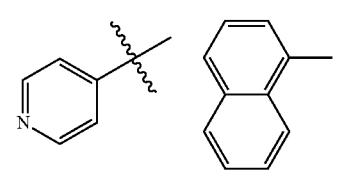 | 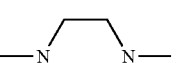 |
| 11 (MW-122) | 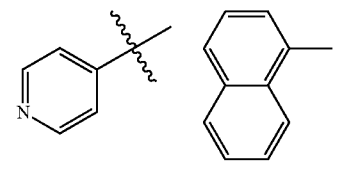 | 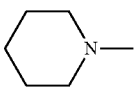 | 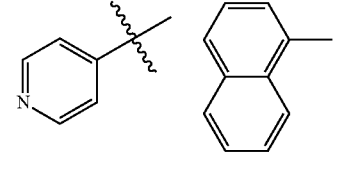 |
| 12 (MW-124) | 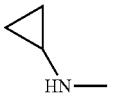 | 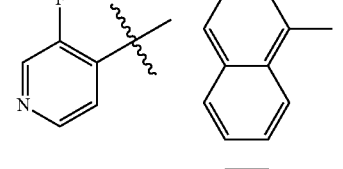 |  |
| 13 (MW-107) | 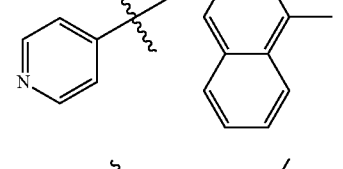 |  | 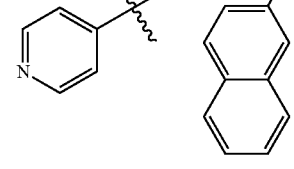 |
| 14 (MW-109) |  | | |
| 15 (MW-156) | | | —NHCH$_3$ |
| 16 (MW-200) | 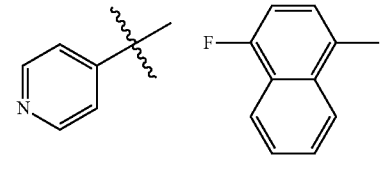 | | —N(H)CH$_3$ |
| 17 (MW-078) |  | | —N(CH$_3$)$_2$ |

TABLE 1-continued
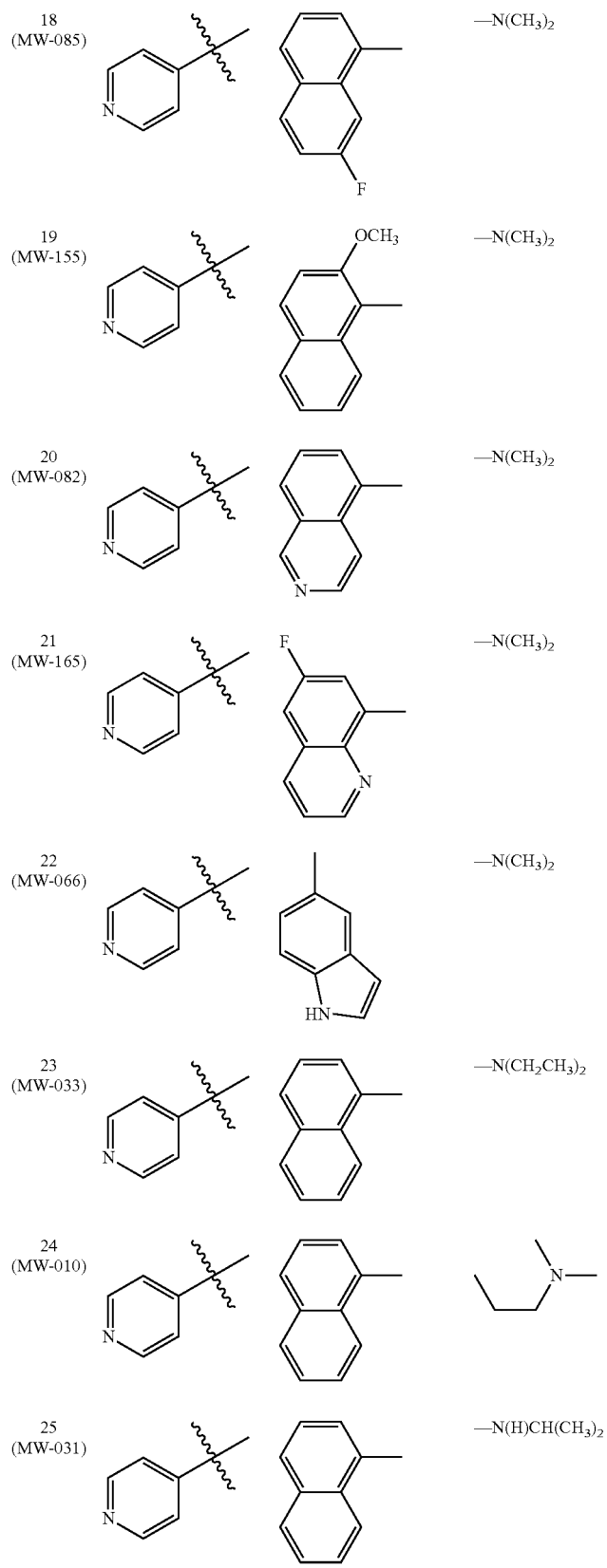

TABLE 1-continued
| | | | |
|---|---|---|---|
| 26 (MW-025) | 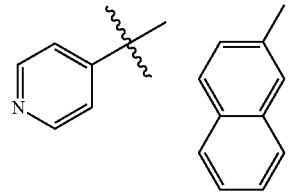 | 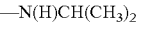 | —N(H)CH(CH$_3$)$_2$ |
| 27 (MW-150) | 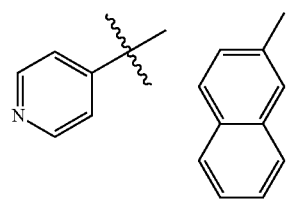 | 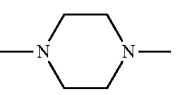 | 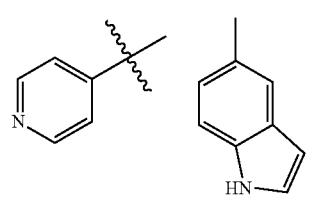 |
| 28 (MW-118) | 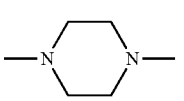 | 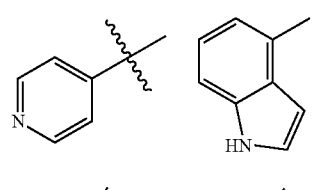 | 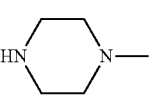 |
| 30 (MW-126) | 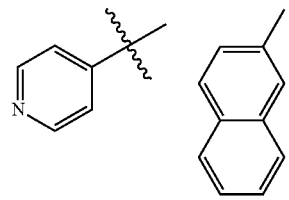 | 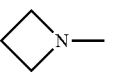 | 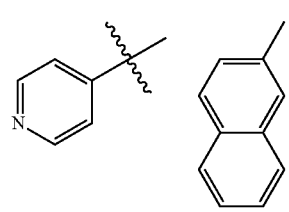 |
| 31 (MW-146) | | | 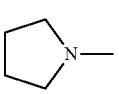 |
| 32 (MW-148) | | | 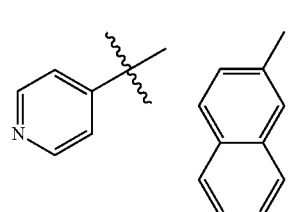 |
| 33 (MW-152) | | | 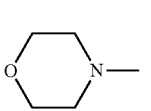 |
| 34 (MW-154) | | 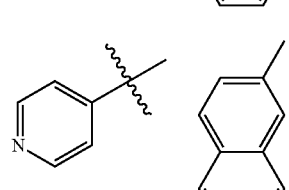 | 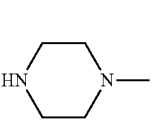 |

TABLE 1-continued
| # | Ar1 | Ar2 | R |
|---|---|---|---|
| 35 (MW-153) | 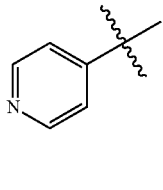 [SMILES: *c1ccncc1] | 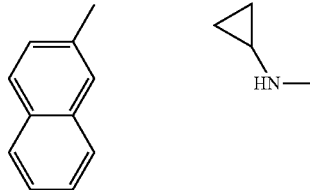 | 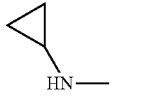 |
| 36 (MW-164) | 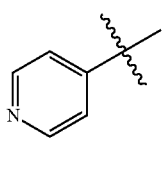 [SMILES: *c1ccncc1] | 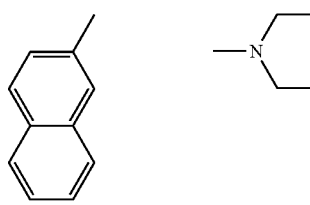 | 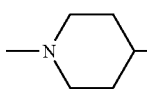 |
| 37 (MW-149) | 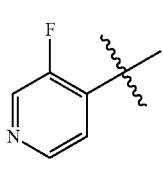 | 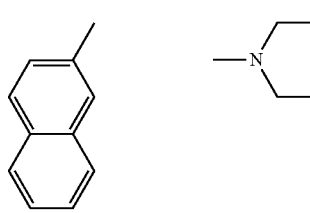 | 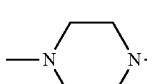 |
| 45 | 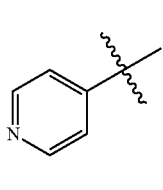 [SMILES: *c1ccncc1] | 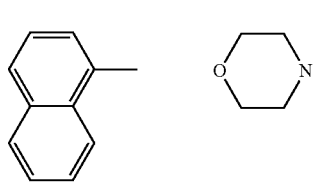 | 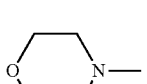 |
| 46 (SRM-137C) | 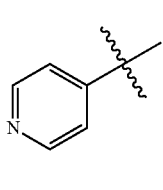 | 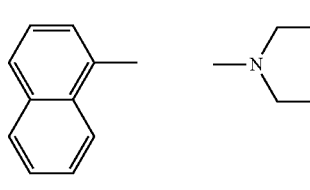 | 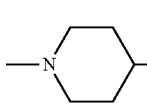 |
| 47 | 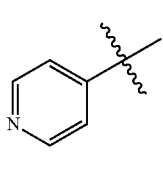 | 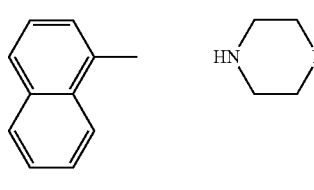 | 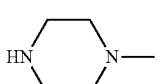 |
| 48 | 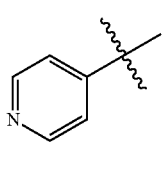 [SMILES: *c1ccncc1] | 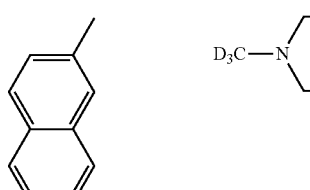 | 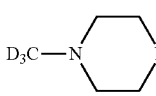 |
| 49 (MW-203) | 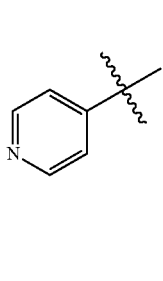 | 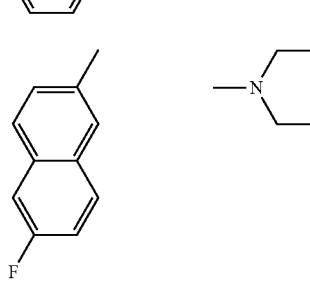 | 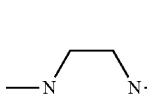 |

TABLE 1-continued
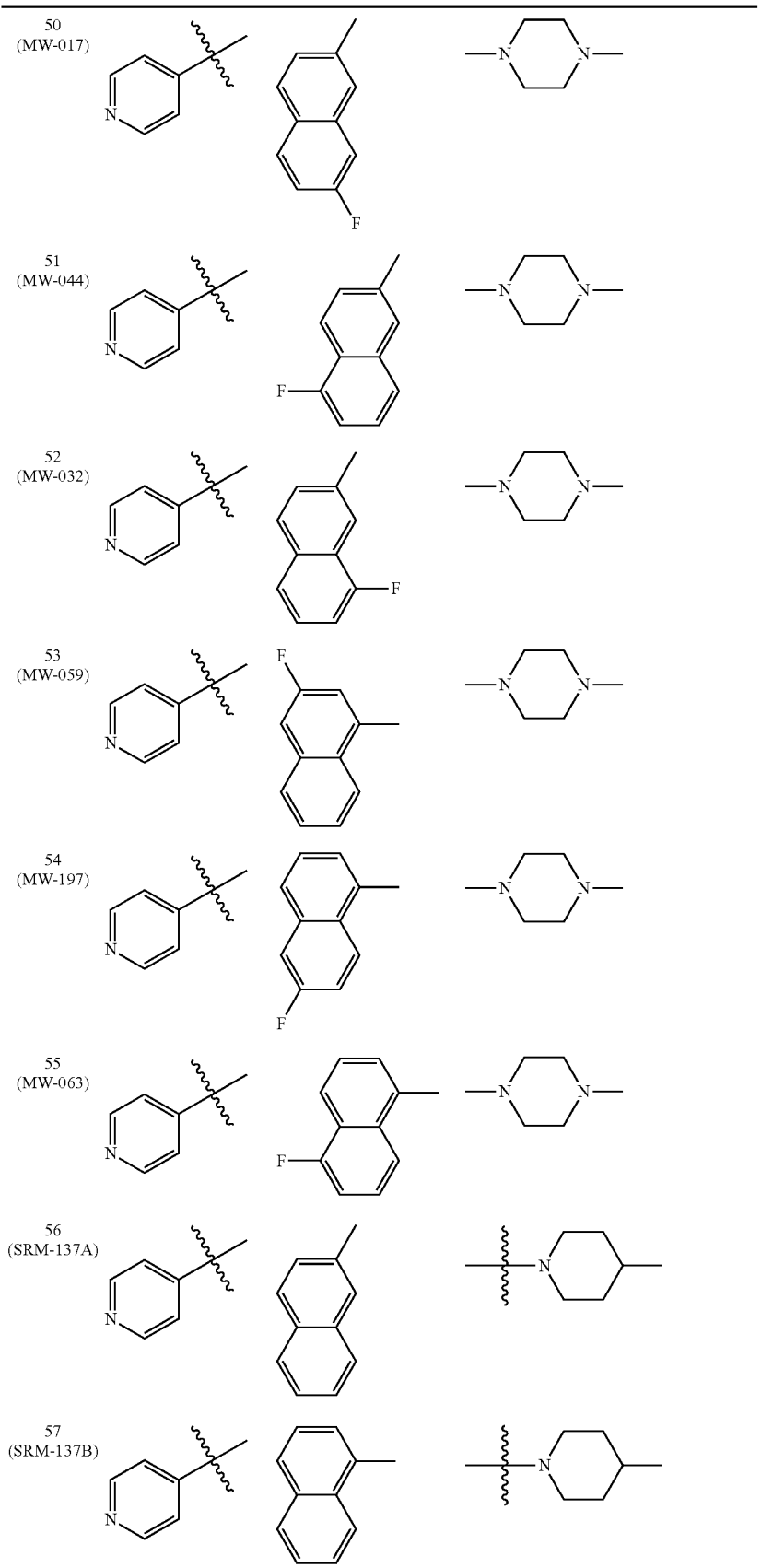

TABLE 1-continued
| # | | | |
|---|---|---|---|
| 59 (SRM-203A) | 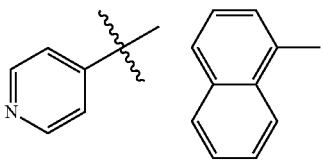 | 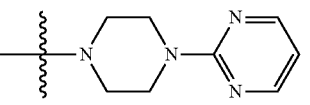 | 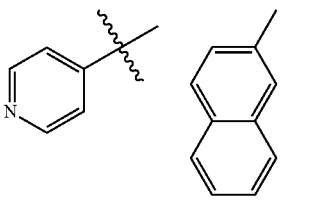 |
| 60 (SRM-203B) | 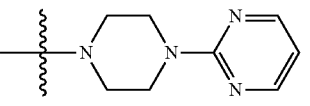 [SMILES: *N1CCN(c2ncccn2)CC1] | 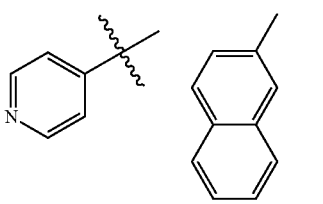 | 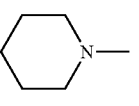 |
| 61 (MW-086) | 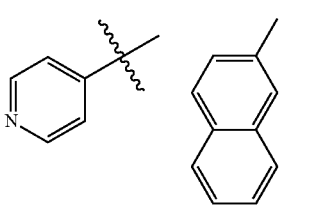 | 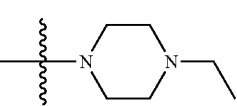 | 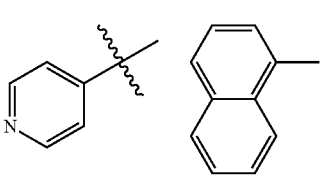 |
| 62 (MW-026) | 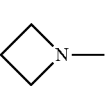 | 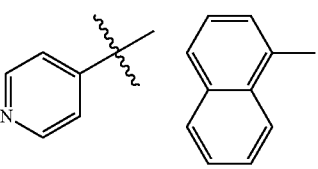 | 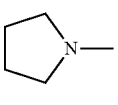 |
| 64 | 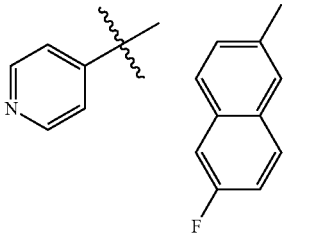 | | |
| 65 | | | |
| 66 | | | —N(CH$_3$)$_2$ |
| 67 | 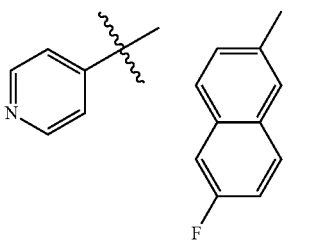 | 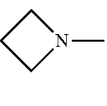 | |

TABLE 1-continued
| | | | |
|---|---|---|---|
| 68 | 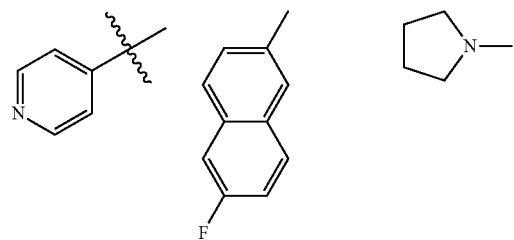 | | |
| 69 | 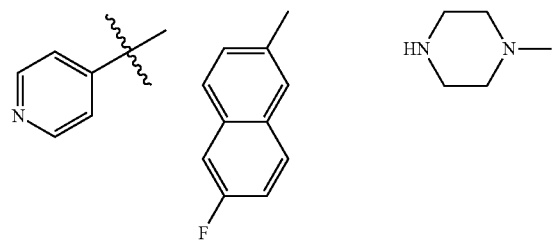 | | |
| 70 | 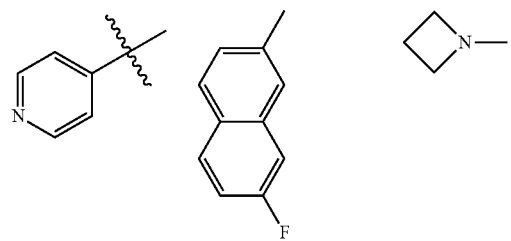 | | |
| 71 | 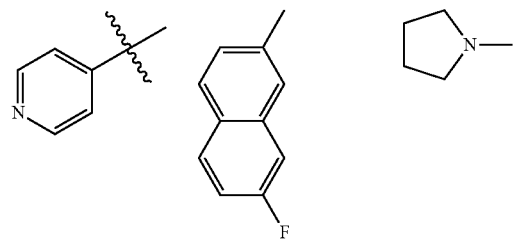 | | |
| 72 | 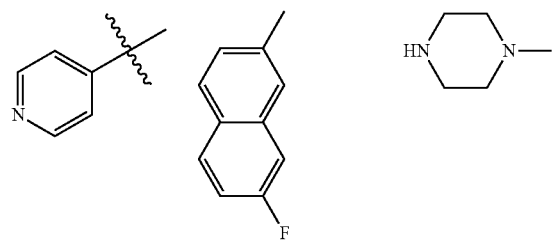 | | |
| 73 | 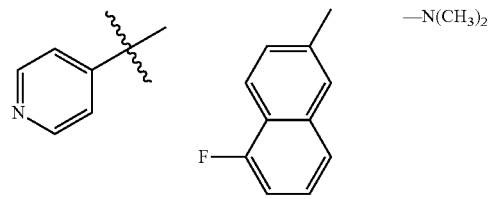 | —N(CH$_3$)$_2$ | |
| 74 | 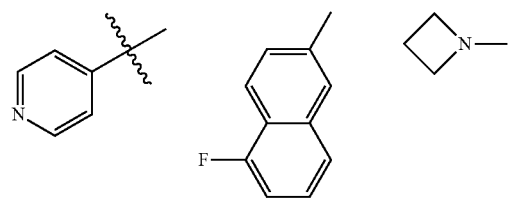 | | |

TABLE 1-continued

| # | Pyridine | Naphthyl | Amine |
|---|---|---|---|
| 75 | 4-pyridyl | 5-fluoro-2-naphthyl | pyrrolidin-1-yl |
| 76 | 4-pyridyl | 5-fluoro-2-naphthyl | 4-methylpiperazin-1-yl |
| 77 | 4-pyridyl | 5-fluoro-2-naphthyl | —N(CH$_3$)$_2$ |
| 78 | 4-pyridyl | 5-fluoro-2-naphthyl | azetidin-1-yl |
| 79 | 4-pyridyl | 5-fluoro-2-naphthyl | pyrrolidin-1-yl |
| 80 | 4-pyridyl | 5-fluoro-2-naphthyl | 4-methylpiperazin-1-yl |

[Structure: 4-pyridyl-pyrazine with R$^1$ and R$^3$ substituents]

| # | Pyridine | Naphthyl | Amine |
|---|---|---|---|
| 44 (MW-064) | 4-pyridyl | 1-naphthyl | —N(CH$_3$)$_2$ |

TABLE 1-continued 63
(SRM-138B)

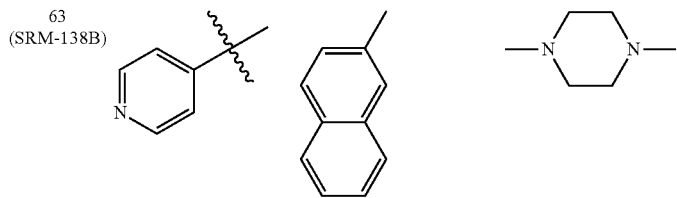

In another aspect, the invention is directed to compositions comprising a compound of formula (I) and a pharmaceutically acceptable carrier.

In another aspect, the invention is directed to a method of inhibiting p38α MAPK comprising contacting MAPK with a compound of formula (I). In some embodiments, the compound of formula (I) exhibits a Ki for p38α MAPK of less than about one micromolar. In some embodiments, the compound of formula (I) exhibits a Ki for p38α MAPK of less than about 500 nM. In some embodiments, the compound of formula (I) exhibits a Ki for p38α MAPK of less than about 200 nM. In some embodiments, the compound of formula (I) exhibits a Ki for p38α MAPK of less than about 100 nM. In some embodiments, the compound of formula (I) exhibits a Ki for p38α MAPK of less than about one micromolar.

In another aspect, the invention is directed to a method of treating diseases or disorders where MAPK is over-expressed or over-activated. In some embodiments, such diseases include, for example, inflammatory diseases, neurodegenerative diseases, skin disorders, etc. Other disorders related to MAPK are described, for example, in U.S. Pat. No. 7,919,485; EP Patent Nos. 1196167, 1606283, and 2426134; U.S. Patent Publication Nos. 2010/0104536 and 20120289511; *Nat. Rev. Drug Disc.* 2003, 2, 717; *Curr. Opin, Drug Disc. Dev.* 2005, 8, 421; *Exp. Opin. Ther. Patents* 2011, 21, 1843; *J. Neuroinflammation* 2007, 4, 21; and *Neuropharmacology* 2010, 58, 561; each herein incorporated by reference in its entirety.

In another aspect, the invention is directed to a method of treating disease in a subject comprising administration of a therapeutically effective amount of a compound of formula (I). In some embodiments, the disease is characterized by inflammation. In some embodiments, the disease comprises ischemia. In some embodiments, the disease is a neurological disorder. In some embodiments, the disease is a neurodegenerative disease. In some embodiments, the neurodegenerative disease is Huntington's Disease, Parkinson's Disease, multiple sclerosis, ALS or Alzheimer's Disease. In some embodiments, the neurodegenerative disease is Huntington's Disease, Parkinson's Disease, ALS or Alzheimer's Disease. In some embodiments, the disease is Alzheimer's Disease.

In another aspect, the invention is directed to a method of treating neurodegenerative disease in a subject comprising administration of a therapeutically effective amount of a composition comprising a compound of formula (I). In some embodiments, the disease is Alzheimer's Disease.

In another aspect, the invention is directed to a method of increasing long-term potentiation in a subject having a neurodegenerative disease comprising administration of a therapeutically effective amount of a compound of formula (I). In some embodiments, the neurodegenerative disease is Alzheimer's Disease.

In another aspect, the invention is directed to a method of increasing long-term potentiation in a subject having a neurodegenerative disease comprising administration of a therapeutically effective amount of a composition comprising a compound of formula (I). In some embodiments, the neurodegenerative disease is Alzheimer's Disease.

In another aspect, the invention is directed to a method of improving memory in a subject having a neurodegenerative disease comprising administration of a therapeutically effective amount of a compound of formula (I). In some embodiments, the neurodegenerative disease is Alzheimer's Disease.

In another aspect, the invention is directed to a method of improving memory in a subject having a neurodegenerative disease comprising administration of a therapeutically effective amount of a composition comprising a compound of formula (I). In some embodiments, the neurodegenerative disease is Alzheimer's Disease.

In another aspect, the invention is directed to a method of improving synaptic function in a subject having a neurodegenerative disease comprising administration of a therapeutically effective amount of a compound of formula (I). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the neurodegenerative disease is Alzheimer's Disease.

In another aspect, the invention is directed to a method of improving synaptic function in a subject having a neurodegenerative disease comprising administration of a therapeutically effective amount of a composition comprising a compound of formula (I). In some embodiments, synaptic function comprises synaptic plasticity. In some embodiments, synaptic plasticity comprises learning, memory, or a combination thereof. In some embodiments, synaptic plasticity comprises long term potentiation (LTP). In some embodiments, the neurodegenerative disease is Alzheimer's Disease.

In another aspect, the invention is directed to a method of improving synaptic function in a subject having ischemia comprising administration of a therapeutically effective amount of a composition comprising a compound of formula (I). In some embodiments, the subject has a neurodegenerative disease. In some embodiments, the neurodegenerative disease ALS, Huntington's Disease, Parkinson's Disease or Alzheimer's Disease. In some embodiments, the ischemia is brain ischemia.

Another aspect of the invention provides a method for increasing memory retention in a subject afflicted with a neurodegenerative disease, the method comprising administering to a subject a therapeutic amount of a compound of formula (I) or a composition comprising a compound of formula (I).

In some embodiments, a compound of formula (I) is administered. In some embodiments, a composition comprising a compound of formula (I) is administered.

Exemplary neurodegenerative diseases comprise Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy. Exemplary neurodegenerative diseases and methods of treatment therefor are also described in WO 2010/074783, WO 2011/072243, and WO 2012/088420; each herein incorporated by reference in its entirety.

In some embodiments, the disease is characterized by altered cellular function, synaptic dysfunction, fast axonal transport, neural degeneration, or neuroinflammation.

In some embodiments, the disorder or disease is Alzheimer's disease, Parkinson's disease, Huntington disease, Down syndrome, head trauma, traumatic brain injury (TBI), brain injury due to cerebral focal ischemia, attention deficit disorder, neuronal degeneration with brain iron accumulation type I (Hallervorden-Spatz disease), Lytico-Bodig disease (Parkinson-dementia complex of Guam), pure autonomic failure, REM sleep behavior disorder, mild cognitive impairment (MCI), cerebral amyloid angiopathy (CAA), mild cognitive deficits, aging, vascular dementias mixed with Alzheimer's disease, any neurodegenerative disease characterized by abnormal amyloid deposition, or any combination thereof, Adrenoleukodystrophy (ALD), Alcoholism, Alexander's disease, Alper's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Rett's syndrome, Tau-positive FrontoTemporal dementia, Tau-negative FrontoTemporal dementia, Dementia pugilistica (chronic traumatic encephalopathy), Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy, Inclusion body myositis, or neuroinflammation. Neuroinflammation has been also found to play a role in psychiatric illnesses. Indeed, a link between psychiatric symptoms and autoimmunity in autoimmune diseases, neuroimmunological abnormalities occur in classical psychiatric disorders (for example, major depressive, bipolar, schizophrenia, and obsessive compulsive disorders).

In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

In some embodiments, the neurodegenerative disease comprises Alzheimer's disease, Amyotrophic lateral sclerosis (Lou Gehrig's Disease), Huntington's disease, or Parkinson's disease.

In some embodiments, the neurodegenerative disease is Alzheimer's disease. In some embodiments, the neurodegenerative disease is Amyotrophic lateral sclerosis. In some embodiments, the neurodegenerative disease is Huntington's disease. In some embodiments, the neurodegenerative disease is Parkinson's disease.

Compounds of formula (I) can be incorporated into pharmaceutical compositions suitable for administration. Such compositions can comprise a compound of formula (I) and a pharmaceutically acceptable carrier. Thus, in some embodiments, the compounds of the invention are present in a pharmaceutical composition.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat or human. In some embodiments, the subject is a mouse. In some embodiments, the subject is a rat. In some embodiments, the subject is a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Pyridazine and pyrazine based compounds are synthesized by methods within the purview of the ordinarily skilled artisan. Exemplary methods by which such derivatives can be synthesized are as follows, in addition to those described in, for example, U.S. Pat. Nos. 8,063,047; 8,158,627; 8,188,096; and 8,367,672; and *Bioorg. Med. Chem. Lett.* 2007, 17, 414; each herein incorporated by reference in its entirety. Additional exemplary methods of preparation for pyridazines and pyrazines are shown in Scheme A and the Examples.

Scheme A. Exemplary Synthesis of Compounds of Formula I.

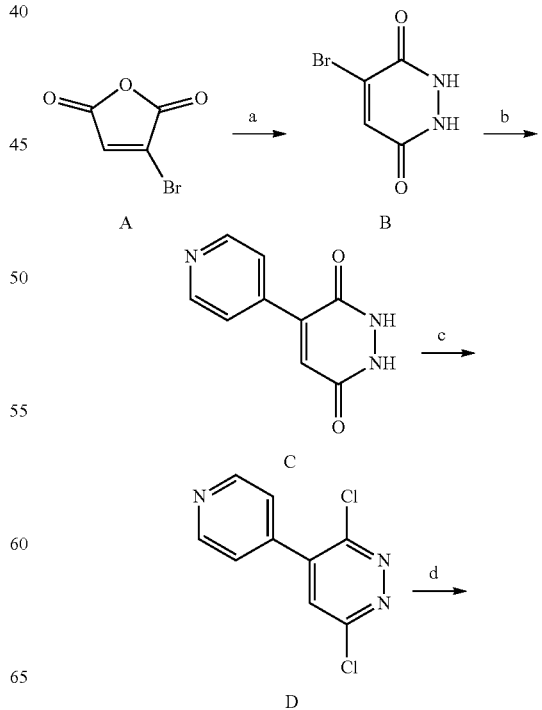

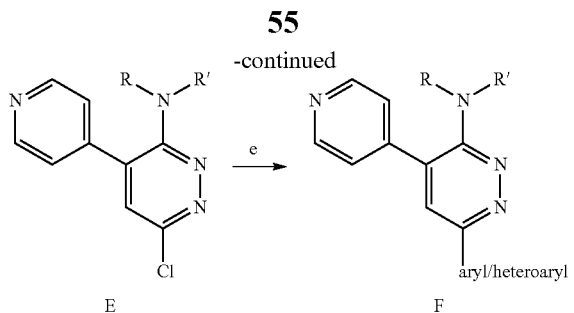

Initially, the starting anhyride A can be treated with hydrazine such as hydrazine sulfate in water and heated to about 100° C. for about 18 hours to provide B. Compound B can then be cross-coupled with a pyridyl derivative such as a pyridyl boronic acid using exemplary reagents Pd(PPh$_3$)$_4$, a carbonate base such as sodium carbonate in a solvent system such as DME/water following typical cross-coupling procedures to provide C. Compound C can then be treated with a chlorine source such as POCl$_3$ in a solvent such as acetonitrile at elevated temperature such as about 90° C. for about 18 hours to provide D. Compound D can then be treated with an amine (HNRR') at elevated temperature, such as about 120° C. for about 12-18 hours to provide E. Compound E can be treated with a arylboronic acid or heteroaryl boronic acid under standard cross-coupling conditions using exemplary reagents such as reagents Pd(PPh$_3$)$_4$, a carbonate base such as sodium carbonate in a solvent system such as DME/water to provide compounds F.

Deuterium enriched compounds of formula (I) can also be synthesized using known intermediates and/or starting materials. For example, compounds containing a CD$_3$ can be made by incorporating building blocks such as CD$_3$I into the exemplary syntheses herein. Deuterium enriched aryl intermediates can also be substituted for non-deuterium enriched aryl intermediates in the methods described herein to obtain compounds of formula (I) comprising deuterium enriched aryl groups. For example, deuterated naphthyl boronic acid or deuterated naphthyl carboxylic acids can be used to generate compounds of formula (I) wherein R$^3$ comprises a deuterated naphthyl group.

It will recognized that one or more features of any embodiments disclosed herein may be combined and/or rearranged within the scope of the invention to produce further embodiments that are also within the scope of the invention. Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Chemicals were purchased from Aldrich (Milwaukee, Wis.) or VWR International (Batavia, Ill.). Solvents were used as received unless stated otherwise. Water was obtained using a Milli-Q Biocel A10 purification system from Millipore Corporation (Bedford, Mass.). High pressure glassware was from Chemglass, (Vineland, N.J.). All syntheses were monitored by HPLC (Dionex System, Sunnyvale, Calif., with UVD170U ultraviolet detector and P680 pump) on a Phenomenex (Torrance, Calif.) Luna C18 column (250×2.0 mm; 5 pin; equipped with guard column) at a flow rate of 0.2 mL/min and using a mobile phase composed of 0.1% (v/v) formic acid (Fluka) in water as reagent A and 80% acetonitrile, 0.08% formic acid/water as reagent B. Synthetic intermediates were screened by electrospray mass spectroscopy (ESI) HPLC (Micromass Quattro II Triple Quadrupole HPLC/MS/MS mass spectrometer). Final compounds were analyzed by HPLC, high-resolution mass spectra (HRMS; VG70-250SE mass spectrometer) and 1H NMR (Bruker Avance-III 500 MHz spectrometer; ambient temperature). Melting point data for compounds were acquired on a Büchi Melting Point B-540 (Flawil, Switzerland). Hydrochloride hydrates (salts) of final compounds were characterized by elemental analysis (Intertek QTI; Whitehouse, N.J.).

Abbreviations used are: MeOH=methanol, CDCl$_3$=deuterated chloroform, CD$_3$OD=deuterated methanol, THF=tetrahydrofuran, DME=1,2-dimethoxyethane, POBr$_3$=phosphorus oxybromide, POCl$_3$=phosphorus oxychloride, Na$_2$CO$_3$=sodium carbonate, EtOAc=ethyl acetate, LDA=lithium diisopropylamide, DIEA=diisopropylethylamine, TEBAC=tetraethylbutyl ammonium chloride, DMSO=dimethylsulphoxide.

HPLC Method A: Gradient—0% to 100% B, 15 min; isocratic 22 min. For purity analysis by HPLC, compounds were analyzed at ~0.50 µg level and peak quantification was performed based upon Relative area % absorption at 260 nm LC/MS method A: LC/MS data were determined with a Waters Alliance 2695 HPLC/MS (Waters Symmetry C18, 4.6×75 mm, 3.5 lm) with a 2996 diode array detector from 210-400 nm; the solvent system is 5-95% MeCN in water (with 0.1% TFA) over nine mins using a linear gradient and retention times are in minutes. Mass spectrometry was performed on a Waters ZQ using electrospray in positive mode.

HPLC method B: Preparative reversed phase chromatography was performed on a Waters Sunfire column (19×50 mm, C18, 5 micron) with a mobile phase of 10% acetonitrile/water to 90% acetonitrile/water with 0.1% TFA as buffer using 214 nm and 254 nm as detection wavelengths. Injection and fraction collection were performed with a Gilson 215 liquid handling apparatus using Trilution LC software.

Animals: All experiments were conducted in accordance with the principles of animal care and experimentation in the Guide For the Care and Use of Laboratory Animals. The Institutional Animal Care and Use Committees of the three universities approved the use of animals in this study. For efficacy experiments, 3- to 4-month-old C57BL/6J male mice from a colony bred in the Columbia University animal facility were used. At the University of Kentucky, the in vivo LPS experiment was done with 2-month-old, female, C57Bl/6J mice from Jackson Laboratory. The p38α MAPK drug-resistant knock-in (p38α$^{T106M}$) mice were generated by replacement of Thr106 in p38α with Met as described in *J. Biol. Chem.* 2007, 282, 34663 (herein incorporated by reference in its entirety). Remaining rodent studies were done at Northwestern University as previously described (*J. Neuroinflamm.* 2007, 4, 21; *Bioorg. Med. Chem. Lett.* 2007, 17, 414; each herein incorporated by reference in its entirety).

Example 1

Synthesis of MW-181 (1) and MW-108 (2)

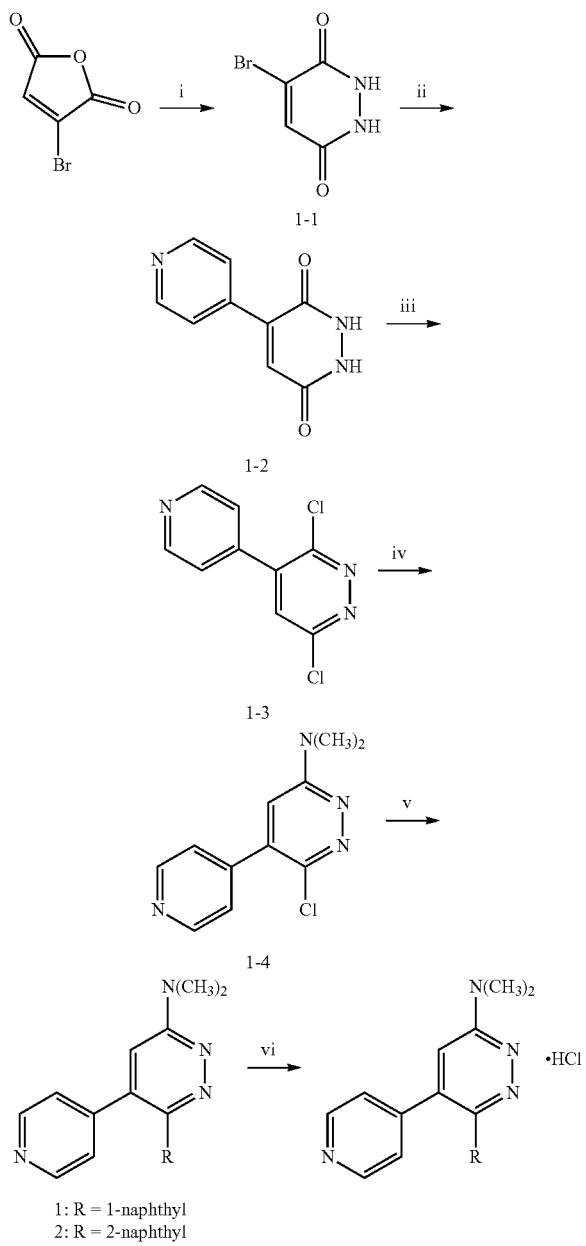

Scheme 1. Synthetic scheme for MW-181 and MW-108 and derivatives.

1: R = 1-naphthyl
2: R = 2-naphthyl

Reagents and conditions: i) Hydrazine sulphate, H₂O, 100° C.; ii) Pyridin-4-ylboronic acid, DME/water, Na₂CO₃, Pd(PPh₃)₄, 110° C.; iii) POCl₃, ACN, 90° C.; iv) Ethanol, amine, reflux; v) 1- or 2-Naphthylboronic acid, DME/water, Na₂CO₃, Pd(PPh₃)₄, 110° C.; vi) conc. HCl, anhydrous isopropanol, 80° C.

4-bromo-1,2-dihydropyridazine-3,6-dione (1-1): Hydrazine sulfate (2.25 g, 17.2 mmol) was dissolved in boiling water (20 mL) with stirring. To this solution, bromomaleic anhydride (2.6 mL, 28.2 mmol) was added dropwise via addition funnel, the mixture heated (100° C.) under reflux for 19 h, then cooled to ambient temperature. The resulting white precipitate was filtered on a medium frit sintered glass funnel, washed with acetone (3×5 ml), and air dried in vacuo to give the desired product 4-bromo-1,2-dihydropyridazine-3,6-dione (2.85 g) as a white powder in 87% yield (gravimetric) with a melting point of 262° C.

4-(pyridin-4-yl)-1,2-dihydropyridazine-3,6-dione (1-2): Essentially as previously described (*J. Neuroinflamm.* 2007, 4, 21; herein incorporated by reference in its entirety), compound 1-1 (2 g, 10.4 mmol, 1 eq) and pyridin-4-yl boronic acid (14.3 mmol, 1.76 g, 1.37 eq) were suspended in dimethoxyethane and water (10:1 v/v) in a heavy wall pressure vessel and purged with argon for 15 min. Tetrakis(triphenylphosphine)palladium (0.1 eq) and sodium carbonate (3 eq) were added, the vessel immediately capped, the reaction mixture heated (110° C.). for 18 h, then cooled to ambient temperature and subjected to filtration on a medium frit sintered glass funnel containing Celite® 545. The filtrate was concentrated in vacuo and the concentrate triturated with hexane. The yellow product 1-2 (2.2 g) exhibited a mass (ESI) of m/z (MeOH)=190.06 (MO, and was taken to the next step without further purification.

3,6-dichloro-4-(pyridin-4-yl)pyridazine (1-3): Essentially as described (*Bioorg. Med. Chem. Lett.* 2007, 17, 414; herein incorporated by reference in its entirety), compound 1-2 (2.2 g, 11.6 mmol) was suspended in 6.25 mL phosphorus oxychloride in a condenser-fitted round bottom flask, heated (90° C.) for 24 h, cooled to ambient temperature and volatiles removed in vacuo. The dark residue was poured onto crushed ice, stirred (2 h), and the mixture neutralized with saturated sodium carbonate solution. The fine precipitate was subjected to replicate extraction with dichloromethane in a separatory funnel, the combined organic phases subjected to drying over anhydrous sodium sulfate, concentrated in vacuo, and subjected to column chromatography on silica gel (200-400 mesh) using a ethyl acetate:hexane (3:2 v/v) eluent. The desired product 1-3 exhibited 97% purity by HPLC and a mass (ESI) of m/z (MeOH)=225.99 (MH⁺). The overall yield (gravimetric) from product 1-1 to 1-3 was approximately 36%.

6-chloro-N,N-dimethyl-5-(pyridin-4-yl)pyridazin-3-amine (1-4): Following published protocol (*Bioorg. Med. Chem. Lett.* 2007, 17, 414; herein incorporated by reference in its entirety), compound 1-3 (11.06 mmol, 1 eq) in ethanol (60 mL) was placed in a heavy wall pressure vessel and 40% dimethylamine (6 eq) added, the vessel capped and heated (110° C.) for 16 h, the mixture allowed to cool to ambient temperature then transferred to a round bottom flask for concentration in vacuo. The residue was treated with 10 mL of water, the aqueous phase subjected to replicate extraction with dichloromethane in a separatory funnel, and the combined organic layers dried (anhydrous sodium sulfate) and evaporated under reduced pressure to yield a yellow adherent solid. The reaction mixture was purified by silica gel (200-400 mesh) column chromatography and the desired product eluted with ethyl acetate:hexane (1:1 v/v). Product 1-4 was obtained as a yellow solid in 89% (gravimetric) yield, with an apparent HPLC purity of 98% and a mass (ESI) m/z (MeOH)=235.10 (MH⁺).

N,N-dimethyl-6-(naphthalen-1-yl)-5-(pyridin-4-yl)pyridazin-3-amine (1=MW-181): Compound 1-4 (1.95 g, 8.5 mmol, 1 eq) and 1-naphthylboronic acid (1.96 g, 11.3 mmol, 1.37 eq) were suspended in dimethoxyethane (DME) and water (10:1, v/v) in a heavy wall pressure vessel and purged with argon for 15 min. Tetrakis(triphenylphosphine)palladium (0.860 g, 9 mol %) and Na₂CO₃ (2.7 g, 25.7 mmol, 3.1 eq) were added, the vessel purged with argon and immediately capped with a Teflon bushing, heated (110° C.) for 17 hr, and cooled to ambient temperature. The reaction mixture was subjected to filtration on a medium frit sintered glass funnel containing Celite® 545. The resultant filtrate was concentrated in vacuo, the residue dissolved in CH$_2$Cl$_2$, and subjected to water extraction (3×30 mL) in a separatory funnel. The organic layer was dried over anhydrous sodium sulfate and concentrated by rotary evaporation under reduced pressure. The crude mixture was subjected to silica gel (200-400 mesh) column chromatography with product elution using ethyl acetate: hexane (2:3 v/v). The product was crystallized from hexane and ethyl acetate. Product 1 (MW-181) was obtained as light yellow crystals in 56% yield (gravimetric). HPLC purity, 98%; ESI m/z (MeOH), 327.10 (MO; MP=189.5-190° C. (uncorrected); HRMS, 326.1526 (calculated for C$_{21}$H$_{18}$N$_4$=326.1531). $^1$H-NMR (500 MHz, CDCl$_3$): δ 8.34 (d, J=5.8 Hz, 2H); 7.83 (d, J=8.2 Hz, 2H); 7.68 (d, J=8.4 Hz, 1H); 7.42-7.26 (m, 4H); 6.99 (dd, J=1.5, 4.6, 2H); 6.84 (s, 1H); 3.33 (s, 6H).

N, N-dimethyl-6-(naphthalen-2-yl)-5-(pyridin-4-yl) pyridazin-3-amine (2=MW-108): Product 2 was produced using the protocol as above for 1 but using 2-naphthylboronic acid (595 mg, 2.9 mmol, 1.37 eq) suspended in DME:water mixture (10:1, v/v). The final product, 2 (MW-108) was obtained as a whitish powder in 52% yield (gravimetric). HPLC purity, 96%; ESI m/z (MeOH), 327.10 (MO; MP=181.5-182° C. (uncorrected); HRMS, 326.1538 (calculated for C$_{21}$H$_{18}$N$_4$=326.1531). $^1$H-NMR (500 MHz, CDCl$_3$): δ 8.55 (d, J=5.65 Hz, 2H); 7.93 (s, 1H); 7.80-7.68 (m, 3H); 7.49-7.34 (m, 3H); 7.19 (d, J=5.95 Hz, 2H); 6.76 (s, 1H); 3.30 (s, 6H).

Hydrochloride Hydrates of Products 1 and 2: This was done as described (*Bioorg. Med. Chem. Lett.* 2007, 17, 414; herein incorporated by reference in its entirety). Approximately 1 mmol of the respective compound was suspended in 8.2 mL of anhydrous isopropanol (99.5%, Aldrich), heated to 85° C. with stirring until dissolved, then 3.1 equiv (2344) of concentrated ultrapure HCl (12N, JT Baker Ultrex® II, Product 6900-05) was added to the clear solution, resulting in immediate generation of a suspension of solids. The suspension was stirred for 10 min (80° C.), allowed to cool to ambient temperature, then the vessel placed on ice for ~2.5 h, then stored (~16 hr) at 4° C. The resulting yellow precipitate was filtered on a medium frit sintered glass funnel under vacuum, washed (3×) with cold anhydrous isopropanol followed by three washes with cold anhydrous ether, and dried under vacuum. The precipitate was stored in vacuo in a glass desiccator containing silica gel until a constant weight was attained. The final products were obtained in approximately 82% yield (gravimetric) compared to the starting material. Hydrochloride hydrate formation was confirmed by elemental analysis. Elemental analysis indicated a ratio of ~2 HCl: compound. EA calculated for C$_{21}$H$_{24}$Cl$_2$N$_4$O$_2$ is: C, 57.94; H, 5.56; N, 12.87; Cl, 16.29; O, 7.35. Experimentally found for MW-181: C, 58.16; H, 5.60; N, 12.51; Cl, 16.52; O, 7.37. Experimentally found for MW-108: C, 56.09; H, 5.65; N, 12.38; Cl, 15.91; O, 10.16.

Example 1-1

Compound 57 (6-(4-methylpiperidin-1-yl)-3-(naphthalen-1-yl)-4-(pyridin-4-yl)pyridazine) (also described herein as SRM-137B) can be prepared in a similar manner as described in Example 1 by using 4-methylpiperidine as the amine and by using 1-naphthylboronic acid instead of 2-naphthylboronic acid.

Example 1-2

Compound 59 (3-(naphthalen-1-yl)-4-(pyridin-4-yl)-6-(4-(pyrimidin-2-yl)piperazin-1-yl)pyridazine) (also described herein as SRM-203A) can be prepared in a similar manner as described in Example 1 by using 2-(piperazin-1-yl) pyrimidine as the amine and by using 1-naphthylboronic acid instead of 2-naphthylboronic acid.

Example 1-3

Compound 56 (6-(4-methylpiperidin-1-yl)-3-(naphthalen-2-yl)-4-(pyridin-4-yl)pyridazine) (also described herein as SRM-137A) can be prepared in a similar manner as described in Example 1 by using 4-methylpiperidine as the amine and by using 2-naphthylboronic instead of 1-naphthylboronic acid.

Example 1-4

Compound 60 (3-(naphthalen-2-yl)-4-(pyridin-4-yl)-6-(4-(pyrimidin-2-yl)piperazin-1-yl)pyridazine) (also described herein as SRM-203B) can be prepared in a similar manner as described in Example 1 by using 2-(piperazin-1-yl) pyrimidine as the amine and by using 2-naphthylboronic instead of 1-naphthylboronic acid.

Example 2

Synthesis of Amino-Pyridazine Analogues

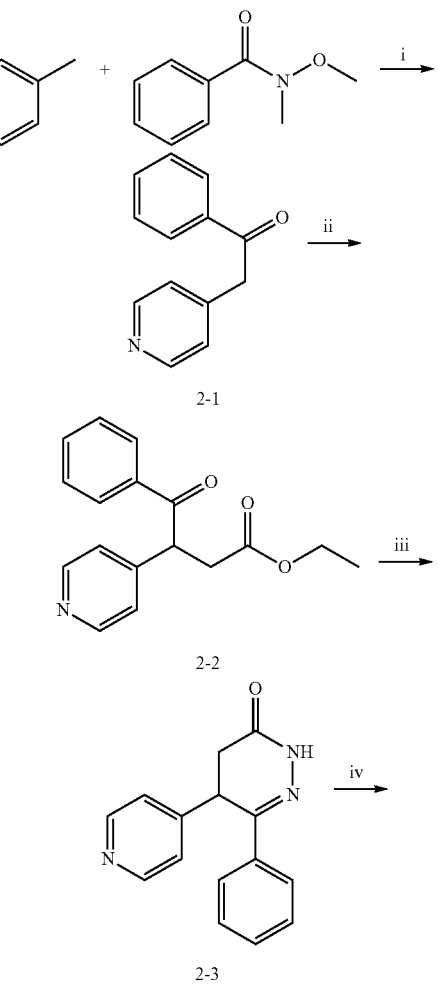

Scheme 2. Synthetic scheme for amino-pyridazine analogues.

-continued

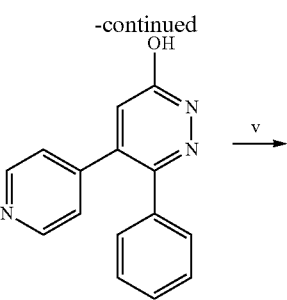

2-4

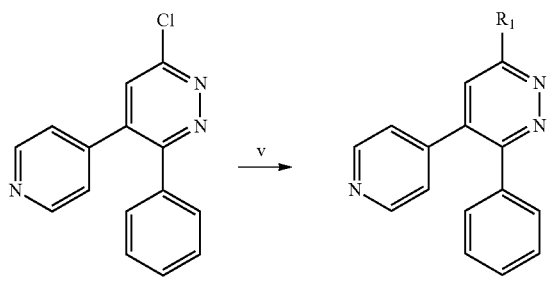

2-5

3: R₁ = 1-methylpiperazine
4: R₁ = diethylamine
5: R₁ = N-methylpropan-1-amine
6: R₁ = dimethylamine Reagents and conditions: i) LDA, THF, -78° C.; ii) 60% NaH, THF, 0° C., ethyl bromoacetate; iii) N₂H₄, ethanol, reflux; iv) Br₂, AcOH, 70° C.; v) POCl₃, 90° C.; vi) 1-butanol, amine, 90-150° C.

Amino-pyridazine analogues described herein are made via approaches described in *Bioorg. Med. Chem. Lett.* 2007, 17, 414; herein incorporated by reference in its entirety.

1-Phenyl-2-(pyridin-4-yl)ethanone (2-1): THF in a round bottom flask was cooled (−78° C.), lithium diisopropylamide added to the flask with stirring under argon atmosphere, and a solution of 4-picoline (in THF) carefully added to the cooled flask under constant stirring. After one hour, a solution of N-methoxy-N-methylbenzamide (in THF) was added over a period of 30 min. Formation of the product was monitored by HPLC and TLC. The reaction mixture was warmed to ambient temperature, during which time the color changed from light yellow to orange, and the reaction quenched with crushed ice addition. THF was removed in vacuo, the reaction mixture was treated with saturated sodium bicarbonate solution, and repeat extraction with ethyl acetate was done in a separatory funnel. The combined organic extracts were treated with brine, dried over anhydrous magnesium sulfate, and concentrated under reduced pressure to yield an oily mixture. The crude mixture was purified by column chromatography on silica gel (200-400 mesh) with product elution using ethyl acetate: hexane (1:4 v/v). The product, ketone 2-1, was obtained as a bright yellow solid in 69% (gravimetric) yield, 90% purity by HPLC and a mass (ESI) of m/z (MeOH)=198.18 (MH⁺).

Ethyl 4-oxo-4-phenyl-3-(pyridin-4-yl)butanoate (2-2): Sodium hydride and chilled anhydrous THF (100 mL) were combined in a round bottom flask under argon at 0° C. Compound 2-1 in anhydrous THF was added dropwise over 1.5 h with constant stirring. After an additional 0.5 h, ethyl bromoacetate in anhydrous THF was added dropwise, the reaction mixture stirred at ambient temperature until completion as monitored by HPLC. The reaction mixture color changed from pale yellow to bright yellow. The reaction was quenched by addition of crushed ice, THF removed in vacuo, the reaction mix decanted into a saturated sodium bicarbonate solution, and the resulting solution subjected to repeat extraction with ethyl acetate using a separatory funnel. The combined organic extracts were treated with brine, dried over anhydrous sodium sulfate, and concentrated under reduced pressure to yield an oily residue. Product 2-2 was obtained by silica gel (200-400 mesh) column chromatography using ethyl acetate: methanol (3:1 v/v) elution. Product 2-2 was obtained as a beige solid in 74% (gravimetric) yield, 90% purity by HPLC, and a mass (ESI) of m/z (MeOH)=284.75 (MH⁺).

6-Phenyl-5-(pyridin-4-yl)-4,5-dihydropyridazin-3(2H)-one (2-3): Compound 2-2 was mixed with ethanol (400 mL) in a round bottom flask, hydrazine added, and the resulting solution was heated (90° C.) under reflux with continuous stirring until completion (~20 h) as monitored by HPLC. The reaction mixture was cooled to ambient temperature and solvent removed under reduced pressure. The residue was treated with ethyl acetate followed by ether addition, and the solution taken to dryness by rotary evaporation. The white foam-like solid contained compound 2-3, with a mass (ESI) of m/z (MeOH)=252.1 (MH⁺), was used for the next step without further purification.

6-Phenyl-5-(pyridin-4-yl)pyridazin-3-ol (2-4): Bromine in acetic acid was added dropwise under continuous stirring to a round bottom flask containing compound 2-3, the mixture refluxed at 70° C. until starting material was no longer detectable (~4 h) as monitored by HPLC. The mixture was cooled to ambient temperature, poured over crushed ice, neutralization with a sodium bicarbonate solution, and subjected to repeat extraction with ethyl acetate. The combined organic layers treated with brine, dried over sodium sulfate and evaporated under reduced pressure to give a deep brown solid. Compound 2-4 was purified by silica gel (200-400 mesh) column chromatography using elution with ethyl acetate: methanol (9:1 v/v). Compound 2-4 was obtained as a light brown solid in 68% (gravimetric) yield, 90% purity by HPLC, and a mass (ESI) m/z (MeOH)= 250.20 (MH⁺).

6-Chloro-3-phenyl-4-(pyridin-4-yl)pyridazine (2-5): Compound 2-5 was obtained following a published protocol (*Bioorg. Med. Chem. Lett.* 2007, 17, 414; herein incorporated by reference in its entirety). Compound 2-4 was suspended in acetonitrile, POCl₃ (Reagent Plus Grade, 99%) added, the mixture heated to 90° C. for 3 h, cooled to ambient temperature, volatiles were removed in vacuo, the residual suspension poured into crushed ice, stirred for 3 h at ambient temperature, and neutralized with 2.5N NaOH. The fine precipitate was subjected to repeat extraction with ethyl acetate, the combined organic phases subjected to drying over anhydrous magnesium sulfate and concentration in vacuo. Product 2-5 was purified from by silica gel (200-400 mesh) column chromatography using ethyl acetate:1% methanol. Product 2-5 was obtained as a white powder in 82% (gravimetric) yield, with an HPLC purity of 98% and a mass (ESI) m/z (MeOH)=268.00 (MH⁺).

Production of Kinase Inhibitors from Common Intermediate (2-5). The various kinase inhibitors were synthesized by reaction of a given amine with compound 2-5 using a published protocol (*Bioorg. Med. Chem. Lett.* 2007, 17, 414; herein incorporated by reference in its entirety). Compound 2-5 and 1-butanol were combined in a round bottom flask with the respective amine, heated to 110° C. for approximately 15 h, cooled to ambient temperature, treated with water, and the aqueous layer subjected to repeat extraction with dichloromethane. The combined organic layers were subjected to drying with anhydrous sodium sulfate and concentration in vacuo. The final products were purified by silica gel column chromatography using volatile solvents for elution and final processing.

6-(4-methylpiperazin-1-yl)-3-phenyl-4-(pyridin-4-yl)pyridazine (3=MW-066): Compound 2-5 was reacted with 1-methylpiperazine and taken through the protocol above to give product 3 as a beige powder in 89% (gravimetric) yield; MP: 190.2-190.7° C. (uncorrected); $^1$H-NMR (500 MHz, CDCl$_3$): δ 8.57 (dd, J=1.55, 4.5 Hz, 2H); 7.34-7.24 (m, 5H); 7.12 (dd, J=1.6, 4.2 Hz, 2H); 6.84 (s, 1H); 3.81 (t, J=4.5, 4.6 Hz, 4H); 2.60 (s, 4H); 2.39 (s, 3H); HPLC (tr/purity): 9.3 min >97% (HPLC method A); ESI m/z (MeOH): 332.1 (MO; HRMS 331.1783 (calculated for $C_{20}H_{22}N_5$ 331.1797).

N, N-diethyl-6-phenyl-5-(pyridin-4-yl)pyridazin-3-amine (4=MW-177): Compound 2-5 was reacted with 10 equivalents of diethylamine and compound 4 obtained by chromatographic elution with ethyl acetate: hexane (2:3 v/v) followed by crystallization in ethyl acetate and hexane to give beige crystals in 70% overall yield (gravimetric). MP: 121.5-122° C. (uncorrected). $^1$H-NMR (500MHz, CDCl$_3$): δ 8.57 (d, J=5.75 Hz, 2H); 7.34-7.23 (m, 5H); 7.14 (dd, J=1.55, 4.45 Hz, 2H); 6.64 (s, 1H); 3.71 (dd, J=7.1, 7.1 Hz, 4H); 1.29 (t, J=7.1, 9 Hz, 6H); HPLC (tr/purity): 12.4 min, >96% (HPLC method A); ESI m/z (MeOH): 305.10 (MH$^+$); HRMS 304.1682 (calculated for $C_{19}H_{20}N_4$ 304.1688).

N-methyl-6-phenyl-N-propyl-5-(pyridin-4-yl)pyridazin-3-amine (5=MW-207): Compound 2-5 was reacted with N-methylpropane-1-amine, processed as above, and the final product obtained via chromatography using ethyl acetate: hexane (1:1 v/v) as solvent, followed by crystallization in ethyl acetate and hexane, to give the desired product 5 as white crystals in 74% (gravimetric) overall yield. MP: 160.5-161° C. (uncorrected). $^1$H-NMR (500MHz, CD$_3$OD): δ 8.47 (dd, J=1.6, 4.55 Hz, 2H); 7.32-7.25 (m, 7H); 7.08 (s, 1H); 3.69 (t, J=7.4, 7.4 Hz, 2H); 3.22 (s, 3H); 1.74 (m, 2H); 0.99 (t, J=7, 7.45 Hz, 3H); HPLC (tr/purity): 12.8 min, >96% (HPLC method A); ESI m/z (MeOH): 305.10 (MO; HRMS 304.1699 (calculated for $C_{19}H_{20}N_4$ 304.1688).

N, N-dimethyl-6-phenyl-5-(pyridin-4-yl)pyridazin-3-amine (6=MW-105) Compound 2-5 was reacted with six equivalents of 40% dimethylamine at 120° C. for 8 h and processed as above. The final product was obtained via crystallization from ethyl acetate and methanol to give the desired product 6 as a light yellow crystalline solid in 90% yield (gravimetric). MP: 155.5-156° C. (uncorrected). $^1$H-NMR (500MHz, CDCl$_3$): δ 8.57 (d, J=5.8 Hz, 2H); 7.34-7.24 (m, 5H); 7.14 (dd, J=1.5, 4.65, 2H); 6.72 (s, 1H); 3.27 (s, 6H); HPLC (tr/purity): 10.3 min >98% (HPLC method A); ESI m/z (MeOH): 277.14 (MO; HRMS 276.1384 (calculated for $C_{17}H_{16}N_4$ 276.1375).

Production of Hydrochloride Hydrate Forms of 3, 4, 5 and 6. This was done following the protocol of Hu et al. (*Bioorg. Med. Chem. Lett.* 2007, 17, 414; herein incorporated by reference in its entirety). Under these conditions for the studies described herein, elemental analyses of each product indicated a mole ratio of HCl:compound of ~2.

MW-066 (3) Hydrochloride Hydrate: EA calculated for $C_{20}H_{23}Cl_2N_5$: C, 59.41; H, 5.73; Cl, 17.54; N, 17.32. experimentally found C, 59.08; H, 5.69; Cl, 17.14; N, 17.11; O, 1.03.

MW-177 (4) Hydrochloride Hydrate: EA calculated for $C_{19}H_{26}Cl_2N_4O_2$: C, 55.21; H, 6.34; Cl, 17.15; N, 13.55; O, 7.74. experimentally found C, 56.30; H, 5.85; Cl, 20.23; N, 13.77; O, 3.32.

MW-207 (5) Hydrochloride Hydrate: EA calculated for $C_{19}H_{26}Cl_2N_4O_2$: C, 55.21; H, 6.34; Cl, 17.15; N, 13.55; O, 7.74. experimentally found C, 55.49; H, 6.17; Cl, 17.92; N, 13.60; O, 3.58.

MW-105 (6) Hydrochloride Hydrate: EA calculated for $C_{17}H_{24}Cl_2N_4O_3$: C, 50.63; H, 6.00; Cl, 17.58; N, 13.89; O, 11.90. experimentally found: C, 50.75; H, 5.89; Cl, 17.75; N, 13.90; O, 12.20.

Example 3

Synthesis of MW-077 (7) and SRM-075 (8)

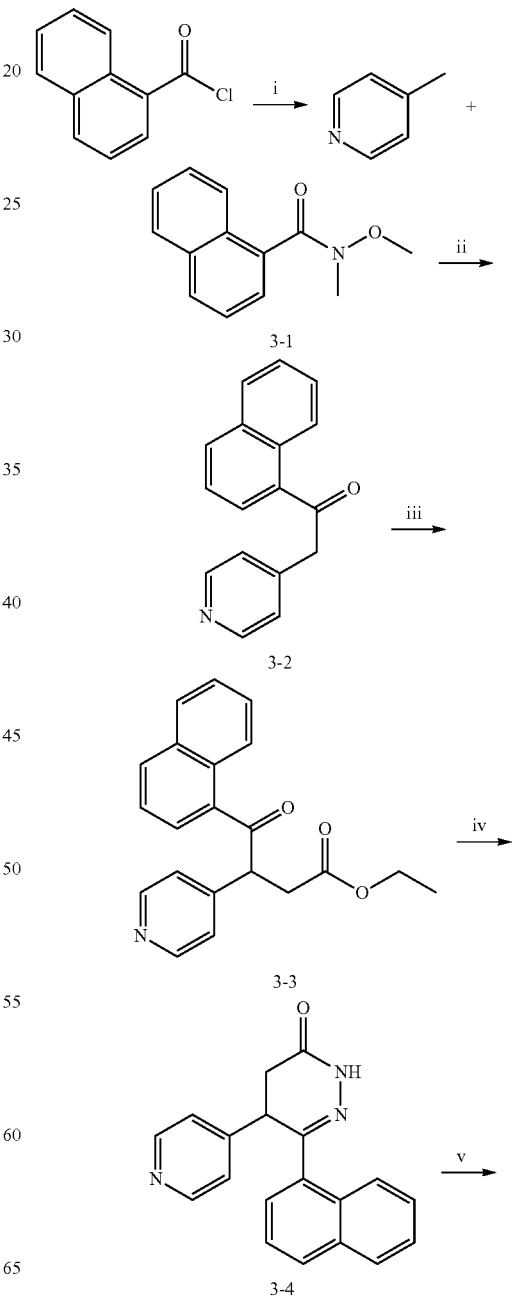

Scheme 3. Synthetic scheme for MW-077 and SRM-075

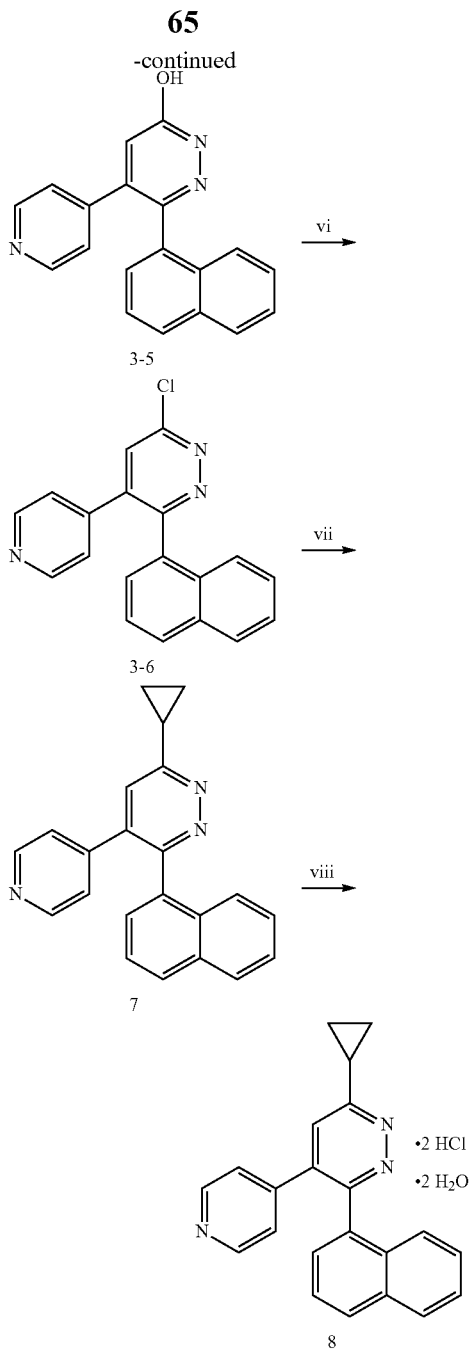

Reagents and conditions:
i) MeNHOMe·HCl, Pyridine, CH$_2$Cl$_2$
ii) LDA, THF, -78° C., 4-picoline;
iii) 60% NaH, DMSO, 0° C., ethyl-2-iodoacetate;
iv) N$_2$H$_4$, ethanol, reflux;
v) Br$_2$, AcOH, 70° C.;
vi) POCl$_3$, 90° C.;
vii) cyclopropylboronic acid, Pd(dppf)Cl$_2$·CH$_2$Cl$_2$, Ag$_2$O, K$_2$CO$_3$, 100° C., 26 h;
viii) 3 eq. conc. HCl, anhydrous isopropanol, 80° C.

N-methoxy-N-methyl-1-naphthamide (3-1): 1-naphthoyl chloride (1 eq), N, O-dimethyl-hydroxylamine hydrochloride (3 eq) and methylene chloride are combined under argon, then cooled in an ice bath. Triethylamine (2.33 eq) is added drop wise with stirring over 0.5 h. The contents of the reaction flask are then warmed to an ambient temperature slowly. After 18 h, the reaction suspension is washed successively with 5% potassium bisulfate, saturated sodium bicarbonate and brine. The organic layer is dried over anhydrous sodium sulfate then concentrated in vacuum to give compound (3-1), yield 100%.

1-(naphthalen-1-yl)-2-(pyridin-4-yl)ethanone (3-2): To a stirring solution of lithium diisopropylamide (1.5 eq) in THF at −78° C. a solution of 4-picoline (1 eq) in THF (10 ml) is added slowly. After 15 min, a solution of N-Methoxy-N-methyl-1-naphthamide (1.2 eq) in THF (10 ml) is added. After stirring for 5 minutes the reaction mixture is slowly allowed to warm to an ambient temperature. The formation of the product is monitored by HPLC. After the reaction is complete, the reaction mixture is poured into saturated aqueous sodium bicarbonate and extracted with ethyl acetate. The organic layers are washed with brine, dried over anhydrous magnesium sulphate and evaporated under reduced pressure to give the crude product. The crude product is then purified by flash column chromatography (25-100% EtOAc-hexane) OR trituration with 10% ether/hexane gave the product (3-2), yield~69-70%.

Ethyl 4-(naphthalen-1-yl)-4-oxo-3-(pyridin-4-yl)butanoate (3-3): In an oven-dried 3-neck round bottom flask fitted with an internal thermometer, argon adapter and rubber septum, sodium hydride (1.1 eq) and anhydrous THF are combined under argon at 0° C. A solution of compound (3-2) (1 eq) in anhydrous THF is added drop wise over 0.5 h using an addition funnel. After stirring an additional 30 min, a solution of ethyl bromoacetate (1.5 eq) in anhydrous THF is added drop-wise. The reaction mixture stirred at an ambient temperature and monitored using HPLC. After 18 h, when complete, the reaction mixture is slowly poured into water. Saturated sodium bicarbonate is added and the resulting solution is extracted several times with ethyl acetate. The combined organic extracts are dried over anhydrous sodium sulphate and then concentrated under reduced pressure to give oil. Purification by flash column chromatography (hexane: ethyl acetate 70:30) gives the product (3-3), yield~20%.

6-(naphthalen-1-yl)-5-(pyridin-4-yl)-4,5-dihydro-pyridazin-3(2H)-one (3-4): The compound (3-3) (1 eq) and ethanol are combined and placed in a round bottom flask and to this hydrazine (2 eq) is added slowly. The resulting solution is heated under reflux with continuous stirring until the reaction is complete as monitored by HPLC. Upon completion the reaction mixture is cooled to an ambient temperature and the solvent evaporated in vacuo. Ethyl acetate is added followed by the addition of ether. The solution is again rotary evaporated to afford a foam-like solid (3-4), which is used for the synthesis of next step without further purification, yield 100%.

6-(naphthalen-1-yl)-5-(pyridin-4-yl)pyridazin-3-ol (3-5): Compound (3-4) is taken in a single-necked round bottom flask in acetic acid and bromine in acetic acid (1.5 eq) is added drop-wise to the solution using an addition funnel. The reaction is refluxed at 70° C. and monitored by HPLC until all starting material consumed. The mixture is then cooled to an ambient temperature and poured into crushed ice to quench the reaction. The pH of the aqueous reaction mixture is adjusted to pH 7 with 0.2N NaOH and then extracted with dichloromethane. The organic layers are combined and purified by flash column chromatography over silica gel column and eluting with dichloromethane and MeOH (5%) to afforded compound (3-5), yield 51%.

6-chloro-3-(naphthalen-1-yl)-4-(pyridin-4-yl)pyridazine (3-6): In a round bottom flask compound 3-5 (1 eq) taken in ACN and POCl$_3$ (10 eq) was added slowly. The reaction mixture was stirred at 90° C., and monitored by HPLC. When the starting materials disappeared, bring it to an ambient temperature and poured into crushed ice. The pH of the mixture adjusted to pH 7 with 10N NaOH. The resulting mixture is then exhaustively extracted with ethyl acetate and dichloromethane. The organic extracts are combined and dried over anhydrous magnesium sulfate. The organic solvent evaporated in vacuo and the product purified by flash column chromatography (Hexane:ethyl acetate) afforded compound (3-6), yield 76%.

6-cyclopropyl-3-(naphthalen-1-yl)-4-(pyridin-4-yl)pyridazine (7=MW-077): Compound 3-6 (2 g, 6.2 mmol, 1 eq) was suspended in THF with 1.4 equiv of cycloprpylboronic acid (760 mg, 8.8 mmol, 1.4 eq) in a heavy wall pressure vessel (Chemglass, Vineland, N.J.) and the reaction mixture was purged with argon for 15 min. To this added 0.1 equiv of Pd (dppf)Cl$_2$CH$_2$Cl$_2$ (565 mg, 0.62 mmol), 2.5 equiv of silver oxide (3.65 g, 15.7 mmol) and 3 equiv of potassium carbonate (2.6 g, 18.8 mmol). The mixture was purged with argon and heated at 100° C. for 26 h in a sealed tube. The reaction mixture was cooled to ambient temperature and quenched with either hydrogen peroxide (33%) or sodium hydroxide (10%). The aqueous layer was extracted several times with ether and the ethereal layers were combined dried over anhydrous sodium sulfate and concentrated in vacuo resulting in a black mass. The crude mixture was purified by column chromatography on silica gel (200-400 mesh) and eluted with ethyl acetate: hexane (2:3 v/v) followed by crystallization with ethyl acetate and hexane to obtained SRM-077 (7) as a white crystals (0.75 g) 36.6% yield (gravimetric). MP 199.5-200 (uncorrected): $^1$H-NMR (500MHz, CDCl$_3$): δ 8.36 (dd, J=1.5, 4.5Hz, 2H); 7.88-7.84 (m, 2H); 7.57 (d, J=8.3Hz, 1H); 7.45-7.29 (m, 5H); 6.98 (dd, J=1.6, 4.5 Hz, 2H); 2.36-2.30 (m, 1H); 1.42-1.35 (m, 2H); 1.31-1.24 (m, 2H). HPLC (tr/purity): 17.26 min/>97%. HRMS calculated for C$_{22}$H$_{17}$N$_3$ 323.1422. found 323.1423.

6-cyclopropyl-3-(naphthalen-1-yl)-4-(pyridin-4-yl)pyridazine hydrochloride hydrate: (8=SRM-075): In a round bottom flask fitted with condenser and dry tube, compound 7 (SRM-077) (0.920 mg, 2.8 mmol) was suspended in (~20 mL) anhydrous isopropanol (99.5%, Aldrich) and heated to 85° C. with stirring until dissolved. To the resulting solution 3 equiv (0.725 μL) of ultrapure HCl (12N, JT Baker Ultrex® II, Product 6900-05) was added at once inducing formation of solids in suspension. The resulting solution was stirred at 80° C. for 10 min, cooled to ambient temperature and placed on ice for 2.5 h. The suspension was then transferred to 4° C. for an additional 16 hr. The resulting yellow precipitate was filtered on a medium frit sintered glass funnel using house vacuum, immediately washed with (3×5 mL) of ice-cold anhydrous isopropanol followed by (3×5) of ice-cold anhydrous ether and air dried by house vacuum for 7 h. The precipitate was then dried in a glass desiccator containing silica gel in vacuo until the compound gave a constant weight. The final product (8=SRM-075) was then transferred using a sterile/pyrogen-free spatula to a sterile storage vial under a Class II, laminar flow containment hood. Compound 8 (SRM-075) was a yellow powder (1.03 g) in 86% yield (gravimetric) compared to starting material. $^1$H NMR (500 MHz, CD$_3$OD): δ 8.70 (t, J=1.5, 5.6 Hz, 2H), 8.40 (s, 1H), 8.10 (d, J=8.2Hz, 1H), 7.96-7.94 (m, 3H), 7.69-7.45 (m, 5H), 2.67-2.61 (m, 1H), 1.61-1.51 (m, 4H). Hydrochloride hydrate formation was confirmed by elemental analysis. Elemental analysis indicated a ratio of ~2. EA calculated for C$_{22}$H$_{23}$C$_2$N$_3$O$_2$: C, 61.12; H, 5.36; N, 9.72; Cl, 16.40; O, 7.40. Found C, 59.54; H, 5.38; N, 9.38; Cl, 15.49; O, 9.46; Pd, 1.4 ppm. MP: 201-210° C. (decomposed) (uncorrected).

Example 3-1

Compound 46 (6-(1-methylpiperidin-4-yl)-3-(naphthalen-1-yl)-4-(pyridin-4-yl)pyridazine) (also described herein as SRM-137C) can be prepared in a similar manner as described in Example 3 by using (1-methylpiperidin-4-yl)boronic acid instead of cyclopropylboronic acid.

Example 4

Synthesis of MW-125 (9)

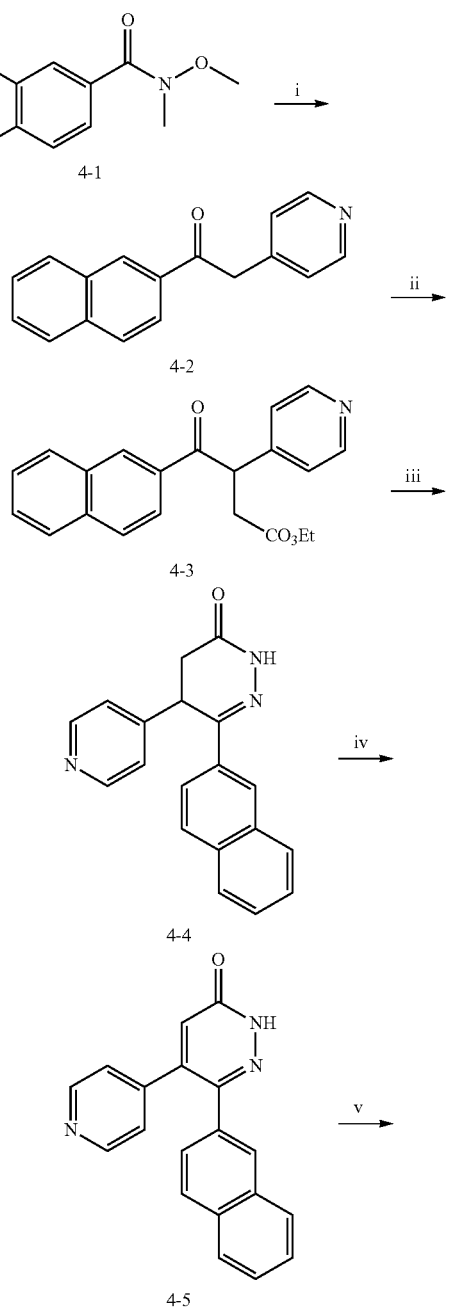

Scheme 4. Synthetic scheme for MW-125

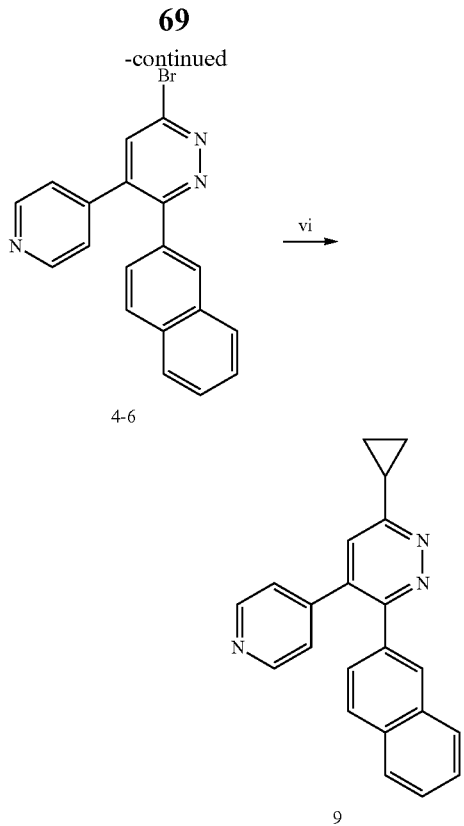

Reagents and conditions:
i) LDA, THF, -78° C., 4-picoline (15);
ii) 60% NaH, ethylbromoacetate;
iii) N$_2$H$_4$, ethanol. reflux;
iv) NBS, DMSO;
v) POBr$_3$, CH$_3$CN, reflux;
vi) cyclopropylboronic acid, Pd(dppf)Cl$_2$·CH$_2$Cl$_2$, Ag$_2$O, K$_2$CO$_3$, 100° C., 26 h;

2-(pyridin-4-yl)-1-(naphthalen-2-yl)ethan-1-one (4-2): A solution of 4-picoline (0.11 g, 1.1 mmol, 0.11 mL) in THF (7 mL) under nitrogen atmosphere at −78° C. was treated with LDA [freshly prepared by treating diisopropylamine (0.12 g, 1.2 mmol, 0.17 mL) in THF (3 mL) with 2.5 M n-BuLi (0.50 mL, 1.25 mmol) in hexanes for 30 minutes under nitrogen atmosphere in an ice bath] for 10 minutes. The mixture stirred 60 minutes and was treated with neat N,O-dimethyl-2-naphthalenehydroxamic acid (4-1, 0.20 g, 0.93 mmol) dropwise over ten minutes. The mixture stirred an additional two hours then saturated aqueous ammonium chloride (2 mL) was added to the mixture and stirring continued an additional two hours while the temperature of the mixture rose to 20° C. The reaction mixture was diluted with ethyl acetate (50 mL) and washed with water (3×50 mL), brine (25 mL), dried (Na$_2$SO$_4$) and evaporated. The product was chromatographed on silica gel eluted with a gradient of ethyl acetate in hexanes (1:1 to 1:2 to 1:3) to leave the purified product 4-2 as a cream colored crystalline solid (153 mg, 67%). $^1$H-NMR (300 MHz, CDCl$_3$) δ 8.58 (dd, J=4.4 Hz, J=1.8 Hz, 2H), 8.53 (s, 1H), 8.05 (dd, J=8.5 Hz, J=1.8 Hz, 1H), 8.00-7.84 (m, 3H), 7.66-7.55 (m, 2H), 7.25 (m, 2H), 4.43 (s, 2H); ESI MS (M+H)$^+$=248; HPLC method A R$_t$=3.37 minutes.

Ethyl 3-(pyridin-4-yl)-4-(naphthalen-2-yl)-4-oxobutanoate (4-3): To a solution of 2-(pyridin-4-yl)-1-(naphthalen-2-yl)ethan-1-one (4-2, 0.15 g, 0.61 mmol) in 1,4-dioxane (6 mL) under nitrogen atmosphere at 20° C. was added sodium hydride (60% in mineral oil, 29 mg, 0.73 mmol) and the mixture stirred for an hour. Ethyl bromoacetate (0.12 g, 0.73 mmol, 81 μL) was added all at once and the mixture stirred for an hour. Saturated aqueous ammonium chloride (2 mL) was added and stirring continued for an hour. The mixture was diluted with ethyl acetate (30 mL), washed with water (2×30 mL), brine (20 mL), dried (Na$_2$SO$_4$) and evaporated to an oily residue that was purified by silica gel chromatography eluted with a gradient of ethyl acetate in hexanes (1:1 to 2:1) to leave the product as a light yellow viscous oil (121 mg, 60%). $^1$H-NMR (300 MHz, CDCl$_3$) δ 8.53 (dd, J=4.4 Hz, J=1.5 Hz, 2H), 8.49 (s, 1H), 7.99 (dd, J=8.5 Hz, J=1.7 Hz, 1H), 7.92 (d, J=7.9 Hz, 1H), 7.87-7.82 (m, 2H), 7.62-7.50 (m, 2H), 7.29 (dd, J=4.4 Hz, J=1.5 Hz, 2H), 5.27 (m, 1H), 4.12 (q, J=7.0 Hz, 2H), 3.42 (dd, J=17.0 Hz, J=9.4 Hz, 1H), 2.78 (dd, J=17.0 Hz, J=5.6 Hz, 1H), 1.21 (t, J=7.0 Hz, 3H); ESI MS (M+H)$^+$=334; HPLC method A R$_t$=3.89 minutes.

6-(naphthalen-2-yl)-5-(pyridin-4-yl)-2,3,4,5-tetrahydropyridazin-3-one (4-4): A solution of Ethyl 3-(pyridin-4-yl)-4-(naphthalen-2-yl)-4-oxobutanoate (4-3, 0.12 g, 0.36 mmol) in ethanol (3 mL) was treated with hydrazine hydrate (0.25 g, 5 mmol, 0.25 mL) and refluxed for 20 hours. The mixture was cooled to 20° C. and purified by reversed phase HPLC (method B). The product fractions were treated with saturated sodium bicarbonate solution (50 mL) and extracted with ethyl acetate (2×50 mL). The combined extracts were washed with brine (50 mL), dried (Na$_2$SO$_4$) and evaporated to leave 48 mg (44%) of beige solid. $^1$H-NMR (300 MHz, CDCl$_3$) δ 8.76 (bs, 1H), 8.57 (d, J=5.3 Hz, 2H), 7.98 (dd, J=8.5 Hz, J=1.8 Hz, 1H), 7.95 (s, 1H), 7.85 (d, J=8.5 Hz, 1H), 7.86-7.76 (m, 2H), 7.55-7.46 (m, 2H), 7.21 (dd, J=4.4 Hz, J=1.2 Hz, 2H), 4.68 (d, J=6.5 Hz, 1H), 3.10 (dd, J=17.0 Hz, J=7.7 Hz, 1H), 2.90 (dd, J=17.0Hz, J=1.8 Hz, 1H); ESI MS (M+H)$^+$=302; HPLC method A R$_t$=3.11 minutes.

6-(Naphthalen-2-yl)-5-(pyridin-4-yl)-2,3-dihydropyridazin-3-one (4-5): A solution of 6-(naphthalen-2-yl)-5-(pyridin-4-yl)-2,3,4,5-tetrahydropyridazin-3-one (4-4, 25 mg, 0.083 mmol) in DMSO (0.5 mL) and water (0.02 mL) was treated with N-bromosuccinimide (75 mg, 0.42 mmol). After a slight exotherm the solution was stirred 72 hours then purified directly by reversed phase HPLC (method B). The combined product fractions were treated with saturated sodium bicarbonate solution (50 mL) and extracted with ethyl acetate (2×25 mL). The combined extracts were washed with brine, dried (Na$_2$SO$_4$) and evaporated to leave a beige solid (17 mg, 69%). $^1$H-NMR (300 MHz, CDCl$_3$) δ 11.13 (bs, 1H), 8.55 (bs, 2H), 7.80 (dd, J=9.1 Hz, J=2.1 Hz, 1H), 7.76-7.68 (m, 3H), 7.55-7.45 (m, 2H), 7.16 (dd, J=8.8 Hz, J=2.0 Hz, 1H), 7.09 (d, J=5.9 Hz, 2H), 7.05 (s, 1H); ESI MS (M+H)$^+$=300; HPLC method A R$_t$=2.88 minutes.

6-Bromo-4-(pyridin-4-yl)-3-(naphthalen-2-yl)pyridazine (4-6): 6-(Naphthalen-2-yl)-5-(pyridin-4-yl)-2,3-dihydropyridazin-3-one (4-5, 0.15 g, 0.50 mmol) was added to a solution of phosphorousoxybromide (0.62 g, 2.0 mmol) in acetonitrile (3 mL) and heated to reflux while stirring for ten hours. The reaction mixture was cooled in an ice bath, treated with ice (2 g) and stirred for an hour. The mixture was neutralized with solid sodium carbonate to a pH=10 followed by dilution with ethyl acetate (20 mL) and water (20 mL). The organic layer was separated, washed with brine (50 mL), dried (Na$_2$SO$_4$) and evaporated. The product was purified by chromatography on silica gel eluted with ethyl acetate in hexanes (3:1). The purified product was isolated as a colorless foamy solid (0.15 g, 83%). $^1$H-NMR (300 MHz, CDCl$_3$) δ 8.59 (dd, J=4.4 Hz, J=1.8 Hz, 1H), 8.04 (d, J=1.2 Hz, 1H), 7.86-7.73 (m, 3H), 7.72 (s, 1H), 7.58-7.47 (m, 2H), 7.33 (dd, J=8.5 Hz, J=1.7 Hz, 1H), 7.15

(dd, J=4.4 Hz, J=1.7 Hz, 2H); ESI MS (M+H)⁺=362, 364; HPLC method A Rt=3.71 minutes.

6-Cyclopropyl-4-(pyridin-4-yl)-3-(naphthalen-2-yl)pyridazine (9): A mixture of 6-bromo-4-(pyridin-4-yl)-3-(naphthalen-2-yl)pyridazine (4-6, 40 mg, 0.11 mmol), cyclopropyl boronic acid (13 mg, 0.15 mmol), PdCl$_2$(dppf)·CH$_2$Cl$_2$ (8 mg, 0.011 mmol), silver oxide (64 mg, 0.28 mmol), potassium carbonate (46 mg, 0.33 mmol) and 1,4-dioxane (1 mL) was stirred and purged with nitrogen. The mixture was heated to 80° C. for 18 hours. The reaction mixture was cooled to 20° C. and filtered through celite (ethyl acetate wash). The filtrate was evaporated to dryness and the crude product was purified by RPHPLC (method B). The product fraction was diluted with saturated sodium bicarbonate solution (50 mL) and the product was extracted with ethyl acetate (2×25 mL). The combined organic layers were washed with brine (2×25 mL), dried (Na$_2$SO$_4$) and evaporated to leave the product as a white solid (16 mg, 45%). ¹H-NMR (300 MHz, CD$_3$OD): δ 8.46 (d, J=4.4 Hz, 2H), 7.93 (d, J=1.5 Hz, 1H), 7.88-7.77 (m, 4H), 7.65 (s, 1H), 7.56-7.46 (m, 2H), 7.37 (dd, J=8.5 Hz, J=1.7 Hz, 1H), 7.33 (dd, J=4.7 Hz, J=1.5 Hz, 1H), 2.4-2.35 (m, 1H), 1.30-1.22 (m, 4H); ESI MS (M+H)⁺=324; HPLC method A R$_t$=3.47 minutes.

Example 5

Synthesis of MW-167 (10)

Scheme 5. Synthetic scheme for MW-167.

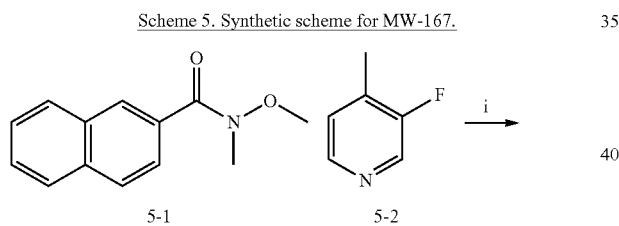

5-1    5-2

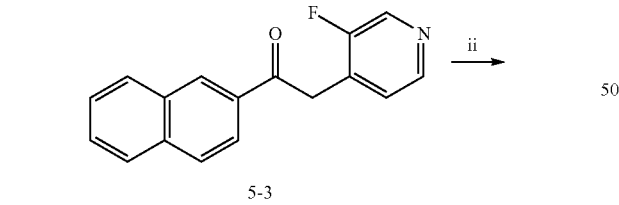

5-3

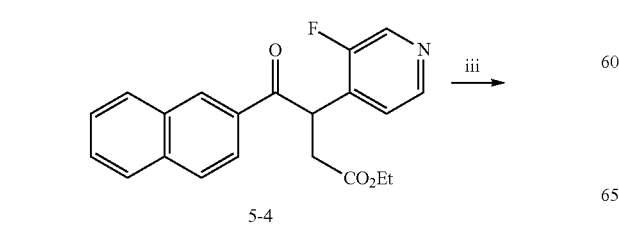

5-4

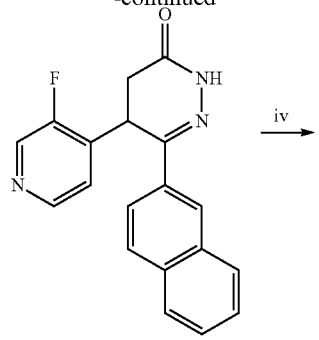

5-5

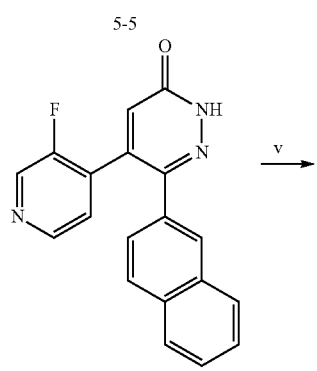

5-6

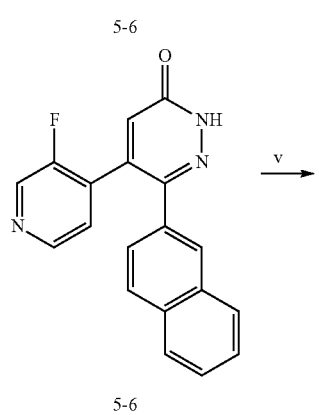

5-6                    5-7                    10

Reagents and conditions: i) LDA, THF, -78° C.; ii) 60% NaH, ethylbromoacetate; iii) N$_2$H$_4$, HOAc, ethanol, reflux; iv) NBS, DMSO; v) POBr$_3$, CH$_3$CN, reflux; vi) cyclopropylboronic acid, Pd(dppf)Cl$_2$·CH$_2$Cl$_2$, Ag$_2$O, K$_2$CO$_3$, 100° C., 26 h.

2-(3-fluoropyridin-4-yl)-1-(naphthalen-2-yl)ethan-1-one (5-3): A solution of 3-fluoro-4-picoline (5-2, 3.2 g, 29 mmol, 2.9 mL) in THF (200 mL) under nitrogen atmosphere at −78° C. was treated with LDA [freshly prepared by treating diisopropylamine (5.3 g, 53 mmol, 7.4 mL) in THF (50 mL) with 2.5 M n-BuLi in hexanes for 30 minutes under nitrogen atmosphere in an ice bath] for 10 minutes. The mixture stirred 60 minutes and was treated with neat N,O-dimethyl-2-naphthalenehydroxamic acid (5-1, 7.5 g, 35 mmol) dropwise over ten minutes. The mixture stirred an additional two hours then saturated aqueous ammonium chloride (20 mL) was added to the mixture and stirring continued an additional two hours while the temperature of the mixture rose to 20° C. Approximately 200 mL of solvent was removed from the mixture in vacuo and the residue was diluted with ethyl acetate (200 mL) and washed with water (3×100 mL). The product was extracted with 1N HCl (6×75 mL) and the combined acidic extracts were neutralized with solid sodium carbonate to pH=9. The product was extracted with ethyl acetate (2×100 mL) and the extracts were dried ($Na_2SO_4$) and evaporated. The product 5-3 was obtained as a light yellow crystalline solid (4.4 g, 57%). $^1$H-NMR (300 MHz, $CDCl_3$): δ 8.57 (s, 1H), 8.50 (d, J=1.5 Hz, 1H), 8.41 (dd, J=4.6 Hz, J=1.0 Hz, 1H), 8.07 (dd, J=8.2 Hz, J=1.5 Hz), 8.01 (d, J=18.7 Hz, 1H), 7.94 (m, 2H), 7.68-7.57 (m, 3H), 4.52 (s, 2H); ESI MS (M+H)$^+$=266; HPLC method A $R_t$=4.29 minutes.

Ethyl 3-(3-fluoropyridin-4-yl)-4-(naphthalen-2-yl)-4-oxobutanoate (5-4): To a solution of 2-(3-fluoropyridin-4-yl)-1-(naphthalen-2-yl)ethan-1-one (5-3, 4.4 g, 17 mmol) in 1,4-dioxane (150 mL) under nitrogen atmosphere at 20° C. was added sodium hydride (60% in mineral oil, 0.80 g, 20 mmol) and the mixture stirred for an hour. Ethyl bromoacetate (3.3 g, 20 mmol, 2.2 mL) was added all at once and the mixture stirred for 18 hours. Saturated aqueous ammonium chloride (20 mL) was added and stirring continued for an hour. The mixture was evaporated in vacuo to approximately 50 mL in volume and diluted with ethyl acetate (200 mL). The mixture was washed with water (2×100 mL), brine (50 mL), dried ($Na_2SO_4$) and evaporated to an oily residue that was purified by silica gel chromatography eluted with a gradient of hexanes/ethyl acetate (3:1 to 2:1) to leave the product as a light yellow viscous oil (4.4 g, 74%). $^1$H-NMR (300 MHz, $CDCl_3$): δ 8.54 (d, J=1.4 Hz, 1H), 8.46 (d, J=1.4 Hz, 1H), 8.31 (dd, J=5.0 Hz, J=0.8 Hz, 1H), 8.00 (dd, J=8.5 Hz, J=1.6 Hz, 1H), 9.94 (bd, J=8.2 Hz, 1H), 7.88-7.82 (m, 2H), 7.62-7.51 (m, 2H), 7.22 (dd, J=5.0 Hz, J=5.0 Hz, 1H), 5.62 (dd, J=9.4 Hz, J=5.3 Hz, 1H), 4.13 (q, J=7.0 Hz, 2H), 3.40 (dd, J=17.1 Hz, J=9.4 Hz, 1H), 2.80 (dd, J=17.1 Hz, J=5.3 Hz, 1H), 1.21 (t, J=7.0 Hz); ESI MS (M+H)$^+$=352; HPLC method A $R_t$=5.38 minutes.

6-(naphthalen-2-yl)-5-(3-fluoropyridin-4-yl)-2,3,4,5-tetrahydropyridazin-3-one (5-5): A solution of Ethyl 3-(3-fluoropyridin-4-yl)-4-(naphthalen-2-yl)-4-oxobutanoate (5-4, 4.4 g, 12.5 mmol) in ethanol (32 mL) and acetic acid (1.5 mL) was treated with hydrazine hydrate (12.5 g, 250 mmol, 12.5 mL) and refluxed for 20 hours. The mixture was cooled to 20° C., water (5 mL) was added and the beige precipitate was filtered, washed with 25% aqueous ethanol and air-dried to leave 1.85 g (46%). $^1$H-NMR (300 MHz, $CDCl_3$): δ 8.92 (bs, 1H), 8.55 (d, J=1.5 Hz, 1H), 8.30 (d, J=5.0 Hz, 1H), 7.99 (dd, J=8.5 Hz, J=1.7 Hz, 1H), 7.90 (d, J=1.5 Hz, 1H), 7.88-7.78 (m, 3H), 7.55-7.45 (m, 2H), 7.04 (dd, J=6.5 Hz, J=5.0 Hz, 1H), 5.02 (dd, J=7.9 Hz, J=1.5 Hz, 1H), 3.10 (dd, J=17.3 Hz, J=7.9 Hz, 1H), 2.90 (dd, J=17.3 Hz, J=1.5 Hz, 1H); ESI MS (M+H)$^+$=320; HPLC method A $R_t$=4.21 minutes.

6-(Naphthalen-2-yl)-5-(3-fluoropyridin-4-yl)-2,3-dihydropyridazin-3-one (5-6): A solution of 6-(naphthalen-2-yl)-5-(3-fluoropyridin-4-yl)-2,3,4,5-tetrahydropyridazin-3-one (5-5, 3.2 g, 10 mmol) in DMSO (80 mL) and water (1.6 mL) was treated with N-bromosuccinimide (8.9 g, 50 mmol). After a slight exotherm the solution was stirred 72 hours then diluted with water (300 mL) and extracted with ethyl acetate (3×150 mL). The combined organic layers were washed with water (200 mL), saturated sodium bicarbonate solution (150 mL) and brine (50 mL). The solution was dried ($Na_2SO_4$) and evaporated. The solid residue was stirred rapidly in saturated sodium bicarbonate solution (50 mL) and water (100 mL) for 18 hours then filtered, washed with water (5×25 mL) and dried under vacuum to leave the product as a tan powder (3.1 g, 97%). $^1$H-NMR (300 MHz, $CDCl_3$): δ 11.69 (bs, 1H), 8.42 (dd, J=5.0 Hz, J=5.0 Hz, 1H), 8.38 (d, J=0.9 Hz, 1H), 7.80 (d, J=7.7 Hz, 1H), 7.74-7.67 (m, 3H), 7.55-7.44 (m, 2H), 7.26 (dd, J=8.5 Hz, J=1.7 Hz, 1H), 7.20-7.13 (m, 1H), 7.11 (s, 1H); ESI MS (M+H)$^+$=318; HPLC method A $R_t$=4.07 minutes.

6-Bromo-4-(3-fluoropyridin-4-yl)-3-(naphthalen-2-yl) pyridazine (5-7): 6-(Naphthalen-2-yl)-5-(3-fluoropyridin-4-yl)-2,3-dihydropyridazin-3-one (5-6, 3.0 g, 9.5 mmol) was added to a solution of phosphorousoxybromide (11 g, 38 mmol) in acetonitrile (100 mL) and heated to reflux while stirring for ten hours. The reaction mixture was cooled in an ice bath, treated with ice (50 g) and stirred for an hour. Approximately half of the solvent was removed in vacuo. The product mixture was diluted with ethyl acetate (100 mL) and saturated sodium bicarbonate solution (300 mL) was cautiously added with stirring until it reached a pH=8. The organic layer was separated, washed with brine (50 mL), dried ($Na_2SO_4$) and evaporated. The product was purified by chromatography on silica gel eluted with a gradient of 40% to 50% ethyl acetate in hexanes. The purified product was isolated as a colorless foamy solid (2.2 g, 61%). $^1$H-NMR (300 MHz, $CDCl_3$): δ 8.47 (d, J=1.2 Hz, 1H), 8.41 (dd, J=5.0 Hz, J=1.0 Hz, 1H), 7.96 (d, J=1.5 Hz, 1H), 7.85-7.73 (m, 4H), 7.57-7.46 (m, 2H), 7.41 (dd, J=8.8 Hz, J=2.1 Hz), 7.15 (dd, J=5.3 Hz, J=4.7 Hz, 1H); ESI MS (M+H)$^+$=380, 382; HPLC method A $R_t$=5.29 minutes.

6-Cyclopropyl-4-(3-fluoropyridin-4-yl)-3-(naphthalen-2-yl)pyridazine (10): A mixture of 6-Bromo-4-(3-fluoropyridin-4-yl)-3-(naphthalen-2-yl)pyridazine (5-7, 2.2 g, 5.8 mmol), cyclopropyl boronic acid (0.70 g, 8.1 mmol), $PdCl_2$(dPPf).$CH_2Cl_2$ (0.42 g, 0.58 mmol), silver oxide (3.36 g, 14.5 mmol), potassium carbonate (2.4 g, 17.4 mmol) and 1,4-dioxane (50 mL) was stirred and purged with nitrogen. The mixture was heated to 80° C. for 18 hours. The reaction mixture was cooled to 20° C. and filtered through celite (ethyl acetate wash). The filtrate was evaporated to dryness and the crude product was purified by chromatography on silica gel eluted with 50% ethyl acetate in hexanes to leave the product as a gum that crystallized upon trituration with hexane (1.1 g, 56%). $^1$H-NMR (300 MHz, $CDCl_3$): δ 8.45 (d, J=1.4 Hz, 1H), 8.38 (dd, J=4.9 Hz, J=1.0 Hz, 1H), 7.95 (m, 1H), 7.84-7.51 (m, 2H), 7.74 (s, 1H), 7.54-7.43 (m, 3H), 7.33 (d, J=1.0 Hz, 1H), 7.14 (dd, J=5.6 Hz, J=5.0 Hz, 1H), 2.27 (m, 1H), 1.38 (m, 2H), 1.24 (m, 2H); ESI MS (M+H)$^+$=342; HPLC method A $R_t$=4.94 minutes.

6-Cyclopropyl-4-(3-fluoropyridin-4-yl)-3-(naphthalen-2-yl)pyridazine hydrochloride (10.HCl): A sample of the cyclopropylpyridazine compound (10, 0.41 g, 1.2 mmol) was dissolved in methanol (20 mL) and treated with 1N HCl (1.4 mL, 1.4 mmol) and evaporated to dryness. The light yellow amorphous solid was triturated in methylene chloride to leave a light yellow crystalline solid (0.41 g). $^1$H-NMR (300 MHz, DMSO-$d_6$): δ 8.51 (d, J=4.7 Hz, 1H), 8.47 (s, 1H), 7.91 (s, 1H), 7.90-7.79 (m, 3H), 7.78 (s, 1H), 7.64 (dd, J=5.6 Hz, J=5.3 Hz, 1H), 7.58-7.46 (m, 2H), 7.42 (d, J=8.2 Hz, 1H), 2.42 (m, 1H), 1.21 (narrow m, 4H).

Example 6

Synthesis of (11) MW-18-122, (12) MW-18-124, (13) MW-15-107, and (7) MW-16-077

Scheme 6

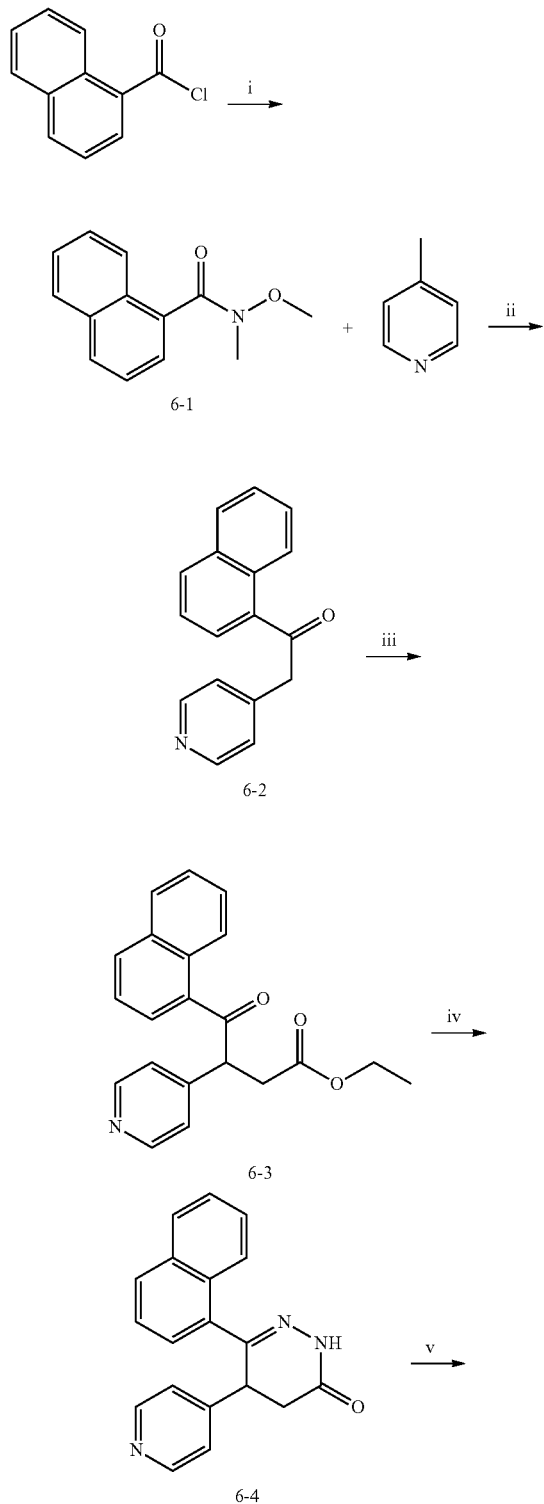

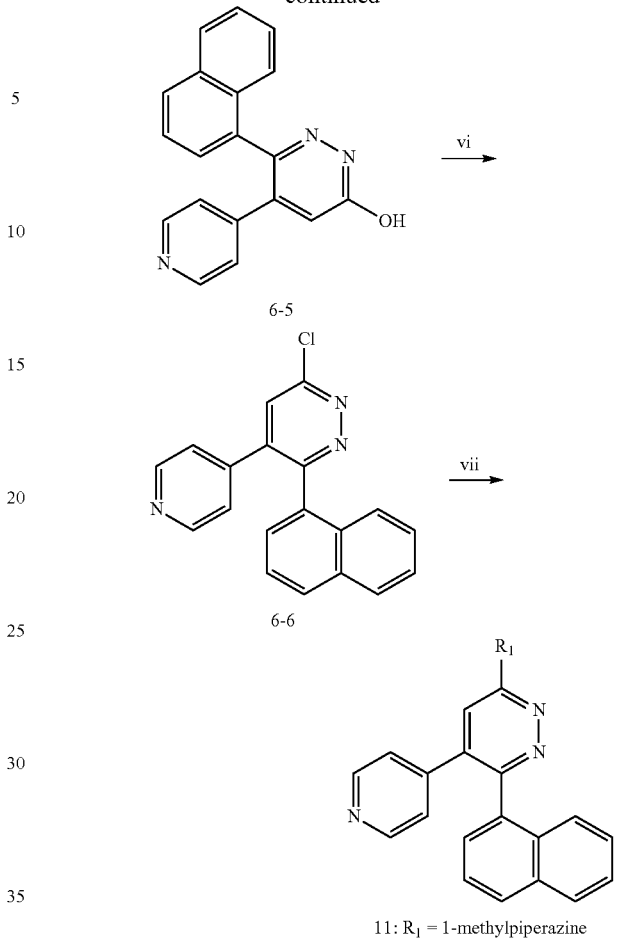

11: $R_1$ = 1-methylpiperazine
12: $R_1$ = piperidine
13: $R_1$ = cyclopropylamine
7: $R_1$ = cyclopropyl Reagents and conditions:
i) MeNHOMe·HCl, pyridine, $CH_2Cl_2$;
ii) LDA, THF, -78° C.;
iii) 60% NaH, DMSO, ethyl-2-iodoacetate, 0° C.-rt;
iv) $N_2H_4$, t-BuOH, reflux, 18 hr;
v) $Br_2$, AcOH, 95° C., 2 h;
vi) $POCl_3$, DIEA, TEBAC, 100° C.;
vii) 1-butanol, amine, 120° C. (XX-XX); cyclopropylboronic acid, Pd(dppf)$Cl_2$, $CH_2Cl_2$, $Ag_2O$, $K_2CO_3$, 100° C., 26 hr (XX).

N-methoxy-N-methyl-1-naphthamide (6-1): An ice cooled mixture of 1-naphthoyl chloride (1 eq) and N,O-dimethyl-hydroxylamine hydrochloride (3 eq) in methylene chloride was treated dropwise with triethylamine (2.33 eq) over 0.5 h under argon. The reaction mixture was warmed slowly to an ambient temperature (20° C.) and stirred an additional 18 h. The solvent was removed under reduced pressure, residue dissolved in ethyl acetate and washed successively with 5% potassium bisulfate, saturated sodium bicarbonate and brine. The organic layer was subjected to drying over anhydrous sodium sulfate and concentrated in vacuo to leave the product 6-1 an oily mass, yield 100%.

1-(naphthalen-1-yl)-2-(pyridin-4-yl)ethanone (6-2): In a 2 L round-bottom flask equipped with a stir bar, under $N_2$, was added 4-methylpyridine (17.6 mL, 180 mmol) followed by anhydrous THF (500 mL). The mixture was then cooled down to -78° C. and LDA (90 mL, 2M in THF) was added dropwise over 1 h. After stirring for 2 h at -78° C. a solution of compound 6-1 (41 g, 190 mmol) in anhydrous THF (200 mL) was added to the reaction mixture drop wise over 30 min while stirring was continued for 1.5 h at −78° C. and 1.5 h at room temperature. The reaction was then diluted with EtOAc and treated with saturated sodium bicarbonate solution and repeat extraction with ethyl acetate was done in a separatory funnel. The combined organic extracts were treated with brine, dried over anhydrous magnesium sulfate and concentrated under reduced pressure to yield an oily mixture. The crude mixture was purified by column chromatography on silica gel (200-400 mesh) with product elution using ethyl acetate: hexane (1:4 v/v). The product, ketone 6-2, was obtained as a bright yellow solid (27.1 g, 61%)(gravimetric) yield.

Ethyl 4-(naphthalen-1-yl)-4-oxo-3-(pyridin-4-yl)butanoate (6-3): In a 1 L, round-bottom flask equipped with a stir bar, under $N_2$, was added 60% NaH (8.16 g, 204 mmol), followed by anhydrous DMSO (300 mL). The reaction mixture was cooled down to 0° C. and stirred for 30 min. The solution of compound 6-2 (42 g, 170 mmol) in anhydrous DMSO (150 mL) was added via addition funnel at a steady drip over 45 min. The heterogeneous solution was stirred for 30 min and then ethyl bromoacetate (24.4 mL, 221 mmol) was added in one portion and the ice bath removed. The reaction was stirred overnight, becoming homogenous. The resulting solution was poured into saturated ammonium chloride and extracted (EtOAc, 3×). The combined organic layers were washed with saturated sodium bicarbonate, 1:1 $H_2O$: brine, followed by brine. The resulting organic layer collected was dried over $Na_2SO_4$ and concentrated under reduced pressure to yield an oily residue. Purification by flash chromatography gives compound 6-3 (11 g, 19%) (gravimetric) yield as a solid.

6-(naphthalen-1-yl)-5-(pyridin-4-yl)-4,5-dihydropyridazin-3(2H)-one (6-4): Compound 6-3 (11 g, 33 mmol) and ethanol (100 mL) were charged into a 350 mL sealed tube with a stir bar, under $N_2$. To this mixture was added hydrazine (2.1 mL, 66 mmol) and resulting solution stirred at 130° C. overnight. The reaction was concentrated under reduced pressure and the crude 6-4 (9.4 g) as a yellow solid that was used for the next step without further purification.

6-(naphthalen-1-yl)-5-(pyridin-4-yl)pyridazin-3-ol (6-5): In a 500 mL round-bottom flask equipped with a stir bar was charged compound 6-4 (9.4 g, 31.2 mmol) and glacial acetic acid (150 mL). The resulting solution was heated at 95° C. for 50 min. To this mixture was added a solution of $Br_2$ (1.8 mL, 34.3 mmol) in glacial acetic acid (10 mL). The reaction was stirred for 1.5 h at 95° C. then concentrated in vacuo. The mixture was cooled to ambient temperature, was added EtOAc (200 mL) and $H_2O$ (100 mL). The aqueous was adjusted to pH 8 by addition of 10% sodium carbonate and subjected to repeat extraction with ethyl acetate. The combined organic layers were washed with saturated sodium bicarbonate followed by brine, dried over anhydrous $Na_2SO_4$ and concentrated under reduced pressure. Compound 6-5 was purified by flash chromatography yielding compound 6-5 (7 g), 75% (gravimetric) yield as off-white solid.

6-chloro-3-(naphthalen-1-yl)-4-(pyridin-4-yl)pyridazine (6-6): In a 500 mL round-bottom flask equipped with a stir bar was charged with compound 6-5 (7 g, 23.4 mmol), tetraethylbutyl ammonium chloride (5.4 g, 23.87 mmol), diisopropylethylamine (4.12 mL, 23.6 mmol) and $POCl_3$ (103 g). The resulting mixture was heated in an oil bath at 100° C. for 2 h then concentrated under reduced pressure. Remaining $POCl_3$ was azeotropically removed using toluene. The crude was suspended in ethyl acetate and iced saturated sodium bicarbonate was added. The aqueous layer was extracted several times with ethyl acetate and the combined organic layers were washed with saturated sodium bicarbonate followed by brine. The organic phases subjected to drying over anhydrous sodium sulfate and concentrated in vacuo and product was purified by silica gel (200-400 mesh) column chromatography using ethyl acetate: hexane (2:3 v/v) as eluent. Product 6-6 was obtained as a beige powder (5.8 g) 78% (gravimetric) yield. $^1$H-NMR (500MHz, $CDCl_3$): δ 8.40 (d, J=5.9 Hz, 2H); 7.93 (dd, J=8.15 Hz, 2H); 7.69 (d, J=3.75Hz, 1H); 7.50-7.32 (m, 5H); 6.99 (dd, J=1.6, 4.5 Hz, 2H). HPLC (tr/purity): 18.07 min, >96.8% (HPLC method A); mass (ESI) m/z (MeOH)=317.0 ($MH^+$).

The above listed compounds (7, 11-13) were synthesized by reaction of a given amine with compound 6-6 using the protocol described in Watterson et al., *PLOS ONE*, 2013, 8, e66226). Compound 6-6 and 1-butanol were combined in a round bottom flask with the respective amine, heated to 110° C. for approximately 15 h, cooled to ambient temperature, treated with water, and the aqueous layer subjected to repeat extraction with dichloromethane. The combined organic layers were subjected to drying with anhydrous sodium sulfate and concentration in vacuo. The final products were purified by silica gel column chromatography using volatile solvents for elution and final processing.

6-(4-methylpiperazin-1-yl)-3-(naphthalen-1-yl)-4-(pyridin-4-yl)pyridazine (11): (MW-18): Compound 6-chloro-3-(naphthalen-1-yl)-4-(pyridin-4-yl)pyridazine (6-6) (0.050 g, 0.157 mmol) and 5 mL 1-butanol were combined in a heavy wall pressure vessel followed by the addition of 1-methylpiperazine (0.078 g, 0.79 mmol). The pressure vessel was capped and heated at 120° C. for 16 h. The reaction mixture was then cooled to ambient temperature, transferred to a round bottom flask and concentrated in vacuo. The residue was treated with 5 ml of Milli-Q water and the aqueous layer was extracted several times with dichloromethane using a separatory funnel. The combined organic layers were dried with anhydrous sodium sulfate and concentrated in vacuo. The crude mixture was purified by column chromatography on silica gel (200-400 mesh) and eluted with ethyl acetate: hexane (3:1 v/v) to give the desired product 11 as a pale yellow powder (45 mg) in 79% yield (gravimetric). $^1$H-NMR (500MHz, $CDCl_3$): δ 8.35 (dd, J=5.0, 5.0 Hz, 2H); 7.85 (dd, J=5.0, 10 Hz, 2H); 7.66 (dd, J=5.0, 7.5, 1H); 7.45-7.34 (m, 3H); 7.28 (dd, J=5.0, 7.5, 1H); 6.97 (dd, J=5.0, 5.0, 3H); 3.90 (s, 4H); 2.70 (s, 4H); 2.46 (s, 3H); HPLC (tr/purity): 11.1 min, >98% (HPLC method A); (ESI) m/z (MeOH)=382.2 ($MH^+$). HRMS calculated for $C_{24}H_{23}N_5$ 381.19535. found 381.19575.

3-(naphthalen-1-yl)-6-(piperidin-1-yl)-4-(pyridin-4-yl)pyridazine (12): (MW-124): Compound 6-chloro-3-(naphthalen-1-yl)-4-(pyridin-4-yl)pyridazine (6-6) (0.050 g, 0.157 mmol) was reacted with piperidine (0.078 g, 0.79 mmol) in 1-butanol, processed as above, and the final product obtained via chromatography using ethyl acetate: hexane (3:1 v/v) as eluent, to give 12 as a beige powder (50 mg) in 89% (gravimetric) yield. $^1$H NMR (500MHz, $CDCl_3$): δ 8.35 (dd, J=5.0, 5.0 Hz, 2H); 7.84-7.82 (m, 2H); 7.69 (d, J=10 Hz, 1H); 7.44-7.28 (m, 4H); 7.01 (t, J=5.0, 5.0 Hz, 2H); 6.96 (s, 1H); 3.83 (t, J=5.0, 5.0 Hz, 4H); 1.77 (s, 6H). HPLC (tr/purity): 16.9 min, >97% (HPLC method A); (ESI) m/z (MeOH)=367.2 ($MH^+$).

N-cyclopropyl-6-(naphthalen-1-yl)-5-(pyridin-4-yl)pyridazin-3-amine (13): (MW-107): Compound 6-chloro-3-(naphthalen-1-yl)-4-(pyridin-4-yl)pyridazine (6-6) (0.600 g, 1.8 mmol) was reacted with cyclopropanamine (0.645 g, 11.3 mmol) in 1-butanol, processed as above, and the final product obtained via column chromatography using ethyl acetate: hexane (4:1 v/v) as eluent, to give 13 as a pale yellow crystals (360 mg) in 59% (gravimetric) yield. $^{1}$H-NMR (500 MHz, CDCl$_3$: MeOD): δ 8.38 (dd, J=5.10 Hz, 2H), 7.85 (dd, J=5.10 Hz, 2H); 7.64 (d, J=10 Hz, 1H); 7.45-7.34 (m, 3H), 7.28 (d, J=10 Hz, 1H), 7.12 (s, 1H), 7.00-6.99 (m, 2H); 5.92 (s, br, 1H); 2.70-2.66 (m, 1H); 0.94-0.90 (m, 2H); 0.74-0.71 (m, 2H). HPLC HPLC (tr/purity): 12.9 min, >96% (HPLC method A); ESI m/z (MeOH)=339.1 (MH$^+$).

6-cyclopropyl-3-(naphthalen-1-yl)-4-(pyridin-4-yl)pyridazine (7): (MW-077): Compound 6-chloro-3-(naphthalen-1-yl)-4-(pyridin-4-yl)pyridazine (6-6) (2 g, 6.2 mmol) was suspended in THF with 1.4 equiv of cyclopropylboronic acid (760 mg, 8.8 mmol in a heavy wall pressure vessel and the reaction mixture was purged with argon for 15 min. To this was added 0.1 equiv of Pd (dppf)Cl$_2$CH$_2$Cl$_2$ (565 mg, 0.62 mmol), 2.5 equiv of silver oxide (3.65 g, 15.7 mmol) and 3 equiv of potassium carbonate (2.6 g, 18.8 mmol). The mixture was purged with argon and heated at 100° C. for 26 h in a sealed tube. The reaction mixture was cooled to ambient temperature and quenched with either hydrogen peroxide (33%) or sodium hydroxide (10%). The aqueous layer subjected to repeat extraction with ether. The combined organic phases subjected to drying over anhydrous sodium sulfate and concentrated in vacuo resulting in a black mass. The crude mixture was purified by silica gel (200-400 mesh) column chromatography using ethyl acetate: hexane (2:3 v/v) eluent, followed by crystallization with ethyl acetate and hexane. Compound 7 was obtained as a white crystalline solid in (1.1 g) 54% (gravimetric) yield; MP 199.5-200° C. (uncorrected); $^{1}$H NMR (500 MHz, CDCl$_3$): δ 8.37 (d, J=5 Hz, 2H), 7.86 (m, 2H), 7.57 (d, J=8.3 Hz, 1H), 7.46-7.34 (m, 4H), 7.31 (dd, J=1.5, 4.6, 1H), 6.99 (dd, J=5 Hz, 2H), 2.35-2.32 (m, 1H), 1.41-1.39 (m, 2H), 1.28-1.25 (m, 2H); HPLC (tr/purity): 17.26 min >97% (HPLC method A); ESI m/z (MeOH): 324.10 (MH$^+$); HRMS 323.1423 (calculated for C$_{22}$H$_{17}$N$_3$ 323.1422).

Example 6-1

Compound 46 (6-(1-methylpiperidin-4-yl)-3-(naphthalen-1-yl)-4-(pyridin-4-yl)pyridazine) (also described herein as SRM-137C) can be prepared in a similar manner as described in Example 6 by using (1-methylpiperidin-4-yl) boronic acid instead of cyclopropylboronic acid.

Example 7

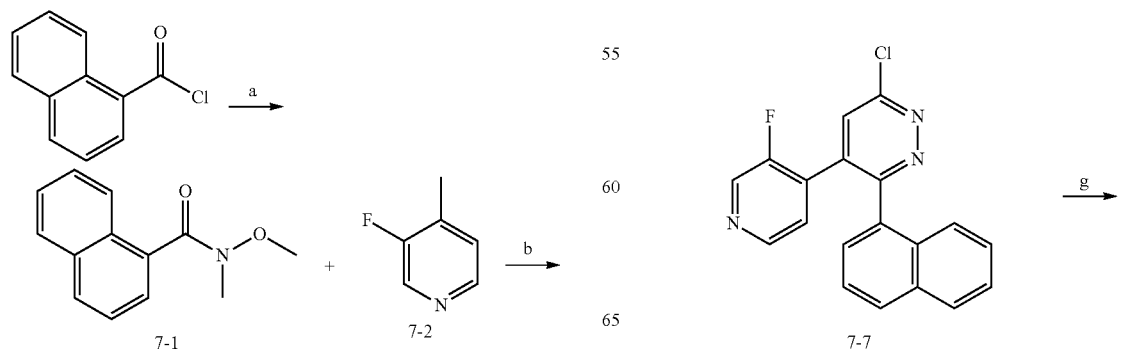

-continued

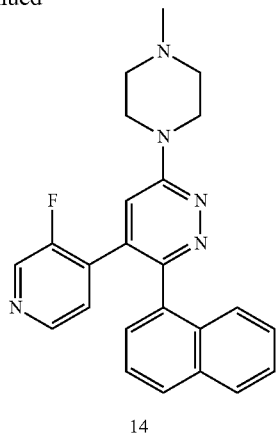

14

Reagents and conditions:
a) HNMe(OMe)HCl, DIPEA, DCM;
b) LDA, THF, -78° C.;
c) 60% NaH, 1,4-dioxane, 20° C., ethyl bromoacetate, 1 h;
d) N₂H₄, ethanol, reflux, 20 h;
e) NBS, DMSO, 72 h;
f) POCl₃, ACN, reflux, 5 h;
g) 1-methylpiperazine, ethanol, reflux.

N-methoxy-N-methyl-1-naphthamide (7-1): A mixture of 1-naphthoyl chloride (5.0 g, 26 mmol) and N,O-dimethylhydroxylamine hydrochloride (2.8 g, 29 mmol) in dichloromethane (250 mL) was stirred and cooled in an external ice bath while it was treated with diisopropylethylamine (7.7 g, 60 mmol, 11 mL) dropwise over 20 minutes. The mixture rose to 20° C. over 2 h and stirred an additional 18 h. The solvents were evaporated in vacuo and the residue was taken up in ethyl acetate (200 ml), washed with 1N HCl (100 mL), water (100 mL) and brine (50 mL). The organic layer was dried (Na₂SO₄) and evaporated to a tan oil (5.6 g, 100%). $^1$H NMR (300 MHz, CDCl₃): δ 7.95-7.85 (m, 3H), 7.58-7.45 (m, 4H), 3.55 (bs, 3H), 3.40 (bs, 3H). LC/MS (method A) $R_t$=4.31 min, purity>95%, (M+H⁺)=216.

2-(3-fluoropyridin-4-yl)-1-(naphthalen-1-yl)ethan-1-one (7-3): A fresh solution of LDA was prepared by treating a solution of diisopropylamine (3.5 g, 35 mmol, 4.8 ml) in anhydrous THF (50 mL) under nitrogen atmosphere in an external ice bath with a solution of n-butyllithium (2.5 M in hexanes, 14 mL, 35 mmol) and allowing it to stir for 30 minutes. The LDA solution was added via cannula to a solution of 3-fluoro-4-picoline (7-2) (2.6 g, 23 mmol, 2.3 mL) in THF (100 ml) under nitrogen atmosphere at −78° C. over 20 minutes followed by additional stirring for 60 minutes. A solution of N-methoxy-N-methyl-1-naphthamide (7-1) (5.5 g, 26 mmol) in THF (50 mL) was added dropwise to the fluoropicoline anion solution over 30 minutes ensuring the temperature did not rise above −70° C. The mixture warmed to 20° C. over 6 h then stirred an additional 12 h. The mixture was treated with saturated ammonium chloride solution (20 mL) and stirred 30 minutes. The solvents were evaporated to 20% of the original volume (approx.) and the residue was dissolved in ethyl acetate (200 mL) and washed with water (100 mL) and brine (50 mL). The organic layer was dried (Na₂SO₄) and evaporated in vacuo. The crude product was chromatographed on silica gel eluted with a gradient of ethyl acetate in hexanes (33%-50%) to leave the product as a light yellow solid (3.2 g, 53%). This product was dissolved in ethyl acetate (50 mL) and extracted with 1N HCl (2×50 mL). The acid layers were cautiously neutralized to pH=9 and extracted with ethyl acetate (2×50 mL). The extracts were dried (Na₂SO₄) and evaporated to leave a beige solid (1.2 g, 17%). $^1$H NMR (300 MHz, CDCl₃): δ 8.65 (d, J=8.5 Hz, 1H), 8.49 (bs, 1H), 8.40 (bs, 1H), 8.05 (d, J=6.8 Hz, 1H), 8.02 (d, J=6.1 Hz, 1H), 7.89 (d, J=8.5 Hz, 1H), 7.63-7.53 (m, 3H), 7.29 (dd, J=5.6 Hz, J=5.2 Hz), 4.46 (s, 2H). LC/MS (method A) $R_t$=4.32 min, purity>90%, (M+H⁺)=266.

Ethyl 3-(3-fluoropyridin-4-yl)-4-(naphthalen-1-yl)-4-oxobutanoate (7-4): A solution of 2-(3-fluoropyridin-4-yl)-1-(naphthalen-1-yl)ethan-1-one (7-3) 1.2 g, 4.5 mmol) in dioxane (25 mL) was treated with sodium hydride (60% in mineral oil, 0.20 g, 5.1 mmol) under nitrogen atmosphere and stirred for 60 minutes. The resulting mixture was treated with ethyl 2-bromoacetate (0.85 g, 5.1 mmol, 0.57 mL) and stirred 3 h. The mixture was treated with saturated aqueous ammonium chloride (5 mL) and stirred 30 minutes. The solvent volume was reduced to 20% of the original volume (approx.) and the residue was dissolved in ethyl acetate (50 mL) and saturated aqueous sodium bicarbonate solution (50 mL). The organic layer was separated, washed with brine (50 mL), dried (Na₂SO₄) and evaporated in vacuo. The residue was dissolved in aqueous methanol (20 mL) and purified by RPHPLC (method B). The product fractions were combined and evaporated to remove acetonitrile. The residue was treated with saturated aqueous sodium bicarbonate solution and extracted with ethyl acetate (2×25 mL). The combined extracts were washed with brine, dried (Na₂SO₄) and evaporated to leave the desired product as an oil (830 mg, 53%). $^1$H NMR (300 MHz, CDCl₃): δ 8.47 (d, J=8.2 Hz, 1H), 8.36 (s, 1H), 8.30 (d, J=4.7 Hz, 1H), 8.01 (d, J=7.0 Hz, 1H), 7.96 (d, J=4.2 Hz, 1H), 7.83 (d, J=7.4 Hz, 1H), 7.60-7.43 (m, 3H), 7.28 (dd, J=5.6 Hz, J=5.6 Hz), 5.50 (dd, J=9.4 Hz, J=5.4 Hz, 1H), 4.18 (q, J=7.0 Hz, 2H), 3.47 (dd, J=17.0 Hz, J=9.4 Hz, 1H), 2.77 (dd, J=17.0 Hz, J=5.4 Hz, 1H), 1.23 (t, J=7.0 Hz, 3H). LC/MS (method A) Rt=5.38 min, purity>95%, (M+H⁺)=352.

5-(3-Fluoropyridin-4-yl)-6-(naphthalen-1-yl)-4,5-dihydropyridazin-3(2H)-one (7-5): A solution of ethyl 3-(3-fluoropyridin-4-yl)-4-(naphthalen-1-yl)-4-oxobutanoate (0.82 g, 2.3 mmol) in ethanol (95%, 10 mL) was treated with 85% hydrazine (4.5 mL) and acetic acid (0.30 mL) and the mixture was heated to reflux for 18 h. The solvents were evaporated and the residue was purified by RPHPLC (method B). The product fraction was treated with saturated sodium bicarbonate solution and extracted with ethyl acetate (2×50 mL). The combined extracts were washed with brine, dried (Na₂SO₄) and evaporated in vacuo to leave a tan solid (180 mg, 25%). $^1$H NMR (300 MHz, CDCl₃): δ 8.85 (bs, 1H), 8.39 (d, J=1.4 Hz, 1H), 8.32 (d, J=5.0 Hz, 1H), 8.29 (d, J=8.5 Hz, 1H), 7.86 (m, 2H), 7.61-7.51 (m, 2H), 7.41-7.31 (m, 2H), 7.18 (dd, J=5.9 Hz, J=5.3 Hz, 1H), 4.79 (dd, J=7.9 Hz, J=4.4 Hz, 1H), 3.20 (dd, J=17.2 Hz, J=7.9 Hz, 1H), 2.93 (dd, J=17.2 Hz, J=4.4 Hz, 1H). LC/MS (method A) Rt=3.89 min, purity>95%, (M+H⁺)=320.

5-(3-Fluoropyridin-4-yl)-6-(naphthalen-1-yl)pyridazin-3(2H)-one (7-6): A solution of 5-(3-fluoropyridin-4-yl)-6-(naphthalen-1-yl)-4,5-dihydropyridazin-3(2H)-one (170 mg, 0.53 mmol) in DMSO (3 mL) and water (85 µL) was treated with N-bromosuccinimide (470 mg, 2.7 mmol). The reaction became slightly exothermic while stirring then cooled to 20° C. and stirred an additional 18 h. The reaction mixture was diluted with ethyl acetate (50 mL), washed with saturated sodium bicarbonate solution (50 mL) and brine (50 mL). The solution was dried (Na₂SO₄) and evaporated. The crude product was purified by RPHPLC (method B) and the product fractions were combined, treated with saturated sodium bicarbonate solution and extracted with ethyl acetate (2×25 mL). The combined extracts were washed with brine (25 mL), dried (Na₂SO₄) and evaporated to leave the product as a white foamy solid (150 mg, 89%). ¹H NMR (300 MHz, CDCl₃): δ 11.66 (bs, 1H), 8.26 (bs, 1H), 8.11 (d, J=5.0 Hz, 1H), 7.85-7.75 (m, 2H), 7.70-7.60 (m, 1H), 7.50-7.27 (m, 4H), 7.14 (s, 1H), 6.86 (dd, J=5.9 Hz, J=5.3 Hz, 1H). LC/MS (method A) $R_t$=3.92 min, purity>95%, (M+H⁺)= 318.

6-chloro-4-(3-fluoropyridin-4-yl)-3-(naphthalen-1-yl) pyridazine (7-7): 6-(Naphthalen-1-yl)-5-(3-fluoropyridin-4-yl)-2,3-dihydropyridazin-3-one (7-6, 0.120 g, 0.37 mmol) and 4 mL acetonitrile was taken in a flask, fitted with condenser and dry tube and added phosphorousoxychloride (145 mg, 0.94 mmoL, 90 μL). Reflux at 90° C. for 5 hr (reaction was monitored by HPLC). Reaction mixture was cooled at ambient temperature and then remove POCl₃ in reduced pressure, added crushed ice and cautiously added 10N NaOH with stirring until it reaches a pH~8. Fine precipitate observed. Extract with dichloromethane several times and dried (Na₂SO₄) and evaporated. Product was purified over a small silica gel filter column eluted with 40% ethyl acetate and Hexane. The purified compound was isolated as light pinkish powder (115 mg), 92% (gravimetric) yield. HPLC (tr/purity): 20.06 min, >95% (HPLC method A), mass (ESI) m/z=336.0 (M+1).

4-(3-fluoropyridin-4-yl)-6-(4-methylpiperazin-1-yl)-3-(naphthalen-1-yl)pyridazine (14): (MW-109): A mixture of 6-chloro-4-(3-fluoropyridin-4-yl)-3-(naphthalen-1-yl) pyridazine (7-7, 0.090 g, 0.26 mmol), 5 mL ethanol and 1-methylpiperazine (0.13 g, 0.15 mL, 1.3 mmol) was taken in a heavy glass vial and blanket with argon and capped immediately. The reaction vial was heated at 120° C. for 26 hr. (reaction was monitored by HPLC). Reaction mixture was cooled to ambient temperature and removes the volatiles under reduced pressure. To the yellow residue added 1 mL water and extracted several times with dichloromethane. The combined organic solvent was dried over anhydrous sodium sulphate and evaporated under reduced pressure. The product 14 was purified over silica gel (200-400 mesh) column with ethyl acetate: hexane (2:3 v/v) eluent. The purified product 14 was isolated as fluffy beige color solid (90 mg), 86% (gravimetric) yield. ¹H-NMR (500 MHz, CDCl₃): δ 8.29 (d, 1H); 8.06 (d, J=5 Hz, 1H); 7.80 (dd, J=5, 10 Hz, 2H); 7.67 (d, J=10 Hz, 1H); 7.42-7.28 (m, 4H); 7.0 (s, 1H); 6.81 (t, J=5, 5 Hz, 1H); 3.92 (bs, 4H); 2.74 (bs, 4H); 2.49 (s, 3H). HPLC (tr/purity): 12.1 min, >97% (HPLC method A), mass (ESI) m/z=400.2. HRMS calculated for $C_{22}H_{22}FN_5$, 399.18592. found 399.18602.

Example 8

Scheme 8.

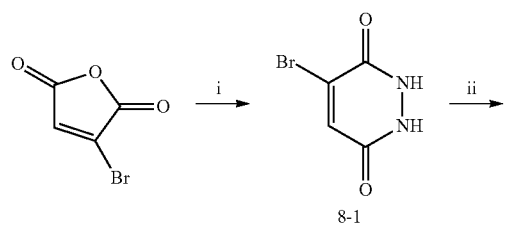

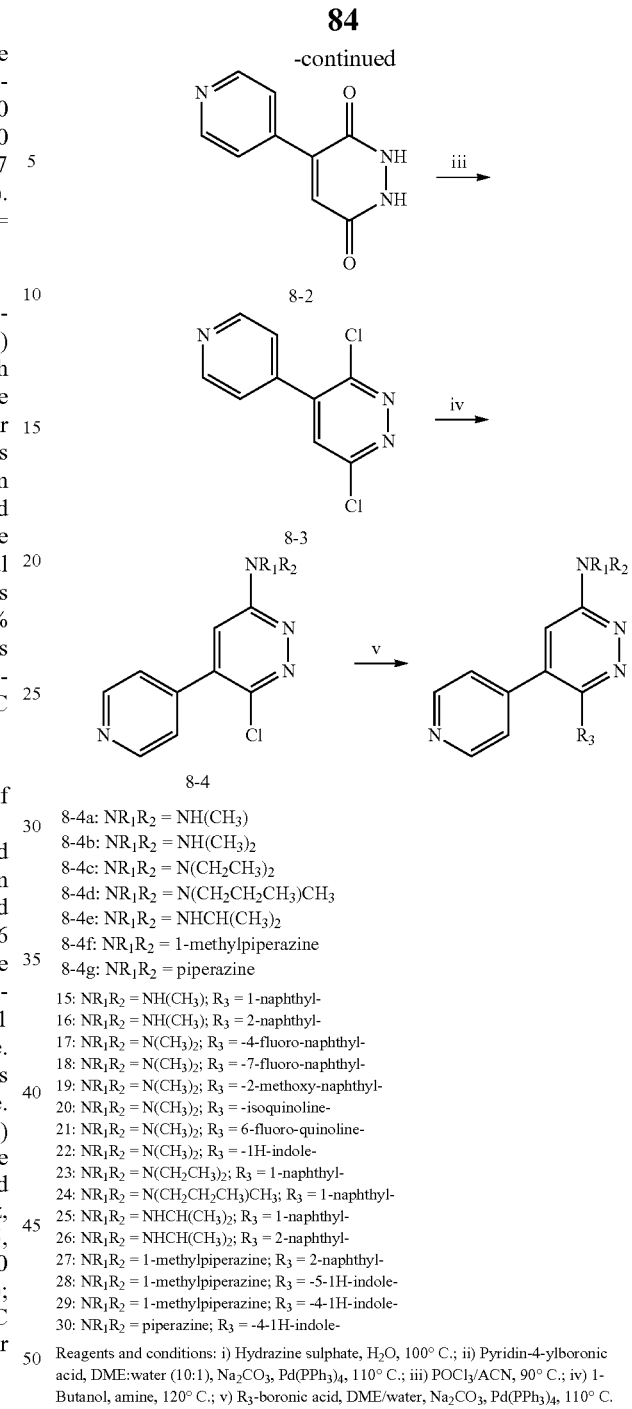

8-4a: NR₁R₂ = NH(CH₃)
8-4b: NR₁R₂ = NH(CH₃)₂
8-4c: NR₁R₂ = N(CH₂CH₃)₂
8-4d: NR₁R₂ = N(CH₂CH₂CH₃)CH₃
8-4e: NR₁R₂ = NHCH(CH₃)₂
8-4f: NR₁R₂ = 1-methylpiperazine
8-4g: NR₁R₂ = piperazine 15: NR₁R₂ = NH(CH₃); R₃ = 1-naphthyl-
16: NR₁R₂ = NH(CH₃); R₃ = 2-naphthyl-
17: NR₁R₂ = N(CH₃)₂; R₃ = -4-fluoro-naphthyl-
18: NR₁R₂ = N(CH₃)₂; R₃ = -7-fluoro-naphthyl-
19: NR₁R₂ = N(CH₃)₂; R₃ = -2-methoxy-naphthyl-
20: NR₁R₂ = N(CH₃)₂; R₃ = -isoquinoline-
21: NR₁R₂ = N(CH₃)₂; R₃ = 6-fluoro-quinoline-
22: NR₁R₂ = N(CH₃)₂; R₃ = -1H-indole-
23: NR₁R₂ = N(CH₂CH₃)₂; R₃ = 1-naphthyl-
24: NR₁R₂ = N(CH₂CH₂CH₃)CH₃; R₃ = 1-naphthyl-
25: NR₁R₂ = NHCH(CH₃)₂; R₃ = 1-naphthyl-
26: NR₁R₂ = NHCH(CH₃)₂; R₃ = 2-naphthyl-
27: NR₁R₂ = 1-methylpiperazine; R₃ = 2-naphthyl-
28: NR₁R₂ = 1-methylpiperazine; R₃ = -5-1H-indole-
29: NR₁R₂ = 1-methylpiperazine; R₃ = -4-1H-indole-
30: NR₁R₂ = piperazine; R₃ = -4-1H-indole- Reagents and conditions: i) Hydrazine sulphate, H₂O, 100° C.; ii) Pyridin-4-ylboronic acid, DME:water (10:1), Na₂CO₃, Pd(PPh₃)₄, 110° C.; iii) POCl₃/ACN, 90° C.; iv) 1-Butanol, amine, 120° C.; v) R₃-boronic acid, DME/water, Na₂CO₃, Pd(PPh₃)₄, 110° C.

4-bromo-1,2-dihydropyridazine-3,6-dione (8-1): Hydrazine sulfate (2.25 g, 17.2 mmol) was dissolved in boiling water (20 mL) with stirring. To this solution, bromomaleic anhydride (2.6 mL, 28.2 mmol) was added drop wise via addition funnel, the mixture heated (100° C.) under reflux for 19 h, then cooled to ambient temperature. The resulting white precipitate was filtered on a medium frit sintered glass funnel, washed with acetone (3×5 mL), and air dried in vacuo to give 4-bromo-1,2-dihydropyridazine-3,6-dione (2.85 g) as a white powder in 87% yield (gravimetric) with a melting point of 262° C.

4-(pyridin-4-yl)-1,2-dihydropyridazine-3,6-dione (8-2): Essentially as previously described in Watterson et al., *PLOS ONE*, 2013, 8, e66226, compound 8-1 (2 g, 10.4 mmol, 1 eq)

and pyridin-4-yl boronic acid (14.3 mmol, 1.76 g, 1.37 eq) were suspended in dimethoxyethane and water (10:1 v/v) in a heavy wall pressure vessel and purged with argon for 15 min. Tetrakis(triphenylphosphine)palladium (0.1 eq) and sodium carbonate (3 eq) were added, the vessel immediately capped, the reaction mixture heated (110° C.). for 18 h, then cooled to ambient temperature and subjected to filtration on a medium frit sintered glass funnel containing Celite® 545. The filtrate was concentrated in vacuo and the concentrate triturated with hexane. The yellow product 8-2 (2.2 g) exhibited a mass (ESI) of m/z (MeOH)=190.06 (MO, and was taken to the next step without further purification.

3,6-dichloro-4-(pyridin-4-yl)pyridazine (8-3): Essentially as described in Watterson et al., PLOS ONE, 2013, 8, e66226, compound 8-2 (2.2 g, 11.6 mmol) was suspended in 6.25 mL phosphorus oxychloride in a condenser-fitted round bottom flask, heated (90° C.) for 24 h, cooled to ambient temperature and volatiles removed in vacuo. The dark residue was poured onto crushed ice, stirred (2 h), and the mixture neutralized with saturated sodium carbonate solution. The fine precipitate was subjected to replicate extraction with dichloromethane in a separatory funnel, the combined organic phases subjected to drying over anhydrous sodium sulfate, concentrated in vacuo, and subjected to column chromatography on silica gel (200-400 mesh) using a ethyl acetate:hexane (3:2 v/v) eluent. The desired product 8-3 exhibited 97% purity by HPLC and a mass (ESI) of m/z (MeOH)=225.99 (MH$^+$). The overall yield (gravimetric) from product 8-1 to 8-3 was approximately 36%.

6-chloro-N-methyl-5-(pyridin-4-yl)pyridazin-3-amine (8-4a): Following the published protocol in Watterson et al., PLOS ONE, 2013, 8, e66226, compound 8-3 (0.750 g, 3.3 mmol, 1 eq) and 25 mL 1-butanol were placed in a heavy wall pressure vessel (Chemglass, Vineland, N.J.) and 40% methylamine (0.618 g, 19.9 mmol, 6 eq) was added, the vessel capped and heated at 110° C. for 4 h. The reaction mixture was cooled to ambient temperature, transferred to a round bottom flask and concentrated in vacuo. The residue was treated with 10 mL of water and the aqueous phase subjected to replicate extraction with ethyl acetate using separatory funnel. The combined organic layers were dried with anhydrous sodium sulfate and evaporated under reduced pressure leaving a yellow solid. The reaction mixture was purified by crystallization with methanol to give product 8-4a as a white crystals (0.500 g) in 68% (gravimetric) yield, HPLC (tr/purity): 10.13 min >95% (HPLC method A), and a mass (ESI) m/z (MeOH)=221.10 (MH$^+$).

N-methyl-6-(naphthalen-1-yl)-5-(pyridin-4-yl)pyridazin-3-amine (15): (MW-156): Compound N-methyl-6-(naphthalen-1-yl)-5-(pyridin-4-yl)pyridazin-3-amine (8-4a) (0.450 g, 2.02 mmol, 1 eq) and 1-napthylboronic acid (0.480 g, 2.79 mmol, 1.37 eq) was suspended in dimethoxyethane (DME) and water mixture (10:1 v/v) in a heavy wall pressure vessel (Chemglass, Vineland, N.J.) and purged with argon for 15 min. Subsequently, Tetrakis(triphenylphosphine)palladium (0.212 g, 9 mol %,) and Na$_2$CO$_3$ (0.670 g, 6.32 mmol, 3.1 eq) were added vessel purged with argon and immediately capped with a Teflon bushing, heated (110° C.) for 16 hr, and cooled to ambient temperature. The reaction mixture was subjected to filtration on a medium frit sintered glass funnel containing Celite® 545. The resultant filtrate was concentrated in vacuo, the residue dissolved in ethyl acetate and subjected to water wash washed (3×10 mL) using a separatory funnel. The organic layer was dried over anhydrous sodium sulfate and concentrated by rotary evaporation under reduced pressure. The crude mixture was subjected to silica gel (200-400 mesh) column chromatography with product elution using ethyl acetate: methanol (19:1 v/v). The product 15 was obtained as pale yellow crystals (464 mg) in 63% yield (gravimetric). $^1$H-NMR (500 MHz, CDCl$_3$): δ 8.33 (dd, J=1.6, 4.5 Hz, 2H); 7.83 (d, J=8.25, 2H); 7.65 (d, J=8.4, 1H); 7.43-7.26 (m, 4H); 6.94 (dd, J=1.6, 4.5 Hz, 2H); 6.75 (s, 1H); 5.29 (m, 1H); 3.13 (d, J=4.95, 3H). HPLC (tr/purity): 11.60 min >97% (HPLC method A); mass (ESI) of m/z (MeOH): 313.10 (MH$^+$); HRMS calculated for C$_{20}$H$_{16}$N$_4$ 312.1375. found 312.1378.

N-methyl-6-(naphthalen-2-yl)-5-(pyridin-4-yl)pyridazin-3-amine (16): (MW-200): Product 16 was produced using the same protocol 'Suzuki' reaction as above for 15 but using 2-napthylboronic acid (427 mg, 2.48 mmol, 1.37 eq) was suspended in dimethoxyethane (DME) and water mixture (10:1 v/v). Product 16 was purified by silica gel (200-400 mesh) column chromatography with product elution using ethyl acetate: hexane (1:1 v/v). The final product 16 was obtained as white crystals (360 mg) in 63% (gravimetric) yield. $^1$H-NMR (500 MHz CDCl$_3$): δ 8.54 (dd, J=1.55, 4.45 Hz, 2H); 7.91 (s, 1H); 7.80-7.68 (m, 3H); 7.49-7.31 (m, 3H); 7.14 (dd, J=1.6, 4.45 Hz, 2H); 6.68 (s, 1H); 5.21 (b, 1H, —NH); 3.15 (d, J=4.95, 3H). HPLC (tr/purity): 12.15 min >97% (HPLC method A); mass (ESI) m/z (MeOH): 313.10 (MH$^+$); HRMS calculated for C$_{20}$H$_{16}$N$_4$ 312.1335. found 312.1375.

6-chloro-N,N-dimethyl-5-(pyridin-4-yl)pyridazin-3-amine (8-4b): Product 8-4b was made following the same protocol described above for 8-4a, using 40% dimethylamine (0.590, 13.2 mmol, 6 eq) in ethanol and heated (110° C.) for 16 h. Product 8-4b was obtained as a yellow solid in 89% (gravimetric) yield, with an apparent HPLC (tr/purity): 11.45 min >98% (HPLC method A), $^1$H NMR (500 MHz, CDCl$_3$): δ 8.76 (d, J=5.0 Hz, 2H); 7.41 (m, 2H); 6.70 (s, 1H); 3.22 (s, 6H); and a mass (ESI) m/z (MeOH)=235.10 (MH$^+$).

6-(4-fluoronaphthalen-1-yl)-N,N-dimethyl-5-(pyridin-4-yl)pyridazin-3-amine (17): MW-078: Product 17 was synthesized using the same 'Suzuki' reaction protocol for 15 as above but using 8-4b. Compound 6-chloro-N,N-dimethyl-5-(pyridin-4-yl)pyridazin-3-amine (8-4b) (1 g, 4.2 mmol) and 4-fluoronaphthalen-1-yl)boronic acid (1.1 g, 5.85 mmol, 1.3 eq) was suspended in dimethoxyethane (DME) and water mixture (10:1 v/v) and followed the above protocol. The final product 17 was purified by silica gel (200-400 mesh) column chromatography using ethyl acetate: hexane (3:7 v/v) eluent. Product 17 was obtained as a crystalline powder (710 mg) in 51% (gravimetric) yield; $^1$H NMR (500MHz, CDCl$_3$): δ 8.37 (d, J=4.6 Hz, 2H); 8.10 (d, J=8.3 Hz, 1H); 7.69 (d, J=8.5 Hz, 1H); 7.50-7.39 (m, 2H); 7.22-7.04 (m, 2H); 6.99 (d, J=5.8 Hz, 2H); 6.84 (s, 1H); 3.33 (s, 6H). HPLC (tr/purity): 13.7 min >97% (method A); mass (ESI) m/z (MeOH): 345.10 (MO; HRMS calculated for C$_{21}$H$_7$FN$_4$ 344.1437. found 344.1442.

6-(7-fluoronaphthalen-1-yl)-N,N-dimethyl-5-(pyridin-4-yl)pyridazin-3-amine (18): (MW-085): Product 18 was synthesized using the same protocol as above for 15. Compound 6-chloro-N,N-dimethyl-5-(pyridin-4-yl)pyridazin-3-amine (8-4b) and (7-fluoronaphthalen-1-yl)boronic acid was suspended in dimethoxyethane (DME) and water (10:1 v/v) and followed the same protocol above. The product 18 was purified by silica gel (200-400 mesh) column chromatography using ethyl acetate and hexane (2:3 v/v) eluent. Product 18 was obtained as light yellow needle-like crystals (200 mg) in 62% (gravimetric) yield. $^1$H NMR (500MHz, CDCl$_3$): δ 8.37 (dd, J=1.6, 4.5 Hz, 2H); 7.83 (m, 1H); 7.35-7.28 (m, 3H); 7.22-7.18 (m, 1H); 6.99 (dd, J=6.2, 4.5

Hz, 2H); 6.84 (s, 1H); 3.33 (s, 6H). LC/MS (tr/purity): 1.82 min, 99.6%; mass (ESI) m/z (MeOH): 345.7 (MH⁺).

6-(2-methoxynaphthalen-1-yl)-N,N-dimethyl-5-(pyridin-4-yl)pyridazin-3-amine (19): (MW-155): Product 19 was synthesized using the same protocol as above for 15. Compound 6-chloro-N,N-dimethyl-5-(pyridin-4-yl)pyridazin-3-amine (8-4b) (0.400 g, 1.7 mmol) and (2-methoxynaphthalen-1-yl)boronic acid (0.334 g, 2.3 mmol) was suspended in dimethoxyethane (DME) and water (10:1 v/v) and followed the same protocol above. The product 19 was purified by silica gel (200-400 mesh) column chromatography using (2:3 v/v) ethyl acetate and hexane followed by crystallization in methanol and hexane. Product 19 was obtained as white crystals (398 mg) in 66% (gravimetric) yield. ¹H NMR (500 MHz, CDCl₃): δ 8.34 (dd, J=5.5 Hz, 2H); 7.83 (d, J=10 Hz, 1H); 7.78 (d, J=5 Hz, 1H); 7.64 (d, J=10 Hz, 1H); 7.40-7.31 (m, 2H); 7.04 (d, J=5 Hz, 1H); 6.95 (dd, J=5, 5 Hz, 2H); 6.81 (s, 1H); 3.47 (s, 3H); 3.30 (s, 6H). HPLC (tr/purity): 12.4 min >97% (method A); exhibited a mass (ESI) m/z (MeOH): 357.10 (MH⁺).

6-(isoquinolin-5-yl)-N,N-dimethyl-5-(pyridin-4-yl)pyridazin-3-amine (20): (MW-082): Product 20 was synthesized using the same protocol as above for 15. Compound 6-chloro-N,N-dimethyl-5-(pyridin-4-yl)pyridazin-3-amine (8-4b) (0.500 g, 2.1 mmol, 1 eq), and isoquinolin-5-ylboronic acid (0.504 g, 2.9 mmol, 1.3 eq) was suspended in dimethoxyethane (DME) and water (10:1 v/v) and followed the same protocol above. The combined organic extracts were dried over anhydrous sodium sulfate, and concentrated under reduced pressure using rotary evaporator. The product 20 was purified by silica gel (200-400 mesh) column chromatography using ethyl acetate and 5% methanol eluent. Product 20 obtained as yellowish-white powder (470 mg) in 68% (gravimetric) yield. ¹H-NMR (500MHz, CDCl₃): δ 9.25 (s, 1H); 8.42-8.38 (m, 3H); 7.97 (d, J=8.0, 1H); 7.59-7.45 (m, 3H); 6.97 (dd, J=1.5, 4.5, 2H); 6.85 (s, 1H); 3.33 (s, 6H). HPLC (tr/purity): 9.2 min >97% (method A); exhibited a mass (ESI) m/z (MeOH): 328.10 (MH⁺).

6-(6-fluoroquinolin-8-yl)-N,N-dimethyl-5-(pyridin-4-yl)pyridazin-3-amine (21): (MW-165): Product 21 was synthesized using the same protocol as above for 15. Compound 6-chloro-N,N-dimethyl-5-(pyridin-4-yl)pyridazin-3-amine (8-4b) (0.400 g, 1.7 mmol, 1 eq), and (6-fluoroquinolin-8-yl)boronic acid (0.437 g, 2.2 mmol, 1.3 eq) was suspended in dimethoxyethane (DME) and water (10:1 v/v) and followed the same protocol above. The product 21 was purified by silica gel (200-400 mesh) column chromatography using ethyl acetate and hexane (4:1 v/v) eluent, followed by crystallization with ethyl acetate. Product 21 obtained as white crystals (250 mg) in 45% (gravimetric) yield. ¹H-NMR (500MHz, CDCl₃): δ 8.4 (dd, J=5.5 Hz, 1H); 8.27 (dd, J=5, 5 Hz, 2H); 7.96 (dd, J=5.5 Hz, 1H); 7.90 (dd, J=5.5 Hz, 1H); 7.44 (d, J=5, 7.5 Hz, 1H); 7.18 (dd, J=5, 10 Hz, 1H); 7.08 (d, J=5 Hz, 2H); 6.80 (s, 1H); 3.30 (s, 6H); HPLC (tr/purity): 10.9 min >97% (method A); exhibited a mass (ESI) m/z (MeOH): 346.10 (MH⁺).

6-(1H-indol-5-yl)-N,N-dimethyl-5-(pyridin-4-yl)pyridazin-3-amine (22): (MW-066): Product 22 was synthesized using the same protocol as above for 15. Compound 6-chloro-N,N-dimethyl-5-(pyridin-4-yl)pyridazin-3-amine (8-4b) (0.500 g, 2.1 mmol, 1 eq), (1H-indol-5-yl)boronic acid (0.470 g, 2.9 mmol, 1.3 eq) was suspended in dimethoxyethane (DME) and water (10:1 v/v) and followed the same protocol above The product 22 was purified by column chromatography on silica gel (200-400 mesh) with product elution using ethyl acetate and methanol (5%) followed by crystallization with ethyl acetate. The product 22 obtained as pale yellow powder (410 mg) in 61% (gravimetric) yield. ¹H NMR (500 MHz CD₃OD): δ 8.42 ((dd, J=1.6, 4.6 Hz, 2H); 7.51 (d, J=1.25 Hz, 2H); 7.29 (m, 4H); 7.15 (s, 1H); 6.95 (dd, J=1.6, 8.4 Hz, 1H); 6.39 (m, 1H); 3.25 (s, 6H). HPLC (tr/purity): 10.2 min >97% (method A); a mass (ESI) of m/z (MeOH): 316.10 (MH⁺).

6-chloro-N, N-diethyl-5-(pyridin-4-yl)pyridazin-3-amine (8-4c): Product 8-4c was made following the same protocol described above for 8-4a, using compound 8-3 (0.600 g, 2.65 mmol) and diethylamine (1.16 g, 15.9 mmol, 6 eq) in 1-butanol and heated (150° C.) for 24 h. Product 8-4c was obtained as a yellow solid (470 mg) in 72% (gravimetric) yield, with an apparent HPLC (tr/purity): 14.6 min >98% (HPLC method A), and a mass (ESI) m/z (MeOH)=263.10 (MH⁺).

N, N-diethyl-6-(naphthalen-1-yl)-5-(pyridin-4-yl)pyridazin-3-amine (23): (MW-033): Product 23 was synthesized using the same 'Suzuki' reaction protocol for 15 as before but using 8-4c. Compound 6-chloro-N, N-diethyl-5-(pyridin-4-yl)pyridazin-3-amine (8-4c) (0.490 g, 1.8 mmol, 1 eq) and 1-napthylboronic acid (0.440 g, 2.56 mmol, 1.37 eq) was suspended in dimethoxyethane (DME) and water mixture (10:1 v/v) and followed the above protocol as described for 15. The product 23 was purified by silica gel (200-400 mesh) column chromatography using ethyl acetate and hexane (1:4 v/v) eluent. Product 23 obtained as pale yellow powder (470 mg) in 69% (gravimetric) yield. ¹H NMR (500MHz, CDCl₃): δ 8.35 (dd, J=1.2, 4.8 Hz, 2H); 7.82 (dd, J=2.7, 8.0 Hz, 2H); 7.74 (d, J=8.4 Hz, 1H); 7.43-7.26 (m, 4H); 6.99 (dd, J=1.5, 4.5 Hz, 2H); 6.76 (s, 1H); 3.76 (dd, J=7.0, 14.1 Hz, 4H); 1.34 (t, J=7.05, 7.05 Hz, 6H). HPLC (tr/purity): 15.01 min >96% (method A); exhibited a mass (ESI) m/z (MeOH): 355.20 (MH⁺).

6-chloro-N-methyl-N-propyl-5-(pyridin-4-yl)pyridazin-3-amine (8-4d): Product 8-4d was made following the same protocol described above for 8-4a, using compound 8-3 (0.600 g, 2.6 mmol) and N-methylpropane-1-amine (1.16 g, 15.9 mmol) 1-butanol and heated (110° C.) for 17 h. Product 8-4d was obtained as a yellow powder (510 mg) in 79% (gravimetric) yield, with an apparent HPLC (tr/purity): 14.9 min >96% (HPLC method A), and a mass (ESI) m/z (MeOH)=263.10 (MH⁺).

N-methyl-6-(naphthalen-1-yl)-N-propyl-5-(pyridin-4-yl)pyridazin-3-amine (24): (MW-010): Product 24 was synthesized using the same 'Suzuki' reaction protocol for 15 as before but using 8-4d. Compound 6-chloro-N-methyl-N-propyl-5-(pyridin-4-yl)pyridazin-3-amine (8-4d) (0.490 g, 1.8 mmol) and 1-napthylboronic acid (0.440 g, 2.56 mmol) was suspended in dimethoxyethane (DME) and water mixture (10:1 v/v). The product 24 was purified by column chromatography on silica gel (200-400 mesh) using ethyl acetate: hexane (2:3 v/v) eluent. The final product 24 was obtained as whitish powder (460 mg) in 69% yield (gravimetric). ¹H NMR (500MHz, CDCl₃): δ 8.35 (dd, J=1.6, 4.57 Hz, 2H); 7.82 (d, J=8.1 Hz, 2H); 7.71 (d, J=8.4 Hz, 1H); 7.43-7.26 (m, 4H); 6.99 (dd, J=1.6, 4.5 Hz, 2H); 6.79 (s, 1H); 3.71 (t, J=7.4, 7.4 Hz, 2H); 3.29 (s, 3H); 1.79 (m, 2H); 1.03 (t, J=7.35, 7.45 Hz, 3H). HPLC (tr/purity): 15.08 min, >96% (method A); exhibited a mass (ESI) m/z (MeOH): 355.10 (MH⁺).

6-chloro-N-isopropyl-5-(pyridin-4-yl)pyridazin-3-amine (8-4e): Product 8-4e was made following the same protocol described above for 8-4a, using compound 8-3 (0.600 g, 2.6 mmol) and isopropyl-amine (0.939 g, 15.9 mmol, 6 eq) in 1-butanol and heated (120° C.) for 25 h. The product 8-4e was purified by column chromatography on silica gel (200-400 mesh) and eluted with ethyl acetate: hexane (9:1 v/v)

followed by crystallization from ethyl acetate and hexane to give the desired product 8-4e as pale yellow crystals (445 mg) in 59% yield, with an apparent HPLC purity of 97% and exhibited a mass (ESI) m/z (MeOH)=249.00 (MH$^+$).

N-isopropyl-6-(naphthalen-1-yl)-5-(pyridin-4-yl) pyridazin-3-amine (25): (MW-031): Product 25 was synthesized using the same 'Suzuki' reaction protocol for 15 as before. Compound 6-chloro-N-isopropyl-5-(pyridin-4-yl)pyridazin-3-amine (8-4e) (0.370 g, 1.48 mmol, 1 eq) and 1-napthylboronic acid (0.350 g, 2.03 mmol, 1.37 eq) was suspended in dimethoxyethane (DME) and water mixture (10:1 v/v) and followed the same above procedure. The product 25 was purified by column chromatography on silica gel (200-400 mesh) using ethyl acetate: hexane (2:3 v/v) eluent. The final product 25 was obtained as light yellow powder (279 mg) in 54% yield (gravimetric). $^1$H-NMR (500 MHz, CDCl$_3$): δ 8.34 (dd, J=1.55, 6.05 Hz, 2H); 7.83 (d, J=8.2 Hz, 2H); 7.67 (d, J=8.4 Hz, 1H); 7.43-7.26 (m, 4H); 6.95 (dd, J=1.6, 6.1, 2H); 6.70 (s, 1H); 5.05 (b, 1H); 4.20 (m, 1H); 1.37 (d, J=6.4 Hz, 6H). HPLC (tr/purity): 12.9 min, >97% (method A); exhibited a mass (ESI) m/z (MeOH): 341.10 (MH$^+$).

N-isopropyl-6-(naphthalen-2-yl)-5-(pyridin-4-yl) pyridazin-3-amine (26): MW-025): Product 26 was synthesized using the same 'Suzuki' reaction protocol for 15 as before. Compound 6-chloro-N-isopropyl-5-(pyridin-4-yl)pyridazin-3-amine (8-4e) (0.500 g, 1.8 mmol, 1 eq) and 2-napthylboronic acid (0.426 g, 2.47 mmol, 1.37 eq) was suspended in dimethoxyethane (DME) and water mixture (10:1 v/v) and followed the same above procedure. The product 26 was purified by column chromatography on silica gel (200-400 mesh) using ethyl acetate: hexane (3:2 v/v) eluent and product 51 obtained as white crystals (390 mg) in 57% (gravimetric) yield. $^1$H NMR (500MHz, CDCl$_3$): δ 8.54 (dd, J=1.55, 4.5 Hz, 2H); 7.92 (s, 1H); 7.80-7.68 (m, 3H); 7.49-7.31 (m, 3H); 7.13 (dd, J=1.55, 4.0 Hz, 2H); 6.61 (s, 1H); 4.92 (b, 1H, —NH); 4.22 (m, 1H); 1.36 (d, J=6.4 Hz, 6H). HPLC (tr/purity): 13.3 min >96% (method A) and exhibited a mass (ESI) m/z (MeOH): 341.10 (MH$^+$).

3-chloro-6-(4-methylpiperazin-1-yl)-4-(pyridin-4-yl) pyridazine (8-4f): Product 8-4f was made following the same protocol described above for 8-4a, using compound 8-3 (0.750 g, 3.3 mmol) and 1-methylpiperazine (1.4 g, 13.2 mmol) in 1-butanol and heated (120° C.) for 17 h. The product 8-4f was purified by column chromatography on silica gel (200-400 mesh) and eluted with 2% methanol and ethyl acetate to give the desired product 8-4f as a beige powder (620 mg) in 78% yield (gravimetric), purity By HPLC >93%; with a mass (ESI) of m/z (MeOH)=290.71 (MH$^+$).

6-(4-methylpiperazine-1-yl)-3-(naphthalen-2-yl)-4-(pyridin-4-yl)pyridazine (27): (MW-150): Product 27 was synthesized using the same 'Suzuki' reaction protocol for 15 as before but using 8-4f. Compound 3-chloro-6-(4-methylpiperazin-1-yl)-4-(pyridin-4-yl)pyridazine (8-4f) (0.187 g, 0.6 mmol, 1 eq) and 2-napthylboronic acid (0.156 g, 0.9 mmol, 1.3 eq) was suspended in dimethoxyethane (DME) and water (10:1 v/v) in a heavy wall pressure vessel and purged with argon for 5 min. Subsequently Tetrakis(triphenylphosphine)palladium (67 mg, 9 mol %), Na$_2$CO$_3$ (0.212 g, 2.0 mmol) were added under argon, and followed the same protocol mentioned above. The product 27 was purified by column chromatography on silica gel (200-400 mesh) using dichloromethane and 5% methanol followed by crystallization with ethyl acetate. The product 27 obtained as beige color crystals in 68% (gravimetric) yield; MP: 187.5-188° C. (uncorrected). $^1$H NMR (500MHz, CDCl$_3$): δ 8.55 (dd, J=1.55, 4.45 Hz, 2H); 7.94 (s, 1H); 7.80-7.69 (m, 3H); 7.49-7.34 (m, 3H); 7.16 (dd, J=1.5, 4.5 Hz, 2H); 6.88 (s, 1H); 3.83 (t, J=4.8, 4.8, 4H); 2.62 (t, J=4.9, 4.9, 4H); 2.39 (s, 3H). HPLC (tr/purity): 11.26 min >97% (method a); ESI m/z (MeOH): 382.2 (MH$^+$); HRMS 381.1949 (calculated for C$_{24}$H$_{23}$N$_5$ 381.1953).

5-(6-(4-methylpiperazin-1-yl)-4-(pyridin-4-yl)pyridazin-3-yl)-1H-indole (28): (MW-118):Product 28 was synthesized using the same 'Suzuki' reaction protocol for 15 as before but using 8-4f. Compound 3-chloro-6-(4-methylpiperazin-1-yl)-4-(pyridin-4-yl)pyridazine (8-4f) (0.5 g, 1.7 mmol) and (1H-indol-5-yl)boronic acid (0.380 g, 2.3 mmol) was suspended in dimethoxyethane (DME) and water (10:1 v/v) and followed the same protocol mentioned above. The product 28 was purified by column chromatography on silica gel (200-400 mesh) with product elution using ethyl acetate and methanol (5%) followed by crystallization with ethyl acetate. The product 28 obtained as fine crystals (465 mg) in 57% (gravimetric) yield; $^1$H-NMR (500MHz, DMSOd$_6$): δ 11.16 (b, 1H); 8.49 (d, J=5 Hz, 2H); 7.49 (d, J=5 Hz, 1H); 7.34 (m, 1H); 7.28-7.23 (m, 4H); 6.93 (dd, J=5.10 Hz, 1H); 6.37 (bs 1H); 3.70 (m, 4H); 2.67 (m, 4H); 2.25 (s, 3H). HPLC (tr/purity): 4.40 min >97% (HPLC methodA); exhibited a mass (ESI) of m/z (MeOH): 371.10 (MH$^+$); HRMS calculated for C$_{22}$H$_{22}$N$_6$ 370.19059. found 370.1909.

4-(6-(4-methylpiperazin-1-yl)-4-(pyridin-4-yl)pyridazin-3-yl)-1H-indole (29): (MW-108): Product 29 was synthesized using the same 'Suzuki' reaction protocol for 15 as before but using 8-4f. Compound 3-chloro-6-(4-methylpiperazin-1-yl)-4-(pyridin-4-yl)pyridazine (8-4f) (130 mg, 0.44 mmol) and (1H-indol-4-yl)boronic acid (98 mg, 0.61 mmol) was suspended in dimethoxyethane (DME) and water (10:1 v/v) and followed the same protocol mentioned above. The product 29 was purified by column chromatography on silica gel (200-400 mesh) with product elution using 5% methanol and ethyl acetate followed by crystallization with ethyl acetate. The product 29 obtained as light yellow color powder (69 mg) in 50% (gravimetric) yield; $^1$H NMR (500MHz, CD$_3$OD): δ 8.30 (d, J=5 Hz, 2H); 7.42-7.36 (m, 2H); 7.25 (dd, J=5,5 Hz, 2H); 7.15 (d, J=5 Hz, 1H); 7.09 (t, J=5,10 Hz, 1H); 6.93 (dd, J=5.5 Hz, 1H); 6.09 (d, J=5 Hz, 1H); 4.97 (b, 1H, —NH); 3.84 (t, J=5, 5 Hz, 4H); 2.67 (t, J=5, 5 Hz, 4H); 2.40 (s, 3H). HPLC (tr/purity): 12.2 min >97% (method A); exhibited a mass (ESI) m/z (MeOH): 371.10 (MH$^+$).

3-chloro-6-(piperazin-1-yl)-4-(pyridin-4-yl)pyridazine (8-4 g):

Product 8-4 g was made following the same protocol described above for 8-4a, using compound 8-3 (0.200 g, 0.88 mmol) and piperazine (0.266 g, 3.0 mmol) in 1-butanol and heated (120° C.) for 17 h. The product 8-4 g was purified by column chromatography on silica gel (200-400 mesh) using ethyl acetate and 5% methanol eluent to give product 8-4 g as a beige powder (209 mg) in 89% yield (gravimetric), HPLC (tr/purity): 4.6 min >93%; exhibited a mass (ESI) of m/z (MeOH)=276.00 (MH$^+$).

4-(6-(piperazin-1-yl)-4-(pyridin-4-yl)pyridazin-3-yl)-1H-indole (30): (MW-126):

Product 30 was synthesized using the same 'Suzuki' reaction protocol for 15. Compound 3-chloro-6-(piperazin-1-yl)-4-(pyridin-4-yl)pyridazine (8-4 g) (200 mg, 0.72 mmol) and (1H-indol-4-yl)boronic acid (159 mg, 0.99 mmol) was suspended in dimethoxyethane (DME) and water (10:1 v/v) and followed the same protocol mentioned above. The product 30 was purified by column chromatography on silica gel (200-400 mesh) using ethyl acetate and methanol (5%) eluent, followed by crystallization with ethyl acetate.

The product 30 obtained as light yellow color powder (110 mg) in 45% (gravimetric) yield; $^1$H NMR (500 MHz, CD$_3$OD): δ 8.30 (d, J=5 Hz, 2H); 7.42-7.36 (m, 2H); 7.25 (dd, J=5,5 Hz, 2H); 7.14 (m, 2H); 6.94 (d, J=5.10 Hz, 1H); 6.09 (d, J=5 Hz, 1H); 3.82 (m, 4H); 3.02 (m,4H); HPLC method A (tr/purity): 12.0 min >97%; ESI m/z (MeOH): 357.10 (MH$^+$).

Example 8-1

Scheme 8A.

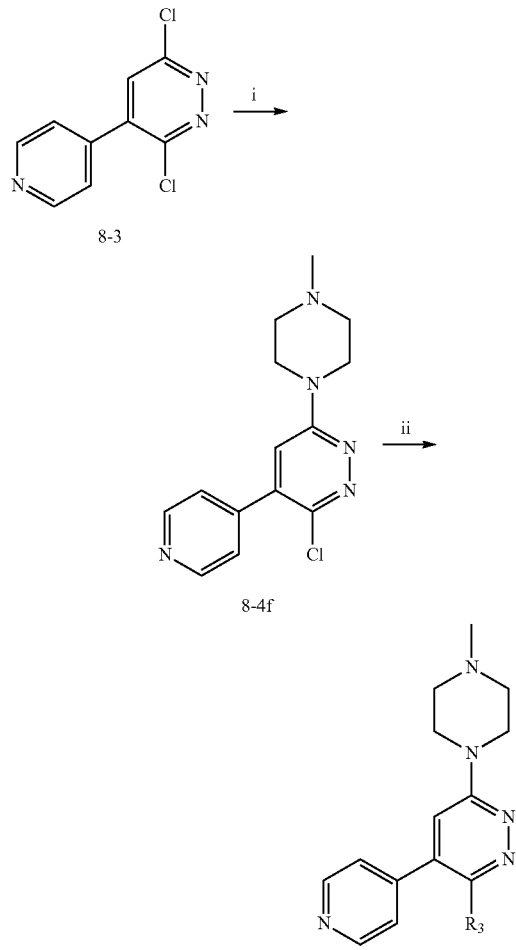

8-3

8-4f

MW208 = R$_3$ = -6-fluoro-naphthyl-2-yl- (49)
MW017 = R$_3$ = -7-fluoro-naphthyl-2-yl- (50)
MW032 = R$_3$ = -8-fluoro-naphthyl-2-yl- (52)
MW044 = R$_3$ = -5-fluoro-naphthyl-2-yl- (51)
MW063 = R$_3$ = -5-fluoro-naphthyl-1-yl- (55)
MW059 = R$_3$ = -3-fluoro-naphthyl-1-yl- (53)
MW197 = R$_3$ = -6-fluoro-naphthyl-1-yl- (54)

Reagents and conditions: i) 1-methylpiperazine< ethanol, 17 h, reflux; ii)fluoro-naphthylboronic acid, DME/eater, Na$_2$CO$_3$•Pd(PPh$_3$)$_4$, 14-15 h, 110° C.

3-Chloro-6-(4-methylpiperazin-1-yl)-4-(pyridin-4-yl)pyridazine (8-4f): Following the published protocol (*Bioorg. Med. Chem Lett.* 17, 414-418), a solution of 3,6-dichloro-4-pyridine-4-yl)pyridazine (8-3, 0.750 g, 3.3 mmol, 1 eq) and 1-methylpiperazine (1.4 g, 13.2 mmol) in 25 ml ethanol were placed in a heavy wall pressure vessel (Chemglass, Vineland, N.J.) and refluxed for 17 h. The product was purified by column chromatography on silica gel (200-400 mesh) and eluted with 2% methanol and ethyl acetate providing product 2 (620 mg, 78%) as a beige powder. $^1$H NMR (300 MHz, CDCl$_3$): δ 8.75 (dd, J=4.4, 1.7 Hz, 2H), 7.38 (dd, J=4.4, 1.7 Hz, 2H), 6.82 (s, 1H), 3.71 (m, 4H), 2.55 (m, 4H), 2.36 (s, 3H); LC/MS ESI positive R$_t$=1.47 min >93%, m/z=290.7 (M+H)$^+$.

3-(6-Fluoronaphthalen-2-yl)-6-(4-methylpiperazin-1-yl)-4-(pyridin-4-yl)pyridazine (49): (MW-203): A mixture of compound 2 (46 mg, 0.16 mmol), (6-fluoronaphthalen-2-yl) boronic acid (*J. Org. Chem.* 70, 611-623) (25 mg, 0.13 mmol), tetrakis(triphenylphosphine)palladium (15 mg, 13 μmol), sodium carbonate (43 mg, 0.40 mmol), water (65 μl) and DME (0.65 ml) was purged with nitrogen, sealed and heated to 80° C. for 14 h. Cooled to 20° C. and ethyl acetate (50 ml) was added. The mixture was washed with brine (25 ml), dried (MgSO$_4$) and evaporated to leave a crystalline solid (26 mg, 41%). $^1$H NMR (300 MHz, CDCl$_3$) δ 8.56 (d, J=5.8 Hz, 2H), 7.94 (s, 1H), 7.71 (dd, J=9.1 Hz, J=5.6 Hz, 1H), 7.64 (d, J=8.5 Hz, 1H), 7.39 (m, 2H), 7.21 (ddd, J=8.8 Hz, J=8.8 Hz, J=2.6 Hz, 1H), 7.15 (dd, J=4.4 Hz, J=1.8 Hz, 2H), 6.87 (s, 1H), 3.82 (m, 4H), 2.61 (m, 4H), 2.39 (s, 3H); LC/MS ESI positive R$_t$=2.82 min >96%, m/z=400.09 (M+H)$^+$; HRMS calculated for C$_{24}$H$_{22}$F N$_5$ 399.1859. found 399.1865.

3-(7-Fluoronaphthalen-2-yl)-6-(4-methylpiperazin-1-yl)-4-(pyridin-4-yl)pyridazine (50): (MW-017): A mixture of compound 2 (46 mg, 0.16 mmol), (7-fluoronaphthalen-2-yl) boronic acid (*J. Med. Chem.* 49, 2222-2231) (25 mg, 0.13 mmol), tetrakis(triphenylphosphine)palladium (15 mg, 13 μmol), sodium carbonate (43 mg, 0.40 mmol), water (65 μl) and DME (0.65 ml) was purged with nitrogen, sealed and heated to 80° C. for 14 h. Cooled to 20° C., water was added (0.5 ml) and the mixture was purified by preparative RPHPLC. The product fractions were combined, treated with saturated sodium bicarbonate solution (20 ml) and extracted with ethyl acetate (2×50 ml). The organic extracts were combined, washed with brine (25 ml), dried (MgSO$_4$) and evaporated to leave a crystalline solid (28 mg, 54%). $^1$H NMR (300 MHz, CDCl$_3$): δ 8.56 (d, J=6.1 Hz, 2H), 7.89 (s, 1H), 7.78 (dd, J=8.8 Hz, J=5.6 Hz, 1H), 7.69 (d, J=8.5 Hz, 1H), 7.37-7.7.22 (m, 3H), 7.15 (dd, J=4.4 Hz, J=1.2 Hz, 2H), 6.88 (s, 1H), 3.83 (m, 4H), 2.62 (m, 4H), 2.40 (s, 3H); LC/MS ESI positive R$_t$=2.79 min >96%, m/z=400.16 (M+H)$^+$; HRMS calculated for C$_{24}$H$_{22}$F N$_5$ 399.1859. found 399.1865.

3-(8-Fluoronaphthalen-2-yl)-6-(4-methylpiperazin-1-yl)-4-(pyridin-4-yl)pyridazine (52): (MW-032): A mixture of compound 2 (46 mg, 0.16 mmol), 2-(8-fluoronaphthalen-2-yl)-4,4,5,5-tetramethyl-1,3,2-dioxaborolane (49 mg, 0.18 mmol), tetrakis(triphenylphosphine)palladium (18 mg, 16 μmol), sodium carbonate (43 mg, 0.40 mmol), water (65 μl) and DME (0.65 ml) was purged with nitrogen, sealed and heated to 80° C. for 14 h. Cooled to 20° C., water was added (0.5 ml) and the mixture was purified by RPHPLC. The product fractions were combined, treated with saturated sodium bicarbonate solution (20 ml) and extracted with ethyl acetate (2×50 ml). The organic extracts were combined, washed with brine (25 ml), dried (MgSO$_4$) and evaporated to leave a crystalline solid (29 mg, 45%). $^1$H NMR (300 MHz, CDCl$_3$) δ 8.55 (d, J=5.8 Hz, 2H), 8.16 (s, 1H), 7.73 (dd, J=8.6,1.5 Hz, 1H), 7.58 (d, J=8.2 Hz, 1H), 7.42 (dd, J=8.4, 1.8 Hz, 1H), 7.43-7.35 (m, 1H), 7.14 (dd, J=4.7, 1.5 Hz, 2H), 7.10 (m, 1H), 6.88 (s, 1H), 3.83 (m, 4H), 2.62 (m, 4H), 2.39 (s, 3H); LC/MS ESI positive R$_t$=2.78 min >96%, m/z=400.16 (M+H)$^+$; HRMS calculated for C$_{24}$H$_{22}$F N$_5$ 399.1859. found 399.1867.

3-(5-Fluoronaphthalen-2-yl)-6-(4-methylpiperazin-1-yl)-4-(pyridin-4-yl)pyridazine (51): (MW-044): A mixture of compound 2 (49 mg, 0.17 mmol), 2-(5-fluoronaphthalen-2-yl)-4,4,5,5-tetramethyl-1,3,2-dioxaborolane (45 mg, 0.17 mmol), tetrakis(triphenylphosphine)palladium (19 mg, 17 µmol), sodium carbonate (45 mg, 0.43 mmol), water (65 µl) and DME (0.65 ml) was purged with nitrogen, sealed and heated to 80° C. for 14 h. Cooled to 20° C., water was added (0.5 ml) and the mixture was purified by RPHPLC. The product fractions were combined, treated with saturated sodium bicarbonate solution (20 ml) and extracted with ethyl acetate (2×25 ml). The organic extracts were combined, washed with brine (25 ml), dried (MgSO$_4$) and evaporated to leave a crystalline solid (19 mg, 28%). $^1$H NMR (300 MHz, CDCl$_3$) δ 8.56 (d, J=5.9 Hz, 2H), 7.96 (dd, J=3.5, 5.0 Hz, 1H), 7.51 (d, J=8.5 Hz, 1H), 7.42 (dd, J=8.5, 1.2 Hz, 2H), 7.40-7.34 (m, 1H), 7.18-7.10 (m, 3H), 6.88 (s, 1H), 3.84 (m, 4H), 2.62 (m, 4H), 2.40 (s, 3H); LC/MS ESI positive R$_t$=2.85 min >97%, m/z=400.16 (M+H)$^+$; HRMS calculated for C$_{24}$H$_{22}$F N$_5$ 399.1859. found 399.1866.

3-(5-fluoronaphthalen-1-yl)-6-(4-methylpiperazin-1-yl)-4-(pyridin-4-yl)pyridazine (55): (MW-063): A mixture of compound 2 (42 mg, 0.14 mmol), (5-fluoronaphthalen-1-yl) boronic acid (32 mg, 0.17 mmol), tetrakis (triphenylphosphine)palladium (16 mg, 14 µmol) and sodium carbonate (44 mg (0.42 mmol) in water (60 µl) and dimethoxyethane (0.60 ml) was purged with nitrogen, sealed tightly and heated to 80° C. for 18 h. The mixture was cooled to 20° C., filtered over celite (methanol wash) and purified by RPHPLC (method C). The product fractions were combined, treated with saturated aqueous sodium bicarbonate solution (25 ml) and extracted with ethyl acetate (2×25 ml). The extracts were washed with brine (25 ml), dried (MgSO$_4$) and evaporated to leave a light yellow solid (22 mg, 39%). $^1$H-NMR (300 MHz, CDCl$_3$): δ 8.36 (d, J=5.8 Hz, 2H), 8.11 (d, J=8.2 Hz, 1H), 7.48-7.41 (m, 2H), 7.75-7.67 (m, 2H), 7.35-7.24 (m, 2H), 7.10 (dd, J=10.3 Hz, J=6.6 Hz, 1H), 6.96 (s, 1H), 6.95 (dd, J=4.4 Hz, J=1.7 Hz, 2H), 3.87-3.82 (m, 4H), 2.67-2.60 (m, 4H), 2.40 (s, 3H); LC/MS method A: ESI MS (M+H)$^+$=400; R$_t$=2.67 minutes.

3-(3-fluoronaphthalen-1-yl)-6-(4-methylpiperazin-1-yl)-4-(pyridin-4-yl)pyridazine (53): (MW-059): A mixture of compound 2 (42 mg, 0.14 mmol), (3-fluoronaphthalen-1-yl) boronic acid (25 mg, 0.13 mmol), tetrakis(triphenylphosphine)palladium (16 mg, 14 µmol), sodium carbonate (44 mg, 0.42 mmol), water (60 µl) and dimethoxyethane (0.6 ml) was purged with a nitrogen atmosphere, sealed and heated to 80° C. for 15 h. Purified by RPHPLC (direct injection, method C). Product fractions were combined, treated with aqueous saturated sodium bicarbonate solution (25 ml) and extracted with ethyl acetate (2×25 ml). The combined extracts were washed with brine, dried (MgSO4) and evaporated to leave a solid (9 mg, 17%). $^1$H-NMR (300 MHz, CDCl$_3$): δ 8.38 (dd, J=4.7 Hz, J=1.5 Hz, 2H), 7.76 (d, J=8.2 Hz, 1H), 7.59 (d, J=8.5 Hz, 1H), 7.48-7.40 (m, 2H), 7.33-7.20 (m, 1H), 7.13 (dd, J=9.0 Hz, J=2.6 Hz, 1H), 6.98 (dd, J=5.0 Hz, J=1.7 Hz, 2H), 6.96 (s, 1H), 3.87 (m, 4H), 2.65 (m, 4H), 2.42 (s, 3H); LC/MS method A: ESI pos. (M+H)$^+$=400, R$_t$=2.63 minutes.

3-(6-fluoronaphthalen-1-yl)-6-(4-methylpiperazin-1-yl)-4-(pyridin-4-yl)pyridazine (54): (MW-197): A mixture of compound 2 (46 mg, 0.16 mmol), (6-fluoronaphthalen-1-yl) boronic acid (25 mg, 0.13 mmol), tetrakis(triphenylphosphine)palladium (15 mg, 13 µmol), sodium carbonate (43 mg, 0.40 mmol), water (65 µl) and DME (0.65 ml) was purged with nitrogen and heated to 80° C. for 14 h. Cooled to 20° C., methanol (1 ml) and water (1 ml) were added and the product was purified by RPHPLC (method). The product fractions were combined, washed with brine (25 ml), dried (MgSO$_4$) and evaporated to leave a crystalline solid (23 mg, 44%). $^1$H-NMR (300 MHz, CDCl$_3$): δ 8.36 (d, J=5.8 Hz, 2H), 7.76 (d, J=8.2 Hz, 1H), 7.71 (dd, J=9.4 Hz, J=5.6 Hz, 1H), 7.44 (dd, J=9.6 Hz, J=2.6 Hz, 1H), 7.39 (dd, J=7.9 Hz, J=7.9 Hz, 1H), 7.21 (dd, J=7.0 Hz, J=0.8 Hz, 1H), 7.13 (ddd, J=10.9 Hz, J=9.1, Hz, J=2.6 Hz, 1H), 6.96 (s, 1H), 6.95 (dd, J=4.7, J=2.0, 2H), 3.86 (m, 4H), 2.64 (m, 4H), 2.41 (s, 3H); LC/MS method A: ESI pos. (M+H)$^+$=400, R$_t$=2.64 minutes.

Example 8-2

Compound 57 (6-(4-methylpiperidin-1-yl)-3-(naphthalen-1-yl)-4-(pyridin-4-yl)pyridazine) (also described herein as SRM-137B) can be prepared in a similar manner as described in Example 8 by using 4-methylpiperidine as the amine and by using 1-naphthylboronic acid as the boronic acid.

Example 8-3

Compound 59 (3-(naphthalen-1-yl)-4-(pyridin-4-yl)-6-(4-(pyrimidin-2-yl)piperazin-1-yl)pyridazine) (also described herein as SRM-203A) can be prepared in a similar manner as described in Example 8 by using 2-(piperazin-1-yl)pyrimidine as the amine and by using 1-naphthylboronic acid as the boronic acid.

Example 8-4

Compound 56 (6-(4-methylpiperidin-1-yl)-3-(naphthalen-2-yl)-4-(pyridin-4-yl)pyridazine) (also described herein as SRM-137A) can be prepared in a similar manner as described in Example 8 by using 4-methylpiperidine as the amine and by using 2-naphthylboronic acid as the boronic acid.

Example 8-5

Compound 60 (3-(naphthalen-2-yl)-4-(pyridin-4-yl)-6-(4-(pyrimidin-2-yl)piperazin-1-yl)pyridazine) (also described herein as SRM-203B) can be prepared in a similar manner as described in Example 8 by using 2-(piperazin-1-yl)pyrimidine as the amine and by using 2-naphthylboronic acid as the boronic acid.

Example 9

Scheme 9.

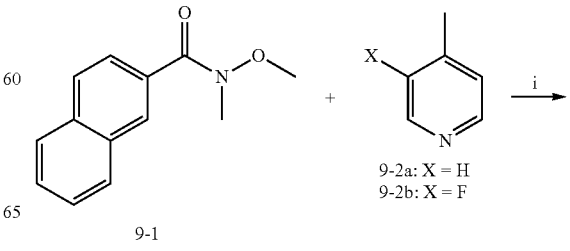

9-1

9-2a: X = H
9-2b: X = F

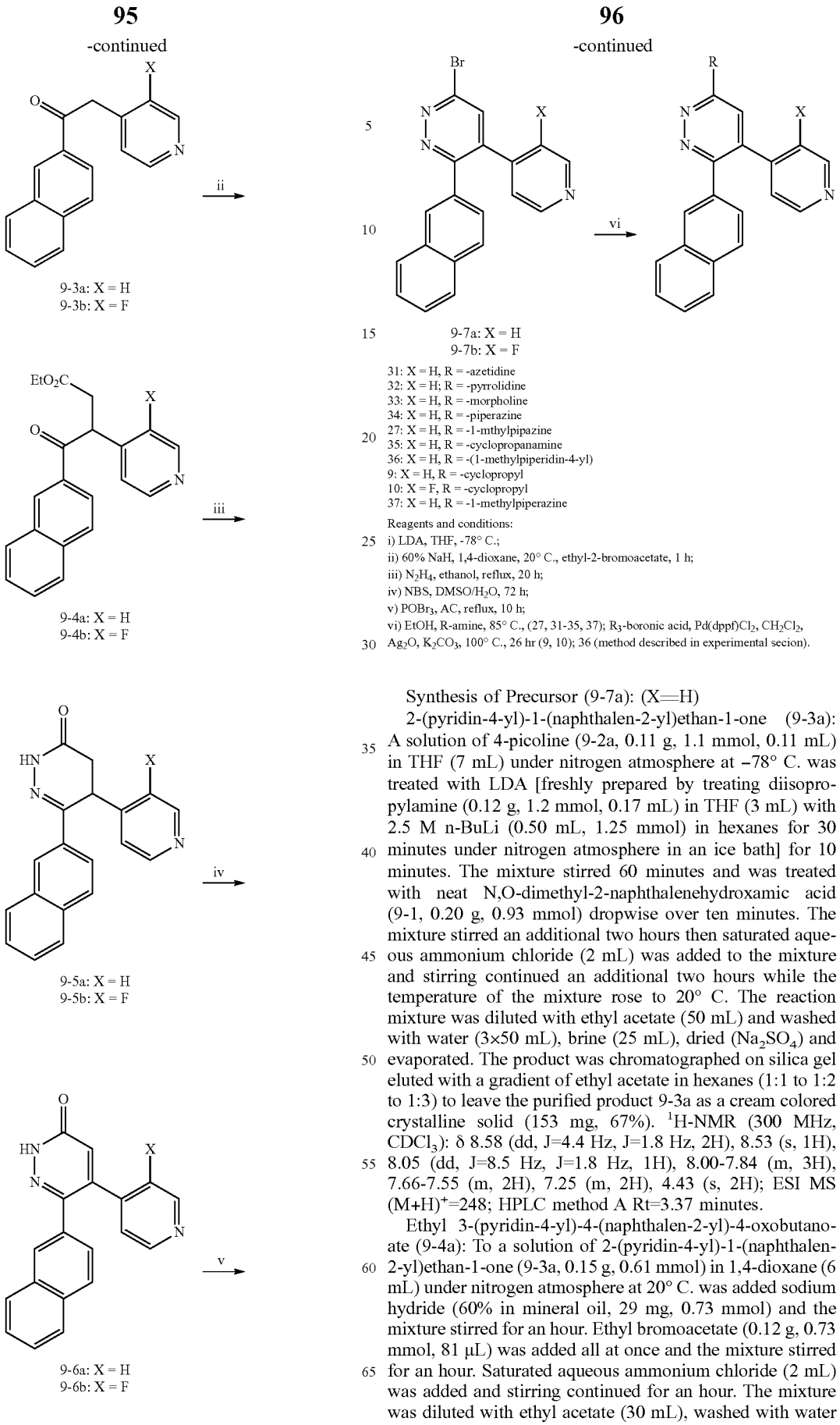

31: X = H, R = -azetidine
32: X = H, R = -pyrrolidine
33: X = H, R = -morpholine
34: X = H, R = -piperazine
27: X = H, R = -1-mthylpipazine
35: X = H, R = -cyclopropanamine
36: X = H, R = -(1-methylpiperidin-4-yl)
9: X = H, R = -cyclopropyl
10: X = F, R = -cyclopropyl
37: X = H, R = -1-methylpiperazine Reagents and conditions:
i) LDA, THF, -78° C.;
ii) 60% NaH, 1,4-dioxane, 20° C., ethyl-2-bromoacetate, 1 h;
iii) N$_2$H$_4$, ethanol, reflux, 20 h;
iv) NBS, DMSO/H$_2$O, 72 h;
v) POBr$_3$, AC, reflux, 10 h;
vi) EtOH, R-amine, 85° C., (27, 31-35, 37); R$_3$-boronic acid, Pd(dppf)Cl$_2$, CH$_2$Cl$_2$, Ag$_2$O, K$_2$CO$_3$, 100° C., 26 hr (9, 10); 36 (method described in experimental secion).

Synthesis of Precursor (9-7a): (X=H)

2-(pyridin-4-yl)-1-(naphthalen-2-yl)ethan-1-one (9-3a): A solution of 4-picoline (9-2a, 0.11 g, 1.1 mmol, 0.11 mL) in THF (7 mL) under nitrogen atmosphere at -78° C. was treated with LDA [freshly prepared by treating diisopropylamine (0.12 g, 1.2 mmol, 0.17 mL) in THF (3 mL) with 2.5 M n-BuLi (0.50 mL, 1.25 mmol) in hexanes for 30 minutes under nitrogen atmosphere in an ice bath] for 10 minutes. The mixture stirred 60 minutes and was treated with neat N,O-dimethyl-2-naphthalenehydroxamic acid (9-1, 0.20 g, 0.93 mmol) dropwise over ten minutes. The mixture stirred an additional two hours then saturated aqueous ammonium chloride (2 mL) was added to the mixture and stirring continued an additional two hours while the temperature of the mixture rose to 20° C. The reaction mixture was diluted with ethyl acetate (50 mL) and washed with water (3×50 mL), brine (25 mL), dried (Na$_2$SO$_4$) and evaporated. The product was chromatographed on silica gel eluted with a gradient of ethyl acetate in hexanes (1:1 to 1:2 to 1:3) to leave the purified product 9-3a as a cream colored crystalline solid (153 mg, 67%). $^1$H-NMR (300 MHz, CDCl$_3$): δ 8.58 (dd, J=4.4 Hz, J=1.8 Hz, 2H), 8.53 (s, 1H), 8.05 (dd, J=8.5 Hz, J=1.8 Hz, 1H), 8.00-7.84 (m, 3H), 7.66-7.55 (m, 2H), 7.25 (m, 2H), 4.43 (s, 2H); ESI MS (M+H)$^+$=248; HPLC method A Rt=3.37 minutes.

Ethyl 3-(pyridin-4-yl)-4-(naphthalen-2-yl)-4-oxobutanoate (9-4a): To a solution of 2-(pyridin-4-yl)-1-(naphthalen-2-yl)ethan-1-one (9-3a, 0.15 g, 0.61 mmol) in 1,4-dioxane (6 mL) under nitrogen atmosphere at 20° C. was added sodium hydride (60% in mineral oil, 29 mg, 0.73 mmol) and the mixture stirred for an hour. Ethyl bromoacetate (0.12 g, 0.73 mmol, 81 µL) was added all at once and the mixture stirred for an hour. Saturated aqueous ammonium chloride (2 mL) was added and stirring continued for an hour. The mixture was diluted with ethyl acetate (30 mL), washed with water (2×30 mL), brine (20 mL), dried (Na$_2$SO$_4$) and evaporated to an oily residue that was purified by silica gel chromatography eluted with a gradient of ethyl acetate in hexanes (1:1 to 2:1) to leave the product 9-4a as a light yellow viscous oil (121 mg, 60%). $^1$H-NMR (300 MHz, CDCl$_3$): δ 8.53 (dd, J=4.4 Hz, J=1.5 Hz, 2H), 8.49 (s, 1H), 7.99 (dd, J=8.5 Hz, J=1.7 Hz, 1H), 7.92 (d, J=7.9 Hz, 1H), 7.87-7.82 (m, 2H), 7.62-7.50 (m, 2H), 7.29 (dd, J=4.4 Hz, J=1.5 Hz, 2H), 5.27 (m, 1H), 4.12 (q, J=7.0 Hz, 2H), 3.42 (dd, J=17.0 Hz, J=9.4 Hz, 1H), 2.78 (dd, J=17.0 Hz, J=5.6 Hz, 1H), 1.21 (t, J=7.0 Hz, 3H); ESI MS (M+H)$^+$=334; HPLC method A R$_t$=3.89 minutes.

6-(naphthalen-2-yl)-5-(pyridin-4-yl)-2,3,4,5-tetrahydropyridazin-3-one (9-5a): A solution of ethyl 3-(pyridin-4-yl)-4-(naphthalen-2-yl)-4-oxobutanoate (9-4a, 0.12 g, 0.36 mmol) in ethanol (3 mL) was treated with hydrazine hydrate (0.25 g, 5 mmol, 0.25 mL) and refluxed for 20 hours. The mixture was cooled to 20° C. and purified by reversed phase HPLC (method B). The product fractions were treated with saturated sodium bicarbonate solution (50 mL) and extracted with ethyl acetate (2×50 mL). The combined extracts were washed with brine (50 mL), dried (Na$_2$SO$_4$) and evaporated to leave 48 mg (44%) of beige solid 9-5a. $^1$H-NMR (300 MHz, CDCl$_3$): δ 8.76 (bs, 1H), 8.57 (d, J=5.3 Hz, 2H), 7.98 (dd, J=8.5 Hz, J=1.8 Hz, 1H), 7.95 (s, 1H), 7.85 (d, J=8.5 Hz, 1H), 7.86-7.76 (m, 2H), 7.55-7.46 (m, 2H), 7.21 (dd, J=4.4 Hz, J=1.2 Hz, 2H), 4.68 (d, J=6.5 Hz, 1H), 3.10 (dd, J=17.0 Hz, J=7.7 Hz, 1H), 2.90 (dd, J=17.0 Hz, J=1.8 Hz, 1H); ESI MS (M+H)$^+$=302; HPLC method A R$_t$=3.11 minutes.

6-(naphthalen-2-yl)-5-(pyridin-4-yl)-2,3-dihydropyridazin-3-one (9-6a): A solution of 6-(naphthalen-2-yl)-5-(pyridin-4-yl)pyridazin-3(2H)-one (9-5a, 25 mg, 0.083 mmol) in DMSO (0.5 mL) and water (0.02 mL) was treated with N-bromosuccinimide (75 mg, 0.42 mmol). After a slight exotherm the solution was stirred 72 hours then purified directly by reversed phase HPLC (method B). The combined product fractions were treated with saturated sodium bicarbonate solution (50 mL) and extracted with ethyl acetate (2×25 mL). The combined extracts were washed with brine, dried (Na$_2$SO$_4$) and evaporated to leave product 9-6a as a beige solid (17 mg, 69%). $^1$H-NMR (300 MHz, CDCl$_3$): δ 11.13 (bs, 1H), 8.55 (bs, 2H), 7.80 (dd, J=9.1 Hz, J=2.1 Hz, 1H), 7.76-7.68 (m, 3H), 7.55-7.45 (m, 2H), 7.16 (dd, J=8.8 Hz, J=2.0 Hz, 1H), 7.09 (d, J=5.9 Hz, 2H), 7.05 (s, 1H); ESI MS (M+H)$^+$=300; HPLC method A R$_t$=2.88 minutes.

6-Bromo-4-(pyridin-4-yl)-3-(naphthalen-2-yl)pyridazine (9-7a): 6-(Naphthalen-2-yl)-5-(pyridin-4-yl)-2,3-dihydropyridazin-3-one (9-6a, 0.15 g, 0.50 mmol) was added to a solution of phosphorousoxybromide (0.62 g, 2.0 mmol) in acetonitrile (3 mL) and heated to reflux while stirring for ten hours. The reaction mixture was cooled in an ice bath, treated with ice (2 g) and stirred for an hour. The mixture was neutralized with solid sodium carbonate to a pH=10 followed by dilution with ethyl acetate (20 mL) and water (20 mL). The organic layer was separated, washed with brine (50 mL), dried (Na$_2$SO$_4$) and evaporated. The product was purified by chromatography on silica gel eluted with ethyl acetate in hexanes (3:1). The purified product 9-7a was isolated as a colorless foamy solid (0.15 g, 83%). $^1$H-NMR (300 MHz, CDCl$_3$): δ 8.59 (dd, J=4.4 Hz, J=1.8 Hz, 1H), 8.04 (d, J=1.2 Hz, 1H), 7.86-7.73 (m, 3H), 7.72 (s, 1H), 7.58-7.47 (m, 2H), 7.33 (dd, J=8.5 Hz, J=1.7 Hz, 1H), 7.15 (dd, J=4.4 Hz, J=1.7 Hz, 2H); ESI MS (M+H)$^+$=362, 364; HPLC method A R$_t$=3.71 minutes.

6-(azetidin-1-yl)-3-(naphthalen-2-yl)-4-(pyridin-4-yl) pyridazine: (31): (MW-146): A solution of 6-bromo-3-(naphthalen-2-yl)-4-(pyridin-4-yl)pyridazine (9-7a) (35 mg, 0.097 mmol) in 200 proof ethanol (1 mL) was treated with azetidine (17 mg, 0.29 mmol, 20 μL). The mixture was sealed and heated to 85° C. for 15 hours then cooled to room temperature. The mixture was diluted with ethyl acetate (25 mL), washed with saturated sodium bicarbonate (25 mL), water (25 mL) and brine (25 mL), dried (MgSO$_4$) and evaporated. The product 31 was triturated with hexane to leave a beige crystalline solid (32 mg, 98%). $^1$H-NMR (300 MHz, CDCl$_3$) δ 8.53 (dd, J=4.4 Hz, J=1.5 Hz, 2H), 7.90 (d, J=1.0 Hz, 1H), 7.82-7.77 (m, 1H), 7.73-7.69 (m, 1H), 7.69 (d, J=8.8 Hz, 1H), 7.51-7.41 (m, 2H), 7.35 (dd, J=8.5 Hz, J=1.8 Hz, 1H), 7.13 (dd, J=4.4 Hz, J=1.5 Hz, 2H), 6.50 (s, 1H), 4.28 (dd, J=7.7 Hz, J=7.7 Hz, 4H), 2.55 (m, 2H); ESI MS (M+H)$^+$=339; HPLC method A R$_t$=2.70 minutes.

3-(naphthalen-2-yl)-4-(pyridin-4-yl)-6-(pyrrolidin-1-yl) pyridazine: (32): (MW-148): A solution of 6-bromo-3-(naphthalen-2-yl)-4-(pyridin-4-yl)pyridazine (9-7a) (50 mg, 0.14 mmol) in 200 proof ethanol (2 mL) was treated with pyrrolidine (40 mg, 0.56 mmol, 46 μL). The mixture was sealed and heated to 85° C. for 15 hours then cooled to room temperature. The mixture was diluted with ethyl acetate (25 mL), washed with saturated sodium bicarbonate (25 mL), water (25 mL) and brine (25 mL), dried (MgSO$_4$) and evaporated. The residue was purified by chromatography on silica gel eluted with a gradient of 75% ethyl acetate in hexane to 100% ethyl acetate. The product 32 fractions were evaporated to leave a beige crystalline solid (41 mg, 83%). $^1$H-NMR (300 MHz, CDCl$_3$) δ 8.54 (dd, J=4.7 Hz, J=1.8 Hz, 2H), 7.92 (s, 1H), 7.82-7.77 (m, 1H), 7.73-7.69 (m, 1H), 7.69 (d, J=8.5 Hz, 1H), 7.50-7.41 (m, 2H), 7.38 (dd, J=8.5 Hz, J=1.7 Hz, 1H), 7.16 (dd, J=4.4 Hz, J=1.5 Hz, 2H), 6.60 (s, 1H), 3.65 (m, 4H), 2.12 (m, 4H); ESI MS (M+H)$^+$=353; HPLC method A Rt=2.78 minutes.

4-(6-(naphthalen-2-yl)-5-(pyridin-4-yl)pyridazin-3-yl) morpholine: (33): (MW-152): A solution of 6-bromo-3-(naphthalen-2-yl)-4-(pyridin-4-yl)pyridazine (9-7a) (50 mg, 0.14 mmol) and morpholine (60 mg, 0.69 mmol) in 95% ethanol was refluxed for 18 h. The reaction mixture was diluted with ethyl acetate (25 mL) and washed with saturated sodium bicarbonate solution (25 mL), water (2×25 mL), brine (25 mL), dried (Na$_2$SO$_4$) and evaporated to a tan solid 33 (50 mg, 97%). $^1$H-NMR (300 MHz, CDCl$_3$): δ 8.56 (bs, 2H), 7.96 (s, 1H), (7.82-7.69 (m, 2H), 7.72 (s, 1H), 7.52-7.43 (m, 2H), 7.35 (dd, J=8.5 Hz, J=1.8 Hz, 1H), 7.15 (d, J=5.3 Hz, 1H), 6.87 (s, 1H), 3.92 (m, 4H), 3.77 (m, 4H). LC/MS (method A) Rt=3.02 mins., purity >95%, (M+H$^+$)=369.

3-(Naphthalen-2-yl)-6-(piperazin-1-yl)-4-(pyridin-4-yl) pyridazine: (34): (MW-154): A solution of 6-bromo-3-(naphthalen-2-yl)-4-(pyridin-4-yl)pyridazine (9-7a) (50 mg, 0.14 mmol) and piperazine (59 mg, 0.69 mmol) in 95% ethanol (1 mL) was refluxed for 18 h. The reaction mixture was diluted with ethyl acetate (25 mL) and washed with saturated sodium bicarbonate solution (25 mL), water (2×25 mL), brine (25 mL), dried (Na$_2$SO$_4$) and evaporated to a beige solid 34 (50 mg, 97%). $^1$H-NMR (300 MHz, CDCl$_3$): δ 8.56 (dd, J=4.7 Hz, J=1.7 Hz, 2H), 7.94 (bs, 1H), 7.82-7.69 (m, 2H), 7.70 (s, 1H), 7.52-7.43 (m, 2H), 7.35 (dd, J=8.0 Hz, J=1.8 Hz, 1H), 7.18-7.12 (m, 2H), 6.93 (d, J=16.7 Hz, 1H), 4.19 (m, 2H), 3.83 (m, 2H), 3.42 (m, 2H), 3.18 (bs, 1H), 2.79 (m, 2H). LC/MS (method A) Rt=2.63 mins., purity >90%, (M+H$^+$)=368.

6-(4-methylpiperazin-1-yl)-3-(naphthalen-2-yl)-4-(pyridin-4-yl)pyridazine: (27): (MW-150): A solution of 6-bromo-3-(naphthalen-2-yl)-4-(pyridin-4-yl)pyridazine (9-7a) (9.0 g, 25 mmol) in ethanol (150 mL) in a 500 mL round bottom flask was treated with N-methylpiperidine (12.4 g, 125 mmol, 13.8 mL) and heated to reflux for 18 h. The solvent was evaporated in vacuo. The residue was dissolved in ethyl acetate (300 mL) and washed with water (2×200 mL) and saturated sodium bicarbonate solution (100 mL). The product precipitated from the organic layer and was collected via filtration on fritted glass. The product was washed with water (20 mL) and ethyl acetate (50 mL) and dried under high vacuum to leave 8.6 g (90%) of 27 as light yellow solid. $^1$H-NMR (300 MHz, CDCl$_3$): δ 8.54 (dd, 2H, J=4.4 Hz, J=1.7 Hz), 7.94 (s, 1H), 7.82-7.68 (m, 3H), 7.51-7.42 (m, 2H), 7.35 (dd, 1H, J=8.5 Hz, J=1.8 Hz), 7.15 (dd, 2H, J=4.4 Hz, J=1.7), 6.88 (s, 1H), 3.82 (dd, 4H, J=5.2 Hz, J=5.0 Hz), 2.60 (dd, 4H, J=5.2 Hz, J=5.0 Hz), 2.39 (s, 3H); ESI MS (M+H)$^+$=382; HPLC method A Rt=2.58 minutes.

N-cyclopropyl-6-(naphthalen-2-yl)-5-(pyridin-4-yl) pyridazin-3-amine: (35): (MW-153): A solution of 6-bromo-3-(naphthalen-2-yl)-4-(pyridin-4-yl)pyridazine (9-7a) (50 mg, 0.14 mmol) and cyclopropylamine (39 mg, 0.69 mmol) in 95% ethanol was refluxed for 18 h in a closed vial. LC/MS analysis (method A) indicated the starting material was half converted to product. Additional cyclopropylamine (39 mg, 0.69 mmol) was added and the mixture was refluxed 18 h. The reaction mixture was diluted with ethyl acetate (25 mL) and washed with saturated sodium bicarbonate solution (25 mL), water (2×25 mL), brine (25 mL), dried (Na$_2$SO$_4$) and evaporated. The product 35 was purified by RPHPLC (method B) and the product fractions were combined, diluted with saturated aqueous sodium bicarbonate solution and extracted with ethyl acetate (2×25 mL). The combined extracts were washed with brine (25 mL), dried (Na$_2$SO$_4$) and evaporated to a light brown solid 35 (37 mg, 76%). $^1$H-NMR (300 MHz, CDCl$_3$): δ 8.56 (bs, 2H), 7.93 (s, 1H), 7.82-7.72 (m, 2H), 7.69 (s, 1H), 7.52-7.43 (m, 2H), 7.32 (dd, J=8.5 Hz, J=1.7 Hz, 1H), 7.17 (d, J=5.9 Hz, 2H), 7.04 (s, 1H), 6.01 (bs, 1H), 2.72-2.62 (m, 1H), 0.97-0.90 (m, 2H), 0.77-0.68 (m, 2H). LC/MS (method A) Rt=2.88 mins., purity >95%, (M+H$^+$)=339.

6-(1-methylpiperidin-4-yl)-3-(naphthalen-2-yl)-4-(pyridin-4-yl)pyridazine: (36): (MW-164): Was made in two steps as follows:

Step-I: 6-(1-Methyl-1,2,3,6-tetrahydropyridin-4-yl)-3-(naphthalen-2-yl)-4-(pyridin-4-yl)pyridazine: A solution of 6-bromo-3-(naphthalen-2-yl)-4-(pyridin-4-yl)pyridazine (9-7a) (100 mg, 0.28 mmol), 1-methyl-4-(4,4,5,5-tetramethyl-1,3,2-dioxaborolan-2-yl)-1,2,3,6-tetrahydropyridine monohydrochloride (110 mg, 0.42 mmol), Pd(dppf) dichloromethane adduct (22 mg, 28 μmol) and potassium carbonate (116 mg, 0.84 mmol) was purged with nitrogen gas then diluted with dioxane (3 mL) and water (0.4 mL). The mixture was purged with nitrogen gas again, tightly capped and heated to 80° C. for 18 h. The mixture was cooled to 20° C., diluted with ethyl acetate (50 mL), washed with water (50 mL), brine (50 mL), dried (Na$_2$SO$_4$) and evaporated. The crude product was purified by RPHPLC (method B) and the product fractions were combined and treated with saturated aqueous sodium bicarbonate solution. The product was extracted with ethyl acetate (2×25 mL) and the combined extracts were washed with brine (25 mL), dried (Na$_2$SO$_4$) and evaporated to leave a light tan solid (100 mg, 94%). $^1$H-NMR (300 MHz, CDCl$_3$): δ 8.58 (dd, J=4.4 Hz, J=1.7 Hz, 2H), 8.08 (bs, 1H), 7.82-7.73 (m, 2H), 7.75 (s, 1H), 7.60 (s, 1H), 7.55-7.45 (m, 2H), 7.41 (dd, J=8.5 Hz, J=1.8 Hz, 1H), 7.19 (dd, J=4.4 Hz, J=1.8 Hz, 2H), 6.82 (m, 1H), 3.29 (m, 2H), 2.98 (m, 2H), 2.80 (dd, J=5.6 Hz, J=5.8 Hz, 2H), 2.49 (s, 3H). LC/MS (method A) Rt=2.73 mins., purity >95%, (M+H$^+$)=379.

Step-II: 6-(1-methylpiperidin-4-yl)-3-(naphthalen-2-yl)-4-(pyridin-4-yl)pyridazine: 6-(1-methyl-1,2,3,6-tetrahydropyridin-4-yl)-3-(naphthalen-2-yl)-4-(pyridin-4-yl) pyridazine (100 mg, 0.26 mmol) was hydrogenated (45 psi) in methanol (5 mL) over 10% Pd/C (20 mg) for 48 h with agitation. The catalyst was filtered and the solvents evaporated. The crude product was purified by RPHPLC to leave 14 mg (14%) of beige solid 36. $^1$H-NMR (300 MHz, CDCl$_3$): δ 8.30 (d, J=5.9 Hz, 2H), 8.06 (bs, 1H), 7.82-7.73 (m, 2H), 7.76 (s, 1H), 7.57-7.48 (m, 2H), 7.43 (s, 1H), 7.38 (dd, J=8.5 Hz, J=1.7 Hz, 1H), 7.16 (dd, J=4.4 Hz, J=1.8 Hz, 2H), 3.23 (m, 4H), 2.52 (s, 3H), 2.44 (m, 1H), 2.22 (m, 4H). LC/MS (method A) Rt=2.69 mins., purity >90%, (M+H$^+$)=381.

6-Cyclopropyl-4-(pyridin-4-yl)-3-(naphthalen-2-yl) pyridazine: (9): (MW-125): A mixture of 6-bromo-3-(naphthalen-2-yl)-4-(pyridin-4-yl)pyridazine (9-7a) (40 mg, 0.11 mmol), cyclopropyl boronic acid (13 mg, 0.15 mmol), PdCl$_2$(dppf).CH$_2$Cl$_2$ (8 mg, 0.011 mmol), silver oxide (64 mg, 0.28 mmol), potassium carbonate (46 mg, 0.33 mmol) and 1,4-dioxane (1 mL) was stirred and purged with nitrogen. The mixture was heated to 80° C. for 18 hours. The reaction mixture was cooled to 20° C. and filtered through celite (ethyl acetate wash). The filtrate was evaporated to dryness and the crude product was purified by RPHPLC (method B). The product fraction was diluted with saturated sodium bicarbonate solution (50 mL) and the product was extracted with ethyl acetate (2×25 mL). The combined organic layers were washed with brine (2×25 mL), dried (Na$_2$SO$_4$) and evaporated to leave the product 9 as a white solid (16 mg, 45%). $^1$H-NMR (300 MHz, CD$_3$OD): δ 8.46 (d, J=4.4 Hz, 2H), 7.93 (d, J=1.5 Hz, 1H), 7.88-7.77 (m, 4H), 7.65 (s, 1H), 7.56-7.46 (m, 2H), 7.37 (dd, J=8.5 Hz, J=1.7 Hz, 1H), 7.33 (dd, J=4.7 Hz, J=1.5 Hz, 1H), 2.4-2.35 (m, 1H), 1.30-1.22 (m, 4H); ESI MS (M+H)$^+$=324; HPLC method A Rt=3.47 minutes.

Synthesis of Precursor (9-7b): (X=F)

2-(3-fluoropyridin-4-yl)-1-(naphthalen-2-yl)ethan-1-one (9-3b): A solution of 3-fluoro-4-picoline (9-2b, 3.2 g, 29 mmol, 2.9 mL) in THF (200 mL) under nitrogen atmosphere at −78° C. was treated with LDA [freshly prepared by treating diisopropylamine (5.3 g, 53 mmol, 7.4 mL) in THF (50 mL) with 2.5 M n-BuLi in hexanes for 30 minutes under nitrogen atmosphere in an ice bath] for 10 minutes. The mixture stirred 60 minutes and was treated with neat N,O-dimethyl-2-naphthalenehydroxamic acid (9-1, 7.5 g, 35 mmol) dropwise over ten minutes. The mixture stirred an additional two hours then saturated aqueous ammonium chloride (20 mL) was added to the mixture and stirring continued an additional two hours while the temperature of the mixture rose to 20° C. Approximately 200 mL of solvent was removed from the mixture in vacuo and the residue was diluted with ethyl acetate (200 mL) and washed with water (3×100 mL). The product was extracted with 1N HCl (6×75 mL) and the combined acidic extracts were neutralized with solid sodium carbonate to pH=9. The product was extracted with ethyl acetate (2×100 mL) and the extracts were dried (Na$_2$SO$_4$) and evaporated. The product 9-3 was obtained as a light yellow crystalline solid (4.4 g, 57%). $^1$H-NMR (300 MHz, CDCl$_3$): δ 8.57 (s, 1H), 8.50 (d, J=1.5 Hz, 1H), 8.41 (dd, J=4.6 Hz, J=1.0 Hz, 1H), 8.07 (dd, J=8.2 Hz, J=1.5 Hz), 8.01 (d, J=18.7 Hz, 1H), 7.94 (m, 2H), 7.68-7.57 (m, 3H), 4.52 (s, 2H); ESI MS (M+H)$^+$=266; HPLC method A R$_t$=4.29 minutes.

Ethyl 3-(3-fluoropyridin-4-yl)-4-(naphthalen-2-yl)-4-oxobutanoate (9-4b): To a solution of 2-(3-fluoropyridin-4-yl)-1-(naphthalen-2-yl)ethan-1-one (9-3b, 4.4 g, 17 mmol) in 1,4-dioxane (150 mL) under nitrogen atmosphere at 20° C. was added sodium hydride (60% in mineral oil, 0.80 g, 20 mmol) and the mixture stirred for an hour. Ethyl bromoacetate (3.3 g, 20 mmol, 2.2 mL) was added all at once and the mixture stirred for 18 hours. Saturated aqueous ammonium chloride (20 mL) was added and stirring continued for an hour. The mixture was evaporated in vacuo to approximately 50 mL in volume and diluted with ethyl acetate (200 mL). The mixture was washed with water (2×100 mL), brine (50 mL), dried ($Na_2SO_4$) and evaporated to an oily residue that was purified by silica gel chromatography eluted with a gradient of hexanes/ethyl acetate (3:1 to 2:1) to leave the product 9-4b as a light yellow viscous oil (4.4 g, 74%). $^1$H-NMR (300 MHz, $CDCl_3$): δ 8.54 (d, J=1.4 Hz, 1H), 8.46 (d, J=1.4 Hz, 1H), 8.31 (dd, J=5.0 Hz, J=0.8 Hz, 1H), 8.00 (dd, J=8.5 Hz, J=1.6 Hz, 1H), 9.94 (bd, J=8.2 Hz, 1H), 7.88-7.82 (m, 2H), 7.62-7.51 (m, 2H), 7.22 (dd, J=5.0 Hz, J=5.0 Hz, 1H), 5.62 (dd, J=9.4 Hz, J=5.3 Hz, 1H), 4.13 (q, J=7.0 Hz, 2H), 3.40 (dd, J=17.1 Hz, J=9.4 Hz, 1H), 2.80 (dd, J=17.1 Hz, J=5.3 Hz, 1H), 1.21 (t, J=7.0 Hz); ESI MS $(M+H)^+$=352; HPLC method A $R_t$=5.38 minutes.

6-(naphthalen-2-yl)-5-(3-fluoropyridin-4-yl)-2,3,4,5-tetrahydropyridazin-3-one (9-5b): A solution of ethyl 3-(3-fluoropyridin-4-yl)-4-(naphthalen-2-yl)-4-oxobutanoate (9-4b, 4.4 g, 12.5 mmol) in ethanol (32 mL) and acetic acid (1.5 mL) was treated with hydrazine hydrate (12.5 g, 250 mmol, 12.5 mL) and refluxed for 20 hours. The mixture was cooled to 20° C., water (5 mL) was added and the beige precipitate was filtered, washed with 25% aqueous ethanol and air-dried to leave the product 9-5b as 1.85 g (46%). $^1$H-NMR (300 MHz, $CDCl_3$): δ 8.92 (bs, 1H), 8.55 (d, J=1.5 Hz, 1H), 8.30 (d, J=5.0 Hz, 1H), 7.99 (dd, J=8.5 Hz, J=1.7 Hz, 1H), 7.90 (d, J=1.5 Hz, 1H), 7.88-7.78 (m, 3H), 7.55-7.45 (m, 2H), 7.04 (dd, J=6.5 Hz, J=5.0 Hz, 1H), 5.02 (dd, J=7.9 Hz, J=1.5 Hz, 1H), 3.10 (dd, J=17.3 Hz, J=7.9 Hz, 1H), 2.90 (dd, J=17.3 Hz, J=1.5 Hz, 1H); ESI MS $(M+H)^+$= 320; HPLC method A $R_t$=4.21 minutes.

6-(Naphthalen-2-yl)-5-(3-fluoropyridin-4-yl)-2,3-dihydropyridazin-3-one (9-6b): A solution of 6-(naphthalen-2-yl)-5-(3-fluoropyridin-4-yl)-2,3,4,5-tetrahydropyridazin-3-one (9-5b, 3.2 g, 10 mmol) in DMSO (80 mL) and water (1.6 mL) was treated with N-bromosuccinimide (8.9 g, 50 mmol). After a slight exotherm the solution was stirred 72 hours then diluted with water (300 mL) and extracted with ethyl acetate (3×150 mL). The combined organic layers were washed with water (200 mL), saturated sodium bicarbonate solution (150 mL) and brine (50 mL). The solution was dried ($Na_2SO_4$) and evaporated. The solid residue was stirred rapidly in saturated sodium bicarbonate solution (50 mL) and water (100 mL) for 18 hours then filtered, washed with water (5×25 mL) and dried under vacuum to leave the product as a tan powder (3.1 g, 97%). $^1$H-NMR (300 MHz, $CDCl_3$): δ 11.69 (bs, 1H), 8.42 (dd, J=5.0 Hz, J=5.0 Hz, 1H), 8.38 (d, J=0.9 Hz, 1H), 7.80 (d, J=7.7 Hz, 1H), 7.74-7.67 (m, 3H), 7.55-7.44 (m, 2H), 7.26 (dd, J=8.5 Hz, J=1.7 Hz, 1H), 7.20-7.13 (m, 1H), 7.11 (s, 1H); ESI MS $(M+H)^+$=318; HPLC method A $R_t$=4.07 minutes.

6-Bromo-4-(3-fluoropyridin-4-yl)-3-(naphthalen-2-yl)pyridazine (9-7b): 6-(Naphthalen-2-yl)-5-(3-fluoropyridin-4-yl)-2,3-dihydropyridazin-3-one (9-6b, 3.0 g, 9.5 mmol) was added to a solution of phosphorousoxybromide (11 g, 38 mmol) in acetonitrile (100 mL) and heated to reflux while stirring for ten hours. The reaction mixture was cooled in an ice bath, treated with ice (50 g) and stirred for an hour. Approximately half of the solvent was removed in vacuo. The product mixture was diluted with ethyl acetate (100 mL) and saturated sodium bicarbonate solution (300 mL) was cautiously added with stirring until it reached a pH=8. The organic layer was separated, washed with brine (50 mL), dried ($Na_2SO_4$) and evaporated. The product was purified by chromatography on silica gel eluted with a gradient of 40% to 50% ethyl acetate in hexanes. The purified product 9-7b was isolated as a colorless foamy solid (2.2 g, 61%). $^1$H-NMR (300 MHz, $CDCl_3$): δ 8.47 (d, J=1.2 Hz, 1H), 8.41 (dd, J=5.0 Hz, J=1.0 Hz, 1H), 7.96 (d, J=1.5 Hz, 1H), 7.85-7.73 (m, 4H), 7.57-7.46 (m, 2H), 7.41 (dd, J=8.8 Hz, J=2.1 Hz), 7.15 (dd, J=5.3 Hz, J=4.7 Hz, 1H); ESI MS $(M+H)^+$=380, 382; HPLC method A $R_t$=5.29 minutes.

6-Cyclopropyl-4-(3-fluoropyridin-4-yl)-3-(naphthalen-2-yl)pyridazine (10): (MW-167): A mixture of 6-Bromo-4-(3-fluoropyridin-4-yl)-3-(naphthalen-2-yl)pyridazine (9-7b, 2.2 g, 5.8 mmol), cyclopropyl boronic acid (0.70 g, 8.1 mmol), $PdCl_2(dppf)\cdot CH_2Cl_2$ (0.42 g, 0.58 mmol), silver oxide (3.36 g, 14.5 mmol), potassium carbonate (2.4 g, 17.4 mmol) and 1,4-dioxane (50 mL) was stirred and purged with nitrogen. The mixture was heated to 80° C. for 18 hours. The reaction mixture was cooled to 20° C. and filtered through celite (ethyl acetate wash). The filtrate was evaporated to dryness and the crude product was purified by chromatography on silica gel eluted with 50% ethyl acetate in hexanes to leave the product 10 as a gum that crystallized upon trituration with hexane (1.1 g, 56%). $^1$H-NMR (300 MHz, $CDCl_3$): δ 8.45 (d, J=1.4 Hz, 1H), 8.38 (dd, J=4.9 Hz, J=1.0 Hz, 1H), 7.95 (m, 1H), 7.84-7.51 (m, 2H), 7.74 (s, 1H), 7.54-7.43 (m, 3H), 7.33 (d, J=1.0 Hz, 1H), 7.14 (dd, J=5.6 Hz, J=5.0 Hz, 1H), 2.27 (m, 1H), 1.38 (m, 2H), 1.24 (m, 2H); ESI MS $(M+H)^+$=342; HPLC method A $R_t$=4.94 minutes.

4-(3-fluoropyridin-4-yl)-6-(4-methylpiperazin-1-yl)-3-(naphthalen-2-yl)pyridazine: (37): (MW-149): A solution of 6-bromo-4-(3-fluoropyridin-4-yl)-3-(naphthalen-2-yl)pyridazine 9-7b (50 mg, 0.13 mmol) and N-methylpiperazine (66 mg, 0.66 mmol) in 95% ethanol (1 mL) was heated to reflux for 18 h. The mixture was diluted with ethyl acetate (25 mL), washed with saturated sodium bicarbonate solution (25 mL), water (2×25 mL), brine (25 mL), dried ($Na_2SO_4$) and evaporated to a light tan solid 37 (50 mg, 96%). $^1$H-NMR (300 MHz, $CDCl_3$): δ 8.44 (d, J=1.5 Hz, 1H), 8.36 (d, J=5.0 Hz, 1H), 7.87 (s, 1H), 7.82-7.69 (m, 2H), 7.72 (s, 1H), 7.51-7.42 (m, 3H), 7.13 (dd, J=6.1 Hz, J=4.7 Hz, 1H), 6.95 (s, 1H), 3.95 (bm, 4H), 2.77 (bm, 4H), 2.49 (s, 3H). LC/MS (method A) $R_t$=3.40 mins., purity >95%, $(M+H^+)$=400.

Formation of Salt Forms of the Base to Hydrochloride Hydrates

Hydrochloride Hydrate of Products of the Base: 7, 9, 15, 16, and 25-27:

This was done as described in Hu et al, *Bioorg Med Chem Lett* 2007, 17: 414-418. Approximately 1 mmol of the respective compound was suspended in 8.2 mL of anhydrous isopropanol (99.5%, Aldrich), heated to 85° C. with stirring until dissolved, then 3.1 equiv (234 μL) of concentrated ultrapure HCl (12N, JT Baker Ultrex® II, Product 6900-05) was added to the clear solution, resulting in immediate generation of a suspension of solids. The suspension was stirred for 10 min (80° C.), allowed to cool to ambient temperature, then the vessel placed on ice for ~2.5 h, then stored (~16 hr) at 4° C. The resulting yellow precipitate was filtered on a medium frit sintered glass funnel under vacuum, washed (3×) with cold anhydrous isopropanol followed by three washes with cold anhydrous ether, and dried under vacuum. The precipitate was stored in vacuo in a glass desiccator containing silica gel until a constant weight was attained. The final products were obtained in approximately 82% yield (gravimetric) compared to the starting material. Hydrochloride hydrate formation was confirmed by elemental analysis. The goal was to obtain a mole ratio of HCl: compound that is >1. Under these conditions for the studies described here, elemental analysis indicated a ratio of ~2.

(MW-077 Hydrochloride Hydrate: (8): EA calculated for $C_{22}H_{23}C_2N_3O_2$: C, 61.12; H, 5.36; N, 9.72; Cl, 16.40; O, 7.40. experimentally found C, 59.54; H, 5.38; N, 9.38; Cl, 15.49; O, 9.46.

MW-156 Hydrochloride Hydrate: (38): EA calculated for $C_{20}H_{22}Cl_2N_4O_2$: C, 57.01; H, 5.26; Cl, 16.83; N, 13.30; O, 7.59. experimentally found C, 58.83; H, 5.56; Cl, 11.87; N, 13.11; O, 5.42.

MW-200 Hydrochloride Hydrate: (39): EA calculated for $C_{20}H_{22}Cl_2N_4O_2$: C, 57.01; H, 5.26; Cl, 16.83; N, 13.30; O, 7.59. experimentally found C, 55.48; H, 5.34; Cl, 16.34; N, 12.69; O, 4.06.

MW-031 Hydrochloride Hydrate: (40): EA calculated for $C_{22}H_{24}Cl_2N_4O$: C, 61.26; H, 5.61; Cl, 16.44; N, 12.99; O, 3.71. experimentally found C, 60.19; H, 5.65; Cl, 15.27; N, 12.83; O, 3.99.

MW-025 Hydrochloride Hydrate: (41): EA calculated for $C_{22}H_{26}C^1{}_2N_4O_2$: C, 58.80; H, 5.83; Cl, 15.78; N, 12.47; O, 7.12. experimentally found C, 58.33; H, 5.92; Cl, 15.19; N, 12.31; O, 6.43.

MW-150 Hydrochloride Hydrate: (42): EA calculated for $C_{24}H_{29}Cl_2N_5O_2$: C, 58.78; H, 5.96; N, 14.28; Cl, 14.46; O, 6.52. experimentally found C, 57.88; H, 5.72; N, 14.03; Cl, 14.31; O, 1.84.

MW-125 Hydrochloride Hydrate: (43): EA calculated for $C_{22}H_{23}Cl_2N_3O_2$: C, 61.12; H, 5.36; N, 9.72; Cl, 16.40; O, 7.40. experimentally found C, 61.15; H, 4.88; N, 9.58; Cl, 15.99; O, 8.01.

Example 9-1

3-(naphthalen-2-yl)-6-(piperidin-1-yl)-4-(pyridin-4-yl)pyridazine (61) (also referred to herein as MW-086) was prepared from compound 9-7a, the synthesis of which is described above in Example 9.

3-(naphthalen-2-yl)-6-(piperidin-1-yl)-4-(pyridin-4-yl)pyridazine (61): (MW-086): A solution of 6-bromo-3-(naphthalen-2-yl)-4-(pyridin-4-yl)pyridazine (9-7a) (25 mg, 69 µmol) and piperidine (29 mg, 0.35 mmol, 34 µl) in ethanol (95%, 1 ml) was heated to reflux for 18 h. The mixture was purified by purified by preparative RPHPLC. The product fractions were combined and neutralized with saturated aqueous sodium bicarbonate solution (25 ml) and the product was extracted with ethyl acetate (2×25 ml). The extracts were washed with brine, dried (MgSO₄) and evaporated to leave 24 mg solid (95%). ¹H NMR (300 MHz, CDCl₃) δ 8.54 (d, J=5.2 Hz, 2H), 7.94 (s, 1H), 7.80 (dd, J=5.6, 2.6 Hz, 1H), 7.75-7.67 (m, 2H), 7.50-7.40 (m, 2H), 7.37 (dd, J=6.5, 1.8 Hz, 1H), 7.16 (dd, J=4.4, 1.4 Hz, 2H), 3.79 (bs, 4H), 1.75 (bs, 6H); LC/MS $R_t$=1.85 min., purity >95%, m/z=367 $(M+H)^+$.

Example 9-2

6-(4-ethylpiperazin-1-yl)-3-(naphthalen-2-yl)-4-(pyridin-4-yl)pyridazine (62) (also referred to as herein MW-026) was prepared from compound 9-7a, the synthesis of which is described above in Example 9.

6-(4-ethylpiperazin-1-yl)-3-(naphthalen-2-yl)-4-(pyridin-4-yl)pyridazine (62) (MW-026): A solution of 6-bromo-3-(naphthalen-2-yl)-4-(pyridin-4-yl)pyridazine (9-7a) (40 mg, 0.11 mmol) in 95% ethanol (1 ml) was treated with N-ethylpiperazine (63 mg, 0.55 mmol, 70 µl) and heated to reflux for 18 h. After cooling to 20° C. ethyl acetate (25 ml) was added and the mixture was washed with water (3×25 ml), dried (MgSO₄) and evaporated to a solid (43 mg, 99%). ¹H-NMR (300 MHz, CDCl₃): δ 8.54 (d, J=5.6 Hz, 2H), 7.94 (s, 1H), 7.80 (d, J=7.8 Hz, 1H), 7.78-7.68 (m, 2H), 7.52-7.41 (m, 2H), 7.36 (dd, J=8.5 Hz, J=1.4 Hz, 1H), 7.15 (d, J=5.6 Hz, 2H), 6.87 (s, 1H), 3.83 (m, 4H), 2.64 (m, 4H), 2.51 (q, J=7.0 Hz, 2H), 1.16 (t, J=7.0 Hz, 3H); LC/MS method A: ESI pos. $(M+H)^+$=396, $R_t$=2.73 minutes.

Munoz L, Ralay Ranaivo H, Roy S M, Hu W, Craft J M, McNamara L K, Wing Chico L, Van Eldik L, and Watterson D M; A novel p38α MAPK inhibitor suppresses brain proinflammatory cytokine up-regulation and attenuates synaptic dysfunction and behavioral deficits in an Alzheimer's disease mouse model. *J Neuroinflammation* 2007, 4: 21.

Schmitt M, Aráujo-Junior JX, Oumouch S, Bourguignon J J; Use of 4-bromo pyridazine 3,6-dione for building 3-amino pyridazine libraries. *Molecular Diversity*, 2006, 10: 429-434

Tamayo N, Liao L, Goldberg M, Powers D, Tudor Y, Yu V, Wong Lu Henkle B, Middleton, S, Syed R; Design and synthesis of potent pyridazine inhibitors of p38 MAP kinase. *Bioorg Med Chem Lett* 2005, 15: 2409-2413.

Example 10

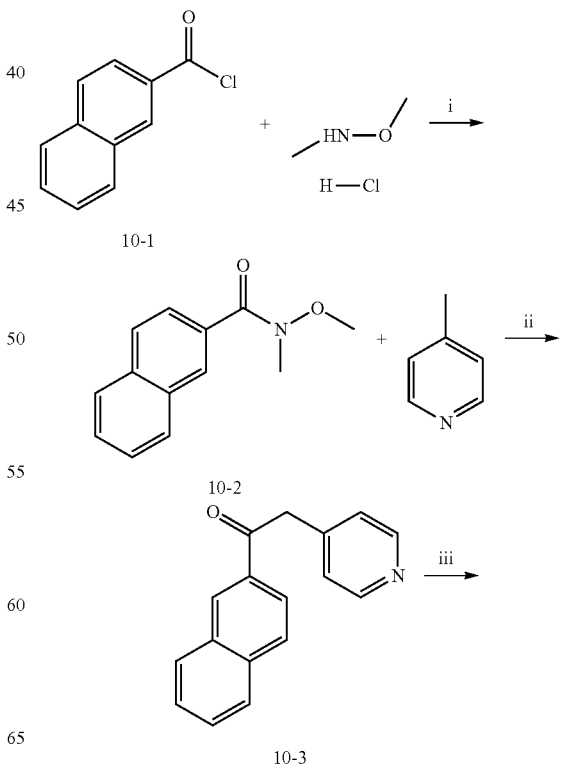

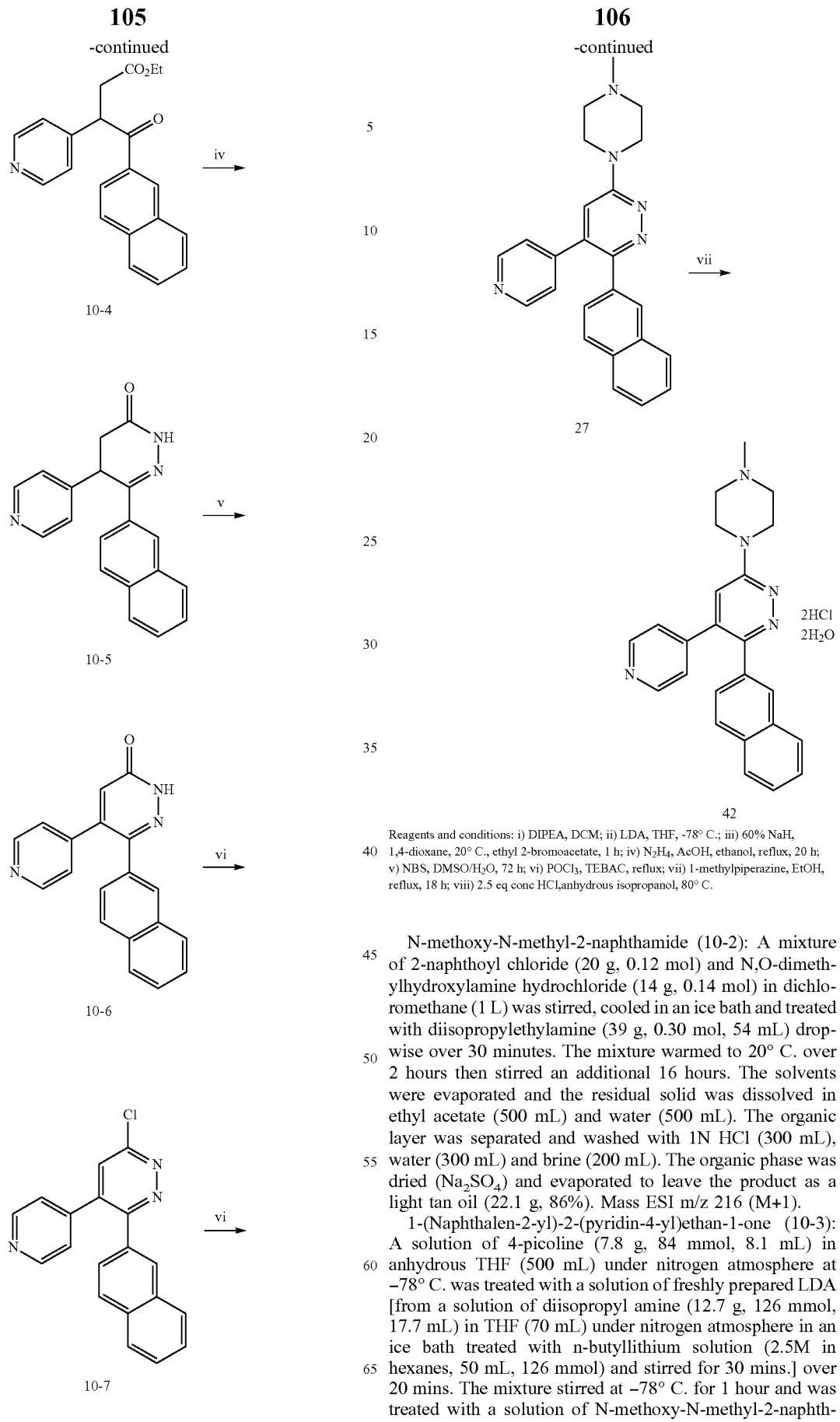

Reagents and conditions: i) DIPEA, DCM; ii) LDA, THF, -78° C.; iii) 60% NaH, 1,4-dioxane, 20° C., ethyl 2-bromoacetate, 1 h; iv) N₂H₄, AcOH, ethanol, reflux, 20 h; v) NBS, DMSO/H₂O, 72 h; vi) POCl₃, TEBAC, reflux; vii) 1-methylpiperazine, EtOH, reflux, 18 h; viii) 2.5 eq conc HCl, anhydrous isopropanol, 80° C.

N-methoxy-N-methyl-2-naphthamide (10-2): A mixture of 2-naphthoyl chloride (20 g, 0.12 mol) and N,O-dimethylhydroxylamine hydrochloride (14 g, 0.14 mol) in dichloromethane (1 L) was stirred, cooled in an ice bath and treated with diisopropylethylamine (39 g, 0.30 mol, 54 mL) dropwise over 30 minutes. The mixture warmed to 20° C. over 2 hours then stirred an additional 16 hours. The solvents were evaporated and the residual solid was dissolved in ethyl acetate (500 mL) and water (500 mL). The organic layer was separated and washed with 1N HCl (300 mL), water (300 mL) and brine (200 mL). The organic phase was dried (Na₂SO₄) and evaporated to leave the product as a light tan oil (22.1 g, 86%). Mass ESI m/z 216 (M+1).

1-(Naphthalen-2-yl)-2-(pyridin-4-yl)ethan-1-one (10-3): A solution of 4-picoline (7.8 g, 84 mmol, 8.1 mL) in anhydrous THF (500 mL) under nitrogen atmosphere at -78° C. was treated with a solution of freshly prepared LDA [from a solution of diisopropyl amine (12.7 g, 126 mmol, 17.7 mL) in THF (70 mL) under nitrogen atmosphere in an ice bath treated with n-butyllithium solution (2.5M in hexanes, 50 mL, 126 mmol) and stirred for 30 mins.] over 20 mins. The mixture stirred at -78° C. for 1 hour and was treated with a solution of N-methoxy-N-methyl-2-naphthamide (10-2, 20 g, 93 mmol) in THF (80 mL) drop-wise over 1.5 hours while ensuring the temperature was maintained at or below −75° C. The mixture was then allowed to warm to 20° C. over 4 hours and stirred an additional 16 hours at this temperature. Saturated ammonium chloride solution (50 mL) was added to the mixture and allowed to stir 30 mins. The solvents were evaporated in vacuo to approximately 20% of the original reaction mixture volume and the residue was dissolved in ethyl aceate (500 mL) and water (300 mL). The organic layer was separated and washed with water (300 mL). The product was extracted from the organic layer with 1N HCl (2×200 mL). The combined acid extracts were neutralized with solid sodium bicarbonate to pH=8. The precipitated product was filtered, washed with water (2×30 mL) and dried under vacuum for 16 hours to leave a light yellow solid. $^1$H-NMR (300 MHz, CDCl$_3$): δ 8.58 (dd, J=4.4 Hz, J=1.8 Hz, 2H), 8.53 (s, 1H), 8.05 (dd, J=8.5 Hz, J=1.8 Hz, 1H), 8.00-7.84 (m, 3H), 7.66-7.55 (m, 2H), 7.25 (m, 2H), 4.43 (s, 2H); ESI MS (M+H)$^+$=248; HPLC method A R$_t$=3.37 minutes.

Ethyl 4-(naphthalen-2-yl)-4-oxo-3-(pyridin-4-yl)butanoate (10-4): A solution of 1-(Naphthalen-2-yl)-2-(pyridin-4-yl)ethan-1-one (10-3, 17 g, 69 mmol) in anhydrous 1,4-dioxane under nitrogen atmosphere was treated with sodium hydride (60% in mineral oil, 3.2 g, 79 mmol) and stirred for 1 hour. The mixture, which now has a precipitate, was treated with ethyl 2-bromoacetate (13 g, 79 mmol, 8.8 mL) and stirred for 18 hours. A solution of saturated ammonium chloride (50 mL) was added and the mixture stirred for 30 mins. The solvents were evaporated to approximately 80% of the original volume and the residue was diluted with ethyl acetate (300 mL) and water (200 mL). The mixture was filtered through celite (ethyl acetate wash) to remove a small amount of yellow precipitate. The organic layer was separated and the product was extracted with 1N HCl (4×100 mL). The combined acid extracts were neutralized with solid sodium carbonate (pH=9) and the product was extracted with ethyl acetate (2×100 mL). The combined organic extracts were washed with brine, dried over Na$_2$SO$_4$ and evaporated. The residue was chromatographed on silica gel (80 g column) eluted with a gradient of ethyl acetate-hexanes (1:1 to 2:1) to leave the product as a light yellow solid (11.5 g, 50%). $^1$H-NMR (300 MHz, CDCl$_3$): δ 8.53 (dd, J=4.4 Hz, J=1.5 Hz, 2H), 8.49 (s, 1H), 7.99 (dd, J=8.5 Hz, J=1.7 Hz, 1H), 7.92 (d, J=7.9 Hz, 1H), 7.87-7.82 (m, 2H), 7.62-7.50 (m, 2H), 7.29 (dd, J=4.4 Hz, J=1.5 Hz, 2H), 5.27 (m, 1H), 4.12 (q, J=7.0 Hz, 2H), 3.42 (dd, J=17.0 Hz, J=9.4 Hz, 1H), 2.78 (dd, J=17.0 Hz, J=5.6 Hz, 1H), 1.21 (t, J=7.0 Hz, 3H); ESI MS (M+H)$^+$=334; HPLC method A R$_t$=3.89 minutes.

6-(Naphthalen-2-yl)-5-(pyridin-4-yl)-4,5-dihydropyridazin-3(2H)-one (10-5): A solution ethyl 4-(naphthalen-2-yl)-4-oxo-3-(pyridin-4-yl)butanoate (10-4, 16 g, 48 mmol) in ethanol (125 mL) and acetic acid (5 mL) was treated with hydrazine hydrate (80 g, 0.96 mol, 80 mL) and refluxed for 20 hours. A precipitate formed. The mixture was cooled and concentrated under reduced pressure to 50% of the original volume. The mixture was cooled in an ice bath and filtered to collect the product which was washed with ice cold methanol (20 mL) and air dried to leave a cream colored powder (12.3 g, 85%). $^1$H-NMR (300 MHz, CDCl$_3$): δ 8.76 (bs, 1H), 8.57 (d, J=5.3 Hz, 2H), 7.98 (dd, J=8.5 Hz, J=1.8 Hz, 1H), 7.95 (s, 1H), 7.85 (d, J=8.5 Hz, 1H), 7.86-7.76 (m, 2H), 7.55-7.46 (m, 2H), 7.21 (dd, J=4.4 Hz, J=1.2 Hz, 2H), 4.68 (d, J=6.5 Hz, 1H), 3.10 (dd, J=17.0 Hz, J=7.7 Hz, 1H), 2.90 (dd, J=17.0 Hz, J=1.8 Hz, 1H); ESI MS (M+H)$^+$=302; HPLC method A R$_t$=3.11 minutes.

6-(Naphthalen-2-yl)-5-(pyridin-4-yl)pyridazin-3(2H)-one (10-6): A round bottom flask equipped with a stir bar was charged 6-(naphthalen-2-yl)-5-(pyridin-4-yl)-4,5-dihydropyridazin-3(2H)-one (10-5, 12 g, 40 mmol), water (6 mL) and DMSO (250 mL). The mixture was stirred and treated with N-bromosuccinimide (35 g, 200 mmol). The reaction mixture turned yellow and a slight exotherm was noted while all solid contents went into solution. After stirring for 20 hours the mixture was poured into a stirring solution of water (1000 mL) and saturated sodium bicarbonate solution (500 mL) at such a rate that effervescence remained under control. The white precipitate that formed was collected on a glass frit, washed with water (2×50 mL) and air dried to leave 11.8 g (98%). $^1$H-NMR (300 MHz, CDCl$_3$): δ 11.13 (bs, 1H), 8.55 (bs, 2H), 7.80 (dd, J=9.1 Hz, J=2.1 Hz, 1H), 7.76-7.68 (m, 3H), 7.55-7.45 (m, 2H), 7.16 (dd, J=8.8 Hz, J=2.0 Hz, 1H), 7.09 (d, J=5.9 Hz, 2H), 7.05 (s, 1H); ESI MS (M+H)$^+$=300; HPLC method A R$_t$=2.88 minutes.

6-Chloro-3-(naphthalen-2-yl)-4-(pyridin-4-yl)pyridazine: (10-7): In a round bottom flask equipped with a stir bar was charged with 6-(Naphthalen-2-yl)-5-(pyridin-4-yl)pyridazin-3(2H)-one (10-6, 11.7 g, 39 mmol), tetraethyl ammonium chloride (9.42 g, 39 mmol), diisopropylethyl amine (6.9 mL) and POCl$_3$ (167 g). The resulting mixture was heated at 100° C. for ~3 hr (reaction monitored by HPLC). The reaction mixture was cooled to ambient temperature and concentrated under reduced pressure. The remaining POCl$_3$ was azeotropically removed using toluene. The reaction mixture was cooled in an ice bath, treated with ice (2 g) and stirred for an hour. The mixture was neutralized with saturated sodium carbonate to a pH=9 followed by extraction with ethyl acetate. The combined organic layer was separated, washed with brine dried (Na$_2$SO$_4$) and evaporated. The product was purified by chromatography on silica gel eluted with ethyl acetate in hexanes (1:1 to 2:1). The purified product 10-7 was isolated as an off-white solid (9.7 g) 78% yield. $^1$H-NMR (300 MHz, CDCl$_3$) δ 8.59 (dd, 2H, J=4.3 Hz, J=1.8 Hz), 8.03 (d, J=1.4 Hz, 1H), 7.85-7.65 (m, 3H), 7.72 (s, 1H), 7.58-7.47 (m, 2H), 7.33 (dd, 1H, J=8.5 Hz, J=1.8 Hz), 7.15 (dd, 2H, J=4.7 Hz, J=1.8); Mass m/z=317.

6-(4-methylpiperazin-1-yl)-3-(naphthalen-2-yl)-4-(pyridin-4-yl)pyridazine: (27): (MW-150): A solution of 6-chloro-3-(naphthalen-2-yl)-4-(pyridin-4-yl)pyridazine (10-7) (9.0 g, 28.3 mmol) in ethanol (150 mL) in a 500 mL round bottom flask was treated with 1-methylpiperazine (14.4 g, 141 mmol) and heated to reflux for 18 h. The solvent was evaporated in vacuo. The residue was dissolved in ethyl acetate (300 mL) and washed with water (2×200 mL) and saturated sodium bicarbonate solution (100 mL). The product precipitated from the organic layer and was collected via filtration on fritted glass. The product was washed with water (20 mL) and ethyl acetate (50 mL) and dried under high vacuum to leave 8.6 g (90%) of 27 as light yellow solid. $^1$H-NMR (300 MHz, CDCl$_3$) δ 8.54 (dd, 2H, J=4.4 Hz, J=1.7 Hz), 7.94 (s, 1H), 7.82-7.68 (m, 3H), 7.51-7.42 (m, 2H), 7.35 (dd, 1H, J=8.5 Hz, J=1.8 Hz), 7.15 (dd, 2H, J=4.4 Hz, J=1.7), 6.88 (s, 1H), 3.82 (dd, 4H, J=5.2 Hz, J=5.0 Hz), 2.60 (dd, 4H, J=5.2 Hz, J=5.0 Hz), 2.39 (s, 3H); ESI MS (M+H)$^+$=382; HPLC method A Rt=2.58 minutes.

Formation of Salt Forms of the Base to Hydrochloride Hydrates 6-(4-Methylpiperazin-1-yl)-3-(naphthalen-2-yl)-4-(pyridin-4-yl)pyridazine dihydrochloride dihydrate (42): In a round bottom flask fitted with condenser and dry tube, compound 6-(4-methylpiperazin-1-yl)-3-(naphthalen-2-yl)-4-(pyridin-4-yl)pyridazine (27) (7.75 g, 20.3 mmol) was suspended in (~70 mL) anhydrous isopropanol (99.5%, Aldrich) and heated to 87° C. with stirring until dissolved. To the resulting solution 2.5 equiv (4.31 uL) of ultrapure HCl (12N, JT Baker Ultrex® II, Product 6900-05) was added in-portion inducing formation of solids in suspension. The resulting solution is stirred at 80° C. for 10 min, cooled to ambient temperature and placed on ice for 2.5 h. The suspension was then transferred to 4° C. for an additional 10 hr. The resulting yellow precipitate was filtered on a medium frit sintered glass funnel using house vacuum, immediately washed with (3×35 mL) of ice-cold anhydrous isopropanol followed by (3×50 mL) of ice-cold anhydrous ether and air dried by house vacuum for 7 h. The product 42 was then dried in a glass desiccator containing silica gel in vacuo until the compound gave a constant weight. Product 42 obtained as a yellow powder 90% (gravimetric) yield, with HPLC purity 98% (HPLC method A); ESI m/z (MeOH): 382.2 (MH$^+$); $^1$H NMR (300 MHz, CDCl$_3$): δ 8.55 (dd, J=1.55, 4.45 Hz, 2H); 7.94 (s, 1H); 7.80-7.69 (m, 3H); 7.49-7.34 (m, 3H); 7.16 (dd, J=1.5, 4.5 Hz, 2H); 6.88 (s, 1H); 3.83 (t, J=4.8, 4.8, 4H); 2.62 (t, J=4.9,4.9, 4H); 2.39 (s, 3H); HRMS 381.1959 (calculated for C$_{24}$H$_{23}$N$_5$ 381.1953).

MW-150 Hydrochloride Hydrate: (42): EA calculated for C$_{24}$H$_{29}$Cl$_2$N$_5$O$_2$: C, 58.78; H, 5.96; N, 14.28; Cl, 14.46; O, 6.52. experimentally found C, 57.88 H, 5.72; N, 14.03; Cl, 14.31; O, 1.84.

Example 10-1

Alternatively, MW-150 hydrochloride hydrate (42) can be prepared as described below.

2-naphthoyl chloride: In a 1 L round bottom flask was charged with 2-naphthoic acid (50 g, 290 mmol) and SOCl$_2$ (375 mL). The solution was refluxed for 4 hours and then concentrated to yield yellow oil, which was used without further purification (55.28 g, 100% yield).

N-methoxy-N-methyl-2-naphthamide (10-2): A mixture of 2-naphthoyl chloride (1 eq, 35 g, 0.18 mol) and N,O-dimethylhydroxylamine hydrochloride (1.2 eq, 21.5 g, 0.22 mol) in dichloro-methane (1 L) was stirred, cooled in an ice bath and treated with diisopropylethylamine (2.5 eq, 58 g, 0.45 mol, 81 mL) drop wise over 30 min. The mixture was warmed to 20° C. over 2 h then stirred an additional 1 h. The solvents were evaporated and the residual solid was dissolved in ethyl acetate (500 mL) and water (500 mL). The organic layer was separated and washed with 1N HCl (300 mL), water (300 mL) and brine (200 mL). The organic phase was dried (Na$_2$SO$_4$) and evaporated to leave the product as light tan oil (10-2, 39.5 g, 100%), mass: m/z 216 (M+H)$^+$.

1-(Naphthalen-2-yl)-2-(pyridin-4-yl)ethan-1-one (10-3): A solution of 4-picoline (1 eq, 15.6 g, 168 mmol, 16.2 mL) in anhydrous THF (1 L) under nitrogen atmosphere at −78° C. was treated with a solution of freshly prepared LDA [from a solution of diisopropyl amine (25.4 g, 252 mmol, 35.4 mL)] in THF (140 mL) under nitrogen atmosphere in an ice bath treated with n-butyllithium solution (2.5M in hexanes, 100 mL, 252 mmol) and stirred for 30 min) over 30 min via cannula. The mixture was stirred at −78° C. for 1 h and was treated with N-methoxy-N-methyl-2-naphthamide (10-2), (1.1 eq, 40 g, 186 mmol) in THF (160 mL) drop wise over 1.5 h while ensuring the temperature was maintained at or below −75° C. The mixture was then allowed to warm to 20° C. over 4 h and stirred an additional 16 h at this temperature. Saturated ammonium chloride solution (100 mL) was added to the mixture and allowed to stir for 30 min. The solvents were evaporated in vacuo to approximately 20% of the original reaction mixture volume and the residue was dissolved in ethyl acetate (1 L) and water (600 mL). The organic layer was separated and washed with water (600 mL). The product was extracted from the organic layer with 1N HCl (2×300 mL). The combined acid extracts were neutralized with solid sodium bicarbonate to pH=8. The precipitated product was filtered, washed with water (2×50 mL) and dried under vacuum for 16 h to leave a light yellow solid 10-3 (34.5 g, 83%). $^1$H NMR (300 MHz, CDCl$_3$) δ 8.58 (dd, J=4.4, 1.8 Hz, 2H), 8.53 (s, 1H), 8.05 (dd, J=8.5, 1.8 Hz, 1H), 8.00-7.84 (m, 3H), 7.66-7.55 (m, 2H), 7.25 (m, 2H), 4.43 (s, 2H); Mass (ESI) m/z 248 (M+H)$^+$.

Ethyl 4-(naphthalen-2-yl)-4-oxo-3-(pyridin-4-yl)butanoate (10-4): In a round-bottom flask equipped with stir bar, an addition funnel and a thermometer was added sodium hydride (60% in mineral oil, 0.930 g, 23.3 mmol, 1.15 eq) and anhydrous THF (60 ml) under argon atmosphere. The mixture was stirred for 30 min at −5 to −10° C. A solution of 1-(Naphthalen-2-yl)-2-(pyridin-4-yl)ethan-1-one (10-3, 5 g, 20.2 mmol, 1 eq) in anhydrous THF (40 ml, cold) was added via an addition funnel with continuous stirring while keeping the temperature ~−5° C. The mixture was stirred for 20-30 min (deep yellow). To this mixture was added a solution of ethyl 2-bromoacetate (3.8 g, 23.3 mmol, 1.15 eq) in anhydrous THF (40 ml, cold) with vigorous stirring (color changed back to yellow). The reaction mixture stirred at ambient temperature for 3-4 h (reaction progress monitored by HPLC, 68-71% product peak after 2.5 h) and was quenched with crushed ice. The solvents were evaporated at reduced pressure to approximately 80% of the original volume and the residue was diluted with a mixture of ethyl acetate and water (30 ml, 3:2 v/v). To this mixture was added cold saturated NaHCO$_3$ solution (~150 ml) to neutralize to pH~8 and the product was extracted with ethyl acetate (2×200 ml). The combined ethyl acetate layers were washed with brine (2×50 ml), dried over anhydrous Na$_2$SO$_4$ and evaporated to a crude sticky residue. Trituration with hexane produced a yellow solid that was collected on a medium glass frit via suction filtration and dried to leave the product 10-4 (5.1 g, 75%). $^1$H NMR (500 MHz, CDCl$_3$) δ 8.53 (d, J=5.0, 2H), 8.49 (bs, 1H), 7.99 (dd, J=8.6 Hz, J=1.8 Hz, 1H), 7.92 (d, J=8.3 Hz, 1H), 7.86-7.82 (m, 2H), 7.60-7.50 (m, 2H), 7.30 (dd, J=1.7, 4.5 Hz, 2H), 5.27 (m, 1H), 4.12 (q, J=7.0 Hz, 2H), 3.42 (dd, J=17.0 Hz, J=9.3 Hz, 1H), 2.80 (dd, J=17.0 Hz, J=5.3 Hz, 1H), 1.21 (t, J=7.1 Hz, 3H); ESI MS (MH)$^+$=334.04.

6-(Naphthalen-2-yl)-5-(pyridin-4-yl)-4,5-dihydro-pyridazin-3(2H)-one (10-5): A solution ethyl 4-(naphthalen-2-yl)-4-oxo-3-(pyridin-4-yl)butanoate (10-4) (4 g, 1 eq) in ethanol in a round bottom flask was cooled to below 10° C. and was treated with hydrazine monohydrate. Reaction mixture was refluxed for ~4-5 h with stirring (until all starting material was consumed, monitored by HPLC). The mixture was cooled to ambient temperature and concentrated under reduced pressure to remove all solvents to get the yellowish orange semi solids. To the flask was added ~10 ml methanol and cooled to ~4° C. (kept in refrigerator for ~3 h). The white solids that formed were collected on a medium glass frit via suction filtration, washed with chilled methanol (2×10 ml) and dried under vacuum to obtain the product 10-5 (3 g, 83%). $^1$H NMR (300 MHz, CDCl$_3$) δ 8.76 (bs, 1H), 8.57 (d, J=5.3 Hz, 2H), 7.98 (dd, J=8.5, 1.8 Hz, 1H), 7.95 (s, 1H), 7.85 (d, J=8.5 Hz, 1H), 7.86-7.76 (m, 2H), 7.55-7.46 (m, 2H), 7.21 (dd, J=4.4, 1.2 Hz, 2H), 4.68 (d, J=6.5 Hz, 1H), 3.10 (dd, J=17.0, 7.7 Hz, 1H), 2.90 (dd, J=17.0, 1.8 Hz, 1H); Mass (ESI) m/z 302 (MH)$^+$; LC/MS method A R$_t$=3.11 min.

6-(Naphthalen-2-yl)-5-(pyridin-4-yl)pyridazin-3(2H)-one (10-6): In a round-bottom flask equipped with stir bar and condenser with dry tube was charged 6-(Naphthalen-2-yl)-5-(pyridin-4-yl)-4,5-dihydropyridazin-3(2H)-one (10-5) (3.2 g, 10.6 mmol, 1 eq) in glacial acetic acid. A solution of bromine (1.78 g, 11.2 mmol, 1.05 eq) in acetic acid was added with vigorous stirring at 70° C. and refluxed until all starting material disappeared ~2.5 h (reaction monitored by HPLC). The reaction mixture was cooled to ambient temperature, concentrated under vacuum, poured onto crushed ice and stirred for 1 h. To this reaction mixture cold 10% sodium carbonate solution was added at such a rate that effervescence remained under control and the pH was adjusted to 9. The white precipitate that formed was collected on a glass frit via suction filtration, washed with water twice (3×20 ml) and dried under vacuum to obtain the product 10-6 (3.1 g, 97%). $^1$H NMR (300 MHz, CDCl$_3$) δ 11.13 (bs, 1H), 8.55 (bs, 2H), 7.80 (dd, J=9.1, 2.1 Hz, 1H), 7.76-7.68 (m, 3H), 7.55-7.45 (m, 2H), 7.16 (dd, J=8.8, 2.0 Hz, 1H), 7.09 (d, J=5.9 Hz, 2H), 7.05 (s, 1H); Mass (ESI) m/z 300 (MH)$^+$; LC/MS method A $^tR$=2.88 min.

6-Chloro-3-(naphthalen-2-yl)-4-(pyridin-4-yl)pyridazine (10-7): A round bottom flask equipped with a stir bar was charged with 6-(Naphthalen-2-yl)-5-(pyridin-4-yl)pyridazin-3(2H)-one 10-6 (2.81 g, 9.4 mmol, 1 eq), dry acetonitrile (60 ml) and POCl$_3$ (17.2 g, 11.2 mmol, 12 eq). The mixture was heated at 90° C. for ~3 h (disappearance of starting material as monitored by HPLC). The reaction was quenched with addition of crushed ice followed by removal of acetonitrile under reduced pressure. The mixture was poured onto crushed ice and stirred for ~1 h, and neutralization done by addition of cold 10% NaOH (pH~9) while stirring. The product precipitated as fine particles which were collected on a glass frit under vacuum, washed with water (3×25 ml) and dried under vacuum to yield the light beige solid compound 10-7 (2.54 g, 85%). $^1$H NMR (CDCl$_3$, 500MHz) δ 8.66 (bs, 2H), 8.09 (s, 1H), 7.90-7.80 (m, 3H), 7.64 (s, 1H), 7.62-7.55 (m, 2H), 7.39 (d, J=8.5Hz, 1H), 7.24 (bs, 2H). Mass (ESI) m/z=317.94 (MH)$^+$.

6-(4-Methylpiperazin-1-yl)-3-(naphthalen-2-yl)-4-(pyridin-4-yl)pyridazine (27): A solution of 6-chloro-3-(naphthalen-2-yl)-4-(pyridin-4-yl)pyridazine (10-7) (2.54 g, 7.9 mmol, 1 eq) in 95% ethanol (40 ml) was reacted with 1-methylpiperazine (4 g, 40 mmol, 5 eq) under reflux for ~18 h. After cooling to ~20° C., ethanol is evaporated under reduced pressure and the resultant residue is dissolved in ethyl acetate: saturated aqueous sodium bicarbonate (2:1) mixture. The separated organic layer was twice washed with water (2×) which yielded the precipitated product in the organic layer. The solid product is harvested on a medium glass frit under vacuum, washed twice with ethyl acetate, and dried under vacuum (up to 12 h). Product 27 (2.6 g, 90%) was obtained as a pale yellow solid. $^1$H NMR (CDCl$_3$, 500MHz) δ 8.53 (dd, J=1.6, 4.4Hz, 2H), 7.92 (s, 1H), 7.78 (dd, J=5, 7.5Hz, 1H), 7.71-7.67 (m, 2H), 7.47-7.41 (m, 2H), 7.34 (dd, J=5, 7.5Hz, 1H), 7.13 (d, J=5, 5Hz, 2H), 6.86 (s, 1H), 3.83 (m, 4H), 2.62 (t, J=5Hz, 4H), 2.39 (s, 3H). Mass (ESI) m/z 382.20 (MH)$^+$; LC/MS method R$_t$=2.58 min.

6-(4-Methylpiperazin-1-yl)-3-(naphthalen-2-yl)-4-(pyridin-4-yl)pyridazine dihydrochloride dihydrate (42): In a round-bottom flask fitted with condenser and dry tube, compound 6-(4-methylpiperazin-1-yl)-3-(naphthalen-2-yl)-4-(pyridin-4-yl)pyridazine (8, 9.1 g, 23.8 mmol) was suspended in 100 mL of anhydrous isopropanol (99.5%, Aldrich) and heated to 81° C. with stirring until dissolved. To the resulting solution, ultrapure HCl (12 N, JT Baker Ultrex II, product 6900-05) (2.5 equiv, 5.1 mL, 59.63 mmol) was added in-portion, inducing formation of solids in suspension. The resulting solution was stirred at 81° C. for 10 min, cooled to ambient temperature, and placed on an ice-bath for 2.5 h. The suspension was then stored at 4° C. for an additional 10 h. The resulting yellow precipitate was filtered on a medium frit sintered glass funnel using a house vacuum, immediately washed three times with ice-cold anhydrous isopropanol (35 mL), followed by ice-cold anhydrous ether (50 mL), and air-dried using house vacuum for 7 h. The product was then dried in a glass desiccator containing silica gel in vacuo until the compound gave a constant weight. Product 42 obtained as a yellow powder (11.12 g, 96%), HPLC purity >98% (LC/MS). ESI m/z=382.2 (MH)$^+$. $^1$H NMR (500 MHz, CD$_3$OD) δ 8.75 (dd, J=1.5, 5.0 Hz, 2H), 7.96 (s, 1H), 7.91-7.83 (m, 6H), 7.58-7.52 (m, 2H), 7.38 (dd, J=1.8, 8.4 Hz, 1H), 4.86 (m, 2H), 3.71 (m, 2H), 3.57 (m, 2H), 3.28 (m, 2H), 3.01 (m, 3H). HRMS (mass) calculated for C$_{24}$H$_{23}$N$_5$: 381.19535. Found: 381.1955. Elemental analysis calculated (%) for C$_{24}$H$_{29}$C$_{12}$N$_5$O$_2$: C, 58.78; H, 5.96; N, 14.28; Cl, 14.46; O, 6.52. Found: C, 58.89; H, 5.89; N, 14.15; Cl, 14.27; O, 7.05. mp 240° C., decomposes.

Example 10-2

Compound 56 (6-(4-methylpiperidin-1-yl)-3-(naphthalen-2-yl)-4-(pyridin-4-yl)pyridazine) (also described herein as SRM-137A) can be prepared in a similar manner as described in Example 10-1 by using 4-methylpiperidine instead of 1-methylpiperazine.

Example 10-3

Compound 60 (3-(naphthalen-2-yl)-4-(pyridin-4-yl)-6-(4-(pyrimidin-2-yl)piperazin-1-yl)pyridazine) (also described herein as SRM-203B) can be prepared in a similar manner as described in Example 10-1 by using 2-(piperazin-1-yl)pyrimidine instead of 1-methylpiperazine.

Example 11

Scheme 11:

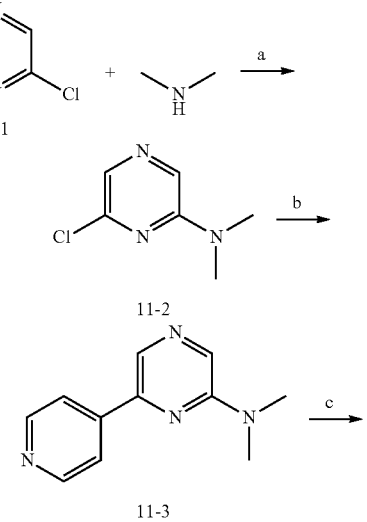

-continued

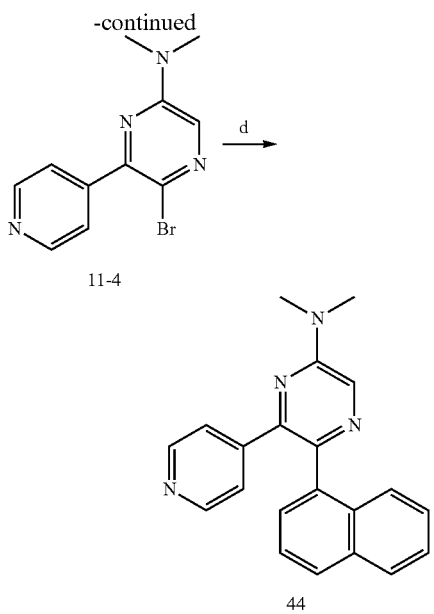

11-4

44

Reagents and conditions: a) Dimethyl amine 40%, 100 C., 6 hr; b) Pyridin-4-ylboronic acid, DME/water, Na$_2$CO$_3$, Pd(PPh$_3$)$_4$, 120° C., 18 hr; c) Br$_2$/acetic acid or NBS/CHCl$_3$; d) 1-Naphthylboronic acid, DME/water, Na$_2$CO$_3$, Pd(PPh$_3$)$_4$, 110° C., 15 hr.

6-chloro-N,N-dimethylpyrazin-2-amine (11-2): A mixture of 2,6-dichloro-pyrazine (1.2 g, 13.4 mmol, 1 eq) and 35 mL acetonitrile was combined in a heavy wall pressure vessel followed by the addition of 40% dimethyl amine (14.7 mmol, 1.1 eq) and K$_2$CO$_3$ (16.1 mmol, 1.2 eq) and purged with argon. The pressure vessel was capped and heated at 900° C. for 4 hr (monitored by TLC/HPLC). The reaction mixture was then cooled to ambient temperature, transferred to a round bottom flask and concentrated in vacuo. The residue was treated with 20 mL of Milli-Q water and the aqueous layer was extracted several times with dichloromethane using a separatory funnel. The combined organic layers were dried with anhydrous sodium sulfate and concentrated in vacuo. The product 2 was purified by column chromatography on silica gel (200-400 mesh) using ethyl acetate: hexane (1:1 v/v) eluent. Product 11-2 was obtained as white solid (1.1 g) in 60% (gravimetric) yield, with an apparent HPLC (tr/purity): 18.4 min, >90% (HPLC method A); (ESI) m/z (MeOH): 158.10 (MH$^+$).

N,N-dimethyl-6-(pyridin-4-yl)pyrazin-2-amine (11-3): A mixture of 6-chloro-N,N-dimethylpyrazin-2-amine (11-2) (1 g, 6.3 mmol) and pyridin-4-yl boronic acid (1.06 g, 8.6 mmol, 1.35 eq) were suspended in dimethoxyethane and water (10:1) in a heavy wall pressure vessel. The reaction mixture was purged with argon for 10 min. Sodium carbonate (2.0 g, 19.6 mmol, 3 eq) and tetrakis(triphenylphosphine)palladium (0.650 g, 0.57 mmol) were added and the reaction mixture was heated at 110° C. for 15 hrs. The reaction mixture was cooled to ambient temperature and filtered though a medium frit sintered glass funnel filled with Celite. The filtrate was concentrated under reduced pressure, dissolved in dichloromethane and washed with water (3×5 mL). The organic layer was dried with sodium sulfate and concentrated under reduced pressure. The product 11-3 was purified over silica gel column using ethylacetate and hexane (2:3 v/v) eluent. The title compound 11-3 was obtained as yellow solid (1.1 g) in 75% (gravimetric) yield. HPLC (tr/purity): 10.7 min, >90% (HPLC method A); ESI m/z (MeOH): 201.10 (MH$^+$).

5-bromo-N,N-dimethyl-6-(pyridin-4-yl)pyrazin-2-amine (11-4): Bromine (282 µL, 54.9 mmol, 1.1 eq) was added dropwise to the solution of N,N-dimethyl-6-(pyridin-4-yl)pyrazin-2-amine (11-3) (1 g, 50 mmol) in 5 mL of acetic acid at room temperature with stirring. The reaction progress was monitored by HPLC until all starting material disappeared (~4 hr). The reaction mixture was poured onto crushed ice and treated with (5%) sodium bisulfate solution to remove the excess bromine. The pH of the aqueous reaction mixture was adjusted to pH 7 with 0.2 N NaOH and the mixture was extracted several times with dichloromethane. The combined organic phase was dried over Na$_2$SO$_4$ (anhydrous) and concentrated under reduced pressure. Product 4 was purified by silica get (200-400 mesh) column chromatography using dichloromethane and 5% MeOH as eluent, Product 11-4 was obtained as pinkish solid (600 mg) in 76% (gravimetric) yield. HPLC (tr/purity): 13.80 min, >90% (HPLC method A); (ESI) m/z (MeOH): 279.10 (MH$^+$).

N,N-dimethyl-5-(naphthalen-1-yl)-6-(pyridin-4-yl)pyrazin-2-amine (44): (MW-064): A mixture of 5-bromo-N,N-dimethyl-6-(pyridin-4-yl)pyrazin-2-amine (11-4) (0.500 g, 1.7 mmol) and 1-napthylboronic acid (0.422 g, 2.4 mmol) were suspended in dimethoxyethane (DME) and water (10:1) in a heavy wall pressure vessel. The reaction mixture was purged with argon for 10 min. Subsequently tetrakis(triphenylphosphine)palladium (0.186 g, 9 mol %) and sodium carbonate (0.588 g, 5.5 mmol) were added and the reaction mixture was heated at 110° C. for 15 hrs. The reaction mixture was cooled to ambient temperature and filtered though a medium frit sintered glass funnel filled with Celite. The filtrate was concentrated under reduced pressure and added ~15 mL MilliQ water and extracted several times in dichloromethane. The combined organic layers was dried over anhydrous sodium sulfate and then concentrated under reduced pressure. The product 44 was purified by column chromatography on silica gel (200-400 mesh) using ethyl acetate and hexane (2:3 v/v) eluent. The product 44 was obtained as pale yellow powder (320 mg) in 45% (gravimetric) yield. $^1$H NMR (500 MHz, CDCl$_3$): δ 8.34 (b, 2H); 8.23 (s, 1H); 7.88 (dd, J=8.4 Hz, 2H); 7.74 (d, J=8.4 Hz, 1H); 7.48-7.36 (m, 3H); 7.26-7.22 (m, 3H); 3.29 (s, 6H). HPLC (tr/purity): 16.3 min >97% (method A); mass (ESI) of m/z (CD$_3$OD): 327.20 (MH$^+$); HRMS calculated for C$_{21}$H$_{18}$N$_4$ 326.1531 found 326.1532.

Example 11-1

Compound 63 (5-(4-methylpiperazin-1-yl)-2-(naphthalen-2-yl)-3-(pyridin-4-yl)pyrazine) (also described herein as SRM-138B) can be prepared in a similar manner as described in Example 11 by using 1-methylpiperazine instead of dimethyl amine and by using 2-naphthylboronic acid instead of 1-naphthylboronic acid.

References

D. Martin Watterson, Valerie L. Gram-Tokars, Saktimayee M. Roy, James P. Schavocky, Brinda D. Bradaric, Adam D. Bachstetter, Bin Xing, Edgardo Dimayuga, Faisal Saeed, Hong Zhang, Agnieszka StanisZewski, Jeffrey C. Pelletier, George Minasov, Wayne F. Anderson, Ottavio Arancio, Linda J. Van Eldic, *PLOS ONE*, 2013, 8, e66226.

Munoz L, Ralay Ranaivo H, Roy S M, Hu W, Craft J M, McNamara L K, Wing Chico L, Van Eldik L, and Watterson D M; A novel p38α MAPK inhibitor suppresses brain proinflammatory cytokine up-regulation and attenuates synaptic dysfunction and behavioral deficits in an Alzheimer's disease mouse model. *J Neuroinflammation* 2007, 4: 21.

Hu W, Ralay Ranaivo H, Roy S M, Behanna H A, Wing L K, Munoz L, Guo L, Van Eldik L J, Watterson D M; Development of a novel therapeutic suppressor of brain proinflammatory cytokine up-regulation that attenuates synaptic dysfunction and behavioral deficits. *Bioorg Med Chem Lett* 2007, 17: 414-418.

Schmitt M, Ara'ujo-J'unior JX, Oumouch S, Bourguignon J J; Use of 4-bromo pyridazine 3,6-dione for building 3-amino pyridazine libraries. *Molecular Diversity*, 2006, 10: 429-434

Tamayo N, Liao L, Goldberg M, Powers D, Tudor Y, Yu V, Wong Lu Henkle B, Middleton, S, Syed R; Design and synthesis of potent pyridazine inhibitors of p38 MAP kinase. *Bioorg Med Chem Lett* 2005, 15: 2409-2413.

Example 12

Kinase Assays

The concentration dependent ability of compounds to inhibit human p38α MAPK, p38βMAPK and CK-1δ were done essentially as described in *J. Neurosci.* 2012, 32, 10201 (herein incorporated by reference in its entirety) and by use of commercially available Millipore® Drug Discovery and Development services. $IC_{50}$ values were calculated by generating a 10-11 point curve and analyzed using nonlinear regression curve fit in GraphPad Prism statistical software. Z-factor (≥0.5) calculation and % CV (<20%) were calculated for each assay. Large-scale kinome screens were done using the commercially available Millipore® Profiler test systems (www.millipore.com) that included >291 protein kinases representative of all major kinome branches as well as isoforms of individual families. The NCBI Entrez identifier for each kinase is provided at the vendor site. A hierarchal analysis was done on inhibitors. First, an initial screen was done where each inhibitor was tested at a fixed concentration (20,000 nM) against a panel of protein kinase targets covering the major branches of the kinome, using an ATP concentration for each kinase at or near their apparent Km. Second, preliminary hits from the profiler screen were validated by a follow-up concentration dependent test of the inhibitor to obtain an $IC_{50}$ value for the inhibitor and a given kinase in order to confirm the hit as positive. Third, kinetic analyses to determine a Ki value were done on confirmed positives with $IC_{50}$ values <1,000 nM.

The commercially available europium competitive active site binding assay (LanthaScreen® Eu Kinase Binding Assay, Invitrogen Life Science Technologies, Grand Island, N.Y., USA) that is based on time-resolved fluorescence resonance energy transfer (TR-FRET) technology was used to test for competitive binding to the non-activated form of p38α MAPK. $IC_{50}$ values were generated from triplicate 12-point curves. Assays were performed in a 384 well plate format (Corning cat No. 3673) in a final volume of 15 μL containing 5 nM kinase (Invitrogen cat No. PV3305), 5 nM tracer (Invitrogen cat No. PV5830), 2 nM antibody (Invitrogen cat No. PV5594). Plates were centrifuged (240 g, 5 min) to mix ingredients, incubation done for 60 min at 25° C., and plates centrifuged (240 g, 5 min) to concentrate reaction mixtures in the plate bottom well. Readings were taken in an En Vision Plate Reader (Perkin Elmer; Waltham Mass., USA) using a dichroic mirror and excitation at wavelength 340 nm (30 nm bandpass) and emission at 665 nm (10 nm bandpass) and 615 nm (10 nm bandpass). Delay time was 100 μs, and integration time 200 μs. The emission ratio was determined by dividing the acceptor/tracer emission (665 nM) by the antibody/donor emission (615 nM). Data were expressed as percent of the maximal binding activity, as determined by the emission ratio, and $IC_{50}$ values were calculated using GraphPad Prism, version 5.0a, by a nonlinear regression data analysis of log inhibitor concentration versus emission ratio.

Off-Target Functional Screens

Compounds were screened in vivo using a standard dose escalation screen in mice coupled with clinical observation and testing based on the SHIRPA mouse phenotype assay paradigm (*Mammalian Genome* 8, 711-719 SHIRPA (1997); herein incorporated by reference in its entirety). To obtain insight into the potential for off-target activity with the largest known family of small molecule drug targets, G-protein coupled receptors (GPCRs), a cell-based functional screen of the final title compounds was done. The Millipore® GPCR Profiler screen employs the ChemiScreen GPCR stable cell line technology used for real-time calcium flux FLIPR assays on a panel of 158 GPCRs. The NCBI Entrez identifier for each GPCR is provided at the vendor site (www.millipore.com). Follow-up validation of any initial hits as being true positives or negatives was done as described above for protein kinases by testing the concentration dependence of any cellular effects. No $IC_{50}$ values <1,000 nM were detected.

p38α MAPK activity retention and improved no adverse effect levels in mice were observed with simplification of the amine. Surprisingly, introduction of bulkier groups, for example naphthyl, at the R3 position of the pyridazine provided improved occupancy at the hydrophobic pocket of the enzyme. The introduction of large groups at this position surprisingly improved p38α MAPK affinity and reduced affinity for Ck1δ (Table 2).

TABLE 2

Target Family Screen:

| Cmpd | p38α MAPK $IC_{50}$(nM) | p38α MAPK $K_i$(nM) | Ck1δ $IC_{50}$ (nM) |
|---|---|---|---|
| 1 (MW-181) | 215 | 184 | >10,000 |
| 2 (MW-108) | 236 | 114 | 6,118 |
| 3 (MW-066) | 481 ± 174 | | 130 ± 40 |
| 4 (MW-177) | 238 ± 49 | | 369 ± 30 |
| 5 (MW-207) | 408 ± 41 | | 284 ± 30 |
| 6 (MW-105) | 543 ± 29 | 657 | 843 ± 42 |
| 7 (MW-077) | 419 | 186 | >10,000 |
| 9 (MW-125) | 412 | 127 | >10,000 |
| 10 (MW-167) | 307 | 86 | >10,000 |
| 11 (MW-122) | 185 | 98 | >10,000 |
| 12 (MW-124) | 191 | | >10,000 |
| 13 (MW-107) | 264 | 91 | >10,000 |
| 14 (MW-109) | 131 | | >10,000 |
| 15 (MW-156) | 289 | 276 | >10,000 |
| 16 (MW-200) | 175 | 100 | 4,984 |
| 17 (MW-078) | 1775 | | >10,000 |
| 18 (MW-085) | 1166 | | |
| 19 (MW-155) | >1600 | | |
| 20 (MW-082) | >3200 | | >10,000 |
| 21 (MW-165) | >1600 | | |
| 22 (MW-066) | 369 | | 4,283 |
| 23 (MW-033) | 162 | | >10,000 |
| 24 (MW-010) | 188 | | >10,000 |
| 25 (MW-031) | 162 | | >10,000 |
| 26 (MW-025) | 130 | | 2,620 |
| 27 (MW-150) | 282 | 101 | 2,802 |
| 28 (MW-118) | 518 | | 403 |
| 29 (MW-108) | 3070 | | 6126 |
| 30 (MW-126) | 753 | | 2628 |
| 31 (MW-146) | 240 | | 6,458 |
| 32 (MW-148) | 185 | | 2,989 |
| 33 (MW-152) | 481 | | |
| 34 (MW-154) | 112 | | 2,162 |
| 35 (MW-153) | 189 | | |

TABLE 2-continued

Target Family Screen:

| Cmpd | p38α MAPK IC$_{50}$(nM) | p38α MAPK K$_i$(nM) | Ck1δ IC$_{50}$ (nM) |
|---|---|---|---|
| 36 (MW-164) | 224 | 101 | 11,227 |
| 37 (MW-149) | 235 | | 4,619 |
| 44 (MW-064) | 456 | 343 | >10,000 |
| 49 (MW-203) | 1176 | | 6,352 |
| 50 (MW-017) | 974 | | 16,752 |
| 51 (MW-044) | 2096 | | 39,869 |
| 52 (MW-032) | 735 | | 17,897 |
| 53 (MW-059) | >20,000 | | 118,989 |
| 54 (MW-197) | 669 | | 135,537 |
| 55 (MW-063) | 526 | | 32,522 |
| 61 (MW-086) | >20,000 | | 9,087 |
| 62 (MW-026) | 520 | | 4,993 |

Example 13

Cell-Based Assays

Quantitative Cell-Based Activity Screen

The ability of compounds to reduce stressor-induced up-regulation of proinflammatory cytokine production was tested in the murine microglial BV-2 cell line stimulated with LPS as previously described (*J. Neuroinfl.* 2011, 8, 79; herein incorporated by reference in its entirety). For experiments, cells were plated in 48-well tissue culture plates at $2 \times 10^4$ cells/well and cultured for 24 hrs. Serum-containing medium was then removed and cells were treated with either saline vehicle control or 100 ng/ml LPS stimulus (LPS from *Salmonella enterica* serotype *typhimurium*; EU/mg 600,000; Sigma L6143) in the absence or presence of increasing concentrations of compound, with at least six concentrations of compound ranging from 0.45 µM to 30 µM. Stock solutions of compounds were made in sterile saline (0.9% sodium chloride) that was free of preservatives (Hospira, Inc., Lake Forest, Ill.: NDC 0409-4888-10). Solutions for cell treatments were prepared by dilution of the stock solutions into serum-free media immediately before adding to the cells. Compound was added to cell cultures just before LPS addition. In some experiments, BV-2 cells were stimulated with other TLR ligands as described previously (*J. Neuroinfl.* 2011, 8, 79; herein incorporated by reference in its entirety). TLR ligands used were TLR2: 10 µg/ml LTA, TLR4: 100 ng/ml LPS, TLR7/8: 500 ng/ml CL097, and TLR9: 500 ng/ml ODN1668. Cells were harvested after 18 hrs of treatment for cytokine measurements.

Levels of IL-1β in cell lysates were measured by ELISA using kits from Meso Scale Discovery (MSD; Gaithersburg, Md.), as previously described (*J. Neuroinfl.* 2011, 8, 79; herein incorporated by reference in its entirety). For the most consistent cytokine measurements with the lowest intra- and interassay variability, cell lysates were frozen at −80° C. for at least one hour, then thawed prior to cytokine assay. Cytokine levels were determined by comparison to standard curves ranging from 2.4 pg/mL to 10,000 pg/mL, and confirmation that sample values were on the linear part of the standard curves. The levels of IL-1β were normalized to the LPS-stimulated vehicle-treated control group for each 48-well tissue culture plate, with data presented as percent of LPS alone. Data represent 3-to-10 independent experiments.

Cell-Based Target Engagement and Activity

The concentration dependent ability of the compounds to inhibit LPS-induced phosphorylation of MK-2, a highly selective p38α MAPK substrate, was examined in BV-2 cells as previously described (*J. Neuroinfl.* 2011, 8, 79; herein incorporated by reference in its entirety). BV-2 cells were plated in 48-well tissue culture plates at $2 \times 10^4$ cells/well and treated in serum containing media with LPS in the absence or presence of compounds as described above. After 60 min of treatment, cell lysates were prepared, and phospho-MK-2 levels were measured by MSD ELISA kits. MSD signal was baseline corrected by subtracting the unstimulated vehicle-treated control group. The data were then normalized to the LPS-stimulated vehicle-treated control group for each 48-well tissue culture plate. Data are presented as percent of LPS alone, and represent 2-to-3 independent experiments.

The loss of inhibitory activity in LPS-induced microglia where the endogenous p38α MAPK gene was disrupted by knock-in of a fully active but drug resistant MAPK mutant, p38αT106M knock-in (*J. Biol. Chem.* 2007, 282, 34663; herein incorporated by reference in its entirety), was tested in primary microglia cultures as previously described (*J. Neuroinfl.* 2011, 8, 79; herein incorporated by reference in its entirety). Mixed glial cultures were prepared from the cerebral cortex of 1-3 day old neonatal C57Bl/6 mice (WT) or p38αT106M knock-in mice, and microglia were isolated from the mixed glial cultures by the shake-off procedure as described (*J. Neuroinfl.* 2011, 8, 79; herein incorporated by reference in its entirety). Microglia were stimulated with LPS (3 ng/mL) or vehicle control for 24 hrs in the absence or presence of inhibitors, and IL-1β levels measured as described above. Data are expressed as a percent of the maximal activity, where activity in the presence of LPS alone is taken as 100%. Data represent 3 independent experiments.

Example 14

In Vivo Efficacy Related to CNS Inflammatory Response

The ability of compounds to inhibit an acute CNS inflammatory response was tested in mice administered LPS to induce brain cytokine production as previously described (*J. Neuroinfl.* 2011, 8, 79; herein incorporated by reference in its entirety). 2-month old, female, C57Bl/6 mice were administered LPS (0.5 mg/kg) by i.p. injection and received compound (20 mg/Kg) or saline vehicle by oral gavage in a volume of 200 µL one hr prior to the LPS injection. At 6 hrs after LPS administration, mice were euthanized, perfused with phosphate-buffered saline (PBS), and brain cortex homogenate supernatants prepared as described (*J. Neuroinfl.* 2011, 8, 79; herein incorporated by reference in its entirety). IL-1β levels in 50 µL of supernatant were determined by MSD ELISA. BCA Protein Assay (Pierce) was used to normalize the total amount of protein in the sample loaded.

Target engagement and validation screens for the glia-based p38α MAPK mediated stress responses that include upregulation of proinflammatory cytokine (PIC) production. These results are summarized in FIG. 1A-1C. The concentration dependent inhibition of increased PIC production over the same range in which phosphorylation of selective downstream substrates is inhibited in a standard mouse glia cell line (BV2). FIG. 1D shows lack of responsiveness to treatment in drug resistant cells from mutant mice in which the endogenous p38α MAPK gene is disrupted by insertion of a transgene encoding a fully active mutant p38α MAPK where the gatekeeper amino acid for the hydrophobic pocket is mutated from small to bulky side chain (T to M), blocking access to the pocket. The bulkier side chain prevents binding of the inhibitors as a key characteristic of target recognition and affinity is entry of the ligand's aromatic group into the hydrophobic pocket of the kinase, which is allowed when a small side chain amino acid is at the gatekeeper but not when a bulky group is present. As a result, the knock-in mice have a p38α MAPK with normal catalytic activity but are resistant to small molecule inhibitors that employ this ligand-target recognition feature. This mechanistic linkage between target engagement in stressed cell modulation related to the disease progression mechanism is a link among inhibitors with good in vitro activity and pharmacokinetic properties. FIG. 1E shows in vivo inhibition of LPS induced PIC increase in the cortex. FIG. 1F shows efficacy with extended administration to a transgenic mouse AD model in which the pathology progress is prolonged and involves early PIC increases.

The ability of MW-108 to engage its target in a cellular assay was done by examining the concentration-dependent inhibition of phosphorylated MK-2, considered a highly selective p38α MAPK substrate. FIG. 2A shows the results with the microglial cell line BV-2 stimulated with the standard glial activating stimulus lipopolysaccharide (LPS). There is a clear decrease in phosphorylated MK-2 in LPS-stimulated cells with increasing concentration of MW-108 (2). LPS activation of the signal transduction pathway involving p38α MAPK and its substrate MK-2 results in a downstream increase in proinflammatory cytokine production. Levels of the proinflammatory cytokine interleukin 1β (IL-1β) as a function of MW-108 (2) concentration (FIG. 2B) were quantified, and showed a coincident decrease over a similar concentration range. The $IC_{50}$ using inhibition of IL-1β overproduction as an end point was 610±20 nM.

To extend the general biological relevance of the initial cellular engagement studies, the ability of MW-108 (2) to inhibit increases in IL-1β levels using different stressors, wild-type and inhibitor resistant primary cells, and in vivo responses was examined. As shown in FIG. 2C, the inhibition of IL-1β production is not limited to LPS as a stressor, but was also seen in BV-2 cells stimulated with diverse TLR ligands (TLR2, TLR4, TLR7/8, TLR9). As shown in FIG. 2D, further validation was provided by demonstrating a loss of MW-108 (2) activity in primary microglia cultures where the endogenous p38α MAPK was removed by targeted knock-in replacement with a fully active but drug resistant mutant p38α T106M MAPK. The knock-in yields catalytically normal kinase, but the replacement of the gatekeeper Thr at residue 106 with a larger side chain Met amino acid renders the mutant p38α T106M MAPK resistant to inhibitors such as MW-108 (2) that exploit the use of the hydrophobic pocket with bulky substituents. To probe the in vivo relevance of the proinflammatory cytokine modulation seen in glia cultures, we tested if oral administration of MW-108 (2) could attenuate stressor induced IL-1β increases in the brain. As shown in FIG. 2E, oral administration of MW-108 (2) restored IL-1β levels in the brain cortex back towards control. Altogether, these results demonstrate that MW-108 engages its molecular target p38α MAPK and modulates the linked cellular response of increased proinflammatory cytokine production, and that this target-related function is evident in vivo.

A prevailing hypothesis in kinase inhibitor development based on analysis of successful campaigns is that in vivo efficacious kinase inhibitors engage a close set of multiple kinases (*Methods Mol. Biol.* 2012, 795, 1; herein incorporated by reference in its entirety). Relatedly, many existing p38α MAPK inhibitors are equivalent or better inhibitors of p38β MAPK, NLK, CK1 and other kinases.

Figure 3C:
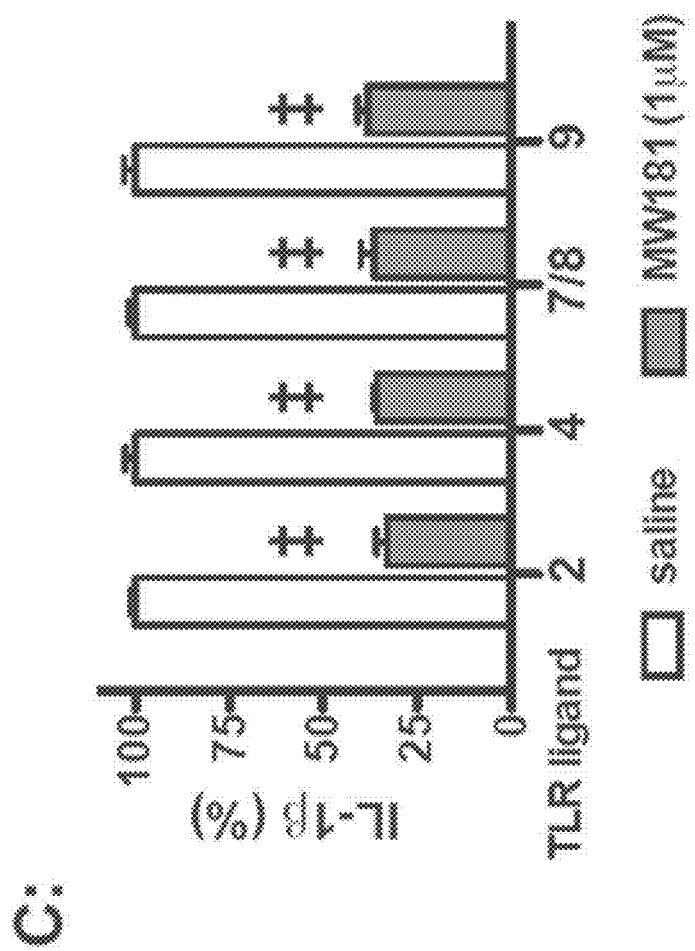

To address whether a mixed p38 MAPK inhibitor that lacks CK1 inhibition would have cellular activities similar to MW-108 (2), the effects of MW-181(1) were examined in the same series of target engagement and mechanism of action studies. MW-181 (1) exhibited activities similar to MW-108 (2), including inhibition of increased cytokine production by glia in response to LPS ($IC_{50}$=820±30 nM) and other TLR ligands, inhibition of MK-2 phosphorylation, loss of activity in drug resistant microglia, and in vivo suppression of increased brain levels of IL-1β after oral administration (FIG. 3). The data indicate that the activity and function of the p38 MAPK family inhibitor, MW-181 (1), reflects its p38α MAPK inhibition in these assays.

Stressor induced responses include activation of endogenous p38α MAPK which, in turn, increases its phosphorylation of endogenous substrates such as pMK2 and pMSK1. This endogenous kinase activity is the proximal step in the in vivo mechanism that yields injurious increases in proinflammatory cytokine production by glia. The phosphorylation state (activation) of the p38α substrates pMK2 (FIG. 4A) and pMSK1 (FIG. 4B) are increased at 1 hr after LPS addition and this increase is attenuated in a dose dependent manner by the inhibitor. Data are expressed as percent of maximal activity (activity with LPS+vehicle), and are representative of at least 2 independent experiments. The log IC50 values and IC50 95% confidence intervals are shown in gray boxes within the graphs.

Concentration-dependent suppression of glia transformation via inhibition of endogenous p38α MAPK phosphorylation of endogenous glia substrates was examined via serial dilutions of MW-181(1) added to glia stimulated with LPS. At 18 h after LPS addition, IL-1β protein levels in cell lysates were measured via ELISA (FIG. 4C).

Figure 5A:
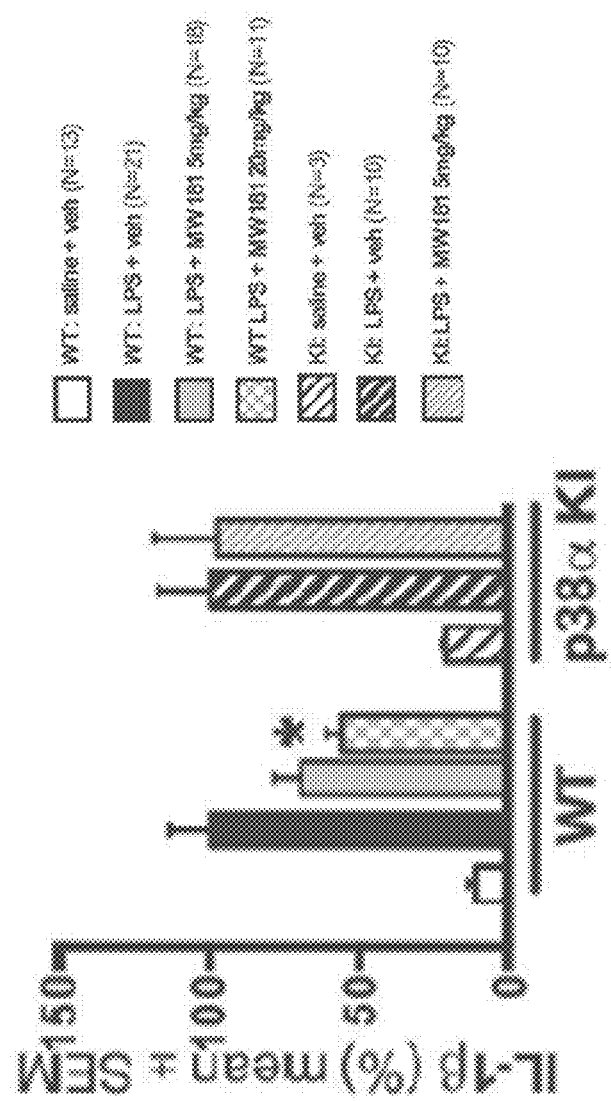
FIGS. 5A-B show linkage of in vitro inhibition to in vivo efficacy. MW-181 reduces IL-1β levels (5A) and IL-6 levels (5B) in stressed wild type (WT) mice but not in drug resistant strains (KI).
Figure 5B:
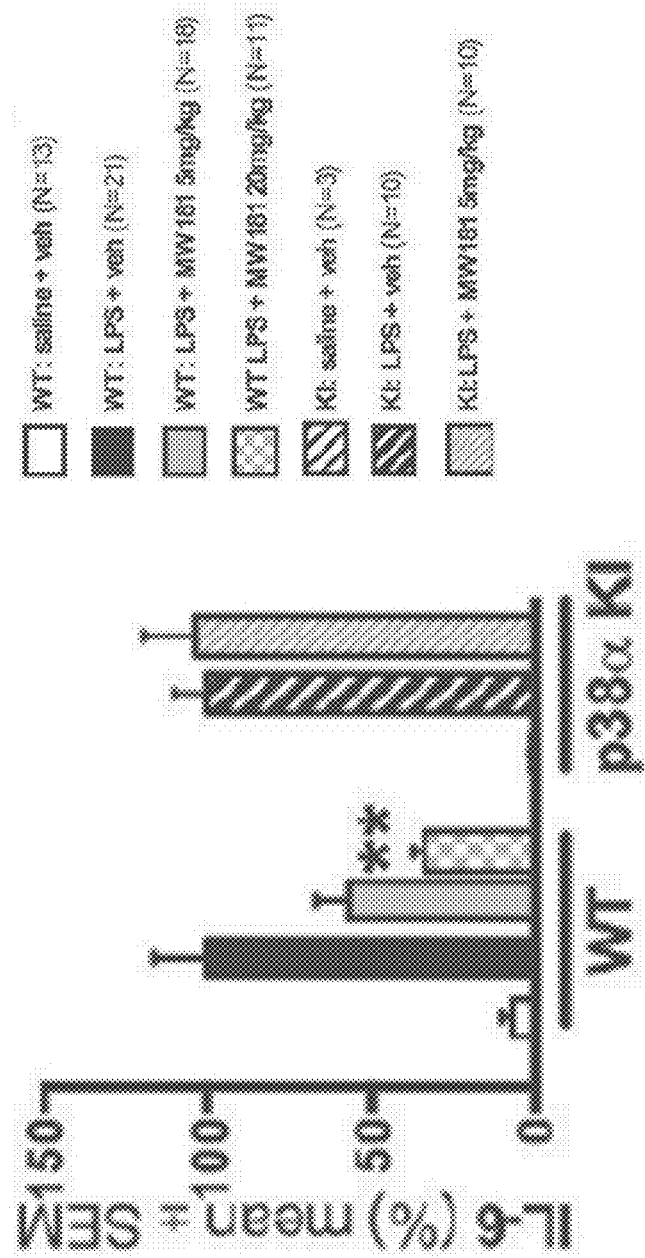

MW-181 (1) reduces brain cytokine levels in stressed wild type (WT) mice but not in drug resistant strains (KI) that have normal p38α MAPK activity but cannot bind the inhibitors due to a designed point mutation that prevents active site binding of the inhibitor. (FIGS. 5A and 5B).

Figure 6A:
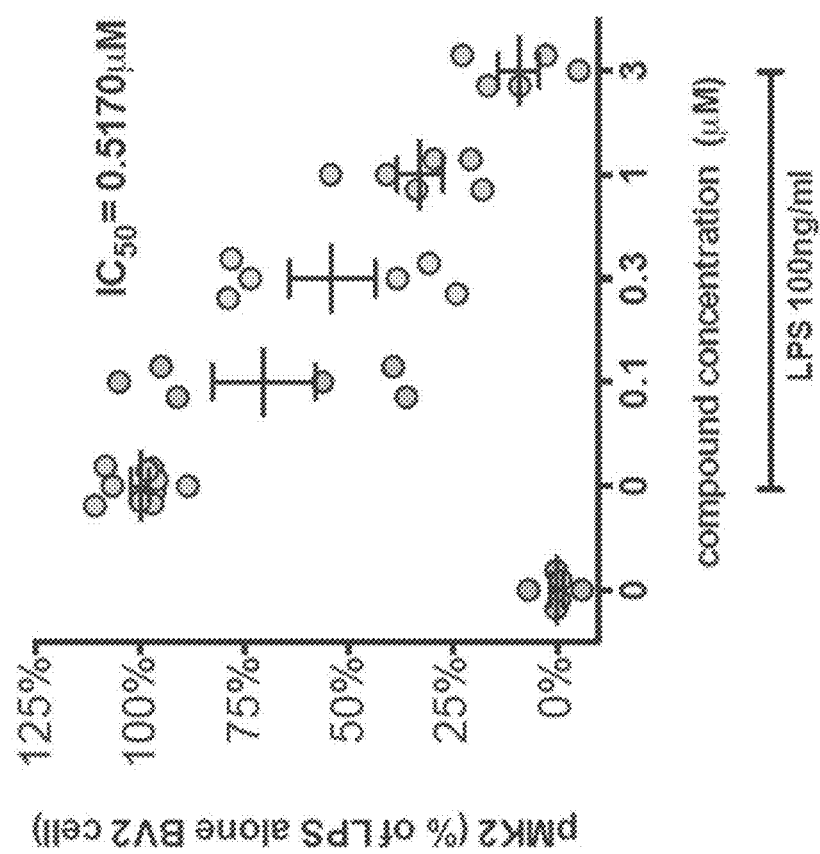
FIGS. 6A-C show (A) phosphorylation state of pMK2 is increased at 1 hr after LPS addition and the increase is attenuated in a dose dependent manner by MW-150 (27); (B) IL-1β protein levels in cell lysates at 18 hrs after LPS addition in MSD ELISA measurements with vehicle, LPS+vehicle and LPS+MW-150; and (C) TNFa protein levels in conditioned media at 18 hrs after LPS addition in MSD ELISA measurements with vehicle, LPS+vehicle and LPS+MW-150.
Figure 6B:
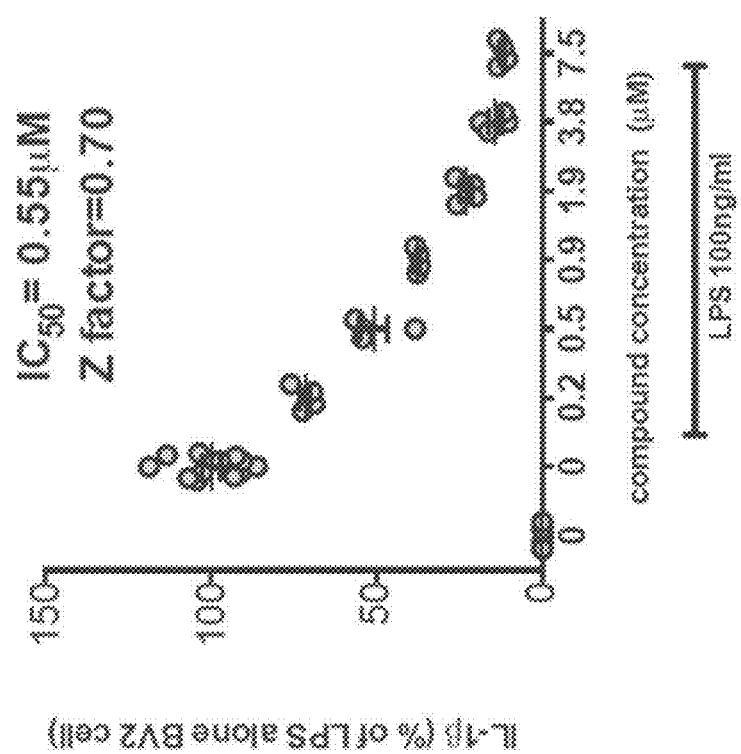
Figure 6C:
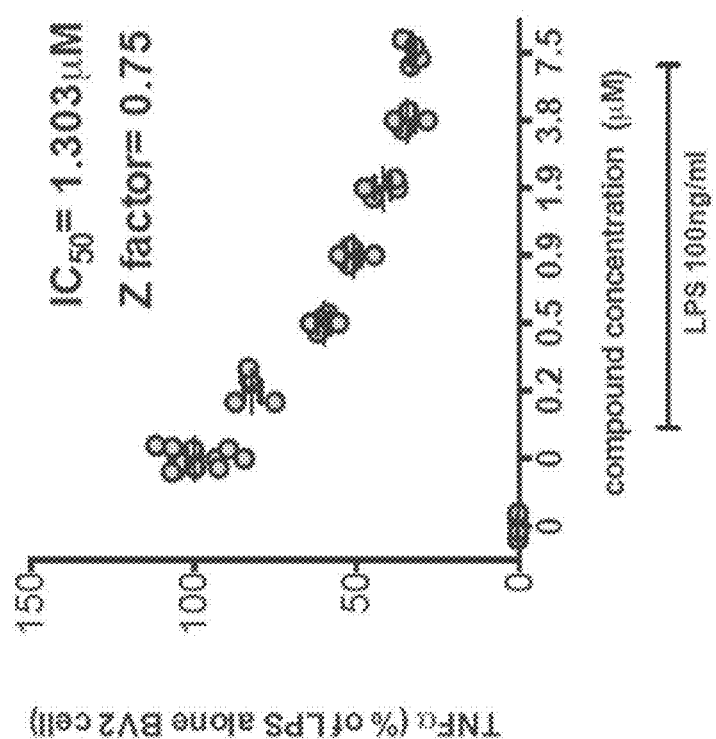

FIG. 6 shows target engagement by MW-150 (27) in glia response pathway. The phosphorylation state (activation) of the p38α substrate pMK2 is increased at 1 hr after LPS addition and this increase is attenuated in a dose dependent manner by MW-150 (27) (FIG. 6A). IL-1β protein levels in cell lysates at 18 hrs after LPS addition in MSD ELISA measurements with vehicle, LPS+vehicle and LPS+MW-150 (FIG. 6B). TNFa protein levels in conditioned media at 18 hrs after LPS addition in MSD ELISA measurements with vehicle, LPS+vehicle and LPS+MW-150 (FIG. 6C). Data are presented as percent of maximal activity (activity with LPS+vehicle) and are representative of at least two independent experiments.

The concentration dependent engagement of endogenous target and its proximal endogenous substrate in living cells, and the concentration dependent effect on upregulated proinflammatory cytokine production in stressed cells provides a strong linkage between in vitro kinase inhibitor activity, pharmacodynamics effects relevant to diverse diseases and the efficacy in biological studies of the compounds.

Example 15

In Vivo Models for Alzheimer's Disease

Animal Models: Two mouse models of the disease were used. In one model, mice overexpressing the mutated transgenes APP and PS1 (termed APP/PS1 mice) were used (*Ann. Neurol.* 2004, 55, 801; herein incorporated by reference in its entirety) and their WT littermates. APP/PS1 mice are well characterized with respect to AD pathology, and begin to show synaptic and memory impairment as early as 3 months of age (*Ann. Neurol.* 2004, 55, 801; *Nat. Med.* 1998, 4, 97; *Exp. Neurol.* 2001, 171, 59; *Neurobiol. Dis.* 1999, 6, 231; and *Neurochem. Res.* 2003, 28, 1009; each herein incorporated by reference in its entirety). In the second model mice that are acutely treated with amyloid-beta are used. APP/PS1 mice are obtained by crossing APP mice with PS1 mice from a breeding colony kept at the animal facility of Columbia University. Animals are genotyped by PCR as described in *Ann. Neurol.* 2004, 55, 801; *Science* 1996, 274, 99 (each herein incorporated by reference in its entirety). All of the mice are maintained on a 12 h light/dark cycle (with lights on at 6:00 AM.) in temperature- and humidity-controlled rooms. Food and water are available ad libitum. Animals are sacrificed by cervical dislocation followed by decapitation.

Aβ Preparation. Oligomeric $A\beta_{42}$ is prepared from a commercially available $A\beta_{42}$ synthetic peptide (American Peptide Co, Sunnyvale, Calif.), as previously described in *J. Biol. Chem.* 2003, 278, 11612; 1 Neurosci. 2008, 28, 14537 (each herein incorporated by reference in its entirety). The lyophilized peptide is resuspended in cold 1,1,1,3,3,3-hexafluoro-2-propanol (HFIP, Sigma) and aliquoted in polypropylene vials. After 24 hrs, the HFIP solution is allowed to evaporate in a fume hood until a thin film of peptide is formed on the bottom of the vials. Peptide films is dried and stored in sealed vials at −20° C. Prior to use, anhydrous DMSO (Sigma) is added to obtain a pure monomeric Aβ/DMSO solution and is sonicated for 10 min (*J. Biol. Chem.* 2003, 278, 11612; herein incorporated by reference in its entirety). Oligomeric $A\beta_{42}$ is obtained by incubating an aliquot of monomeric Aβ/DMSO solution in sterile PBS at 4° C. overnight. The quality of Aβ preparation is routinely assessed using immunoblot analysis with the anti-human Aβ monoclonal antibody 6E10 (Signet Lab) that recognizes monomeric and oligomeric forms of $A\beta_{42}$.

Cannula Infusion Technique. Following anaesthesia with 20 mg/kg Avertin, mice are implanted with a 26-gauge guide cannula into the dorsal part of the hippocampi (coordinates: P=2.46 mm, L=1.50 mm to a depth of 1.30 mm) (Paxinos, G., *Mouse Brain in Stereotaxic Coordinates, 2$^{nd}$ Ed.* 1998, New York: Academic Press; herein incorporated by reference in its entirety). The cannulas are fixed to the skull with acrylic dental cement (made from Paladur powder). After 6-8 days, miceare bilaterally infused with oligomeric forms of $A\beta_{42}$ or vehicle.

Treatment of the APP/PS1 Mice: APP/PS1 mice are treated with the test compounds 2.5 mg/Kg (p.o.) by oral gavage starting from the age of two months. The treatment lasts until the behavioral and electrophysiological tests are completed. Behavioral tests are started at 3 months of age and last for 3 weeks. Electrophysiological tests start after the behavioral tests and last about 21 days.

Acute Treatment with Amyloid-Beta: For behavioral testing mice are infused with amyloid beta through cannulas implanted into dorsal hippocampi. For electrophysiological tests, slices taken from mouse hippocampi are perfused with amyloid beta. The test compounds are given immediately prior to the behavioral testing or to induction of LTP with the theta burst.

Behavioral Tests include two types of tasks: a) fear conditioning, and b) 2 day radial arm water maze.

Fear Conditioning (FC) is assessed as described in *Cell* 2006, 126, 775 and *J. Clin. Invest.* 2004, 114, 1624 (each herein incorporated by reference in its entirety). First, sensory perception of electric foot shock is examined in different groups of mice through the threshold assessment test. The animals are placed in the conditioning chamber and the electric current (0.1 mA for 1 sec) is increased at 30 s intervals from 0.1 mA to 0.7 mA. Threshold to flinching (first visible response to shock), jumping (first extreme motor response), and vocalized response is quantified for each animal by averaging the shock intensity at which each animal shows the behavioral response to that type of shock. No differences in the threshold assessment among the different groups of mice should be found if treatments with the new chemical entity does not affect animals' sensory threshold. For FC training, mice are placed in a conditioning chamber for 2 min before the onset of a tone (Conditioned Stimulus (CS), 30 sec, 85 dB sound at 2800 Hz). In the last 2 sec of the CS, mice are given a 2 sec, 0.7 mA mild foot shock (Unconditioned Stimulus, (US)) through the bars of the floor. After the US, the mice are left in the chamber for another 30 s. Freezing behavior, defined as the absence of movements except for that needed for breathing, is scored using Freezeview software (Med Associates, St. Albans, Vt.). Contextual fear learning, a type of memory for which hippocampal function is indispensable, is evaluated 24 hrs after training by measuring freezing responses for 5 min in the same chamber where the mice have been trained. Cued fear learning, a type of memory that depends on amygdala function, is evaluated 24 hrs after contextual testing. The mice are placed in a novel context for 2 min (pre-CS test), after which they are given a CS for 3 min (CS test), and freezing behavior is measured during the first 30 sec that mimic the CS-US conditioning and the remaining 2.5 min. In addition, the open-field test is conducted to evaluate exploratory behavior in different groups of mice (*Neuroscience* 2007, 147, 28; *J. Neurosci.* 2008, 28, 14537 (each herein incorporated by reference in its entirety). The open field consists of a squared arena (72×72×33 cm) made of white acrylic. A 36×36 cm area in the center is defined as the 'central compartment'. At the beginning of the test, mice are placed in the center of the open field arena and allowed to move freely for 1 hour. Amount of time spent in the center compartment vs. the periphery and number of entries into the center compartment is scored. After 24 hours mice are retested for an additional hour.

Radial Arm Water Maze (RAWM). It has been established that this task is altered both in Aβ-infused mice and in APP/PS1 animals (see FIG. 7A-B). Reference memory was studied with the 2-day RAWM as described in *Nat. Protoc.* 2006, 1, 1671 (herein incorporated by reference in its entirety). For these experiments, visible platform testing was conducted to exclude that visual, motor and motivation deficits affect the mouse performance (*Ann. Neurol.* 2004, 55, 801; herein incorporated by reference in its entirety). The task is a hybrid of the Morris Water Maze (MWM) and the radial arm land maze. The motivation for the animals is the immersion in water. The mouse needs to swim in 6 alleys (arms) radiating from a central area until it finds a hidden (submerged) platform at the end of one of the arms, based on visual cues placed in the room. In the old RAWM version of the task, the goal arm varies from day to day, requiring 21 days of training in wild-type mice to reach the learning criterion. In the new version of the task, the goal arm is kept constant for all trials, with a different start arm on successive trials, such that the learning criterion is reached in 2 days The first day of the protocol is a training day. Mice are trained to identify the platform location by alternating between a visible and a hidden platform in a goal arm. The final 3 trials on day 1 and all 15 trials on day 2 use a hidden escape platform to force mice to use spatial cues to identify the location of the goal arm. To avoid learning limitations imposed by exhausting practice and to avoid fatigue that may result from consecutive trials, spaced practice training is established by running the mice in cohorts of 4 and alternating different cohorts through the 15 training trials over 3 hours testing periods each day. On day 1, a visible platform is placed in a goal location. Mouse 1 of cohort 1 is gently placed in the pool near the perimeter of the wall of the first start arm (specified on a score sheet) and facing the center of the pool. The number of incorrect arm entries (entries in arms with no platform) is counted. If the animal enters the incorrect arm it is gently pulled back to the start arm. Each trial lasts up to 1 min. Failure to select an arm after 15 sec is counted as an error and the mouse is returned to the start arm. After 1 min, if the platform has not been located, the mouse is guided gently through the water by placing a hand behind it to direct it towards the platform. The mouse rests on the platform for 15 sec. After completing the trial, the mouse is removed from the pool, gently towel dried and placed back into its cage under a heat lamp. The goal platform location is different for each mouse. After all the mice in the first cohort have had a trial to locate a visible platform, the platform is switched from visible to hidden. After each mouse from cohort 1 completes six alternating trials between visible and hidden platforms, the mice are left to rest under a heating source, and mice from the second cohort are tested in the same way. After completing the six alternating trials, mice from cohort 2 are returned to their cages to rest. Next, mice from the first cohort complete trials 7-12 again using the alternating visible-hidden platform location. During resting time for mice from the first cohort, mice from the second cohort complete trials 7-12. At this point, all mice will have performed 3 hidden platform trials. On day 2, the same procedure is repeated as on day 1 for all 15 trials using only the hidden platform. For data analysis, averages for each mouse are calculated using blocks of 3 trials.

Electrophysiological Tests include a study of long-term potentiation (LTP). Transverse hippocampal slices (400 mm) are cut with a tissue chopper (EMS, PA) and maintained in an interface chamber at 29° C. for 90 min prior to recording, as described in Proc. Natl. Acad. Sci. U.S.A. 2002, 99, 13217, herein incorporated by reference in its entirety. The extracellular bath solution consists of 124.0 mM NaCl, 4.4 mM KCl, 1.0 mM $Na_2HPO_4$, 25.0 mM $NaHCO_3$, 2.0 mM $CaCl_2$, 2.0 mM $MgSO_4$, and 10.0 mM glucose, continuously aerated with 95% $O_2$/5% $CO_2$ to a final pH of 7.4. Field extracellular postsynaptic responses (fEPSPs) are recorded by placing the stimulating and recording electrodes in CA1 stratum radiatum. A bipolar tungsten electrode (FHC, Bowdoin, Me.) is used as a stimulating electrode, and a glass pipette filled with bath solution is used as a recording electrode. BST is first assessed by plotting the stimulus voltages (V) against slopes of fEPSP, or by plotting the peak amplitude of the fiber volley response against the slope of fEPSP to generate input-output relations. For LTP experiments, a 15 min baseline is first recorded every minute at an intensity that evokes a response at approximately 35% of the maximum evoked response. LTP is induced using a theta-burst stimulation (4 pulses at 100 Hz, with the bursts repeated at 5 Hz, and each tetanus consisting of 3 ten-burst trains separated by 15 sec). Responses are measured as fEPSP slopes expressed as percentage of baseline.

Example 16

Efficacy Tests for Cognitive Deficit Attenuation in Aβ Infused Mouse Models

Animals. Three- to four-month-old C57BL/6J male mice derived from a colony which was bred in our animal facility. They were maintained on a 12 h light/dark cycle in temperature- and humidity-controlled rooms. Animals were killed by cervical dislocation followed by decapitation.

Aβ preparation. Aβ42 was prepared as previously described in J. Neurosci 2005, 25, 6887 (herein incorporated by reference in its entirety), starting from lyophilized peptide (American Peptide) which was suspended in 100% 1,1,1,3,3,3-hexafluoro-2-propanol (Sigma-Aldrich) and allowed to evaporate. The resulting clear peptide film was stored at 20° C. Twenty-four hours prior to its use, the film was added to DMSO (Sigma-Aldrich) and sonicated for 10 min. This preparation was diluted into the bath solution, vortexed for 30 sec, and incubated at 4° C. for 24 hrs. Western blot analysis was routinely utilized to check the biochemistry of this aged synthetic Aβ as previously described in J. Neurosci 2005, 25, 6887 (herein incorporated by reference in its entirety).

Electrophysiological Studies. Brain slices (400 µm) were cut and maintained in an interface chamber at 29° C. for 90 min prior to recording, as previously described in J. Neurosci 2005, 25, 6887 (herein incorporated by reference in its entirety). CA3-CA1 responses were recorded by means of a stimulating electrode, a bipolar tungsten electrode, placed at the level of the Schaeffer collateral fibers, and a recording electrode, a glass electrode filled with bath solution. Following assessment of basal synaptic transmission by plotting the stimulus voltages against slopes of field EPSP, a 15 min baseline was recorded every minute at an intensity that evokes a response ~35% of the maximum evoked response. Then, LTP was evoked through a θ-burst stimulation (4 pulses at 100 Hz, with the bursts repeated at 5 Hz and each tetanus including three 10-burst trains separated by 15 sec).

Behavioral Studies. A) Reference memory was studied with the 2-day RAWM as described in Nat. Protoc. 2006, 1, 1671 (herein incorporated by reference in its entirety). For these experiments, visible platform testing was conducted to exclude that visual, motor and motivation deficits affect the mouse performance (Ann. Neurol. 2004, 55, 801; herein incorporated by reference in its entirety). B) Fear Conditioning to examine both contextual and cued learning were assessed, as previously described (J. Clin. Invest. 2004, 114, 1624; herein incorporated by reference in its entirety). For these experiments, threshold assessment test was performed to check sensory perception of electric shock in different groups of mice, as previously described (J. Clin. Invest. 2004, 114, 1624; herein incorporated by reference in its entirety). In addition, the open-field test was conducted to evaluate exploratory behavior, as previously described (J. Neurosci. 2008, 28, 14537; herein incorporated by reference in its entirety).

Statistics. Experiments were performed in blind (results expressed as SEM). Significance of differences between 2 groups was determined by t-test for pairwise comparisons or a 2-way ANOVA with repeated measures for multiple comparisons. Significance was set at $p<0.05$.

Figure 8A:
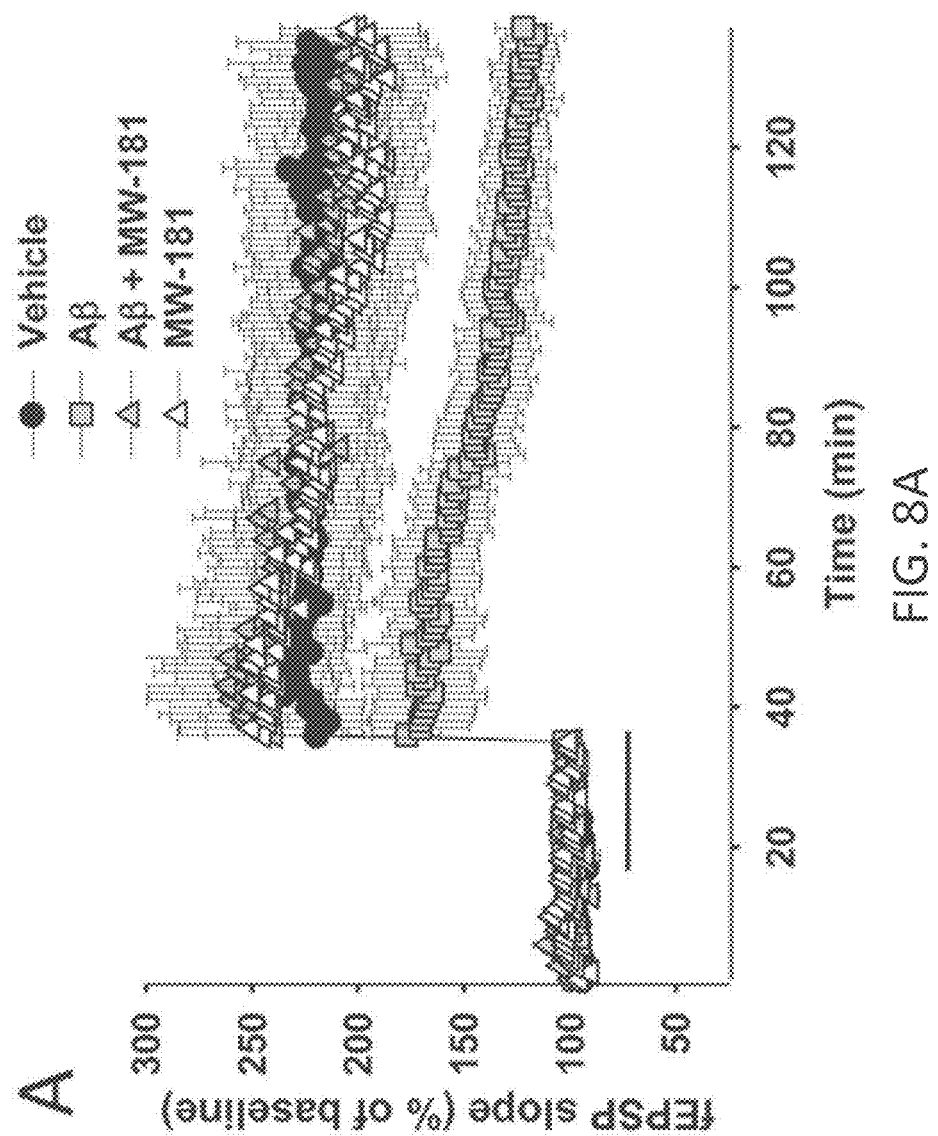
Figure 8B:
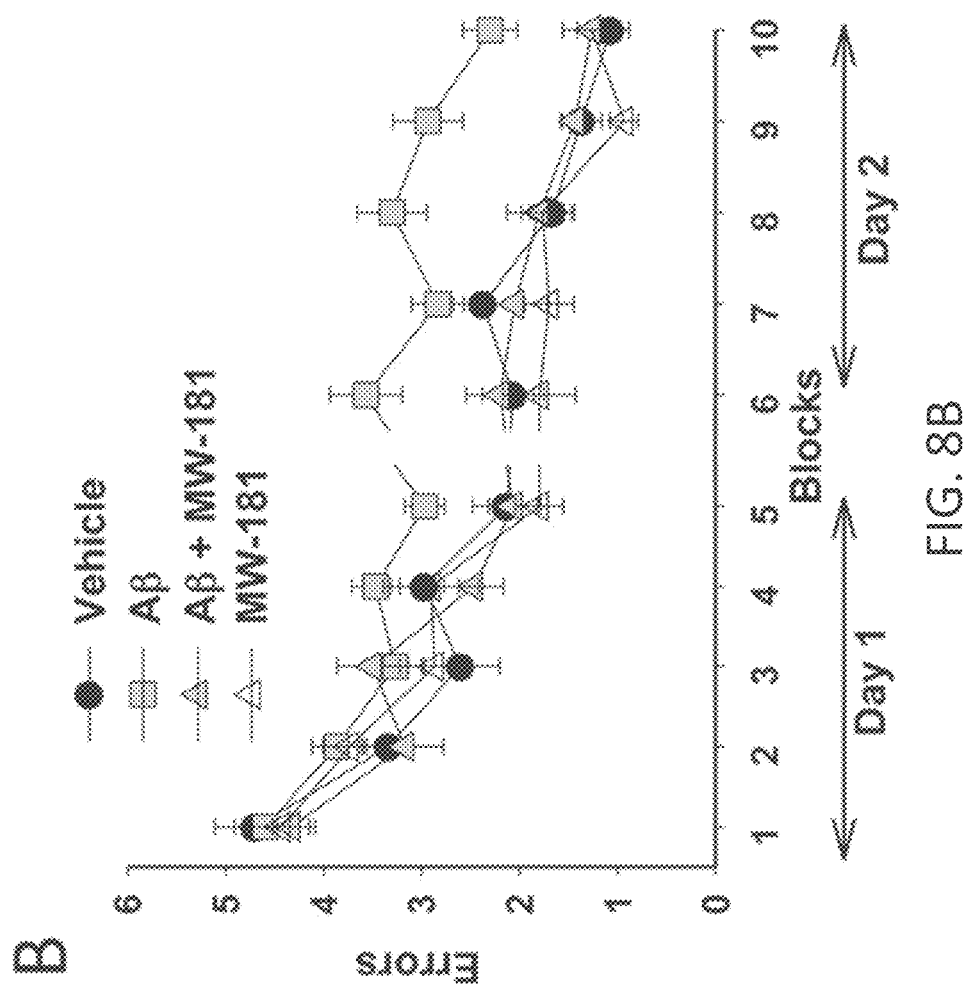
Figure 8C:
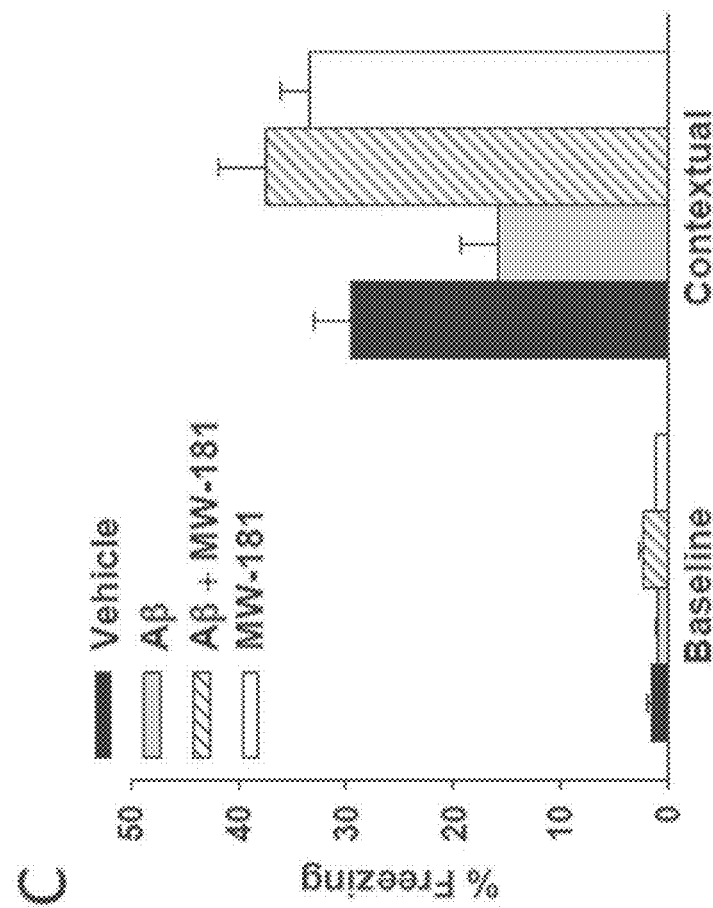
Figure 8D:
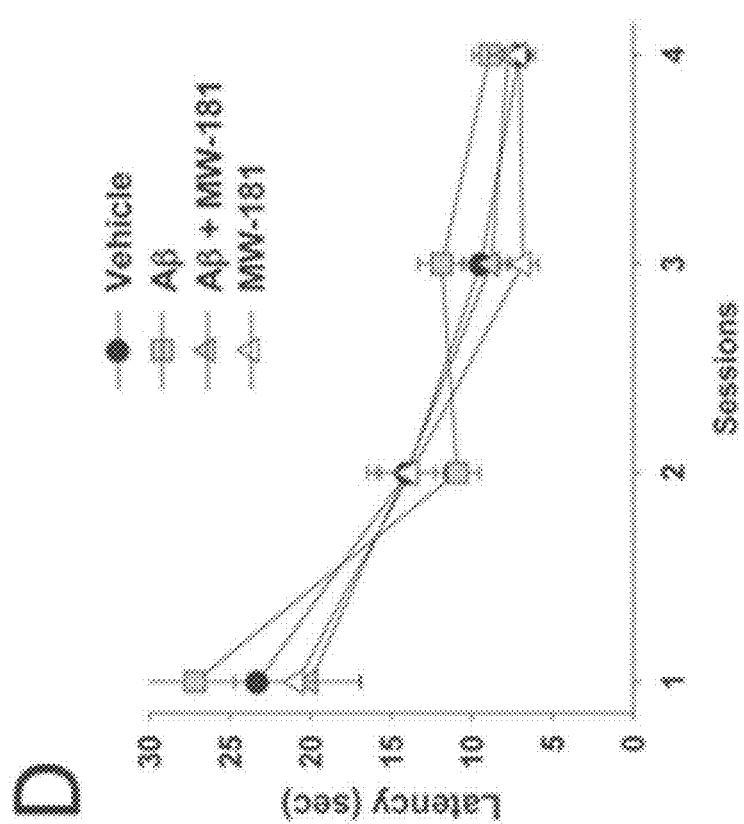

In a series of experiments, LTP was induced in the presence of oligomeric $Aβ_{42}$, a peptide that accumulates in the brains of AD patients. In these experiments, 200 nM $Aβ_{42}$ or vehicle were perfused through the bath solution for 20 min prior to application of the θ-burst. As previously demonstrated, Aβ reduced LTP (FIG. 8A) (*Neuroreport* 1997, 8, 3213; *Eur. J. Pharmacol.* 1999, 382, 167; *Nature* 2002, 416, 535; *Proc. Natl. Acad. Sci. U.S.A.* 2002, 99, 13217; *J. Neurosci.* 2005, 25, 6887; *Nat. Med.* 2005, 11, 556; *Proc. Natl. Acad. Sci. U.S.A.* 1998, 95, 6448; each herein incorporated by reference in its entirety). However, MW-181 (1; 10 µM, for 20 min prior to the θ-burst) ameliorated the electrophysiological deficit (FIG. 8A). The relevance to AD pathology of these results was validated by assessing both reference memory and contextual fear memory, two types of memory that are affected in AD patients. A$\beta_{42}$ (200 nM, in a final volume of 1 µl over 1 min) or vehicle were bilaterally infused 20 min prior to the 1st trial [for the 1st group of tests in a 2-day radial arm water maze (RAWM) test assessing reference memory (*Nat. Protoc.* 2006, 1, 1671; herein incorporated by reference in its entirety) and 20 min prior to the 7th trial (for the 2nd group of tests of the RAWM), into dorsal hippocampus of the animal that had been pre-implanted with a cannula the week before or 20 min prior to the foot shock. Aβ reduced the two types of memory (FIGS. 8B and 8C). However, MW-181 (1; 5 mg/Kg, i.p., 30 min before the 1st and 2nd group of tests for the RAWM or before training for fear conditioning) rescued the memory defects (FIGS. 8B and 8C). The effects of the compounds were really due to changes in hippocampal memory mechanisms because in control experiments including visible platform test, open field, sensory threshold assessment and cued learning, no difference across groups was found (FIGS. 8D-8I).

Efficacy studies were performed using a second p38α MAPK inhibitor, MW-108 (2), that is more selective than MW-181(1) as it does not hit the p38β isoform or atypical MAPK, CKs and is negative in the Millipore large scale kinase and GPCR screens. The compound was used at a concentration of 10 µM (bath perfusion) for the LTP experiments and 5 mg/Kg (i.p.) for the behavioral experiments using the same experimental paradigms as for MW-181 (1). These experiments showed that MW-108 (2) was still capable of rescuing the LTP deficits, as well as the defects in contextual fear memory and reference memory due to exogenous Aβ42 application (FIG. 9A-I).

LTP was induced in the presence of oligomeric A$\beta_{42}$. As expected from previous studies, Aβ reduced LTP (FIG. 9A) (*J. Clin. Invest.* 2004, 114, 1624; 1 Neurosci. 2005, 25, 6887; *Ann. Neurol.* 2004, 55, 801; *J. Neurobiol. Aging* 2009, 30, 257; *Eur. J. Med. Chem.* 2013, 60, 348; each herein incorporated by reference in its entirety). Importantly, MW-108 (2) ameliorated the Aβ-induced electrophysiological deficit (FIG. 9A), indicative of rescue of synaptic plasticity impairment.

Figure 9A:
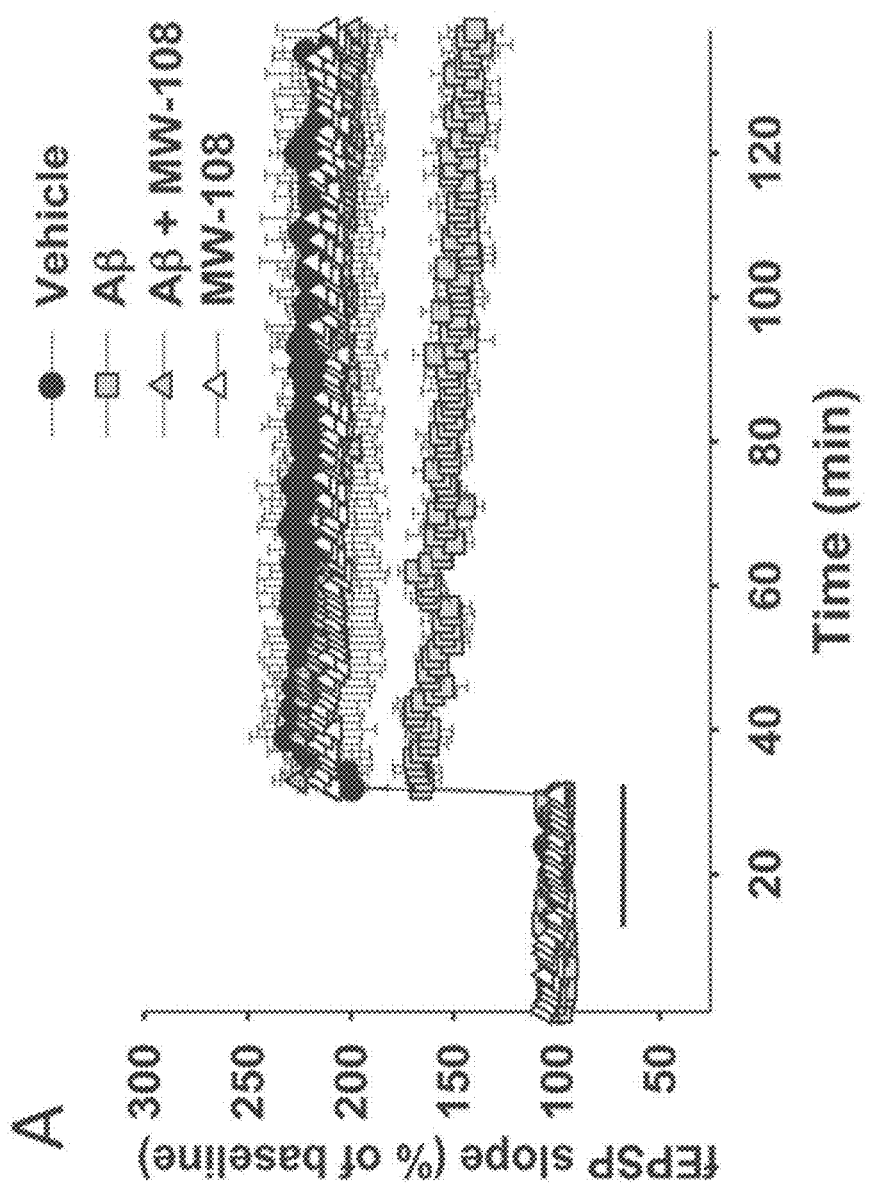
Figure 9B:
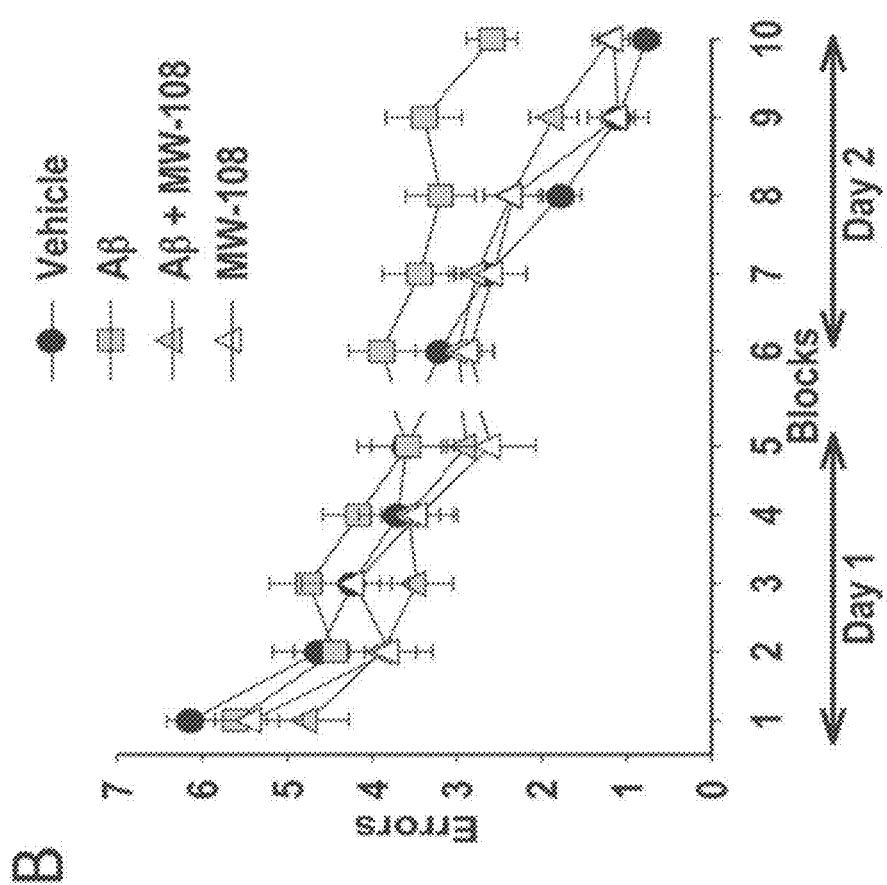
Figure 9C:
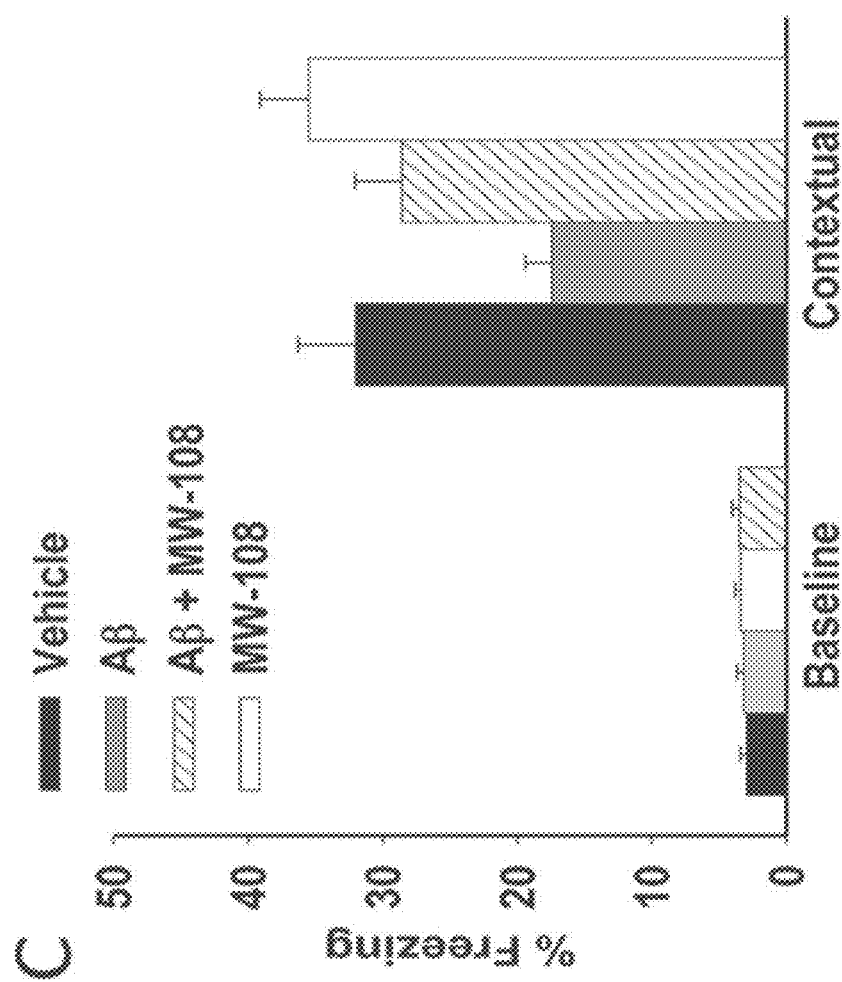
Figure 11A:
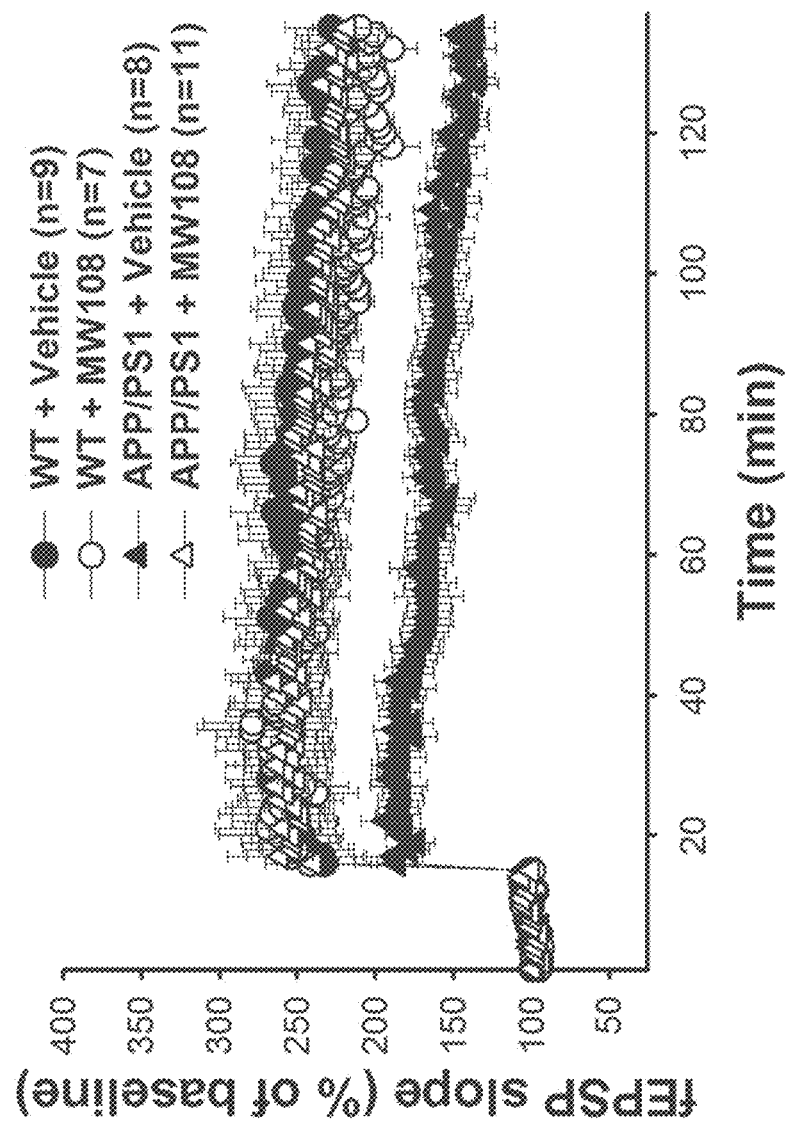
Figure 11B:
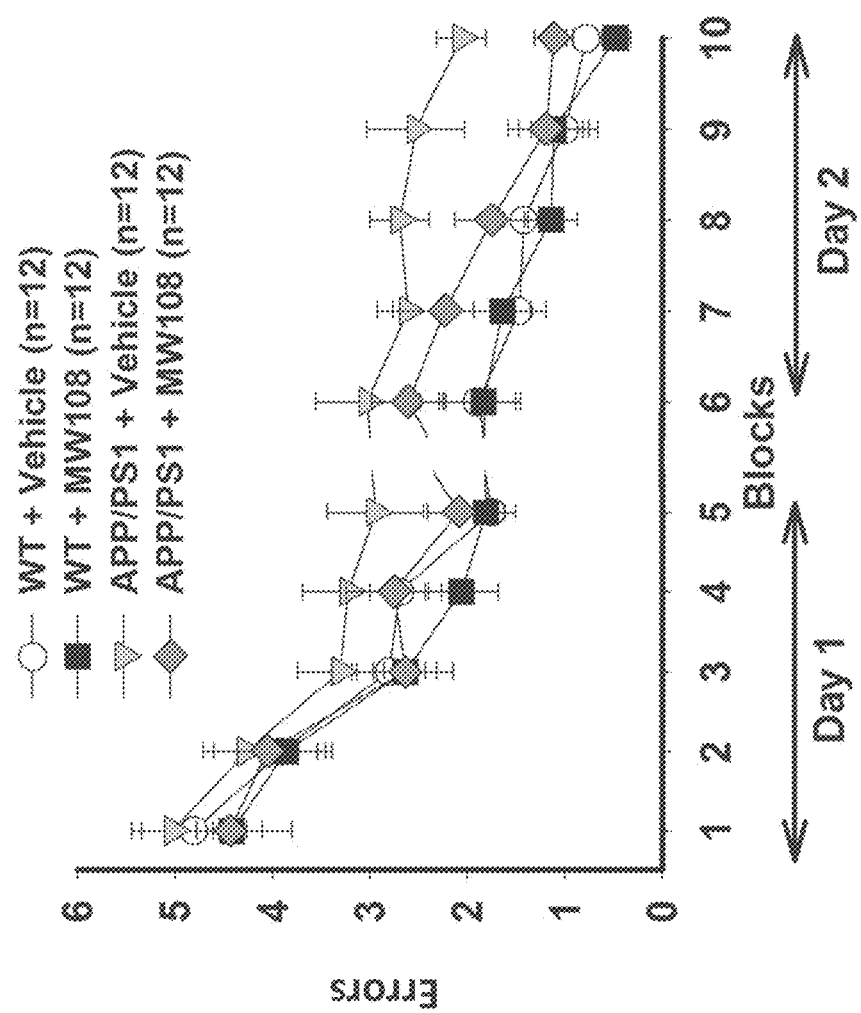
Figure 11C:
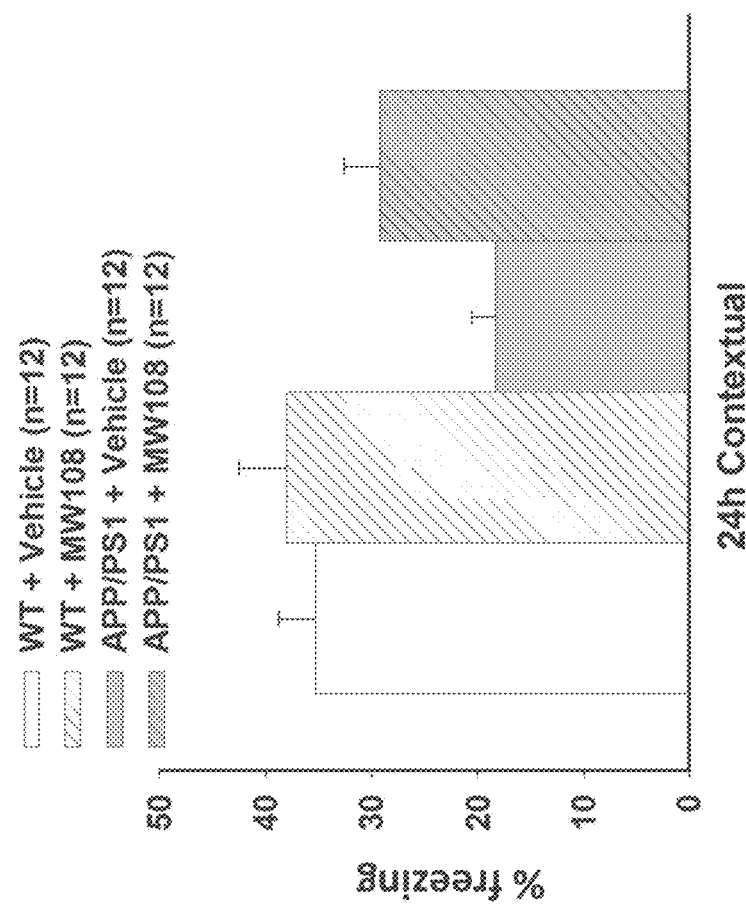
Figure 11D:
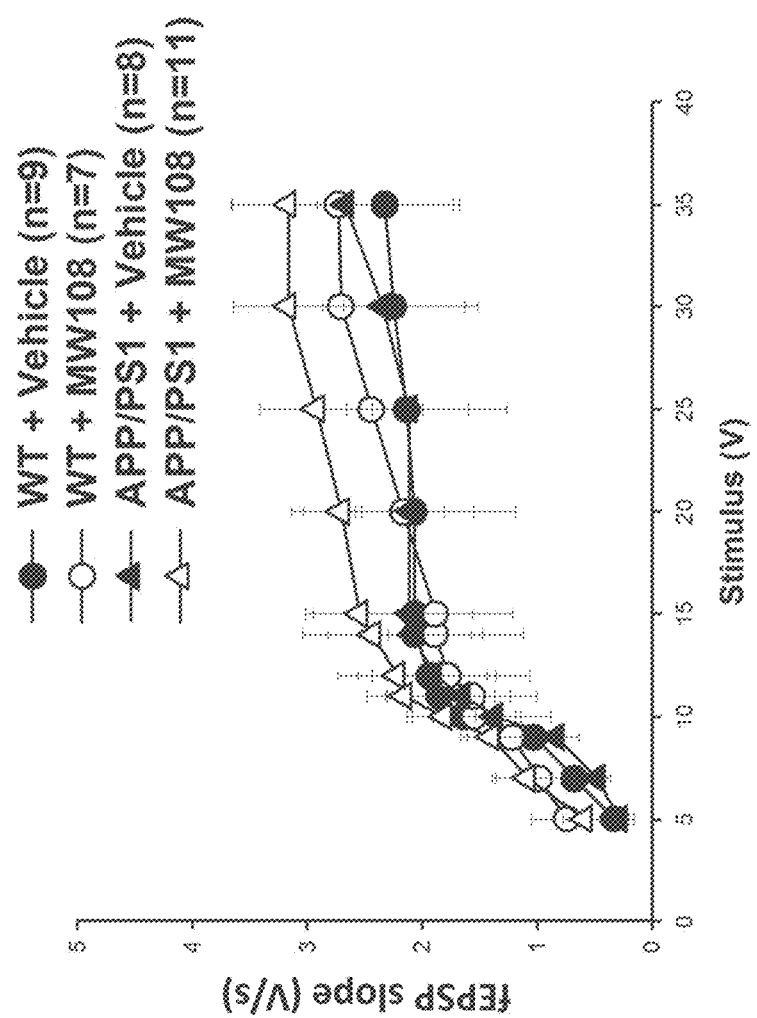
Figure 11E:
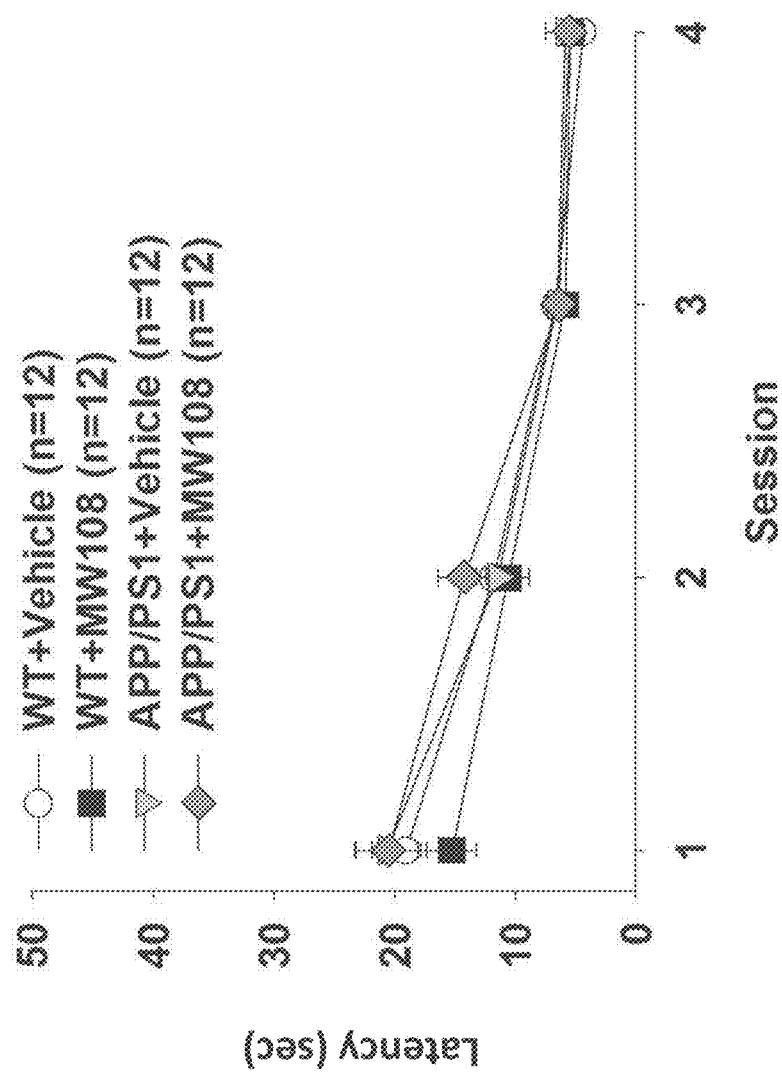
Figure 11F:
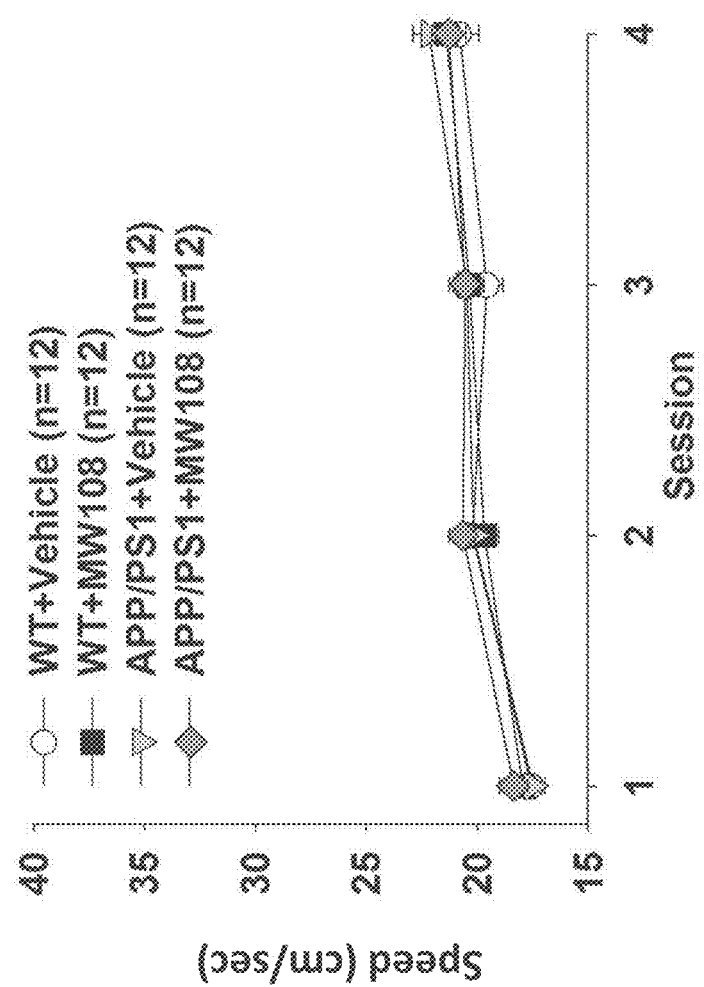
Figure 11G:
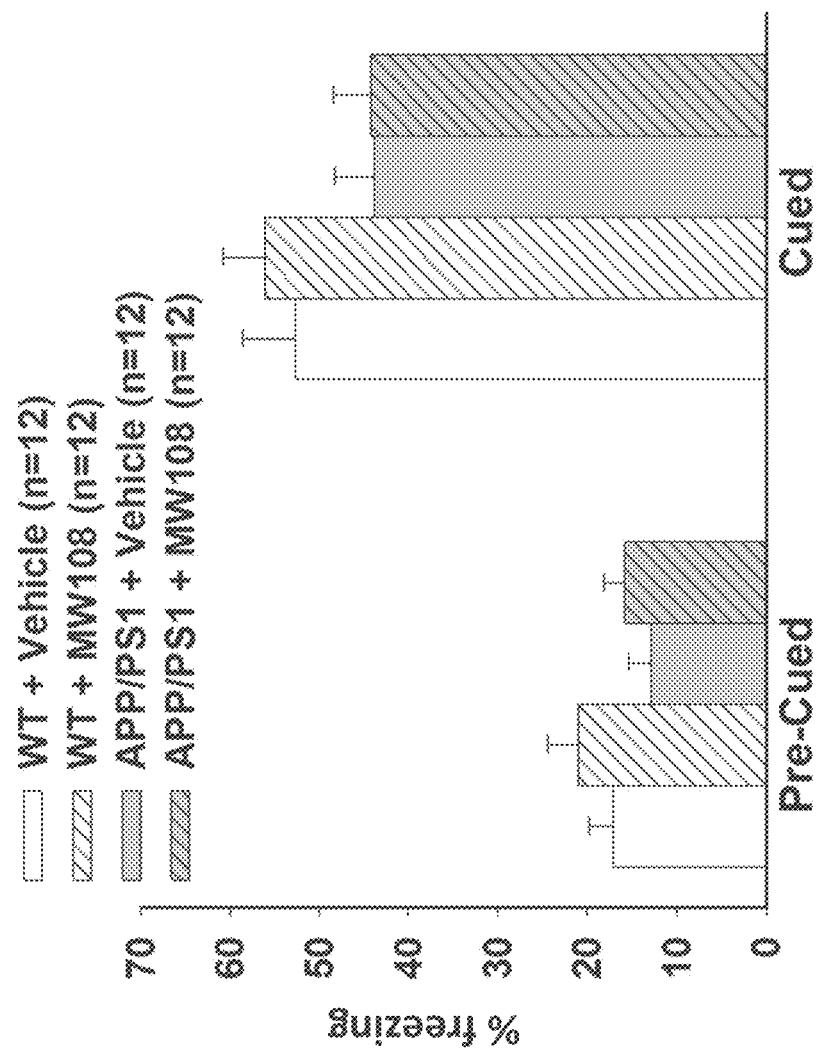
Figure 11I:
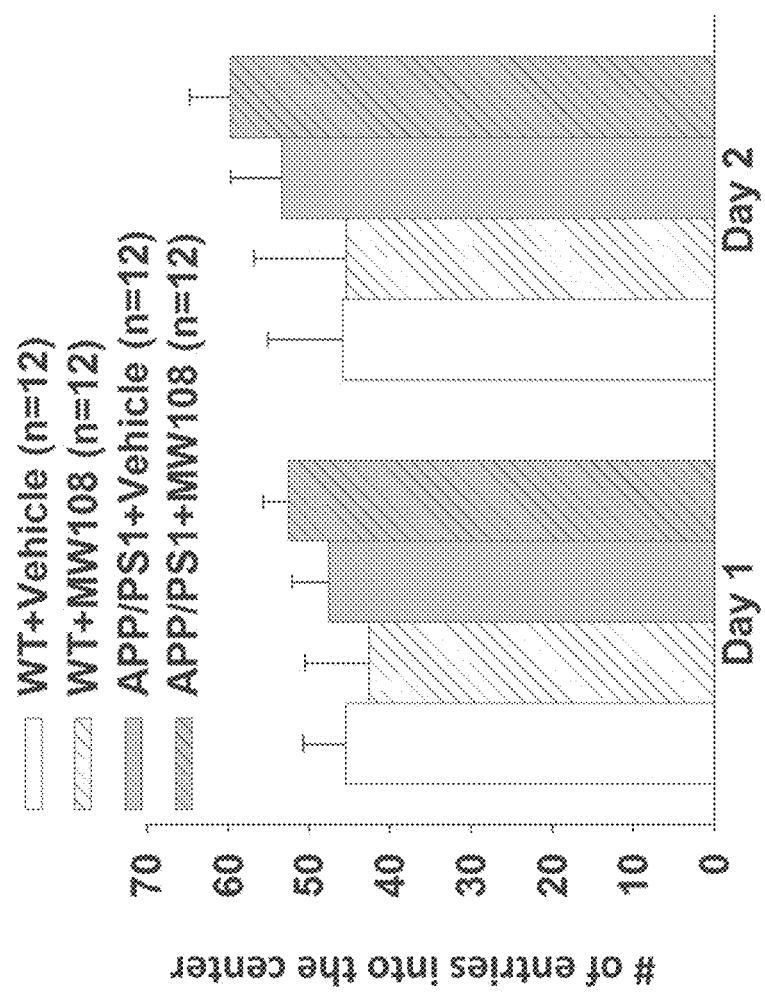
Figure 11J:
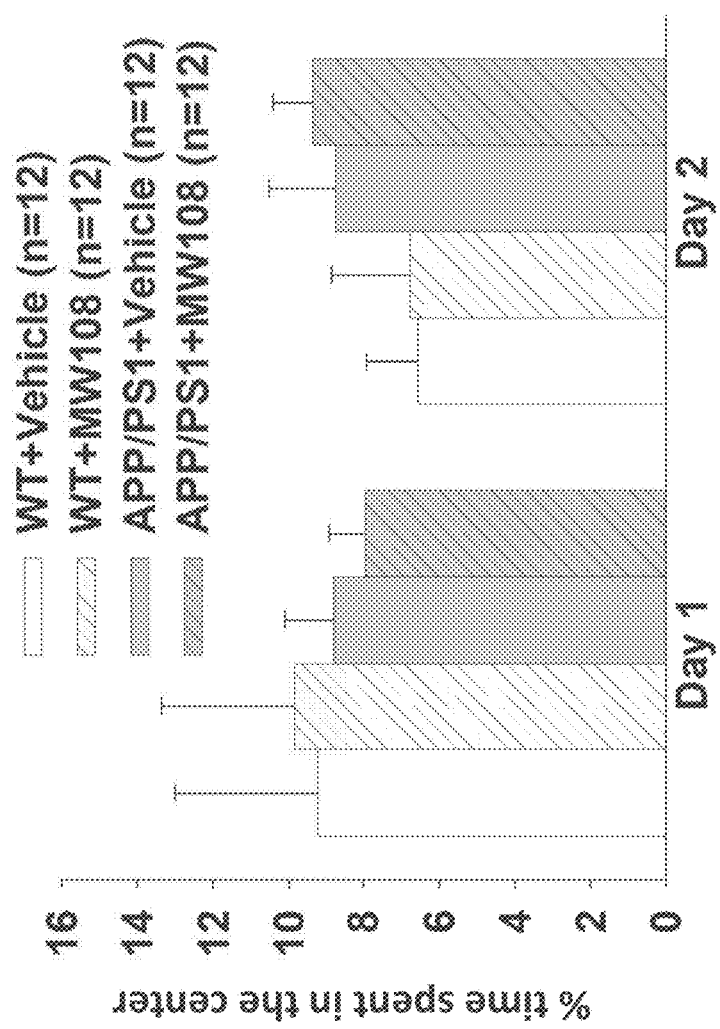

The initial results were extended by testing whether MW-108 (2) could attenuate cognitive deficits in two AD-relevant behavioral tasks that measure two types of memory dysfunction: the radial arm water maze (RAWM) to measure reference memory (*Eur. J. Med. Chem.* 2013, 60, 348; herein incorporated by reference in its entirety) and fear conditioning to measure contextual fear memory (*J. Clin. Invest.* 2004, 114, 1624; herein incorporated by reference in its entirety). A$\beta_{42}$ or vehicle was bilaterally infused into the dorsal hippocampus of mice. Aβ-infused mice showed memory deficits, exhibiting more performance errors compared to vehicle-infused mice (FIG. 9B). Treatment with MW-108 (2) rescued the memory defects (FIG. 9B). In the fear conditioning task, A$\beta_{42}$ caused a contextual fear memory deficit which was prevented by MW-108 (2) administration (FIG. 9C). Control experiments, including visible platform test, open field, sensory threshold assessment and cued learning, showed no differences across groups (FIG. 9D). These data document that MW-108 (2) attenuates AD-relevant impairments in synaptic plasticity and memory.

Example 17

Efficacy Tests in Transgenic Mouse Models

Experiments were also validated in an Aβ depositing mouse model, the APP/PS1 mouse (*Nat. Med.* 1998, 4, 97, herein incorporated by reference in its entirety). These mice are well characterized with respect to AD pathology, and begin to show synaptic and memory impairment as early as 3 months of age (*Ann. Neurol.* 2004, 55, 801; *Nat. Med.* 1998, 4, 97; *Exp. Neurol.* 2001, 171, 59; *Neurobiol. Dis.* 1999, 6, 231; and *Neurochem. Res.* 2003, 28, 1009; each herein incorporated by reference in its entirety). In these experiments, (1) (MW-181) was given daily, p.o. (2.5 mg/kg) from the age of 2 months until 3-4 months of age.

As shown in FIG. 10, compound 1 (MW-181) ameliorated the electrophysiological deficits without affecting WT mice (FIG. 10A). Additionally, WT mice exhibited ~1 error at the end of the second day with the RAWM task. APP/PS1 in turn failed to learn and made ~3 errors. Treatment with compound 1 (MW-181) reduced the memory deficit in double Tgs without affecting memory in WT mice (FIG. 10B). Similar results were observed when double Tgs mice performed FC to assess contextual fear memory (FIG. 10C). Regarding the behavioral experiments, control experiments were performed including visible platform test, open field and sensory threshold assessment which did not reveal any difference across groups.

As shown in FIG. 11, MW-108 (compound 2) was also tested in the APP/PS1 mouse model and rescues deficits in LTP, fear memory and reference memory in amyloid depositing mice.

Representative compounds MW-077 (7), MW-125 (9) and MW-150 (27) were tested to rescue defects of synaptic plasticity and memory in APP/PS1 mice. Daily p.o. treatment starting from 8 weeks of age until the end of the experiment at 3-4 months of age, at a concentration of 2.5 mg/kg, recued impairment of LTP and memory, including contextual fear and short term reference memory. The beneficial effects of the compounds regarding LTP and memory were due to an effect on the mechanism underlying the defects in these phenomena and not to an additive effect on them because administration of the drug to WT littermates did not change the amounts of LTP and behavorial performance. Controls were performed using cued conditioning the check for impairment of amygdala function, threshold assessment test to check sensory perception of electric shock in different groups of mice, visible platform testing to exclude that visual, motor and motivation deficits affect performance, and the open-field test to evaluate exploratory behavior. None of these tests showed an effect of the compounds, indicating that the effect is due to true action on the cognitive mechanisms.

Figure 12A:
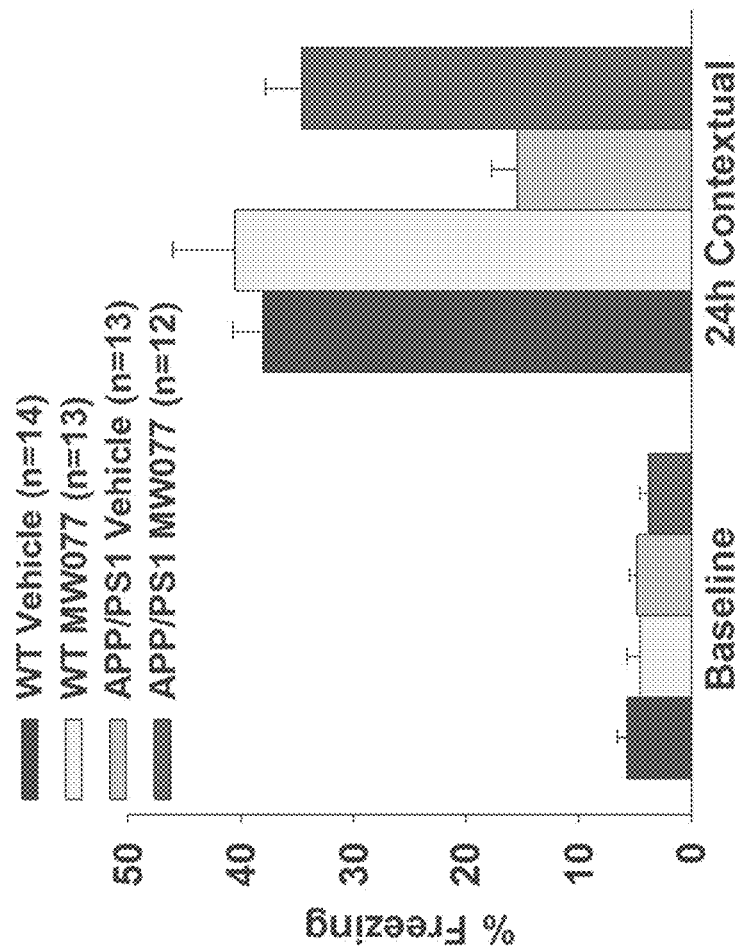
FIGS. 12A-C show contextual fear conditioning results for (A) WT+vehicle, APP/PS1+vehicle, WT+MW-077 (7), and APP/PS1+MW-077 treated mice (WT+vehicle: n=14; APP/PS1+vehicle: n=13; WT+MW-077: n=13; APP/PS1+MW-077: n=12). At 24 hours, statistical analyses showed: APP/PS1 vehicle vs. APP/PS1+MW-077: p=0.00006099; APP/PS1 vehicle vs. WT-vehicle: p=0.00000094; (B) WT+vehicle, APP/PS1+vehicle, WT+MW-125 (9), and APP/PS1+MW-125 treated mice (WT+vehicle: n=14; APP/PS1+vehicle: n=13; WT+MW-125: n=13; APP/PS1+MW-125: n=12). At 24 hours, statistical analyses showed: APP/PS1 vehicle vs. APP/PS1+MW-125: p=0.00224081; APP/PS1 vehicle vs. WT-vehicle: p=0.00000094; and (C) WT+vehicle, APP/PS1+vehicle, WT+MW-150 (27), and APP/PS1+MW-150 treated mice (WT+vehicle: n=10; APP/PS1+vehicle: n=10; WT+MW-150: n=11; APP/PS1+MW-150: n=10). At 24 hours, statistical analyses showed: APP/PS1 vehicle vs. APP/PS1+MW-125: p=0.00148599; APP/PS1 vehicle vs. WT-vehicle: p=0.00032711.
Figure 12B:
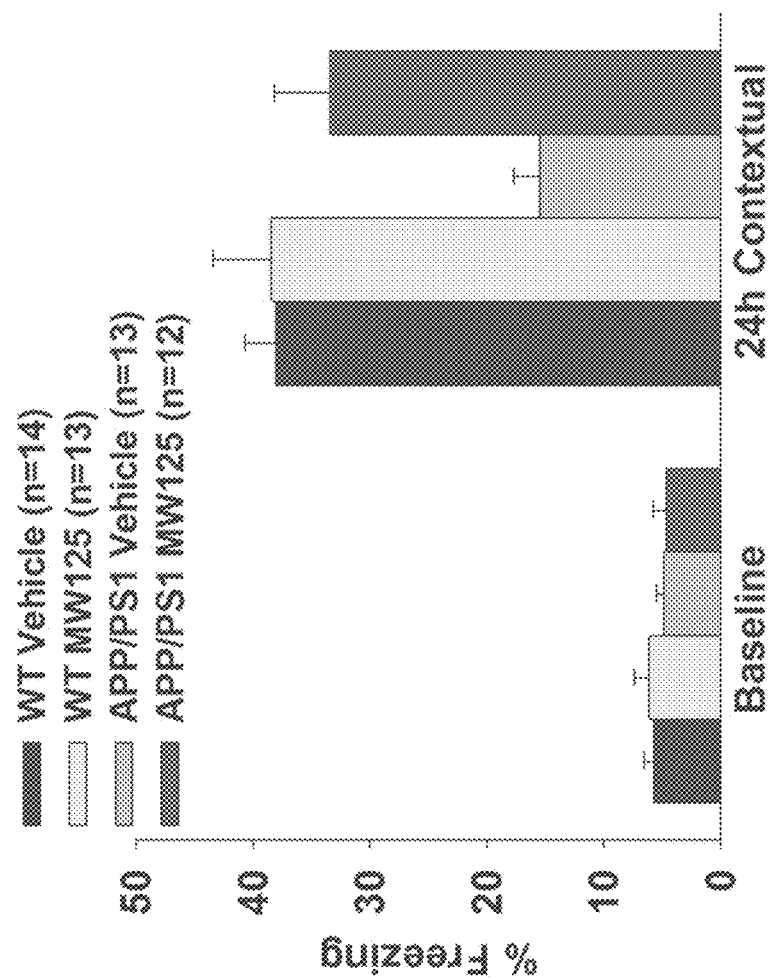
Figure 12C:
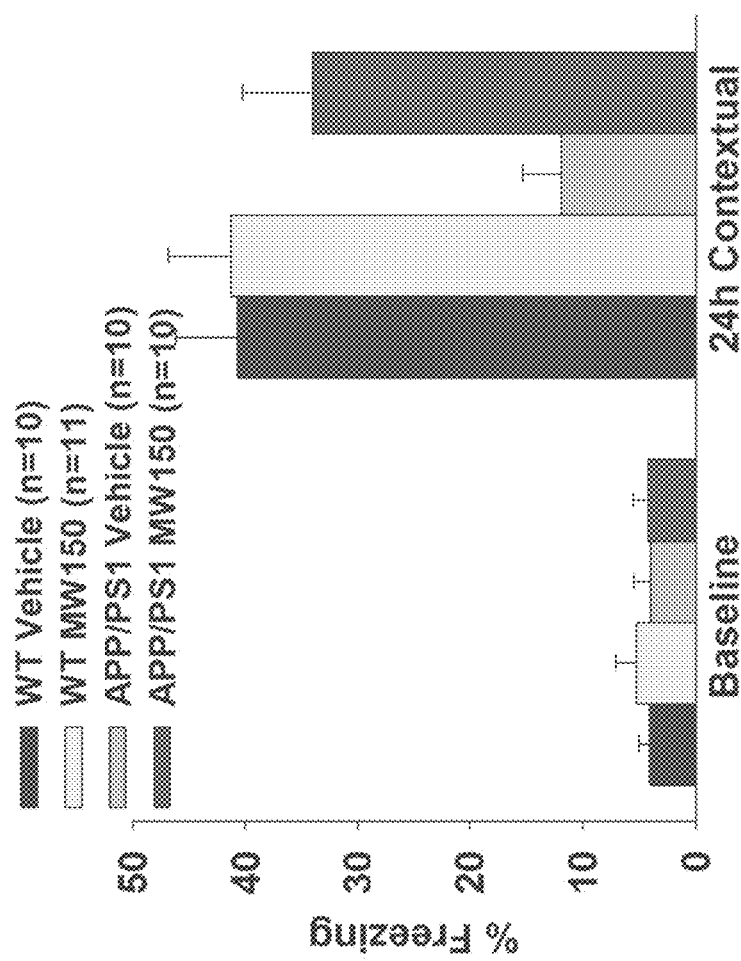

As shown in FIG. 12A-C, MW-077 (7), MW-125 (9) and MW-150 (27) rescue the defect in contextual fear learning in APP/PS1 mice. The compounds did not affect the performance in WT littermates. Mice were treated (2.5 mg/kg, daily, oral gavage) with the compound from the age of 2 months until behavioral testing that occurred at ~3 months of age.

Figure 13A:
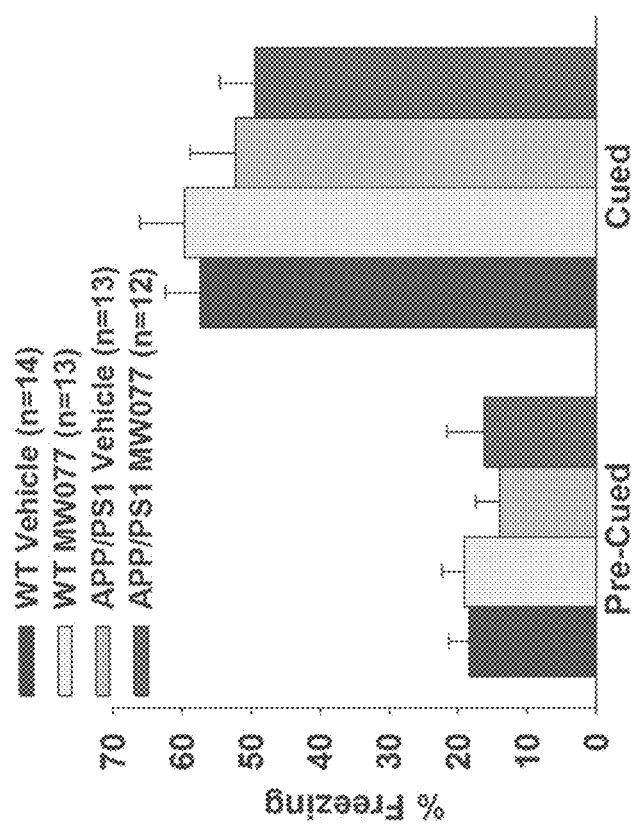
FIGS. 13A-C show cued fear conditioning results for (A) WT+vehicle, APP/PS1+vehicle, WT+MW-077(7), and APP/PS1+MW-077 treated mice (WT+vehicle: n=14; APP/PS1+vehicle: n=13; WT+MW-077: n=13; APP/PS1+MW-077: n=12); (B) WT+vehicle, APP/PS1+vehicle, WT+MW-125 (9), and APP/PS1+MW-125 treated mice (WT+vehicle: n=14; APP/PS1+vehicle: n=13; WT+MW-125: n=13; APP/PS1+MW-125: n=12); and (C) WT+vehicle, APP/PS1+vehicle, WT+MW-150 (27), and APP/PS1+MW-150 treated mice (WT+vehicle: n=10; APP/PS1+vehicle: n=10; WT+MW-150: n=11; APP/PS1+MW-150: n=10).
Figure 13B:
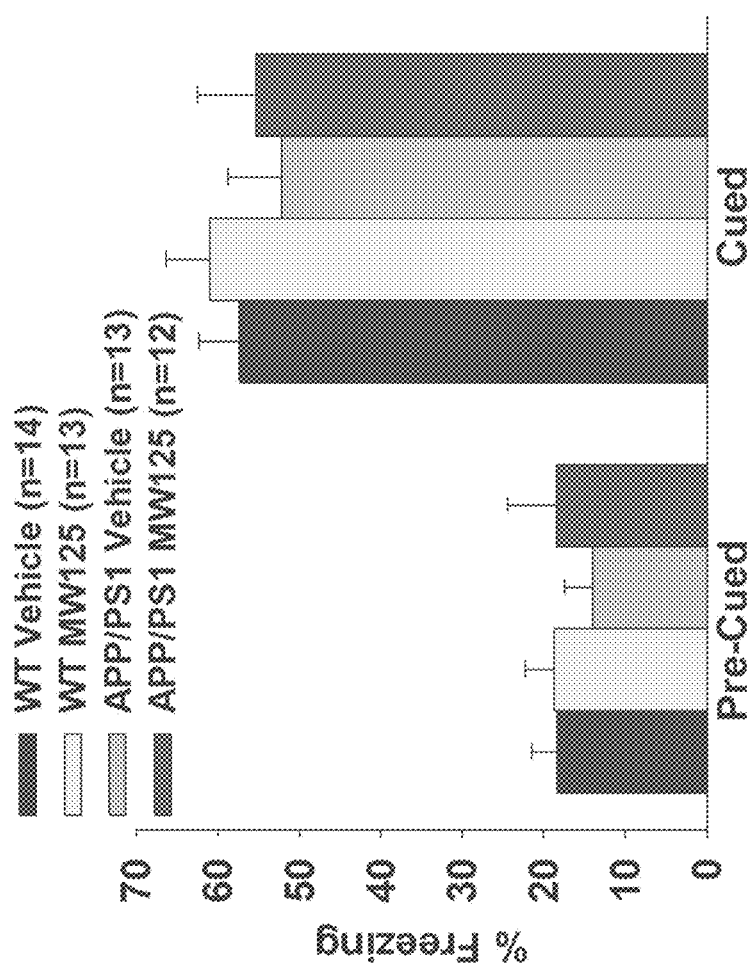
Figure 13C:
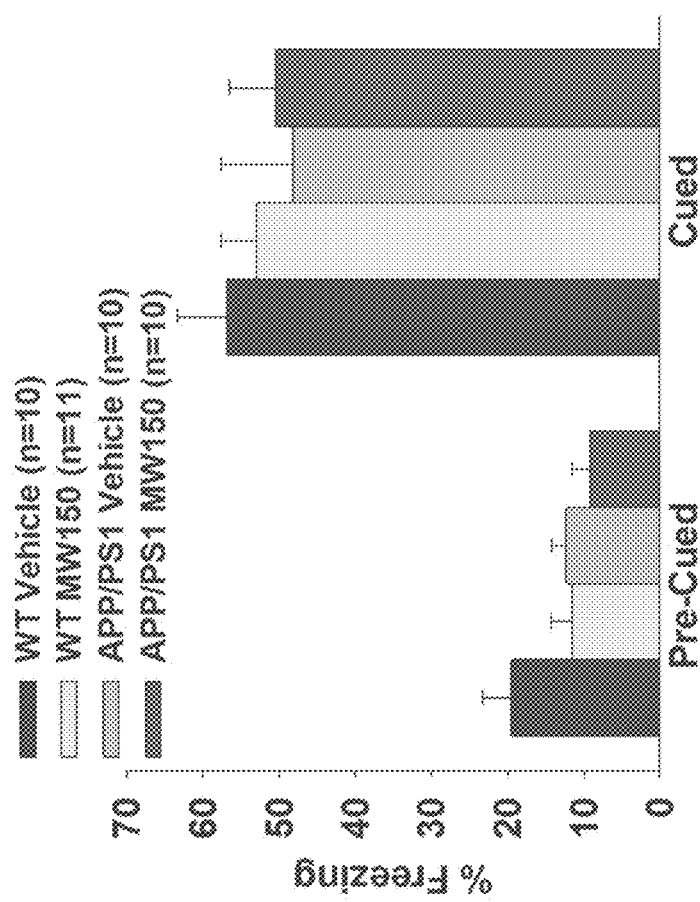
Figure 14A:
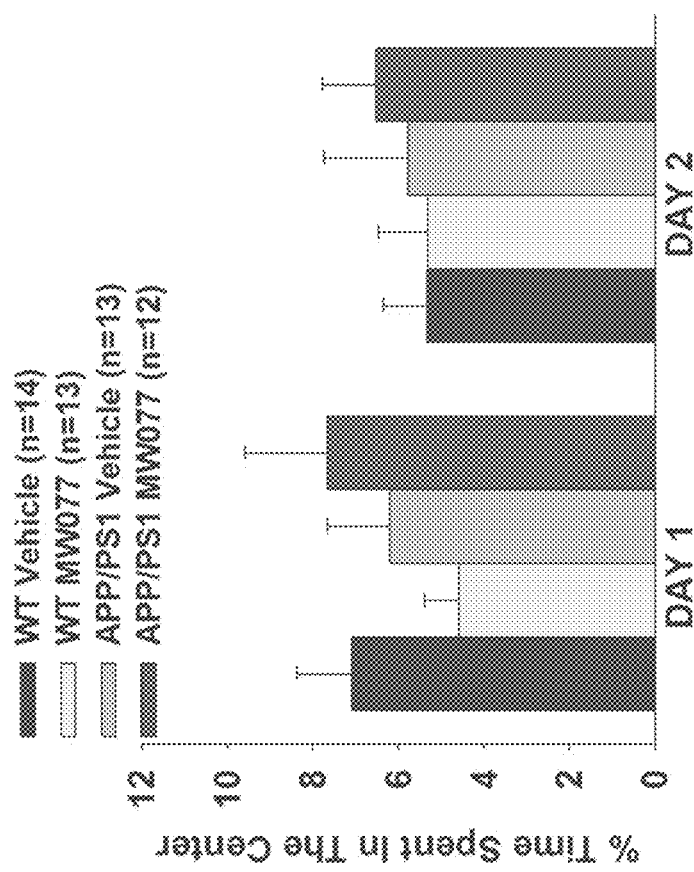
FIGS. 14A-B show open field results for (A) time spent in the center, and (B) number of entries into center for WT+vehicle, APP/PS1+vehicle, WT+MW-077 (7), and APP/PS1+MW-077 treated mice (WT+vehicle: n=14; APP/PS1+vehicle: n=13; WT+MW-077: n=13; APP/PS1+MW-077: n=12).
Figure 14B:
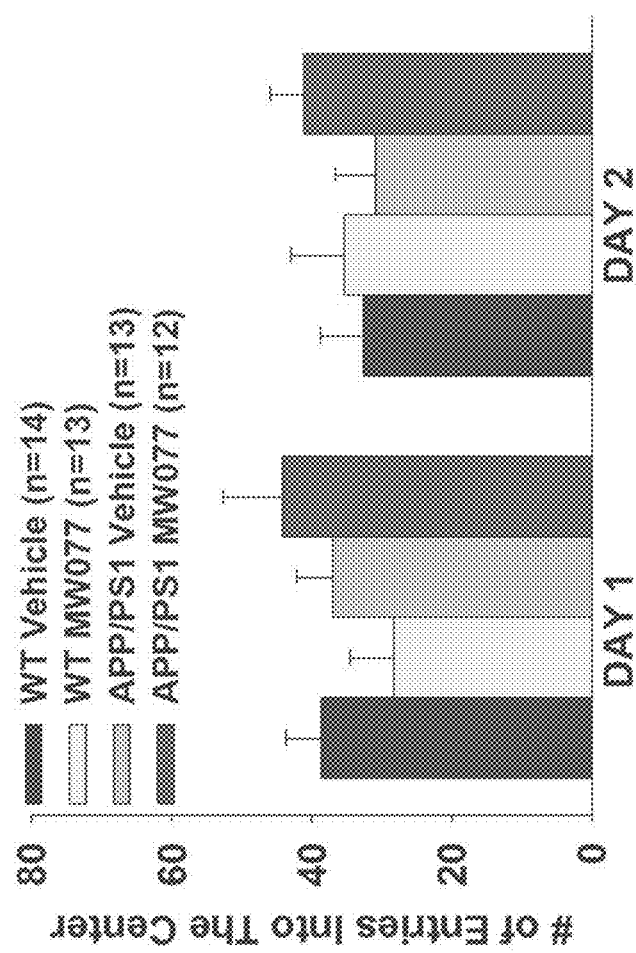
Figure 15A:
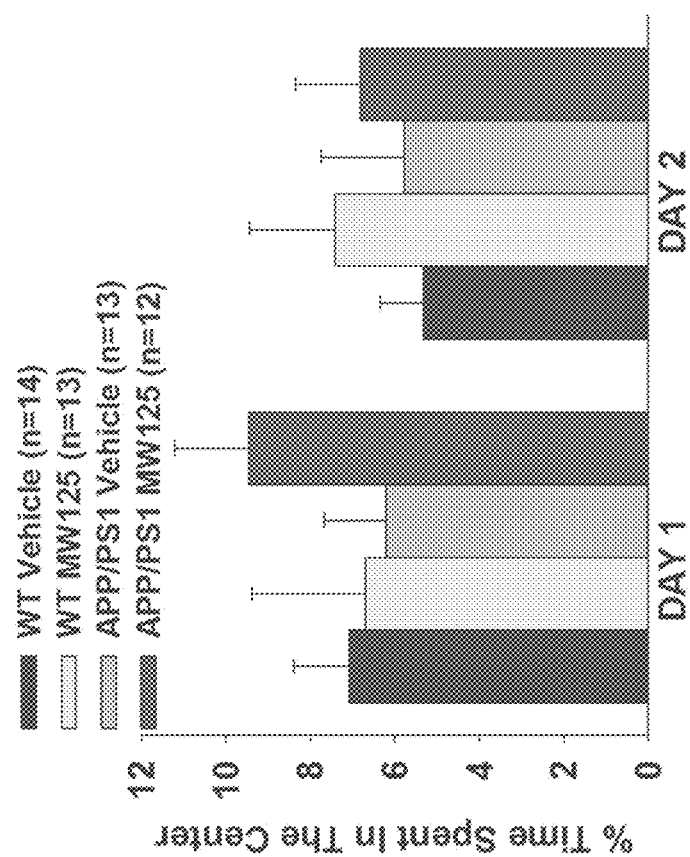
FIGS. 15A-B show open field results for (A) time spent in the center, and (B) number of entries into center for WT+vehicle, APP/PS1+vehicle, WT+MW-125 (9), and APP/PS1+MW-125 treated mice (WT+vehicle: n=14; APP/PS1+vehicle: n=13; WT+MW-125: n=13; APP/PS1+MW-125: n=12).
Figure 15B:
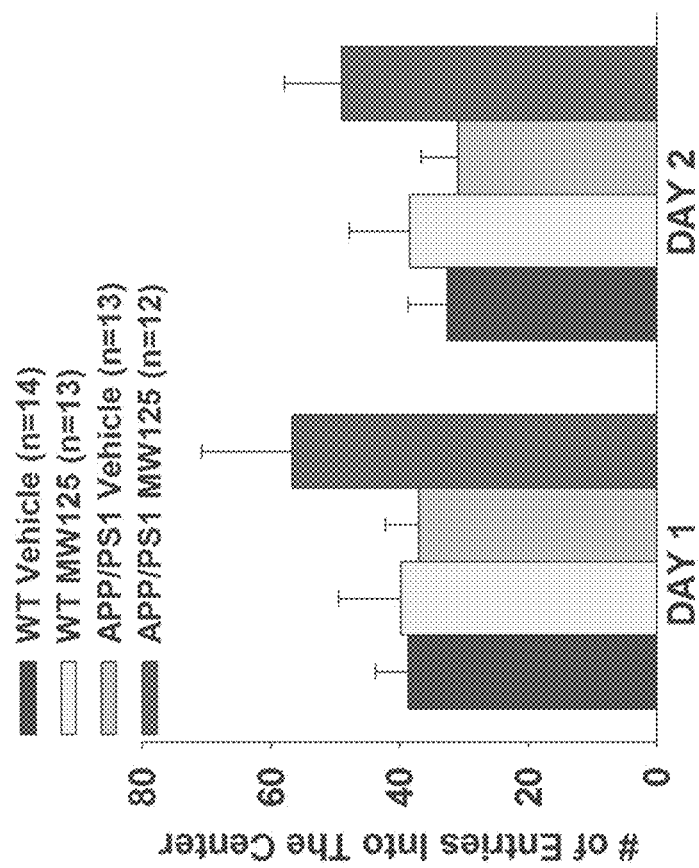
Figure 16A:
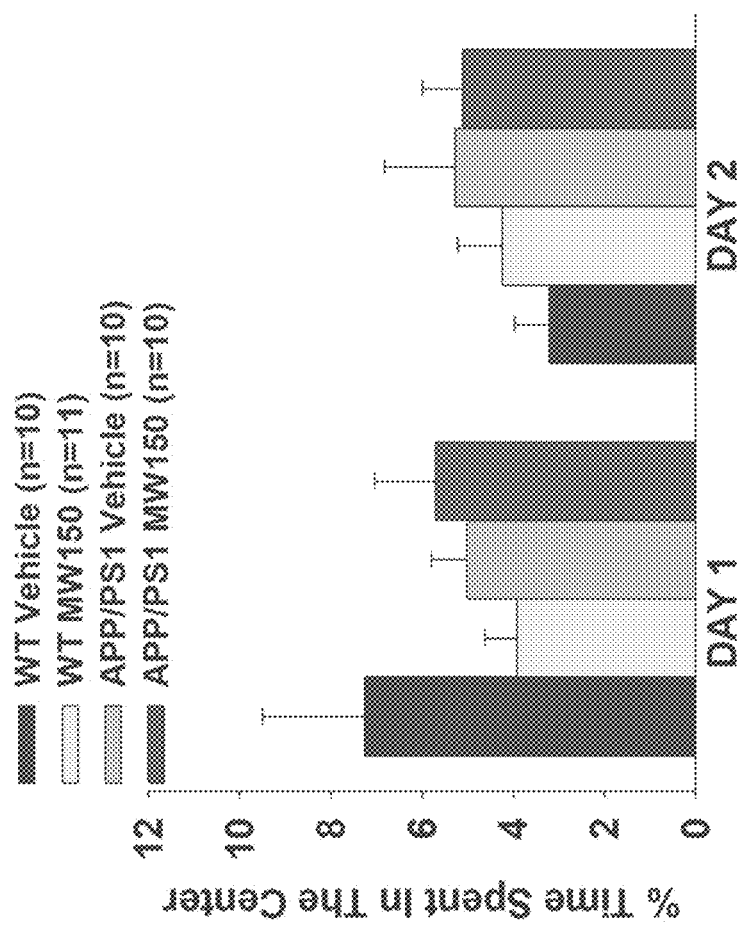
FIGS. 16A-B show open field results for (A) time spent in the center, and (B) number of entries into center for WT+vehicle, APP/PS1+vehicle, WT+MW-150 (27), and APP/PS1+MW-150 treated mice (WT+vehicle: n=10; APP/PS1+vehicle: n=10; WT+MW-150: n=11; APP/PS1+MW-150: n=10).
Figure 16B:
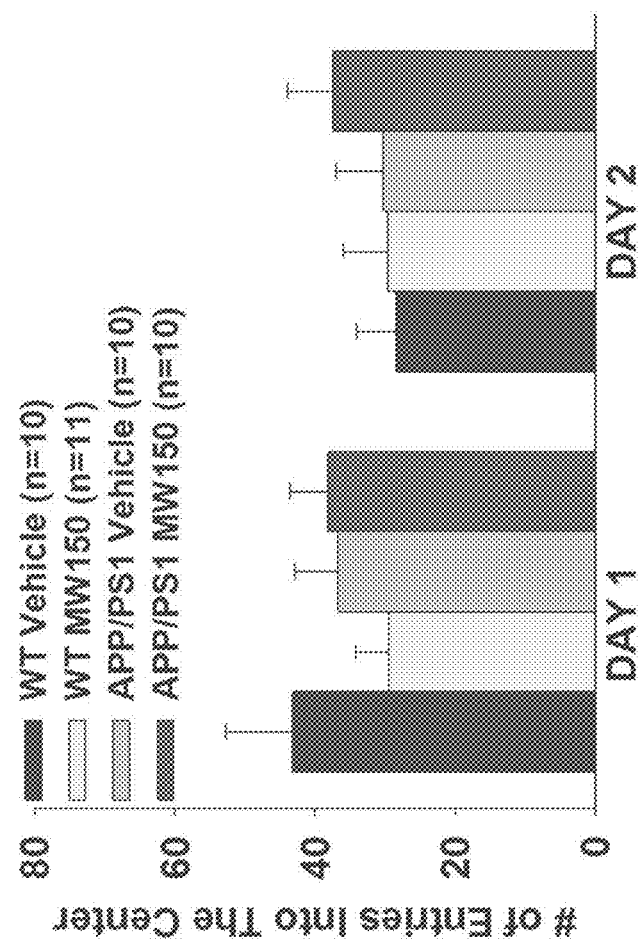
Figure 17:
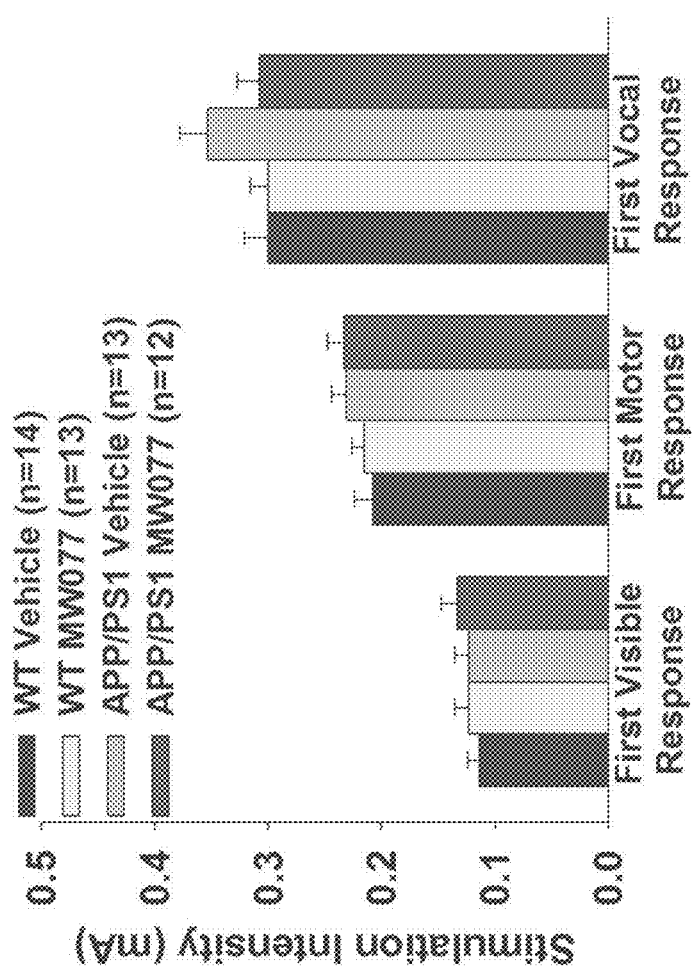
FIG. 17 shows sensory threshold assessment results for WT+vehicle, APP/PS1 vehicle, WT+MW-077 (7), and APP/PS1+MW-077 treated mice (WT: n=14; APP/PS1: n=13; WT+MW-077: n=13; APP/PS1+MW-077: n=12).
Figure 18:
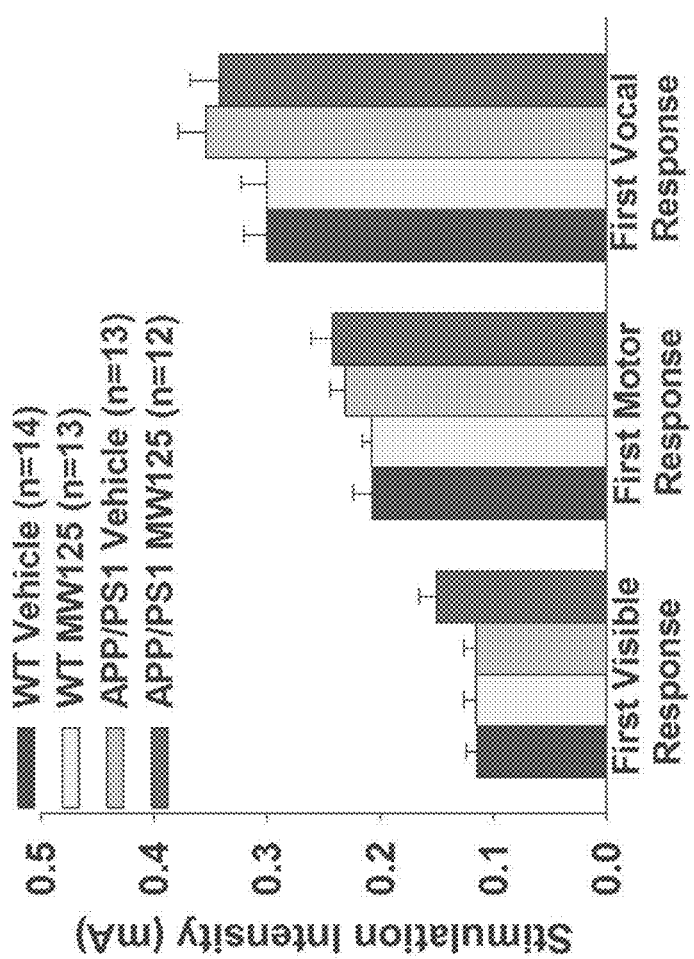
FIG. 18 shows sensory threshold assessment results for WT+vehicle, APP/PS1+vehicle, WT+MW-125 (9), and APP/PS1+MW-125 treated mice (WT+vehicle: n=14; APP/PS1+vehicle: n=13; WT+MW-125: n=13; APP/PS1+MW-125: n=12).
Figure 19:
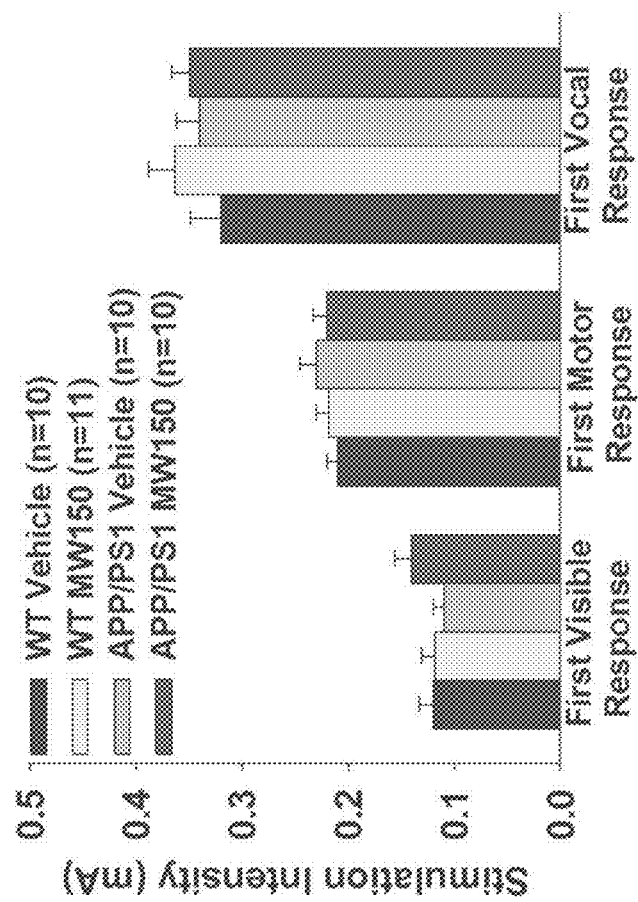
FIG. 19 shows sensory threshold assessment results for WT+vehicle, APP/PS1+vehicle, WT+MW-150 (27), and APP/PS1+MW-150 treated mice (WT+vehicle: n=10; APP/PS1+vehicle: n=10; WT+MW-150: n=11; APP/PS1+MW-150: n=10).

As shown in FIG. 13A-C, MW-077 (7), MW-125 (9) and MW-150 (27) (2.5 mg/kg, daily, oral gavage) do not affect cued fear memory in APP/PS1 mice.

As shown in FIG. 14-19, MW-077 (7), MW-125 (9) and MW-150 (27) (2.5 mg/kg, daily, oral gavage) did not animal performance with open field (FIGS. 14-16) and sensory threshold (FIGS. 17-19), meaning that the compounds do not affect anxiety status of the animal and its ability to feel the noxius stimulus.

Figure 20A:
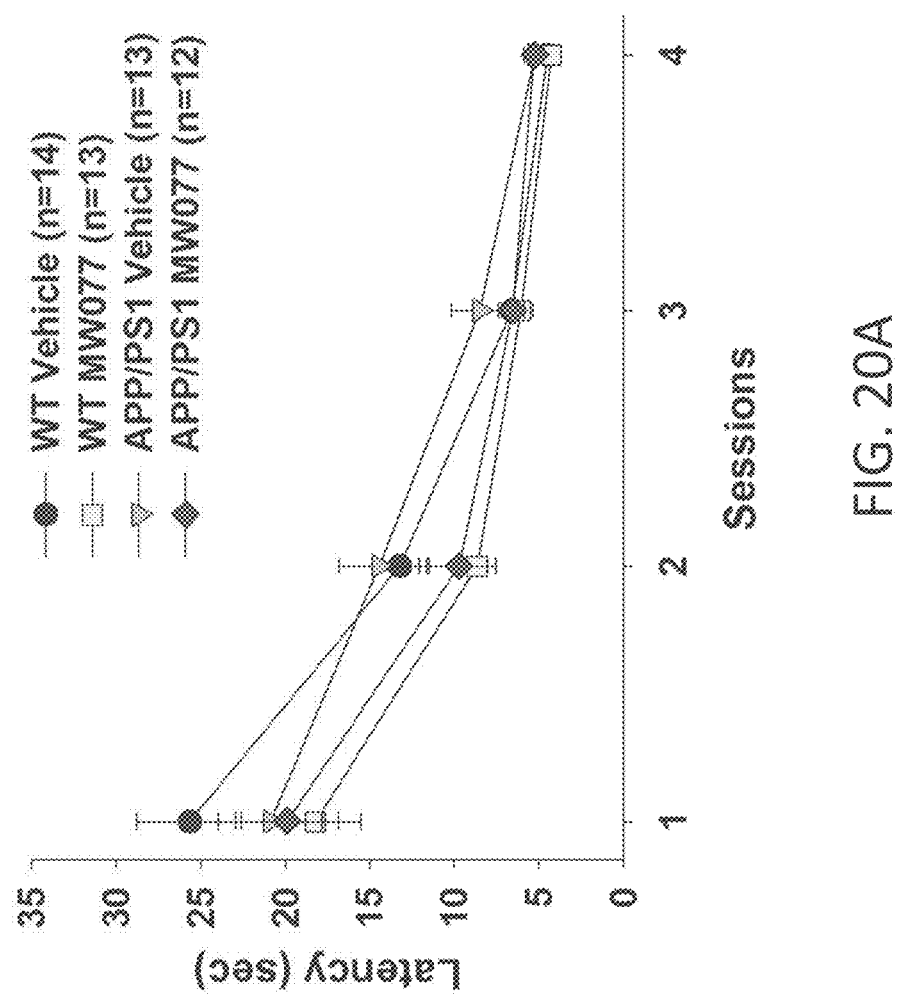
FIGS. 20A-C show time to platform results in visible platform test in (A) WT+vehicle, APP/PS1+vehicle, WT+MW-077 (7), and AP/PS1+MW-077 treated mice (WT+vehicle: n=14; APP/PS1+vehicle: n=13; WT+MW-077: n=13; APP/PS1+MW-077: n=12); (B) WT+vehicle, APP/PS1+vehicle, WT+MW-125 (9), and AP/PS1+MW-125 treated mice (WT+vehicle: n=14; APP/PS1+vehicle: n=13; WT+MW-125: n=13; APP/PS1+MW-125: n=12); and (C) WT+vehicle, APP/PS1+vehicle, WT+MW-150 (27), and AP/PS1+MW-150 treated mice (WT+vehicle: n=10; APP/PS1+vehicle: n=10; WT+MW-150: n=11; APP/PS1+MW-150: n=10).
Figure 20B:
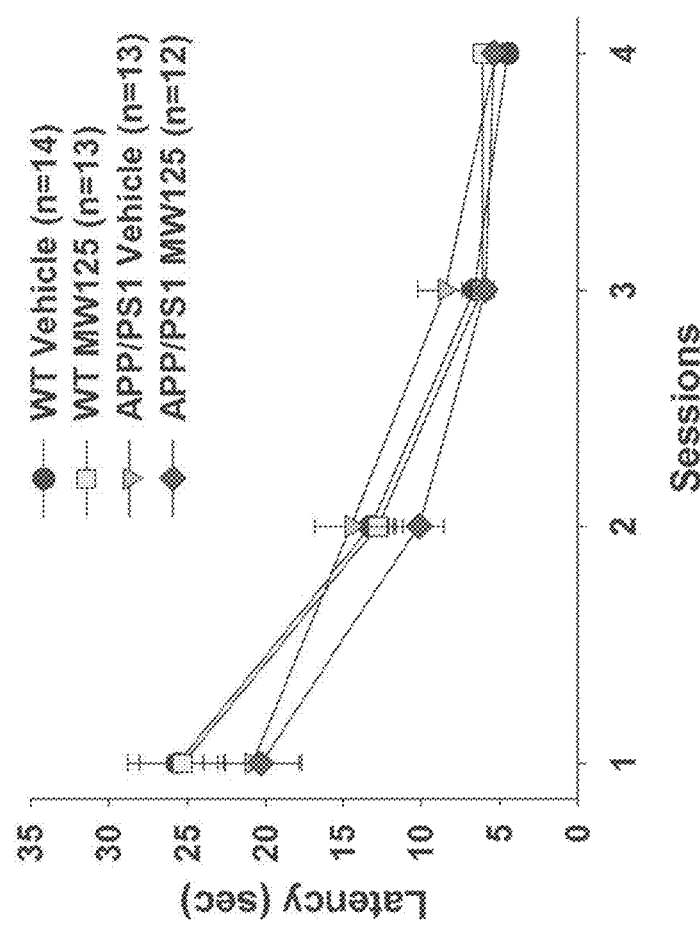
Figure 20C:
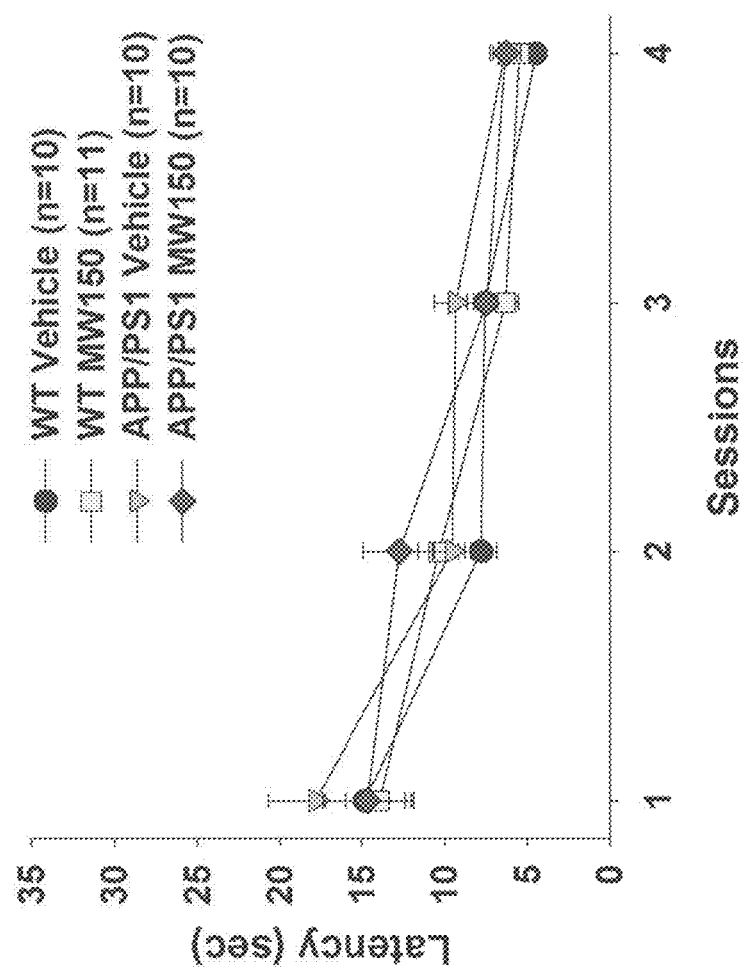
Figure 21A:
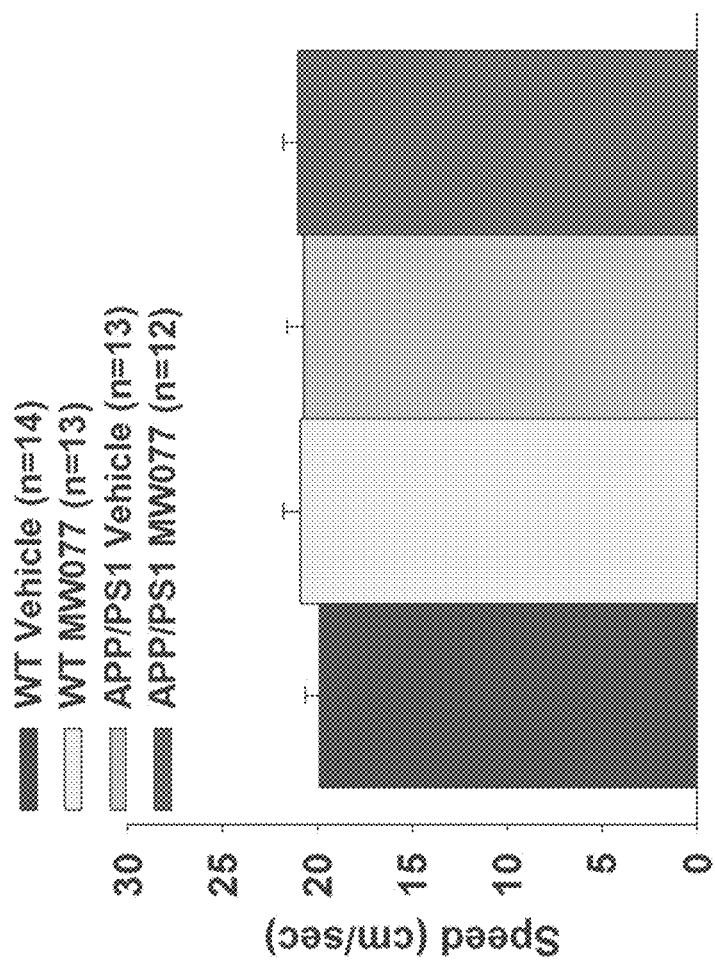
FIGS. 21A-C show speed to platform results in visible platform test in (A) WT+vehicle, APP/PS1+vehicle, WT+MW-077 (7), and AP/PS1+MW-077 treated mice (WT+vehicle: n=14; APP/PS1+vehicle: n=13; WT+MW-077: n=13; APP/PS1+MW-077: n=12): (B) WT+vehicle, APP/PS1+vehicle, WT+MW-125 (9), and AP/PS1+MW-125 treated mice (WT+vehicle: n=14; APP/PS1+vehicle: n=13; WT+MW-125: n=13; APP/PS1+MW-125: n=12): and (C) WT+vehicle, APP/PS1+vehicle, WT+MW-150 (27), and AP/PS1+MW-150 treated mice (WT+vehicle: n=10; APP/PS1+vehicle: n=10; WT+MW-150: n=11; APP/PS1+MW-150: n=10).
Figure 21B:
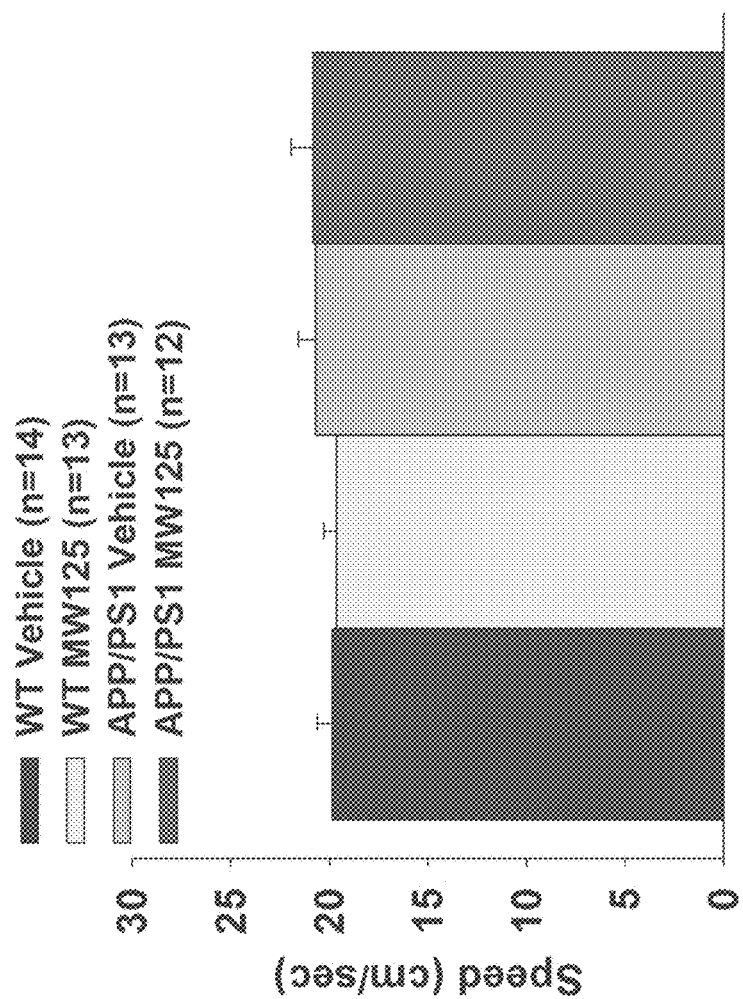
Figure 21C:
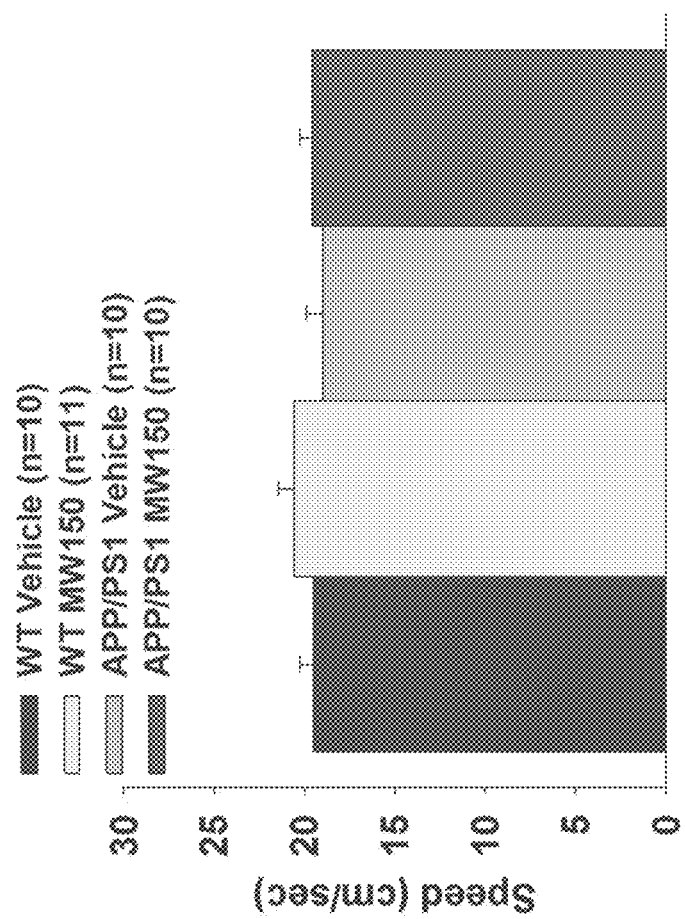

As shown in FIGS. 20-21, controls of visible platform testing show that MW-077 (7), MW-125 (9) and MW-150 (27) (2.5 mg/kg, daily, oral gavage) do not affect performance with visible platform tasks in APP/PS1 mice.

Figure 22A:
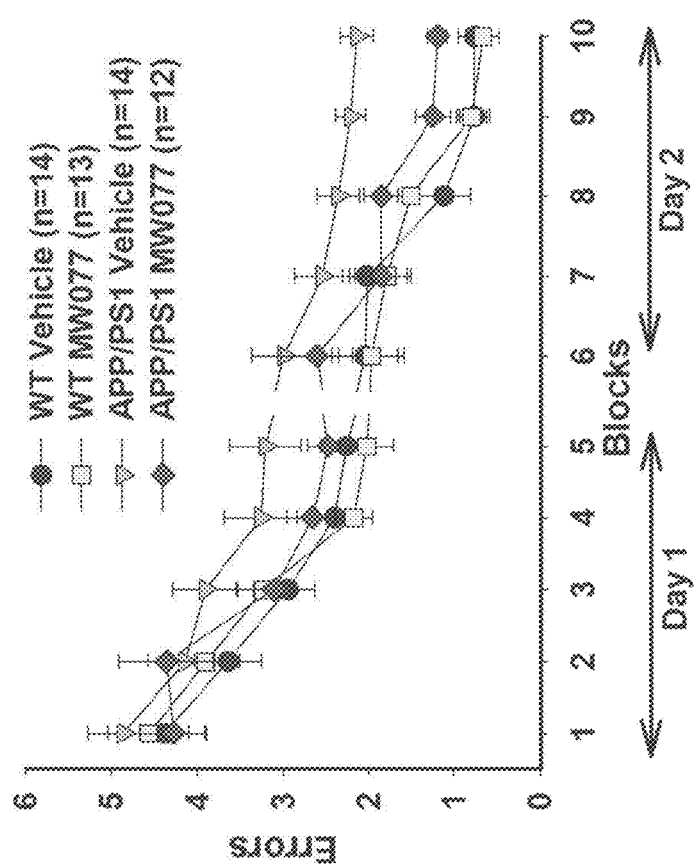
FIGS. 22A-C show RAWM results in (A) WT+vehicle, APP/PS1+vehicle, WT+MW-077 (7), and AP/PS1+MW-077 treated mice (WT+vehicle: n=14; APP/PS1+vehicle: n=14; WT+MW-077: n=13; APP/PS1+MW-077: n=12). Statistical analyses showed: APP/PS1 vehicle vs. APP/PS1+MW-077: p=0.14056485 ($3^{rd}$ last point), 0.00166180 ($2^{nd}$ last point), 0.00039962 (last point); APP/PS1 vehicle vs. WT-vehicle: p=0.00354140 ($3^{rd}$ last point), 0.00007920 ($2^{nd}$ last point), 0.00000630 (last point): (B) WT+vehicle, APP/PS1+vehicle, WT+MW-125 (9), and AP/PS1+MW-125 treated mice (WT+vehicle: n=14; APP/PS1+vehicle: n=14; WT+MW-125: n=13; APP/PS1+MW-125: n=12). Statistical analyses showed: APP/PS1 vehicle vs. APP/PS1+MW-125: p=0.01969560 ($3^{rd}$ last point), 0.00269137 ($2^{nd}$ last point), 0.00079845 (last point); APP/PS1 vehicle vs. WT-vehicle: p=0.00354140 ($3^{rd}$ last point), 0.00007920 ($2^{nd}$ last point), 0.00000630 (last point); and (C) WT+vehicle, APP/PS1+vehicle, WT+MW-150 (27), and AP/PS1+MW-150 treated mice (WT+vehicle: n=10; APP/PS1+vehicle: n=10; WT+MW-150: n=11; APP/PS1+MW-150: n=10). Statistical analyses showed: APP/PS1 vehicle vs. APP/PS1+MW-150: p=0.04494522 ($3^{rd}$ last point), 0.12684352 ($2^{nd}$ last point), 0.02070092 (last point); APP/PS1 vehicle vs. WT-vehicle: p=0.01189036 ($3^{rd}$ last point), 0.04848323 ($2^{nd}$ last point), 0.00119455 (last point).
Figure 22B:
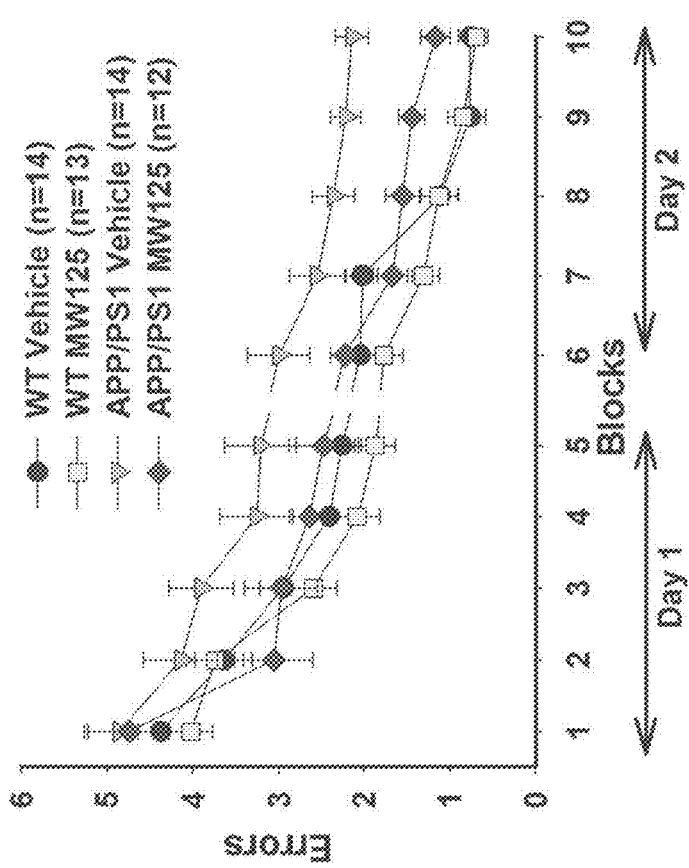
Figure 22C:
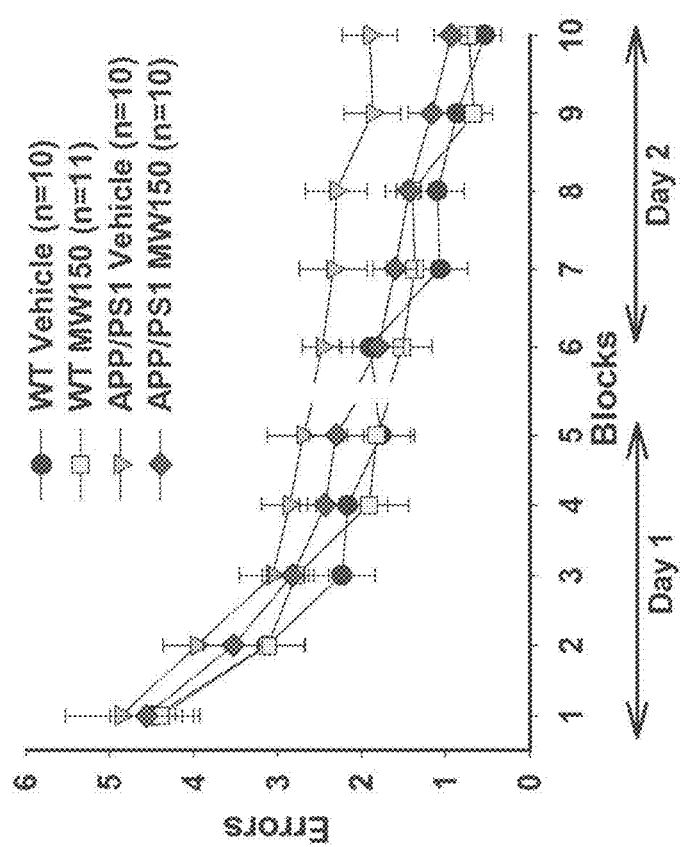

As shown in FIG. 22, MW-077 (7), MW-125 (9) and MW-150 (27) rescue defects in spatial memory in APP/PS1 mice. The compounds did not affect performance in WT littermates. Mice were treated with the compounds (2.5 mg/kg, daily, oral gavage) from the age of 2 months until behavioral testing that occurred at ~3 months of age.

Figure 23A:
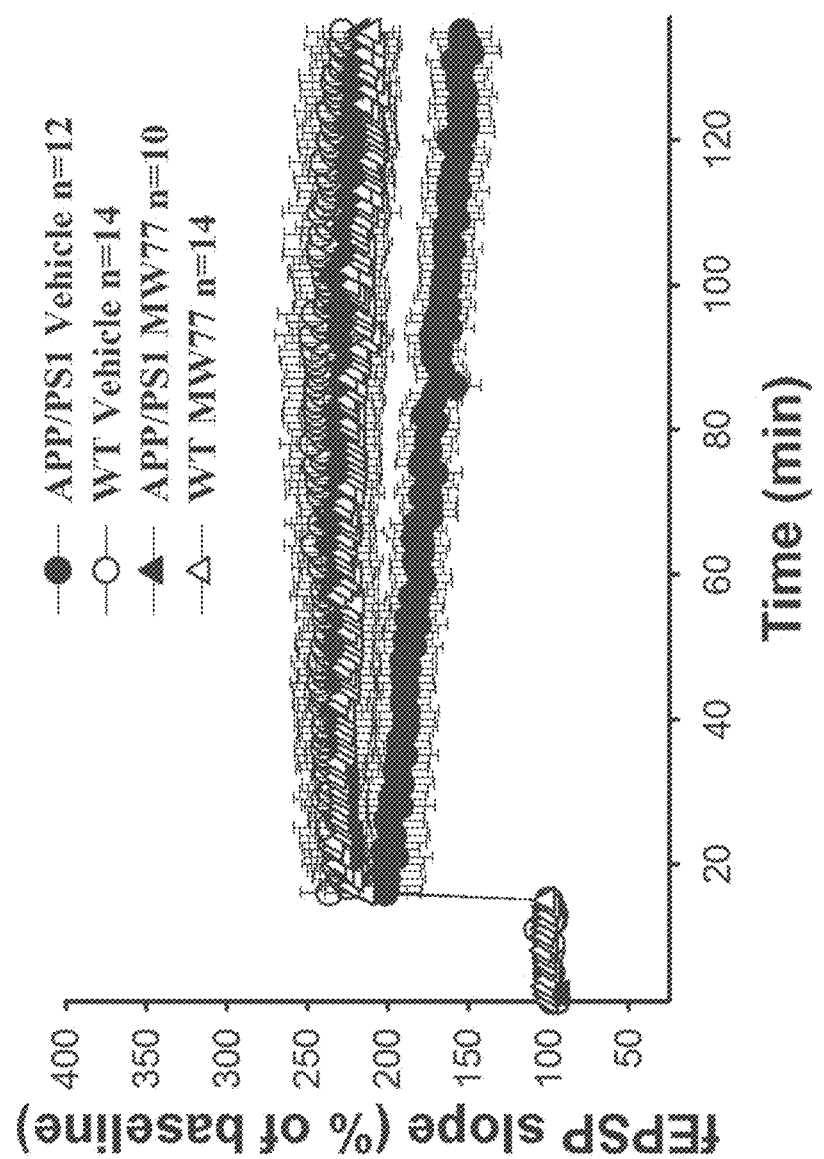
FIGS. 23A-C show potentiation as a percent of baseline in (A) APP/PS1+vehicle (n =12), APP/PS1+MW-077 (7) (n=10), WT+vehicle (n=14), WT+MW-077 (n=14). APP/PS1 vehicle vs. APP/PS1+MW-077: Two-way ANOVA F(1, 19)=5.163, p=0.0349. APP/PS1 vehicle vs. WT+vehicle: F(1,24)=5.967, p=0.0223; (B) APP/PS1+vehicle (n=12), APP/PS1+MW-125 (9) (n=9), WT+vehicle (n=14), WT+MW-125 (n=7). APP/PS1 vehicle vs. APP/PS1+MW-077: Two-way ANOVA F(1,19)=9.357 p=0.0065. APP/PS1 vehicle vs. WT+vehicle: F(1,24)=5.967, p=0.0223; and (C) APP/PS1+vehicle (n=12), APP/PS1+MW-150 (27) (n=7), WT+vehicle (n=14), and WT+MW-150 (n=9). APP/PS1 vehicle vs. APP/PS1+MW-077: Two-way ANOVA F(1,17)= 6.780 P=0.0185. APP/PS1 vehicle vs. WT+vehicle: F(1,24)=5.967, p=0.0223.
Figure 23B:
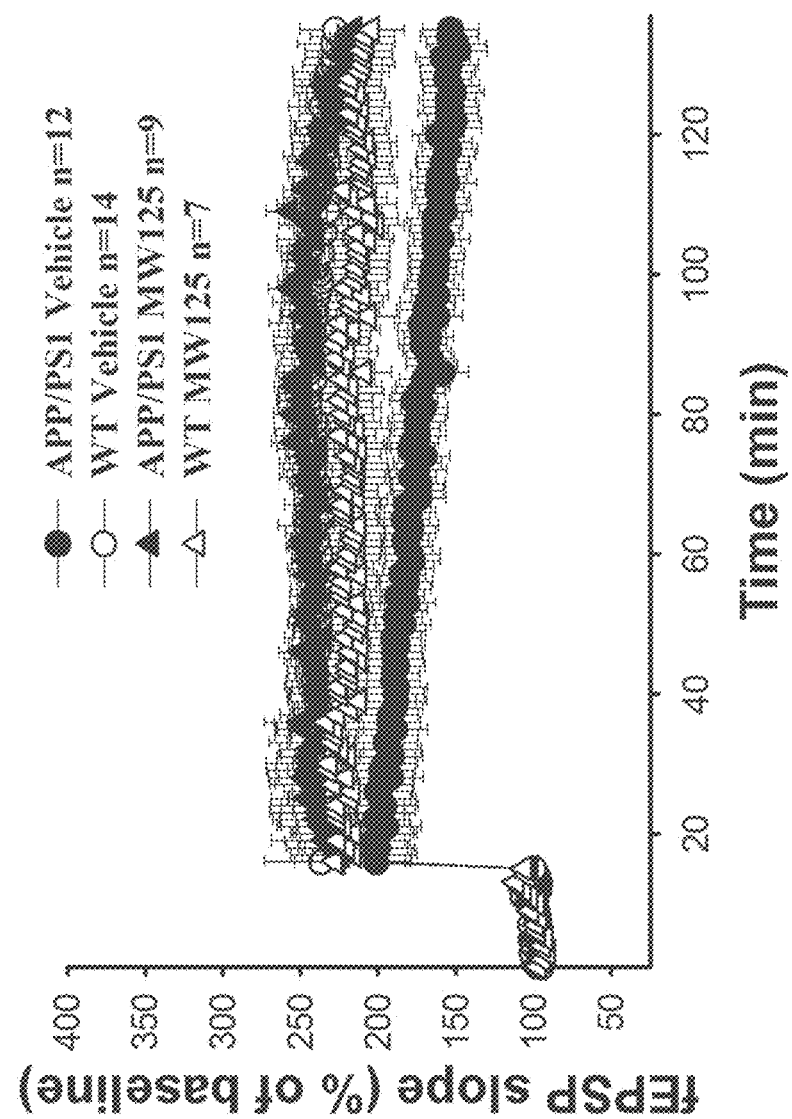
Figure 23C:
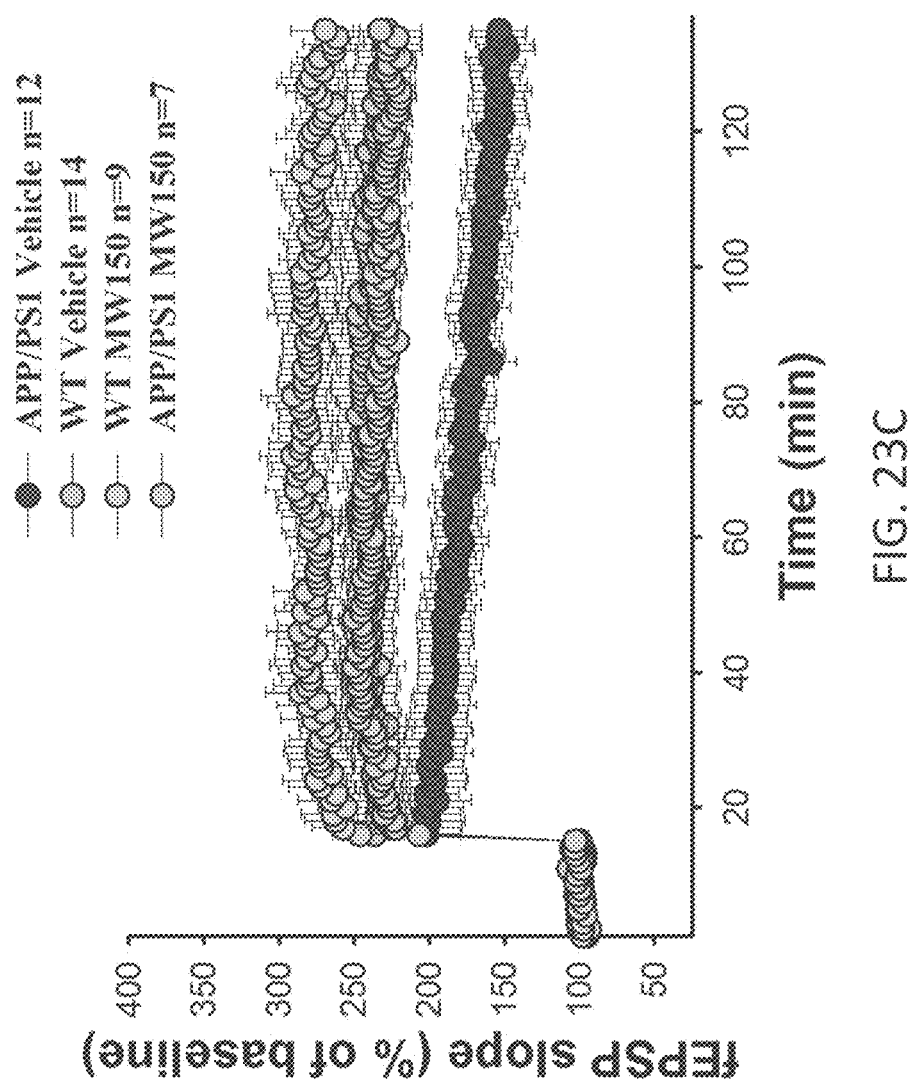

As shown in FIG. 23, MW-077 (7), MW-125 (9) and MW-150 (27)_rescue defects in LTP in APP/PS1 mice. The compounds did not affect LTP in WT littermates. Mice were treated with the compounds (2.5 mg/kg, daily, oral gavage) from the age of 2 months until the sacrifice of the animals which occurred between 3-4 months.

Methods to screen compounds for treatment of Alzheimer's Disease are also described, for example, in WO 11/072243 and WO12/088420, each herein incorporated by reference in its entirety.

Example 18

Amyotrophic Lateral Sclerosis (ALS)

Animal Models: SOD1 transgenic mice are used as a model for ALS. These mice have the mutant human SOD1 (G93A) substitution. Motor impairment starts at 12 weeks of age and includes changes in body weight, reduction in grip strength and general motor activity, which can be assessed using the tests outlined below. This phenotype continues to progress until death at about 19 weeks.

Body Weight: The body weight of the mice is recorded at regular intervals throughout the duration of the study. SOD1 (G93A) mice exhibit a reduction in bodyweight starting at 12 weeks of age in males and 16 weeks of age in females. Body weight loss continues to progress with disease progression.

Grip Strength: Grip strength is used to assess muscular strength in limb muscles. The mouse is lowered toward the platform and gently pulled backwards with consistent force by the experimenter until it releases its grip. The grip force is recorded through a strain gauge. SOD1 (G93A) mice exhibit a decline in forelimb grip strength, from about 9 weeks of age, and continuing to decline as the disease progresses. SOD1 (G93A) mice also show a decline in hind limb grip strength, starting at about 9 weeks of age, and continuing to decline with disease progression. Finally, SOD1 (G93A) mice exhibit a decline in hind limb grip strength, starting from around 9 weeks of age, and continuing to decline with disease progression.

Rotarod: Motor coordination and exercise capacity are assessed through the rotarod. Tests are performed on separate days, with multiple trials per day. Mice are placed on the rotarod and the speed of the rotation of the rod is gradually and uniformly increased over a maximum period of time. The time that each mouse remains on the rotating rod before falling is recorded. SOD1 (G93A) mice demonstrate a decline in motor function from 12 weeks of age.

Survival: Survival of the mice is recorded and can be cumulatively followed as the population in the various treatment groups decline. SOD1 (G93A) mice begin to show decreased survival at about 120 days, with an increasingly steep decline and zero survival at about 150 days.

Treatment with the test compound starts from the age of two months. The treatment lasts until the death of the animal.

Example 19

Parkinson's Disease (PD)

Animal Model: The MPTP mouse model of Parkinson's disease is thought to mimic more closely the behavioral pathology of Parkinson's disease, compared to other models. Mice exhibit Parkinson's-like symptoms following systemic injection of the pyridine toxin MPTP, which produces a loss of striatal dopamine (DA) nerve terminal markers and, at higher doses, death of DA neurons in the substantia nigra. The process of terminal loss and degeneration takes 6-9 days following MPTP injection.

Treatment: The test compounds can be administered both before the MPTP is given (to evaluate neuroprotection), and/or while the toxin is active in the first week post-injection (to evaluate preservation of dopamine function).

Neurochemical Assay: Tyrosine Hydroxylase (TH) Immunohistochemistry (Quantitative Morphology) and Dopamine turnover. Determination of DA, DOPAC and HVA concentrations in the striata of control and MPTP-lesioned mice. The DA and DOPAC levels are significantly reduced, in MPTP-lesioned mice as compared to control groups.

Behavior Testing: In mice, MPTP injections produce a temporary increase in hyperactivity, a long-lasting increase in wall-supported rearing in the open field enclosure (relative to "free" rearing in the center), a lasting increase in foot slippage (foot faults in a grid-walking test) and a lasting impairment in treadmill activity (using several measures of gait). The hyperactivity returns to baseline after 2 weeks but the other three measures of impaired balance remain abnormal indefinitely. Improvements in the latter measures following drug treatment correlate with increased dopamine neuron presence (increased numbers of TH-positive cells) in the substantia nigra and increased dopamine activity in the striatum.

Methods to screen compounds for treatment of Parkinson's Disease are also described, for example, in WO 11/072243 and WO12/088420, each herein incorporated by reference in its entirety.

Example 20

Huntington's Disease (HD)

Animal Model. Several mouse models of HD have been engineered. Out of all of them, YAC128 is advantageous because a) it expresses the full length protein, and thus Lysine 444; b) it has a faster age of onset than knock-in model; c) the aggregation pattern is more reminiscent to adult onset HD; and d) reports of some neuronal loss as measured by dark cell degeneration in the striatum. This model will therefore permit simultaneous testing of the importance of transcriptional dysregulation in HD as well as the importance of selective degradation of mutant huntingtin protein.

Treatment: The test compound is administered by gavage daily to 8 week old mice up to 10 months. The primary endpoints of therapeutic effectiveness are evaluated by testing monthly motor behaviors including rotarod, gait analyses and open field, starting at 10 weeks of age as described in Cell 2000, 101, 57, herein incorporated by reference in its entirety, to determine if the new compound administration leads to a delay in phenotype onset. To determine if the new compound administration leads to a decrease of mutant htt protein levels, a small cohort of (n=3) mice is sacrificed after 1 month and analyzed for SDS-soluble and insoluble mutant htt protein using EM48 (Chemicon) and 3B5H10 (Sigma). EM48-positive intracellular inclusions, stereological counts of striatal neurons (NeuN-positive), dark cell degeneration and brain weights are collected starting at 12 months of age. Part of the brains is utilized for measuring histone acetylation levels. For behavioral experiments mice are divided into different cohorts of 12 mice per group (see group distribution below). Although the study continues up to the age of 12 months, within 4 months of the study one will learn whether chronic administration of the new compound has a positive input in mutant huntingtin protein levels, as well as whether the new compound can delay the age of phenotypic onset.

The Phenotypic Analysis of these Mice Includes: Rotarod, Open Fieldmeasurement of SDS-soluble and insoluble mutant htt protein, EM48-positive intracellular inclusions, stereological counts of striatal neurons (NeuN-positive) and brain weights.

Accelerating Rotarod: This assay is a common assay used to monitor motor coordination in mouse models of Huntington's disease (HD). After a training period to acclimatize the mice to the apparatus, mice are placed on a rod rotating at 5 rpm. Over the test period of 300 sec, the rod increases its rotational speed from 5 rpm to 40 rpm. The time at which the mouse falls off of the rod is recorded. Each mouse is subject to 3 runs per day (shown as a per day average) across 3 days (d1, d2, d3). Typically 8 to 12 mice per group are used in this assay.

Open Field: This assay is a common assay used to monitor total spontaneous locomotor activity and exploratory behavior in mouse models of Huntington's disease (HD). The spontaneous locomotor activity of the animals is measured using an automated photo-beam open-field system (Med-Associates, St Albans, Vt.). Mice are placed individually in the center of a clear open-field chamber (27.9 cm×27.9 cm×20 cm), and their horizontal and vertical activities are measured immediately for 30 min with three 16-beam I/R arrays. Locomotor activity is assessed as the distance traveled in 5-min intervals.

Methods to screen compounds for treatment of Huntington's Disease are also described, for example, in WO 11/072243 and WO 12/088420, each herein incorporated by reference in its entirety.

Example 21

Oxygen Glucose Deprivation

Figure 24:
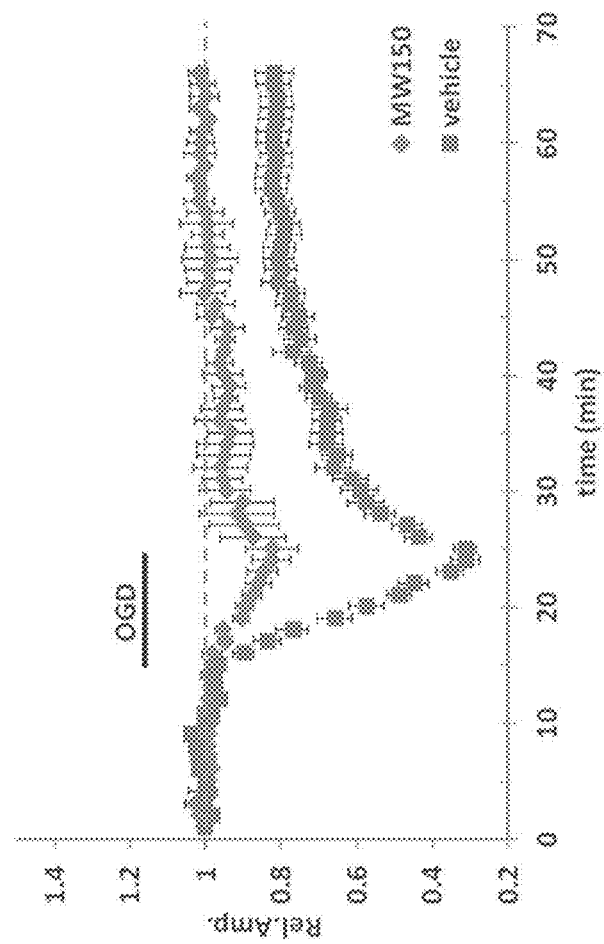
FIG. 24 shows synaptic depression induced by oxygen glucose deprivation (OGD) is ameliorated by MW-150 (27). After 15 min of stable baseline, oxygen glucose deprivation was applied for 10 min (dark bar).

Slice preparation. Animals were anesthetized using urethane (20% solution, 1 mL/100 g body weight) via intraperitoneal injection and then decapitated after disappearance of the tail pinch reflex. After brain removal, horizontal sections (400 μm in thickness), containing the entorhinal area, were made on a Vibratome. All steps were performed in ice-cold oxygenated ACSF solution. Before recording, slices were stored for at least 1 h in a recovery chamber containing oxygenated ACSF solution at room temperature. For electrophysiology, slices were perfused at a rate of 2.5-3 mL/min with oxygenated ACSF at 33±1° C. Extracellular field potentials (FPs) were evoked in layer II/III in 3 response to electrical stimulation of layer II (Origlia et al., Receptor for advanced glycation end product-dependent activation of p38 mitogen-activated protein kinase contributes to amyloid-β-mediated cortical synaptic dysfunction. J Neurosci 2008, 28:3521-3530; Origlia et al., Microglial Receptor for Advanced Glycation End Product-Dependent Signal Pathway Drives β-Amyloid-Induced Synaptic Depression and Long-Term Depression Impairment in Entorhinal Cortex, Journal Neurosci 2010, 30(34): 11414-11425; each herein incorporated by reference in its entirety). The amplitude of the FPs was used as a measure of the evoked population excitatory current. All FPs had peak latency between 4.5 and 6 ms. Baseline responses were obtained with a stimulation intensity that yielded 50-60% of maximal amplitude. After 15 min of stable baseline recordings slices were perfused for 10 minutes with deoxygenated glucose-free ACSF (glucose was substituted with D-mannitol at equimolar concentration), to obtain a transient oxygen/glucose deprivation (OGD). The amplitude of FP was monitored every 20 s and averaged every three responses by online data acquisition software. Effects on synaptic function were evaluated either during ischemia (as the average of FPs amplitude during the last 3 min of 10 min OGD application) or as the recovery of FPs calculated as the averaged relative amplitude of FPs respect to the baseline values after reintroduction of regular ACSF (from 41st to 50th min after the end of OGD). Synaptic depression induced by OGD is ameliorated by MW-150 (FIG. 24). Slices were continuously perfused with ACSF containing 10 μM of the compound.

Example 22

Figure 25A:
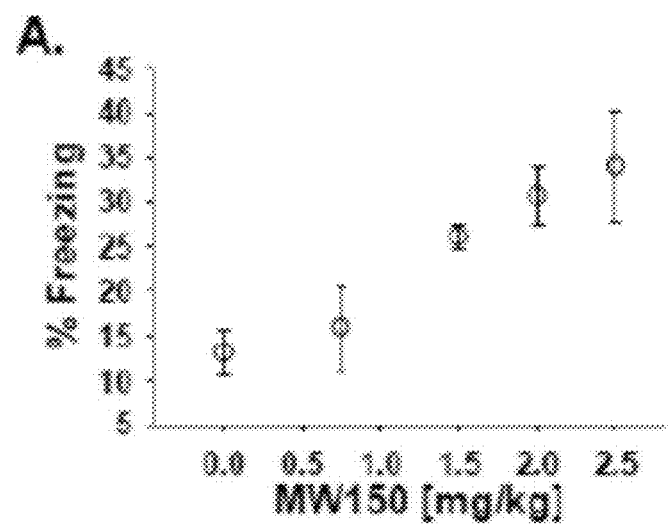
FIGS. 25A-25B show effect of MW-150 treatment for behavior end points. Dose response curve for MW-150 during assessment of associative and spatial memory deficit in APP/PS1 transgenic mice. Mice were administered orally either saline vehicle or different concentrations of MW-150 daily from 8 weeks of age until 3-4 months when associative and spatial memories were assessed through contextual fear memory (FIG. 25A) and RAWM (FIG. 25B). RAWM errors correspond to the number of errors that mice (3-15 per test) made at the last set of trials.
Figure 25B:
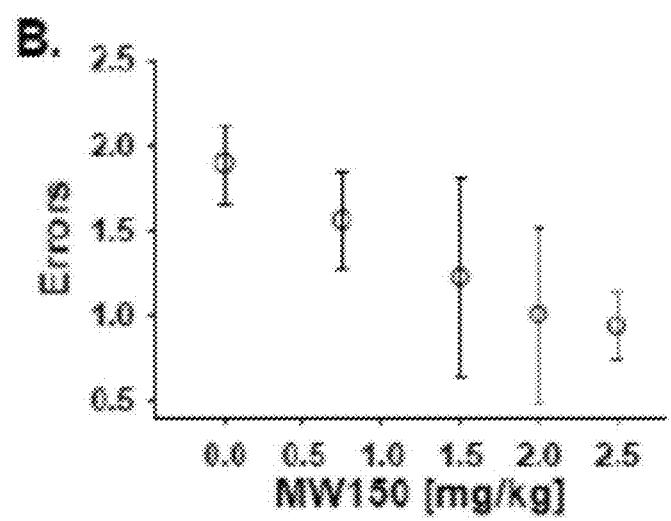

Dose response curve for MW-150 during assessment of associative and spatial memory deficit in APP/PS1 transgenic mice. Mice were administered orally either saline vehicle or different concentrations of MW-150 daily from 8 weeks of age until 3-4 months when associative and spatial memories were assessed through contextual fear memory (FIG. 25A) and RAWM (FIG. 25B). RAWM errors correspond to the number of errors that mice (3-15 per test) made at the last set of trials.

Example 23

Results in two distinct pathology progression models demonstrate the ability bring about pharmacological efficacy with MW-150 repeat dosing. Further, the results in a battery of behavioral tests are consistent with a true hippocampus-dependent mechanism of action in attenuation of memory deficits. Repeat dosing with MW-150 did not bring about any observed adverse events within the targeted physiological axis or control behaviors in aged or diseased animals. The selective improvement in cognitive behavior was also brought about with no effect on amyloid plaque load (Wilcock, D. M., and Colton, C. A. (2009) Immunotherapy, vascular pathology and microhemorrhages in transgenic mice. CNS Neurol. Disord.: Drug Targets 8, 50-64, herein incorporated by reference in its entirety).

Histopathology. Immunohistochemistry was performed using the Ventana BenchMark Ultra automated platform. Tissue sections were first deparaffinized using Ventana's "ez-prep" solution. Antigen retrieval was performed by treatment at 95° C. for 54 minutes using Ventana's CC1 (pH 7.3) solution, followed by treatment with 0.3% hydrogen peroxide to block endogenous peroxidase. Tissue sections were then incubated in protein-free block (Biocare's background sniper) for 15 min to inhibit nonspecific binding. Primary antibody (anti-Aβ 6E10 at 1:400, Biocare Medical) was incubated for 32 min at room temperature. Detection was performed using Ventana's ultraview DAB kit, and counterstaining with Gill hematoxylin solution. A boardcertified neuropathologist, who was blinded to the treatment versus the control group, analyzed a sagittal section from each mouse and counted the total number of well-formed β-amyloid plaques.

Figure 26A:
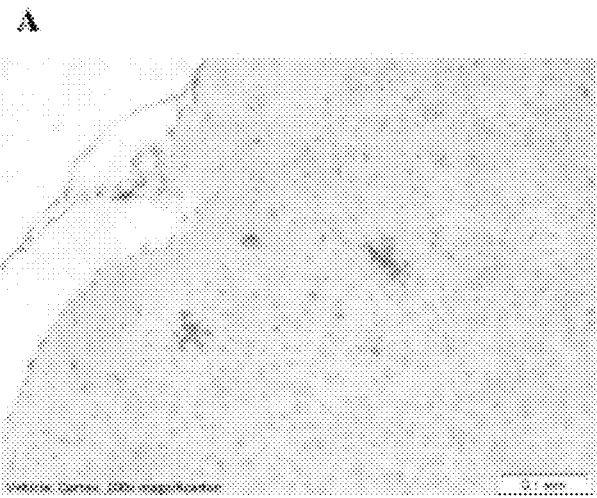
FIGS. 26A-26D show effect of MW-150 treatment on cognitive performance in the absence of effect on A-β plaque burden. Sections of cortex from APP/PS1 transgenic mice treated with vehicle (FIG. 26A) or MW-150 (FIG. 26B) were stained with 6E10 anti-Aβ antibody (10× objective; 100× magnification).
Figure 26B:
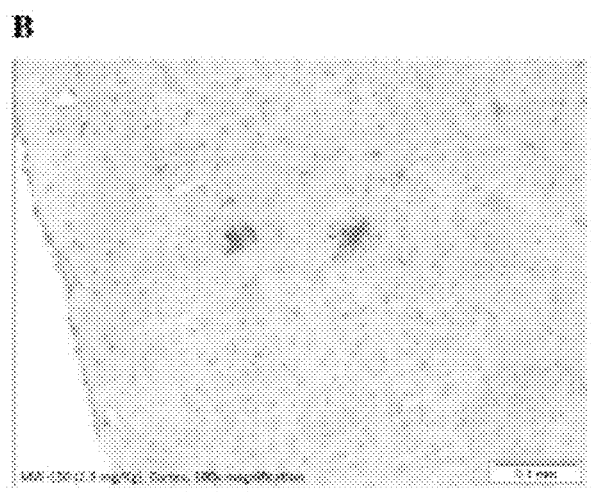
Figure 26C:
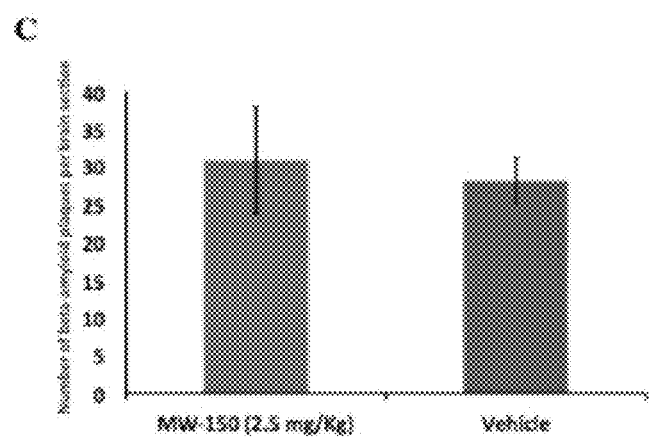
Figure 26D:
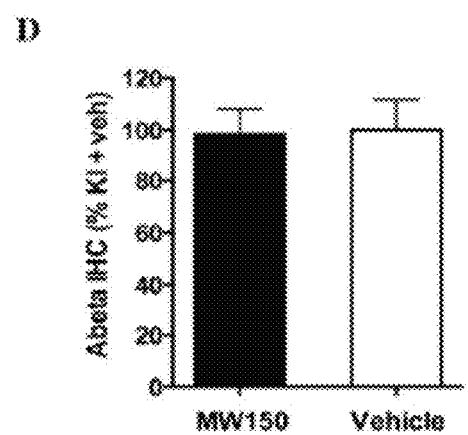

MW-150 treatment improves cognitive performance in the absence of effect on AP plaque burden. Sections of cortex from APP/PS1 transgenic mice treated with vehicle (FIG. 26A) or MW-150 (FIG. 26B) were stained with 6E10 anti-Aβ antibody (10× objective; 100× magnification). (FIG. 26C) Quantification by a board-certified neuropathologist blinded to the treatment groups was done by analysis of a brain sagittal section from each mouse in which the total number of well formed β-amyloid plaques in the entire section were counted. Error bars show standard error of the mean (n=4 for each group). (FIG. 26D) In a separate experiment with APP/PS1 knock-in (KI) mice, Aβ plaques were quantified from KI mice treated with MW-150 or vehicle. In both AD mouse S15 models, there are no effects of MW-150 treatment on the amyloid plaque burden.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:
1. A compound of formula (I),

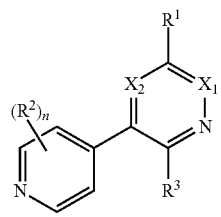

(I)

wherein
$X_1$ is N and $X_2$ is CH, or $X_1$ is CH and $X_2$ is N;
$R^1$ is -$N(R^4)_2$, cyclopropyl, or $R^5$-piperidin-4-yl;
$R^2$ is independently D or halogen;
$R^3$ is naphthyl, quinolinyl, or isoquinolinyl, wherein said naphthyl, quinolinyl, or isoquinolinyl is optionally independently substituted with at least one D, halogen, $(C_1-C_3)$-alkoxy, or $(C_1-C_3)$-alkoxy substituted with at least one D;
$R^4$ is independently H, $(C_1-C_4)$-alkyl, $(C_1-C_4)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S, and wherein the 3-7 membered heterocyclic ring is optionally substituted with a $(C_1-C_3)$-alkyl;
$R^5$ is H or $(C_1-C_3)$-alkyl, or $(C_1-C_3)$-alkyl substituted with at least one D;
$R^6$ is H, $(C_1-C_3)$-alkyl, $(C_1-C_3)$-alkyl substituted with at least one D, or pyrimidin-2-yl; and
n is an integer from 0-4; or a pharmaceutically acceptable salt thereof.

2. The compound of claim 1, wherein
$R^4$ is independently H, $(C_1-C_3)$-alkyl, $(C_1-C_3)$-alkyl substituted with at least one D, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S; and
$R^6$ is H, $(C_1-C_3)$-alkyl, or $(C_1-C_3)$-alkyl substituted with at least one D.

3. The compound of claim 2, wherein
$R^3$ is naphthyl, quinolinyl, or isoquinolinyl, wherein said naphthyl, quinolinyl, or isoquinolinyl is optionally independently substituted with at least one D, halogen, $(C_1-C_3)$-alkoxy, or $(C_1-C_3)$-alkoxy substituted with at least one D.

4. The compound of claim 3, wherein
$R^2$ is independently halogen;
$R^3$ is naphthalen-1-yl, naphthalen-2-yl, quinolin-8-yl, or isoquinolin-5-yl, wherein said naphthalen-1-yl, naphthalen-2-yl, quinolin-8-yl, or isoquinolin-5-yl, is optionally independently substituted with at least one halogen or $(C_1-C_3)$-alkoxy;
$R^4$ is independently H, $(C_1-C_3)$-alkyl, $(C_3-C_5)$-cycloalkyl, or each $R^4$ together with the nitrogen to which they are attached form a 3-7 membered heterocyclic ring, wherein one of the carbon atoms is optionally replaced with $NR^6$, O or S;
$R^5$ is H or $(C_1-C_3)$-alkyl; and
$R^6$ is H or $(C_1-C_3)$-alkyl.

5. The compound of claim 4, wherein
$R^1$ is -$N(R^4)_2$ or cyclopropyl;
$R^2$ is fluorine;
$R^3$ is naphthalen-1-yl or naphthalen-2-yl;
$R^4$ is independently H, $(C_1-C_3)$-alkyl, $(C_3-C_5)$-cycloalkyl, or each $R^4$ together with the nitrogen to which they are attached form

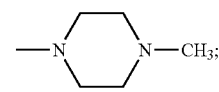

and
n is 0 or 1.

6. The compound of claim 2, wherein
$X_1$ is N and $X_2$ is CH.

7. The compound of claim 6, wherein
$R^1$ is -$N(R^4)_2$ or cyclopropyl;
$R^2$ is independently halogen;

$R^3$ is naphthalen-1-yl, naphthalen-2-yl, quinolin-8-yl, or isoquinolin-5-yl, wherein naphthalen-1-yl, naphthalen-2-yl, quinolin-8-yl, or isoquinolin-5-yl is optionally independently substituted with one or more fluorine atoms;

$R^4$ is independently H, $(C_1-C_3)$-alkyl, $(C_3-C_5)$-cycloalkyl, or each $R^4$ together with the nitrogen to which they are attached form $NR^6$-piperazine, piperidine, pyrrolidine, azetidine, or morpholine;

$R^6$ is H, methyl or $CD_3$; and n is an integer from 0-2.

8. The compound of claim 7, wherein
$R^1$ is

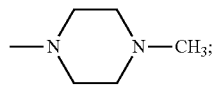

$R^3$ is naphthalen-1-yl or naphthalen-2-yl; and
n is 0.

9. The compound of claim 8, wherein the compound is

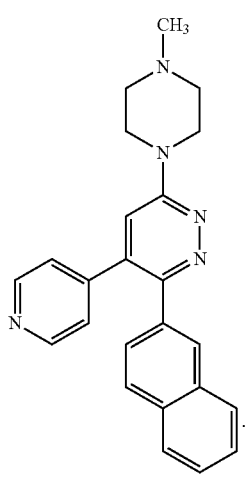 [SMILES: CN1CCN(c2cc(-c3ccncc3)c(-c3ccc4ccccc4c3)nn2)CC1]

10. The compound of claim 7, wherein the compound is selected from

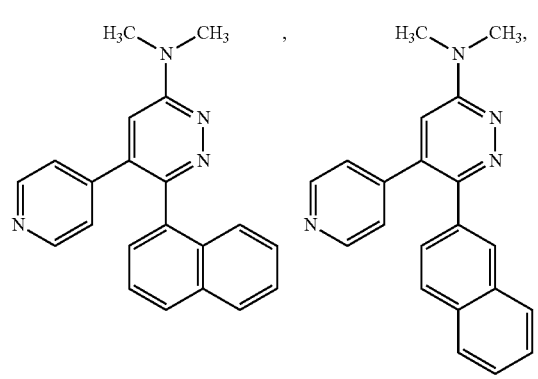

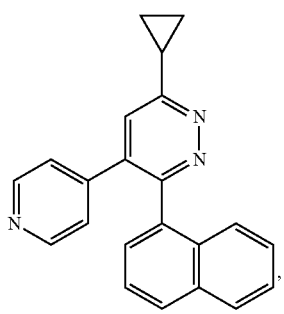

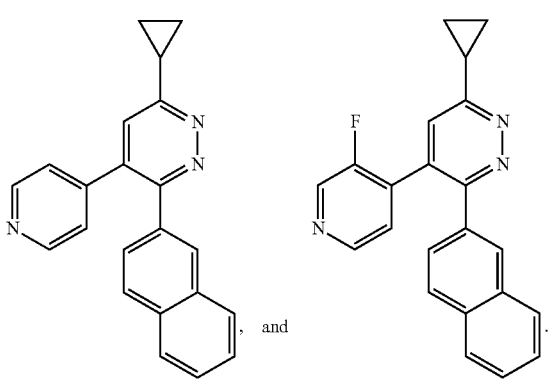

11. The compound of claim 10, wherein the compound is

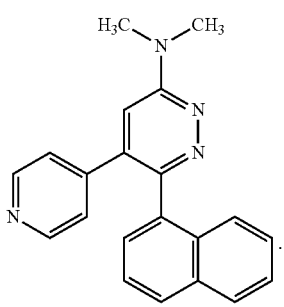 [SMILES: CN(C)c1cc(-c2ccncc2)c(-c2cccc3ccccc23)nn1]

12. The compound of claim 10, wherein the compound is

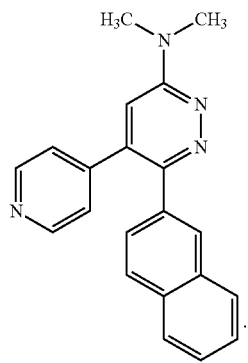 [SMILES: CN(C)c1cc(-c2ccncc2)c(-c2ccc3ccccc3c2)nn1]

13. The compound of claim 10, wherein the compound is

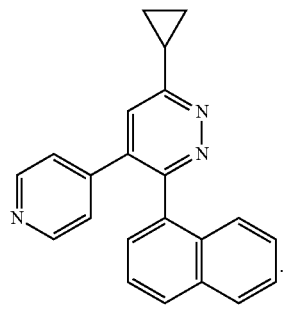 [SMILES: c1ccc2c(-c3nnc(C4CC4)cc3-c3ccncc3)cccc2c1]

14. The compound of claim 10, wherein the compound is

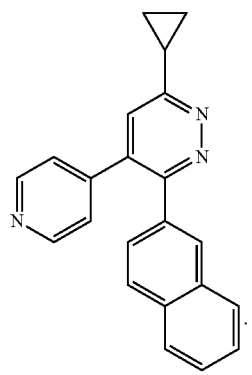 [SMILES: c1ccc2cc(-c3nnc(C4CC4)cc3-c3ccncc3)ccc2c1]

15. The compound of claim 10, wherein the compound is

16. The compound of claim 2, wherein
$X_1$ is CH and $X_2$ is N;
$R^1$ is -N(CH$_3$)$_2$, cyclopropyl, or

—N⌐⌐N—R$^6$;

$R^3$ is naphthalen-1-yl or naphthalen-2-yl;
$R^6$ is H, methyl or CD$_3$; and
n is 0.

17. A composition comprising a compound of claim 1 and a pharmaceutically acceptable carrier.

* * * * *